US012420016B2

(12) United States Patent
Edwards et al.

(10) Patent No.: US 12,420,016 B2
(45) Date of Patent: *Sep. 23, 2025

(54) MEDICAMENT DELIVERY DEVICES FOR ADMINISTRATION OF A MEDICAMENT WITHIN A PREFILLED SYRINGE

(71) Applicant: kaleo, Inc., Richmond, VA (US)

(72) Inventors: Eric S. Edwards, Moseley, VA (US); Evan T. Edwards, Charlottesville, VA (US); Mark J. Licata, Doswell, VA (US); Paul F. Meyers, Fishers, IN (US)

(73) Assignee: kaleo, Inc., Richmond, VA (US)

( * ) Notice: Subject to any disclaimer, the term of this patent is extended or adjusted under 35 U.S.C. 154(b) by 139 days.

This patent is subject to a terminal disclaimer.

(21) Appl. No.: 17/869,570

(22) Filed: Jul. 20, 2022

(65) Prior Publication Data

US 2022/0355034 A1 Nov. 10, 2022

Related U.S. Application Data

(63) Continuation of application No. 16/504,725, filed on Jul. 8, 2019, now Pat. No. 11,426,520, which is a
(Continued)

(51) Int. Cl.
*A61M 5/20* (2006.01)
*A61M 5/315* (2006.01)
*A61M 5/32* (2006.01)

(52) U.S. Cl.
CPC ............ *A61M 5/2033* (2013.01); *A61M 5/20* (2013.01); *A61M 5/315* (2013.01);
(Continued)

(58) Field of Classification Search
CPC ...... A61M 5/2033; A61M 5/20; A61M 5/315; A61M 5/3202; A61M 5/2066;
(Continued)

(56) References Cited

U.S. PATENT DOCUMENTS 2,409,656 A 10/1946 Austin
D168,131 S 11/1952 Touart
(Continued)

FOREIGN PATENT DOCUMENTS

DE 2019296 11/1971
DE 20 2009 003 009 7/2009
(Continued)

OTHER PUBLICATIONS

"Solutions for Medical Devices," 3M Brochure, © 3M, (2006), 80-6201-3490-0, 8 pages.
(Continued)

*Primary Examiner* — Bhisma Mehta
*Assistant Examiner* — Hamza A Darb

(57) ABSTRACT

An apparatus includes a housing, a medicament container and a movable member. The medicament container is movable within the housing between a first position and a second position in response to a force produced by an energy storage member. A proximal end portion of the medicament container includes a flange and has a plunger disposed therein. A first shoulder of the movable member exerts the force on the flange to move the medicament container from the first position to the second position. A portion of the first shoulder deforms when the medicament container is in the second position such that at least a portion of the force is exerted upon the plunger. A second shoulder of the movable member exerts a retraction force on the flange to move the medicament container from the second position towards the first position.

15 Claims, 90 Drawing Sheets

Related U.S. Application Data continuation of application No. 16/280,488, filed on Feb. 20, 2019, now Pat. No. 10,342,924, which is a continuation of application No. 14/803,821, filed on Jul. 20, 2015, now Pat. No. 10,238,806, which is a continuation of application No. 13/357,935, filed on Jan. 25, 2012, now Pat. No. 9,084,849.

(60) Provisional application No. 61/436,301, filed on Jan. 26, 2011.

(52) U.S. Cl.
CPC ... *A61M 5/3202* (2013.01); *A61M 2005/2013* (2013.01); *A61M 2005/206* (2013.01); *A61M 5/2066* (2013.01); *A61M 2005/2073* (2013.01); *A61M 2005/208* (2013.01); *A61M 2005/2086* (2013.01); *A61M 5/3204* (2013.01)

(58) Field of Classification Search
CPC ........ A61M 5/3204; A61M 2005/2013; A61M 2005/206; A61M 2005/2073; A61M 2005/208; A61M 2005/2086; A61M 2005/14252; A61M 2005/1585; A61M 5/34; A61M 5/328
See application file for complete search history.

(56) References Cited

U.S. PATENT DOCUMENTS

| | | |
|---|---|---|
| 2,960,087 A | 11/1960 | Uytenbogaart |
| 3,055,362 A | 9/1962 | Uytenbogaart |
| 3,115,133 A | 12/1963 | Morando |
| 3,426,448 A | 2/1969 | Sarnoff |
| 3,563,373 A | 2/1971 | Paulson |
| 3,565,070 A | 2/1971 | Hanson et al. |
| 3,688,765 A | 9/1972 | Gasaway |
| 3,768,472 A | 10/1973 | Hodosh et al. |
| 3,795,061 A | 3/1974 | Sarnoff et al. |
| 3,797,489 A | 3/1974 | Sarnoff |
| 3,941,130 A | 3/1976 | Tibbs |
| 3,945,379 A | 3/1976 | Pritz et al. |
| 4,031,889 A | 6/1977 | Pike |
| 4,108,177 A | 8/1978 | Pistor |
| 4,124,024 A | 11/1978 | Schwebel et al. |
| 4,226,235 A | 10/1980 | Sarnoff et al. |
| 4,227,528 A | 10/1980 | Wardlaw |
| 4,258,713 A | 3/1981 | Wardlaw |
| 4,360,019 A | 11/1982 | Portner et al. |
| 4,378,015 A | 3/1983 | Wardlaw |
| 4,424,057 A | 1/1984 | House |
| 4,425,120 A | 1/1984 | Sampson et al. |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,664,653 A | 5/1987 | Sagstetter et al. |
| 4,666,430 A | 5/1987 | Brown et al. |
| 4,673,657 A | 6/1987 | Christian |
| 4,681,567 A | 7/1987 | Masters et al. |
| 4,689,042 A | 8/1987 | Sarnoff et al. |
| 4,693,708 A | 9/1987 | Wanderer et al. |
| 4,781,697 A | 11/1988 | Slaughter |
| 4,782,841 A | 11/1988 | Lopez |
| 4,784,652 A | 11/1988 | Wikström |
| 4,790,824 A | 12/1988 | Morrow et al. |
| 4,795,433 A | 1/1989 | Sarnoff |
| 4,822,340 A | 4/1989 | Kamstra |
| 4,826,489 A | 5/1989 | Haber |
| 4,853,521 A | 8/1989 | Claeys et al. |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,955,871 A | 9/1990 | Thomas |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,042,977 A | 8/1991 | Bechtold et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,842 A | 3/1992 | Bechtold et al. |
| 5,092,843 A | 3/1992 | Monroe et al. |
| 5,104,380 A | 4/1992 | Holman et al. |
| 5,125,898 A | 6/1992 | Kaufhold, Jr. et al. |
| 5,147,311 A | 9/1992 | Pickhard |
| 5,167,641 A | 12/1992 | Schmitz |
| 5,199,949 A | 4/1993 | Haber et al. |
| 5,224,936 A | 7/1993 | Gallagher |
| D338,727 S | 8/1993 | Rand et al. |
| 5,240,146 A | 8/1993 | Smedley et al. |
| 5,244,465 A | 9/1993 | Michel |
| 5,271,527 A | 12/1993 | Haber et al. |
| 5,281,198 A | 1/1994 | Haber et al. |
| 5,286,258 A | 2/1994 | Haber et al. |
| 5,295,965 A | 3/1994 | Wilmot |
| 5,298,023 A | 3/1994 | Haber et al. |
| 5,298,024 A | 3/1994 | Richmond |
| 5,312,326 A | 5/1994 | Myers et al. |
| 5,314,412 A | 5/1994 | Rex |
| 5,318,544 A | 6/1994 | Drypen et al. |
| 5,336,180 A | 8/1994 | Kriesel et al. |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,358,489 A | 10/1994 | Wyrick |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,383,864 A | 1/1995 | van den Heuvel |
| 5,394,866 A | 3/1995 | Ritson et al. |
| 5,395,345 A | 3/1995 | Gross |
| 5,399,163 A | 3/1995 | Peterson et al. |
| 5,405,362 A | 4/1995 | Kramer et al. |
| 5,417,660 A | 5/1995 | Martin |
| 5,451,210 A | 9/1995 | Kramer et al. |
| 5,466,217 A | 11/1995 | Myers et al. |
| 5,478,316 A | 12/1995 | Bitdinger et al. |
| 5,514,097 A | 5/1996 | Knauer |
| 5,514,135 A | 5/1996 | Earle |
| 5,527,287 A | 6/1996 | Miskinyar |
| 5,540,664 A | 7/1996 | Wyrick |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,615,771 A | 4/1997 | Hollister |
| 5,616,132 A | 4/1997 | Newman |
| 5,645,534 A | 7/1997 | Chanoch |
| 5,658,259 A | 8/1997 | Pearson et al. |
| 5,662,612 A | 9/1997 | Niehoff |
| 5,681,291 A | 10/1997 | Galli |
| 5,681,292 A | 10/1997 | Tober et al. |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,728,074 A | 3/1998 | Castellano et al. |

(56) References Cited

U.S. PATENT DOCUMENTS

| | | |
|---|---|---|
| 5,772,635 A | 6/1998 | Dastur et al. |
| 5,779,677 A | 7/1998 | Frezza |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,814,020 A | 9/1998 | Gross |
| 5,820,602 A | 10/1998 | Kovelman |
| 5,823,346 A | 10/1998 | Weiner |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,848,990 A | 12/1998 | Cirelli et al. |
| 5,852,590 A | 12/1998 | de la Huerga |
| 5,853,292 A | 12/1998 | Eggert et al. |
| 5,858,001 A | 1/1999 | Tsals et al. |
| 5,865,795 A | 2/1999 | Schiff et al. |
| 5,868,711 A | 2/1999 | Kramer et al. |
| 5,868,713 A | 2/1999 | Klippenstein |
| 5,868,721 A | 2/1999 | Marinacci |
| D407,487 S | 3/1999 | Greubel et al. |
| 5,876,380 A | 3/1999 | Manganini et al. |
| 5,899,879 A | 5/1999 | Umbaugh |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,970,457 A | 10/1999 | Brant et al. |
| 5,971,953 A | 10/1999 | Bachynsky |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,050,977 A | 4/2000 | Adams |
| 6,056,728 A | 5/2000 | von Schuckmann |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,080,130 A | 6/2000 | Castellano |
| 6,083,199 A | 7/2000 | Thorley et al. |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,120,786 A | 9/2000 | Cheikh |
| 6,123,685 A | 9/2000 | Reynolds |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,179,812 B1 | 1/2001 | Botich et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,258,063 B1 | 7/2001 | Haar et al. |
| 6,258,068 B1 | 7/2001 | Kirchhofer et al. |
| 6,259,654 B1 | 7/2001 | de la Huerga |
| 6,264,629 B1 | 7/2001 | Landau |
| 6,270,479 B1 | 8/2001 | Bergens et al. |
| 6,280,421 B1 | 8/2001 | Kirchhofer et al. |
| 6,312,412 B1 | 11/2001 | Saied et al. |
| 6,317,630 B1 | 11/2001 | Gross et al. |
| 6,334,070 B1 | 12/2001 | Nova et al. |
| 6,364,866 B1 | 4/2002 | Furr et al. |
| 6,371,939 B2 | 4/2002 | Bergens et al. |
| 6,383,168 B1 | 5/2002 | Landau et al. |
| 6,387,078 B1 | 5/2002 | Gillespie, III |
| 6,405,912 B2 | 6/2002 | Giannou |
| 6,406,455 B1 | 6/2002 | Willis et al. |
| 6,411,567 B1 | 6/2002 | Niemiec et al. |
| 6,413,236 B1 | 7/2002 | Van Dyke |
| 6,419,656 B1 | 7/2002 | Vetter et al. |
| 6,425,897 B2 | 7/2002 | Overes et al. |
| 6,427,684 B2 | 8/2002 | Ritsche et al. |
| 6,428,517 B1 | 8/2002 | Hochman et al. |
| 6,428,528 B2 | 8/2002 | Sadowski |
| 6,475,181 B1 | 11/2002 | Potter et al. |
| 6,478,771 B1 | 11/2002 | Lavi et al. |
| 6,482,186 B1 | 11/2002 | Douglas et al. |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,540,672 B1 | 4/2003 | Simonsen et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,565,533 B1 | 5/2003 | Smith et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,599,272 B1 | 7/2003 | Hjertman et al. |
| 6,613,010 B2 | 9/2003 | Castellano |
| 6,613,011 B2 | 9/2003 | Castellano |
| 6,616,627 B2 | 9/2003 | Willis et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,648,850 B2 | 11/2003 | Landau |
| 6,656,163 B1 | 12/2003 | Marshall et al. |
| 6,659,980 B2 | 12/2003 | Moberg et al. |
| 6,673,035 B1 | 1/2004 | Rice et al. |
| 6,676,630 B2 | 1/2004 | Landau et al. |
| 6,679,862 B2 | 1/2004 | Diaz et al. |
| 6,689,093 B2 | 2/2004 | Landau |
| 6,692,469 B1 | 2/2004 | Weekes et al. |
| 6,702,778 B2 | 3/2004 | Hill et al. |
| 6,706,019 B1 | 3/2004 | Parker et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,657 B1 | 4/2004 | Dedig et al. |
| 6,726,661 B2 | 4/2004 | Munk et al. |
| 6,736,796 B2 | 5/2004 | Shekalim |
| 6,743,203 B1 | 6/2004 | Pickhard |
| 6,743,635 B2 | 6/2004 | Neel et al. |
| 6,749,437 B2 | 6/2004 | Chan |
| 6,752,781 B2 | 6/2004 | Landau et al. |
| 6,764,469 B2 | 7/2004 | Broselow |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,805,686 B1 | 10/2004 | Fathallah et al. |
| 6,808,514 B2 | 10/2004 | Schneider et al. |

(56) References Cited

U.S. PATENT DOCUMENTS

| | | | |
|---|---|---|---|
| 6,809,653 B1 | 10/2004 | Mann et al. | |
| 6,817,986 B2 | 11/2004 | Slate et al. | |
| 6,830,560 B1 | 12/2004 | Gross et al. | |
| 6,839,304 B2 | 1/2005 | Niemiec et al. | |
| 6,872,200 B2 | 3/2005 | Mann et al. | |
| 6,875,195 B2 | 4/2005 | Choi | |
| 6,883,222 B2 | 4/2005 | Landau | |
| 6,923,764 B2 | 8/2005 | Aceti et al. | |
| 6,936,029 B2 | 8/2005 | Mann et al. | |
| 6,936,032 B1 | 8/2005 | Bush, Jr. et al. | |
| 6,937,150 B2 | 8/2005 | Medema et al. | |
| 6,942,646 B2 | 9/2005 | Langley et al. | |
| 6,946,299 B2 | 9/2005 | Neel et al. | |
| 6,949,082 B2 | 9/2005 | Langley et al. | |
| 6,952,604 B2 | 10/2005 | DeNuzzio et al. | |
| 6,953,445 B2 | 10/2005 | Wilmot et al. | |
| 6,953,693 B2 | 10/2005 | Neel et al. | |
| 6,958,691 B1 | 10/2005 | Anderson et al. | |
| 6,959,247 B2 | 10/2005 | Neel et al. | |
| 6,961,285 B2 | 11/2005 | Niemiec et al. | |
| 6,964,650 B2 | 11/2005 | Alexandre et al. | |
| 6,969,259 B2 | 11/2005 | Pastrick et al. | |
| 6,979,316 B1 | 12/2005 | Rubin et al. | |
| 6,979,326 B2 | 12/2005 | Mann et al. | |
| 6,985,870 B2 | 1/2006 | Martucci et al. | |
| 6,997,911 B2 | 2/2006 | Klitmose | |
| 7,014,470 B2 | 3/2006 | Vann | |
| 7,074,211 B1 | 7/2006 | Heiniger et al. | |
| 7,104,972 B2 | 9/2006 | Moller et al. | |
| 7,113,101 B2 | 9/2006 | Peterson et al. | |
| 7,116,233 B2 | 10/2006 | Zhurin | |
| 7,118,553 B2 | 10/2006 | Scherer | |
| 7,126,879 B2 | 10/2006 | Snyder | |
| 7,158,011 B2 | 1/2007 | Brue | |
| 7,191,916 B2 | 3/2007 | Clifford et al. | |
| 7,299,981 B2 | 11/2007 | Hickle et al. | |
| 7,329,241 B2 | 2/2008 | Horvath et al. | |
| 7,357,790 B2 | 4/2008 | Hommann et al. | |
| 7,416,540 B2 | 8/2008 | Edwards et al. | |
| 7,465,294 B1 | 12/2008 | Vladimirsky | |
| 7,500,963 B2 | 3/2009 | Westbye et al. | |
| 7,500,967 B2 | 3/2009 | Thorley et al. | |
| 7,503,907 B1 | 3/2009 | Lesch, Jr. | |
| 7,544,188 B2 | 6/2009 | Edwards et al. | |
| 7,611,491 B2 | 11/2009 | Pickhard | |
| 7,611,495 B1 | 11/2009 | Gianturco | |
| 7,637,891 B2 | 12/2009 | Wall | |
| 7,648,482 B2 | 1/2010 | Edwards et al. | |
| 7,648,483 B2 | 1/2010 | Edwards et al. | |
| 7,654,983 B2 | 2/2010 | De La Serna et al. | |
| 7,674,246 B2 | 3/2010 | Gillespie et al. | |
| 7,686,788 B2 | 3/2010 | Freyman et al. | |
| 7,731,686 B2 | 6/2010 | Edwards et al. | |
| 7,731,690 B2 | 6/2010 | Edwards et al. | |
| 7,749,194 B2 | 7/2010 | Edwards et al. | |
| 7,758,550 B2 | 7/2010 | Bollenbach et al. | |
| 7,771,397 B1 | 8/2010 | Olson | |
| 7,806,866 B2 | 10/2010 | Hommann et al. | |
| 7,850,662 B2 | 12/2010 | Veasey et al. | |
| 7,871,393 B2 | 1/2011 | Monroe | |
| 7,901,377 B1 | 3/2011 | Harrison et al. | |
| 7,901,384 B2 | 3/2011 | Kleyman et al. | |
| 7,918,823 B2 | 4/2011 | Edwards et al. | |
| 7,918,832 B2 | 4/2011 | Veasey et al. | |
| 7,931,614 B2 | 4/2011 | Gonnelli et al. | |
| 7,938,802 B2 | 5/2011 | Bicknell et al. | |
| 7,938,808 B2 | 5/2011 | Pessin | |
| 7,947,017 B2 | 5/2011 | Edwards et al. | |
| 8,016,788 B2 | 9/2011 | Edwards et al. | |
| 8,021,335 B2 | 9/2011 | Lesch, Jr. | |
| 8,105,281 B2 | 1/2012 | Edwards et al. | |
| 8,105,293 B2 | 1/2012 | Pickhard | |
| 8,123,719 B2 | 2/2012 | Edwards et al. | |
| 8,162,886 B2 | 4/2012 | Sadowski et al. | |
| 8,172,082 B2 | 5/2012 | Edwards et al. | |
| 8,172,790 B2 | 5/2012 | Hunter et al. | |
| 8,206,360 B2 | 6/2012 | Edwards et al. | |
| 8,231,573 B2 | 7/2012 | Edwards et al. | |
| 8,313,466 B2 | 11/2012 | Edwards et al. | |
| 8,361,029 B2 | 1/2013 | Edwards et al. | |
| 8,409,141 B2 | 4/2013 | Johansen et al. | |
| 8,425,462 B2 | 4/2013 | Edwards et al. | |
| 8,608,698 B2 | 12/2013 | Edwards et al. | |
| 8,632,504 B2 | 1/2014 | Young | |
| 8,647,306 B2 | 2/2014 | Schwirtz et al. | |
| 8,662,349 B2 | 3/2014 | Genosar et al. | |
| 8,663,188 B2 | 3/2014 | Genosar et al. | |
| 8,684,968 B2 | 4/2014 | Genosar | |
| 8,690,827 B2 | 4/2014 | Edwards et al. | |
| 8,728,042 B2 | 5/2014 | Pickhard | |
| 8,734,394 B2 | 5/2014 | Adams et al. | |
| 8,747,357 B2 | 6/2014 | Stamp et al. | |
| 8,900,197 B2 | 12/2014 | Crow | |
| 8,920,377 B2 | 12/2014 | Edwards et al. | |
| 8,939,959 B2 | 1/2015 | Baney et al. | |
| 8,945,048 B2 | 2/2015 | Thorley et al. | |
| 8,961,455 B2 | 2/2015 | Holmqvist et al. | |
| 8,992,477 B2 | 3/2015 | Raday et al. | |
| 9,022,980 B2 | 5/2015 | Edwards et al. | |
| 9,044,549 B2 | 6/2015 | Niklasson | |
| 9,056,170 B2 | 6/2015 | Edwards et al. | |
| 9,084,849 B2 | 7/2015 | Edwards et al. | |
| 9,149,579 B2 | 10/2015 | Edwards et al. | |
| 9,173,999 B2 | 11/2015 | Edwards et al. | |
| 9,289,563 B2 | 3/2016 | Pickhard et al. | |
| 9,345,831 B2 | 5/2016 | Raday et al. | |
| 9,352,099 B2 | 5/2016 | Roberts et al. | |
| 9,586,011 B2 | 3/2017 | Roberts et al. | |
| 9,820,913 B2 | 11/2017 | Genosar | |
| 10,028,886 B2 | 7/2018 | Genosar | |
| 10,071,203 B2 | 9/2018 | Edwards et al. | |
| 10,105,499 B2 | 10/2018 | Schwirtz et al. | |
| D833,065 S | 11/2018 | Alarcon | |
| 10,716,901 B2 | 7/2020 | Genosar | |
| 10,864,139 B2 | 12/2020 | Genosar | |
| 10,981,713 B2 | 4/2021 | Genosar | |
| 11,001,435 B2 | 5/2021 | Genosar | |
| D921,190 S | 6/2021 | Shor et al. | |
| 11,185,634 B2 | 11/2021 | Genosar | |
| 11,426,520 B2 * | 8/2022 | Edwards | A61M 5/3202 |
| 11,638,794 B2 | 5/2023 | Genosar | |
| 11,648,180 B2 | 5/2023 | Genosar | |
| 2001/0005781 A1 | 6/2001 | Bergens et al. | |
| 2001/0037087 A1 | 11/2001 | Knauer | |
| 2002/0016567 A1 | 2/2002 | Hochman et al. | |
| 2002/0042596 A1 | 4/2002 | Hartlaub et al. | |
| 2002/0055711 A1 | 5/2002 | Lavi et al. | |
| 2002/0074345 A1 | 6/2002 | Schneider et al. | |
| 2002/0076679 A1 | 6/2002 | Aman | |
| 2002/0079326 A1 | 6/2002 | Fuchs | |
| 2002/0095120 A1 | 7/2002 | Larsen et al. | |
| 2002/0096543 A1 | 7/2002 | Juselius | |
| 2003/0015191 A1 | 1/2003 | Armstrong et al. | |
| 2003/0028145 A1 | 2/2003 | Duchon et al. | |
| 2003/0040717 A1 | 2/2003 | Saulenas et al. | |
| 2003/0105430 A1 | 6/2003 | Lavi et al. | |
| 2003/0106824 A1 | 6/2003 | Wilmot et al. | |
| 2003/0120222 A1 | 6/2003 | Vaillancourt | |
| 2003/0132128 A1 | 7/2003 | Mazur | |
| 2003/0135388 A1 | 7/2003 | Martucci et al. | |
| 2003/0233070 A1 * | 12/2003 | De La Serna | A61M 5/2053 604/141 |
| 2004/0015125 A1 | 1/2004 | Alexandre et al. | |
| 2004/0019326 A1 | 1/2004 | Gilbert et al. | |
| 2004/0024361 A1 | 2/2004 | Fago et al. | |
| 2004/0024367 A1 | 2/2004 | Gilbert | |
| 2004/0039336 A1 | 2/2004 | Amark et al. | |
| 2004/0039337 A1 | 2/2004 | Letzing | |
| 2004/0039368 A1 | 2/2004 | Reilly et al. | |
| 2004/0054327 A1 | 3/2004 | Gillespie, III | |
| 2004/0073169 A1 | 4/2004 | Amisar et al. | |
| 2004/0092874 A1 | 5/2004 | Mazidji | |
| 2004/0094146 A1 | 5/2004 | Schiewe et al. | |
| 2004/0116854 A1 | 6/2004 | Abulhaj et al. | |

(56) References Cited

U.S. PATENT DOCUMENTS

| | | |
|---|---|---|
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0210199 A1 | 10/2004 | Atterbury et al. |
| 2004/0220524 A1 | 11/2004 | Sadowski et al. |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0049561 A1 | 3/2005 | Hommann et al. |
| 2005/0062603 A1 | 3/2005 | Fuerst et al. |
| 2005/0070848 A1 | 3/2005 | Kim |
| 2005/0090781 A1 | 4/2005 | Baba et al. |
| 2005/0090782 A1 | 4/2005 | Marshall et al. |
| 2005/0101912 A1 | 5/2005 | Faust et al. |
| 2005/0134433 A1 | 6/2005 | Sweeney, II |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0182358 A1 | 8/2005 | Veit et al. |
| 2005/0183982 A1 | 8/2005 | Giewercer |
| 2005/0192530 A1 | 9/2005 | Castellano |
| 2005/0192534 A1 | 9/2005 | Wolbring et al. |
| 2005/0197654 A1 | 9/2005 | Edman et al. |
| 2005/0203466 A1 | 9/2005 | Hommann et al. |
| 2005/0222539 A1 | 10/2005 | Gonzales et al. |
| 2005/0261742 A1 | 11/2005 | Nova et al. |
| 2005/0267403 A1 | 12/2005 | Landau et al. |
| 2005/0273059 A1 | 12/2005 | Mernoe et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0084908 A1 | 4/2006 | Bonney et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129089 A1 | 6/2006 | Stamp |
| 2006/0129090 A1 | 6/2006 | Moberg et al. |
| 2006/0173408 A1 | 8/2006 | Wyrick |
| 2006/0184133 A1 | 8/2006 | Pessin |
| 2006/0189938 A1 | 8/2006 | Hommann et al. |
| 2006/0200077 A1 | 9/2006 | Righi et al. |
| 2006/0223027 A1 | 10/2006 | Smith et al. |
| 2006/0235354 A1 | 10/2006 | Kaal et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0021720 A1 | 1/2007 | Guilllermo |
| 2007/0074722 A1 | 4/2007 | Giroux et al. |
| 2007/0079777 A1 | 4/2007 | Hurlstone et al. |
| 2007/0088268 A1* | 4/2007 | Edwards ............ A61M 5/2033 604/151 |
| 2007/0100288 A1 | 5/2007 | Bozeman et al. |
| 2007/0129686 A1 | 6/2007 | Daily et al. |
| 2007/0135767 A1 | 6/2007 | Gillespie, III et al. |
| 2007/0173772 A1 | 7/2007 | Liversidge |
| 2007/0184847 A1 | 8/2007 | Hansen et al. |
| 2007/0210147 A1 | 9/2007 | Morrone et al. |
| 2007/0213598 A1 | 9/2007 | Howard et al. |
| 2007/0233001 A1 | 10/2007 | Burroughs et al. |
| 2007/0265568 A1 | 11/2007 | Tsals et al. |
| 2007/0276320 A1 | 11/2007 | Wall et al. |
| 2007/0293826 A1 | 12/2007 | Wall et al. |
| 2008/0111685 A1 | 5/2008 | Olson et al. |
| 2008/0147006 A1 | 6/2008 | Brunnberg et al. |
| 2008/0154200 A1 | 6/2008 | Lesch |
| 2008/0171995 A1 | 7/2008 | Vitullo et al. |
| 2008/0188798 A1 | 8/2008 | Weber |
| 2008/0208114 A1 | 8/2008 | Landau et al. |
| 2008/0228143 A1 | 9/2008 | Stamp |
| 2008/0255513 A1 | 10/2008 | Kaal et al. |
| 2008/0262443 A1 | 10/2008 | Hommann et al. |
| 2009/0093759 A1 | 4/2009 | Judd et al. |
| 2009/0192486 A1 | 7/2009 | Wilmot et al. |
| 2009/0209939 A1 | 8/2009 | Verespej et al. |
| 2009/0221962 A1 | 9/2009 | Kaal et al. |
| 2009/0240200 A1 | 9/2009 | Heneveld et al. |
| 2009/0299279 A1 | 12/2009 | Richter |
| 2009/0318361 A1 | 12/2009 | Noera et al. |
| 2010/0010454 A1 | 1/2010 | Marshall et al. |
| 2010/0049125 A1 | 2/2010 | James et al. |
| 2010/0137808 A1 | 6/2010 | Wilmot et al. |
| 2010/0152659 A1 | 6/2010 | Streit et al. |
| 2010/0160894 A1 | 6/2010 | Julian et al. |
| 2010/0185148 A1 | 7/2010 | Gillespie, III et al. |
| 2010/0185178 A1 | 7/2010 | Sharp et al. |
| 2010/0211005 A1 | 8/2010 | Edwards et al. |
| 2010/0280460 A1 | 11/2010 | Markussen |
| 2010/0286612 A1 | 11/2010 | Cirillo |
| 2011/0046565 A1 | 2/2011 | Radmer et al. |
| 2011/0077589 A1 | 3/2011 | Karlsson et al. |
| 2011/0092917 A1 | 4/2011 | Wei et al. |
| 2011/0092954 A1 | 4/2011 | Jennings |
| 2011/0098655 A1 | 4/2011 | Jennings et al. |
| 2011/0201999 A1 | 8/2011 | Cronenberg |
| 2011/0202011 A1 | 8/2011 | Wozencroft |
| 2011/0213314 A1 | 9/2011 | Guillermo |
| 2011/0245761 A1 | 10/2011 | Jennings et al. |
| 2011/0270220 A1 | 11/2011 | Genosar |
| 2011/0319864 A1 | 12/2011 | Beller et al. |
| 2012/0046613 A1 | 2/2012 | Plumptre |
| 2012/0056019 A1 | 3/2012 | Renz et al. |
| 2012/0078180 A1* | 3/2012 | Fujioka ............ A61J 1/20 604/131 |
| 2012/0101446 A1 | 4/2012 | Heald |
| 2012/0101449 A1 | 4/2012 | Holmqvist |
| 2012/0101475 A1 | 4/2012 | Wilmot et al. |
| 2012/0103462 A1 | 5/2012 | Levy |
| 2012/0107783 A1 | 5/2012 | Julian et al. |
| 2012/0116319 A1 | 5/2012 | Grunhut |
| 2012/0130318 A1 | 5/2012 | Young |
| 2012/0143144 A1 | 6/2012 | Young |
| 2012/0172804 A1 | 7/2012 | Plumptre |
| 2012/0172817 A1 | 7/2012 | Bruggemann et al. |
| 2012/0191049 A1 | 7/2012 | Harms et al. |
| 2012/0209200 A1 | 8/2012 | Jones et al. |
| 2012/0233834 A1 | 9/2012 | Szechinski et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0268741 A1 | 10/2012 | Pommerau et al. |
| 2012/0271243 A1 | 10/2012 | Plumptre et al. |
| 2012/0283648 A1 | 11/2012 | Veasey et al. |
| 2012/0283651 A1 | 11/2012 | Veasey et al. |
| 2012/0283662 A1 | 11/2012 | MacDonald et al. |
| 2012/0289906 A1 | 11/2012 | Jones et al. |
| 2012/0289929 A1 | 11/2012 | Boyd et al. |
| 2012/0310168 A1 | 12/2012 | Plumptre et al. |
| 2012/0310206 A1 | 12/2012 | Kouyoumjian et al. |
| 2012/0323186 A1 | 12/2012 | Karlsen et al. |
| 2012/0325865 A1 | 12/2012 | Forstreuter et al. |
| 2012/0330244 A1 | 12/2012 | Helmer et al. |
| 2013/0060231 A1 | 3/2013 | Adlon et al. |
| 2013/0060232 A1 | 3/2013 | Adlon et al. |
| 2013/0079718 A1 | 3/2013 | Shang et al. |
| 2013/0079725 A1 | 3/2013 | Shang et al. |
| 2013/0096512 A1 | 4/2013 | Ekman et al. |
| 2013/0110050 A1 | 5/2013 | Boyd et al. |
| 2013/0131602 A1 | 5/2013 | Kemp et al. |
| 2013/0138049 A1 | 5/2013 | Kemp et al. |
| 2013/0150800 A1 | 6/2013 | Kemp et al. |
| 2013/0172822 A1 | 7/2013 | Ekman et al. |
| 2013/0204199 A1 | 8/2013 | Hourmand et al. |
| 2013/0218074 A1 | 8/2013 | Holmqvist et al. |
| 2013/0226084 A1 | 8/2013 | Samandi et al. |
| 2013/0236872 A1 | 9/2013 | Laurusonis et al. |
| 2013/0245562 A1 | 9/2013 | Kouyoumjian et al. |
| 2013/0266919 A1 | 10/2013 | Baker et al. |
| 2013/0274662 A1 | 10/2013 | Hourmand et al. |

(56) References Cited

U.S. PATENT DOCUMENTS

| | | | |
|---|---|---|---|
| 2013/0274707 A1 | 10/2013 | Wilmot et al. |
| 2013/0296796 A1 | 11/2013 | Hourmand et al. |
| 2013/0317427 A1 | 11/2013 | Brereton et al. |
| 2013/0317477 A1 | 11/2013 | Edwards et al. |
| 2013/0317480 A1 | 11/2013 | Reber et al. |
| 2014/0008366 A1 | 1/2014 | Genosar |
| 2014/0025014 A1 | 1/2014 | Radmer et al. |
| 2014/0031760 A1 | 1/2014 | Mercer et al. |
| 2014/0046259 A1 | 2/2014 | Reber et al. |
| 2014/0103075 A1 | 4/2014 | Bennison et al. |
| 2014/0114250 A1 | 4/2014 | DeSalvo et al. |
| 2014/0128840 A1 | 5/2014 | Rao et al. |
| 2014/0135705 A1 | 5/2014 | Hourmand et al. |
| 2014/0257185 A1 | 9/2014 | Bechmann et al. |
| 2014/0367288 A1 | 12/2014 | Ziegner |
| 2015/0238695 A1 | 8/2015 | Edwards et al. |
| 2015/0283323 A1 | 10/2015 | Young et al. |
| 2016/0015907 A1 | 1/2016 | Edwards et al. |
| 2016/0045670 A1 | 2/2016 | Edwards et al. |
| 2016/0184521 A1 | 6/2016 | Edwards et al. |
| 2016/0250414 A1 | 9/2016 | Edwards et al. |
| 2017/0290982 A1 | 10/2017 | Edwards et al. |
| 2018/0008774 A1 | 1/2018 | Edwards et al. |
| 2018/0235840 A1 | 8/2018 | Genosar |
| 2019/0151548 A1 | 5/2019 | Edwards et al. |
| 2019/0175837 A1 | 6/2019 | Edwards et al. |
| 2019/0275253 A1 | 9/2019 | Edwards et al. |
| 2019/0282763 A1 | 9/2019 | Edwards et al. |
| 2019/0328971 A1 | 10/2019 | Edwards et al. |
| 2019/0358399 A1 | 11/2019 | Edwards et al. |
| 2019/0381245 A1 | 12/2019 | Edwards et al. |
| 2020/0197612 A1 | 6/2020 | Edwards et al. |
| 2020/0360231 A1 | 11/2020 | Genosar |
| 2021/0138152 A1 | 5/2021 | Edwards et al. |
| 2021/0213201 A1 | 7/2021 | Meyers et al. |
| 2021/0292073 A1 | 9/2021 | Genosar |
| 2021/0402097 A1 | 12/2021 | Genosar et al. |
| 2022/0071844 A1 | 3/2022 | Genosar |
| 2022/0088310 A1 | 3/2022 | Genosar |
| 2023/0076855 A1 | 3/2023 | Edwards et al. |
| 2023/0099753 A1 | 3/2023 | Genosar |

FOREIGN PATENT DOCUMENTS

| | | |
|---|---|---|
| EP | 1287840 A1 | 3/2003 |
| EP | 1462134 A1 | 9/2004 |
| EP | 1518575 A1 | 3/2005 |
| EP | 1712178 A2 | 10/2006 |
| EP | 1095668 | 4/2007 |
| FR | 1514210 | 2/1968 |
| FR | 2506161 | 11/1982 |
| FR | 2509615 | 1/1983 |
| FR | 2700959 | 2/1993 |
| GB | 2490807 | 11/2012 |
| MX | PA04009276 | 1/2005 |
| WO | WO 91/04760 | 4/1991 |
| WO | WO 92/18176 | 10/1992 |
| WO | WO 93/02720 | 2/1993 |
| WO | WO 93/23096 | 11/1993 |
| WO | WO 95/13838 | 5/1995 |
| WO | WO 95/26009 | 9/1995 |
| WO | WO 95/35126 | 12/1995 |
| WO | WO 98/52632 | 11/1998 |
| WO | WO 99/10031 | 3/1999 |
| WO | WO 2001/024690 | 4/2001 |
| WO | WO 2001/026020 | 4/2001 |
| WO | WO 2001/041849 | 6/2001 |
| WO | WO 2001/088828 | 11/2001 |
| WO | WO 2001/093926 | 12/2001 |
| WO | WO 2002/083205 | 10/2002 |
| WO | WO 2002/083212 | 10/2002 |
| WO | WO 2002/100469 | 12/2002 |
| WO | WO 2003/011378 | 2/2003 |
| WO | WO 2003/013632 | 2/2003 |
| WO | WO 2003/095001 | 11/2003 |
| WO | WO 2003/097133 | 11/2003 |
| WO | WO 2004/041330 | 5/2004 |
| WO | WO 2004/047890 | 6/2004 |
| WO | WO 2004/047891 | 6/2004 |
| WO | WO 2004/047892 | 6/2004 |
| WO | WO 2004/047893 | 6/2004 |
| WO | WO 2004/054644 | 7/2004 |
| WO | WO 2005/050526 | 6/2005 |
| WO | WO 2005/070481 | 8/2005 |
| WO | WO 2005/077441 | 8/2005 |
| WO | WO 2005/039673 | 5/2006 |
| WO | WO 2006/058426 | 6/2006 |
| WO | WO 2006/109778 | 10/2006 |
| WO | WO 2006/125692 | 11/2006 |
| WO | WO 2008/005315 | 1/2008 |
| WO | WO 2008/082704 | 7/2008 |
| WO | WO 2008/148864 | 12/2008 |
| WO | WO 2009/095735 | 8/2009 |
| WO | WO 2010/033806 | 3/2010 |
| WO | WO 2011/157930 | 12/2011 |
| WO | WO 2012/164402 A2 | 12/2012 |
| WO | WO 2013/044172 | 3/2013 |

OTHER PUBLICATIONS

Tingelstad, M., "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint&ArticleID=CA6332947>, 3 pages.

"Flexible circuits / Flex circuits / Flexible Technology Ltd.," Flexible Technology Limited [online] [retrieved on Aug. 28, 2006] Retrieved from the Internet <URL: http://www.flexibletechnology.com/ >, 2 pages.

"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible circuits Capability.htm >, 2 pages.

"Flex Circuits/flexible circuits design guide," [online] [retrieved on Aug. 28, 2006] Retrieved from the Internet <URL: http://flexiblecircuit.co.uk/Flex Circuits Design Guide.htm >, 7 pages.

"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >, 3 pages.

"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/product catalogue.asp >, 9 pages.

"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >, 3 pages.

Allan, R., "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>, 3 pages.

RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >, 2 pages.

"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?. v=8>, 3 pages.

Scholz, O., "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true>, 1 page.

Heartsine Technology, samaritan™ Pad Accessories [online] [retrieved on Jun. 1, 2007] Retrieved from the Internet <URL: http://www.heartsine.com/aboutsam-accessories.htm>, 4 pages.

CliniSense Corporation, "Drug delivery devices A potentially harsh environment for drugs," Stability [online] [retrieved on Jun. 1, 2007] Retrieved from the Internet <URL: http://www.clinisense.com/devices.htm>, 2 pages.

(56) References Cited

OTHER PUBLICATIONS

CliniSense Corporation, "LifeTrack Technology A new method to detect improper storage." Stability [online] [retrieved on Jun. 1, 2007] Retrieved from the Internet <URL: http://www.clinisense.com/tech.htm>, 2 pages.
AED Professionals ™ Brochure [online] [retrieved on Jun. 1, 2007] Retrieved from the Internet <URL: http://www.aedprofessionals.com>, 4 pages.
Ruppar, D., "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8 >, 8 pages.
Office Action for Canadian Patent Application No. 2,586,525, mailed Aug. 17, 2010.
Examination Report for British Patent Application No. GB 0708523.6, mailed Dec. 8, 2008.
Examination Report for British Patent Application No. GB 0822532.8, mailed Jan. 21, 2009.
Examination Report for British Patent Application No. GB 0822532.8, mailed May 21, 2009.
Office Action for U.S. Appl. No. 11/562,061, mailed Feb. 3, 2009.
Office Action for U.S. Appl. No. 11/758,393, mailed May 13, 2009.
Search Report and Written Opinion for International Patent Application No. PCT/US07/84891 mailed Sep. 15, 2008, 7 pages.
Office Action for U.S. Appl. No. 12/138,987, mailed Oct. 5, 2009.
Office Action for U.S. Appl. No. 13/053,451, mailed Nov. 15, 2012.
International Search Report and Written Opinion for International Patent Application No. PCT/US06/03415, mailed Jul. 13, 2006, 10 pages.
International Search Report and Written Opinion for International Patent Application No. PCT/US07/007626, mailed Sep. 29, 2008.
Office Action for U.S. Appl. No. 12/119,016, mailed Nov. 3, 2011.
Examination Report for Australian Patent Application No. 2012211307, mailed Mar. 3, 2014, 3 pages.
Supplementary Search Report for European Patent Application No. 12740010.9, mailed Aug. 5, 2014.
International Search Report and Written Opinion for International Application No. PCT/US2012/022675, mailed May 25, 2012.
Office Action for Japanese Patent Application No. 2013-551324, mailed Jan. 13, 2016.
Third Party Observations filed in European Patent Application No. 07864490.3, mailed Aug. 22, 2016.
Office Action for Israel Patent Application No. 227617, mailed Sep. 19, 2016.
Office Action for U.S. Appl. No. 15/696,287, mailed Nov. 16, 2017.
Office Action for Canadian Patent Application No. 2,825,600, mailed Feb. 1, 2018.
Office Action for U.S. Appl. No. 14/803,821, mailed Feb. 9, 2018.
Office Action for U.S. Appl. No. 14/803,821, mailed Aug. 27, 2018.
Office Action for U.S. Appl. No. 15/631,076, mailed Apr. 8, 2019.
Office Action for U.S. Appl. No. 16/438,203, mailed Jul. 18, 2019.
Office Action for U.S. Appl. No. 15/738,008, mailed Aug. 22, 2019.
Office Action for U.S. Appl. No. 16/426,412, mailed Sep. 17, 2019.
First Examination Report for IN Application No. 6573/DELNP/2013, mailed Jan. 7, 2020.
Office Action for U.S. Appl. No. 16/504,725, mailed May 19, 2021.
Final Office Action for U.S. Appl. No. 16/504,725, mailed Jan. 7, 2022.

\* cited by examiner

MEDICAMENT DELIVERY DEVICES FOR ADMINISTRATION OF A MEDICAMENT WITHIN A PREFILLED SYRINGE

CROSS-REFERENCE TO RELATED APPLICATIONS

This application is a continuation of U.S. patent application Ser. No. 16/504,725, now U.S. Pat. No. 11,426,520, entitled "Medicament Delivery Devices for Administration of a Medicament within a Prefilled Syringe," filed on Jul. 8, 2019, which is a continuation of U.S. patent application Ser. No. 16/280,488, now U.S. Pat. No. 10,342,924, entitled "Medicament Delivery Devices for Administration of a Medicament within a Prefilled Syringe," filed on Feb. 20, 2019, which is a continuation of U.S. patent application Ser. No. 14/803,821, now U.S. Pat. No. 10,238,806, entitled "Medicament Delivery Devices for Administration of a Medicament within a Prefilled Syringe," filed on Jul. 20, 2015, which is a continuation of U.S. patent application Ser. No. 13/357,935, now U.S. Pat. No. 9,084,849, entitled "Medicament Delivery Devices for Administration of a Medicament within a Prefilled Syringe," filed on Jan. 25, 2012, which claims priority to U.S. Provisional Application Ser. No. 61/436,301, entitled "Devices and Methods for Delivering Lyophilized Medicaments," filed Jan. 26, 2011, the disclosures of each of which are incorporated herein by reference in their entireties.

BACKGROUND

The embodiments described herein relate to medicament delivery devices. More particularly, the embodiments described herein relate to medicament delivery devices for delivery of medicaments contained within a prefilled syringe.

Known prefilled syringes are commonly used to contain and inject medicaments. Known prefilled syringes include a syringe body, often constructed from glass, within which a medicament is contained. The distal end portion of some known prefilled syringes includes a staked needle (i.e., a needle that is permanently coupled to the syringe body during manufacture), the end of which is disposed within a needle cover to maintain the sterility of the needle prior to use. Other known prefilled syringes include a Luer fitting or adapted such that the distal end portion of the syringe body can be coupled to a needle. The proximal end portion of the syringe body of known prefilled syringes includes a plunger (usually constructed from an elastomer) that defines a portion of the container closure, and that can be moved within the syringe body to inject the medicament. The proximal end portion also includes a flange to allow the user to grasp the syringe body and manually apply a force to a piston to move the plunger, thereby causing injection of the medicament.

Although prefilled syringes can be cost effective devices for storing and delivering medicaments, known methods for using prefilled syringes include manually inserting the needle into the body followed by manually applying the injection force. Moreover, upon completion of the injection, known methods include covering the needle to avoid needle sticks. Thus, known prefilled syringes are often used by healthcare professionals that are trained in such procedures. To facilitate the self-administration of medicaments contained in prefilled syringes, some known autoinjectors have been adapted to contain prefilled syringes. In this manner, the autoinjector provides a source of stored energy for inserting the needle and/or injecting the medicament.

Known autoinjectors, however, are often designed for a medicament container having a specific size and/or shape, and are therefore often not configured to receive known prefilled syringes. For example, using a prefilled syringe within a known autoinjector can often result in high forces being applied to the flange of the syringe body during the insertion operation, which can lead to breakage of the syringe flange or body. Moreover, because many known prefilled syringes include a staked needle that is in fluid communication with the medicament, applying a force to the plunger during storage and/or during an insertion operation is undesirable. For example, the application of a force against the plunger during storage, which can result, for example, when a spring-loaded member is placed in contact with the plunger, can cause in leakage of the medicament. As another example, the application of a force against the plunger during a needle insertion event can result in the injection of the medicament before the needle is inserted to the desired location. Similarly stated, some known autoinjectors are not configured to control the force applied to the plunger within the syringe body during storage and/or needle insertion.

Thus, a need exists for improved methods and devices for delivering medicaments contained within a prefilled syringe.

SUMMARY

Medicament delivery devices for administration of medicaments contained within a prefilled syringe are described herein. In some embodiments, an apparatus includes a housing, a medicament container and a movable member. The medicament container is configured to move within the housing between a first position and a second position in response to a force produced by an energy storage member. A proximal end portion of the medicament container includes a flange and has a plunger disposed therein. The movable member is configured to move within the housing. A first shoulder of the movable member is configured to exert the force on the flange to move the medicament container from the first position to the second position. A portion of the first shoulder is configured to deform when the medicament container is in the second position such that at least a portion of the force is exerted upon the plunger. A second shoulder of the movable member is configured to exert a retraction force on the flange to move the medicament container from the second position towards the first position.

DETAILED DESCRIPTION

Figure 1:
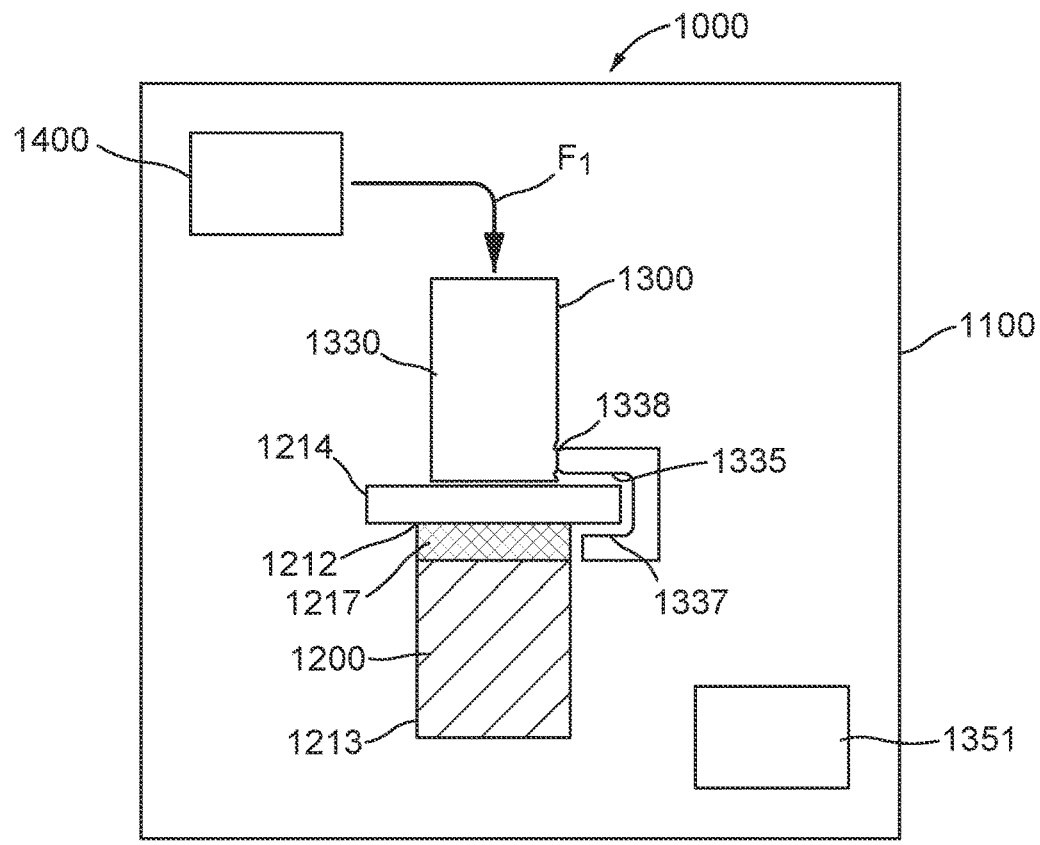
FIGS. 1-4 are schematic illustrations of a medicament delivery device according to an embodiment, in a first, second, third and fourth configuration, respectively.

Medicament delivery devices for administration of medicaments contained within a prefilled syringe are described herein. In some embodiments, an apparatus includes a housing, a medicament container and a movable member. The medicament container, which can be, for example, a prefilled syringe, is configured to move within the housing between a first position and a second position in response to a force produced by an energy storage member. The energy storage member can be, for example, a spring, a compressed gas container, an electrical energy storage member or the like. A proximal end portion of the medicament container includes a flange and has a plunger disposed therein. The movable member is configured to move within the housing. A first shoulder of the movable member is configured to exert the force on the flange to move the medicament container from the first position to the second position. A portion of the first shoulder is configured to deform when the medicament container is in the second position such that at least a portion of the force is exerted upon the plunger. A second shoulder of the movable member is configured to exert a retraction force on the flange to move the medicament container from the second position towards the first position.

In some embodiments, a medicament delivery device includes a housing, a medicament container, a movable member and an energy storage member. The medicament container is configured to move within the housing between a first position and a second position in response to a force produced by the energy storage member. A proximal end portion of the medicament container includes a flange and has a plunger disposed therein. The movable member is configured to exert the force on the medicament container to move the medicament container from the first position to the second position. An engagement portion of the movable member is configured to limit movement of a piston surface relative to the plunger when the medicament container moves from the first position to the second position such that the piston surface is spaced apart from the plunger. The engagement portion is configured to deform when the medicament container is in the second position such that the piston surface is in contact with the plunger.

In some embodiments, a medicament delivery device includes a housing, a medicament container, a first movable member and a second movable member. The medicament container is configured to move within the housing between a first position and a second position in response to a force produced by an energy storage member. A proximal end portion of the medicament container includes a flange and has a plunger disposed therein. The first movable member is configured to move within the housing, and is operably coupled to the energy storage member such that a first portion of the first movable member is configured to exert at least a portion of the force on the flange to move the medicament container from the first position to the second position. A second portion of the first movable member is configured to deform when the medicament container is in the second position such that at least a portion of the force is exerted upon the plunger. The second movable member is configured to move with the medicament container when the medicament container moves from the first position to the second position. The second movable member is configured to move relative to the medicament container to move the plunger within the medicament container after the second portion of the first movable member is deformed.

In some embodiments, a medical device includes a carrier configured to be disposed within a housing of the medical device. The carrier is configured to contain at least a proximal portion of a medicament container, such as, for example a prefilled syringe having a flange. A first shoulder of the carrier is in contact with a proximal surface of the flange and a second shoulder of the carrier is in contact with a distal surface of the flange. The carrier has a first engagement portion configured to engage a movable member such that when a first force is exerted by the movable member on the first engagement portion, the first shoulder transfers at least a portion of the first force to the proximal surface of the flange. The carrier has a second engagement portion configured to engage a retraction spring such that when a second force is exerted by the retraction spring on the second engagement portion, the second shoulder transfers at least a portion of the second force to the distal surface of the flange.

In some embodiments, the medical device further includes a damping member disposed between the first shoulder of the carrier and the proximal surface of the flange of the medicament container, or between the second shoulder of the carrier and the proximal surface of the flange of the medicament container. The damping member can be disposed such that a portion of the first force or a portion of the second force is received and/or absorbed by the damping member to reduce the possibility of damage to the medicament container and/or flange.

In some embodiments, a medical device includes a housing, a movable member and a medicament container. The movable member is disposed within the housing and has a first engagement portion, a second engagement portion and a retraction portion. The first engagement portion is configured to be coupled to an energy storage member. The second engagement portion is configured to be coupled to the medicament container such that a shoulder of the second engagement portion exerts a first force produced by the energy storage member on the medicament container to move the medicament container within the housing in a first direction. The retraction portion is configured to produce a second force to move the medicament container within the housing in a second direction. In some embodiments, the retraction portion includes a spring that is monolithically constructed with at least the second engagement portion.

As used in this specification and the appended claims, the words "proximal" and "distal" refer to direction closer to and away from, respectively, an operator of the medical device. Thus, for example, the end of the medicament delivery device contacting the patient's body would be the distal end of the medicament delivery device, while the end opposite the distal end would be the proximal end of the medicament delivery device.

FIGS. 1-4 are schematic illustrations of a medicament delivery device 1000 according to an embodiment in a first, second, third and fourth configuration, respectively. The medicament delivery device 1000 includes a housing 1100, a medicament container 1200, a movable member 1300, an energy storage member 1400 and a retraction member 1351. The housing 1100 can be any suitable size, shape, or configuration and can be made of any suitable material. For example, in some embodiments, the housing 1100 is an assembly of multiple parts formed from a plastic material and defines a substantially rectangular shape when assembled.

The medicament container 1200 is disposed within the housing 1100, and contains (i.e., is filled or partially filled with) a medicament. The medicament container 1200 includes a proximal end portion 1212 that has a flange 1214 and a distal end portion 1213 that is coupled to a needle (not shown in FIGS. 1-4). The medicament container 1200 includes an elastomeric member 1217 (also referred to herein as a "plunger"). The elastomeric member 1217 is formulated to be compatible with the medicament housed within the medicament container 1200. Similarly stated, the elastomeric member 1217 is formulated to minimize any reduction in the efficacy of the medicament that may result from contact (either direct or indirect) between the elastomeric member 1217 and the medicament. For example, in some embodiments, the elastomeric member 1217 can be formulated to minimize any leaching or out-gassing of compositions that may have an undesired effect on the medicament. The elastomeric member 1217 is disposed within the medicament container 1200 to seal the proximal end portion 1212 of the medicament container 1200. In some embodiments, the elastomeric member 1217 can be formulated to maintain its chemical stability, flexibility and/or sealing properties when in contact (either direct or indirect) with a medicament over a long period of time (e.g., for up to six months, one year, two years, five years or longer). The medicament container 1200 can be any container suitable for storing the medicament. In some embodiments, the medicament container 1200 can be, for example, a prefilled syringe having a staked needle at the distal end thereof. In those embodiments in which the medicament container 1200 is a prefilled syringe, the elastomeric member 1217 can be disposed within the medicament container 1200 during the fill process (e.g., before being placed in the housing 1100).

The energy storage member 1400 can be any suitable device or mechanism that, when actuated, produces a force $F_1$ to deliver the medicament contained within the medicament container 1200. Similarly stated, the energy storage member 1400 can be any suitable device or mechanism that produces the force $F_1$ such that the medicament is conveyed from the medicament container 1200 into a body of a patient. More specifically, the energy storage member 1400 produces the force $F_1$ that moves the medicament container 1200 from a first position to a second position in a first direction indicated by the arrow AA in FIG. 2 and/or that moves the plunger 1217 from a first plunger position to a second plunger position as shown by the arrow BB in FIG. 3. The medicament can be conveyed into a body via any suitable mechanism, such as, for example, by injection. By employing the energy storage member 1400 to produce the force $F_1$ rather than relying on a user to manually produce the delivery force, the medicament can be delivered into the body at the desired pressure and/or flow rate, and with the desired delivery characteristics. Moreover, this arrangement reduces the likelihood of partial delivery (e.g., that may result if the user is interrupted or otherwise rendered unable to manually produce the force to complete the delivery).

In some embodiments, the energy storage member 1400 can be a mechanical energy storage member, such as a spring, a device containing compressed gas, a device containing a vapor pressure-based propellant or the like. In other embodiments, the energy storage member 1400 can be an electrical energy storage member, such as a battery, a capacitor, a magnetic energy storage member or the like. In yet other embodiments, the energy storage member 1400 can be a chemical energy storage member, such as a container containing two substances that, when mixed, react to produce energy.

The energy storage member 1400 can be disposed within the housing in any position and/or orientation relative to the medicament container 1200. In some embodiments, for example, the energy storage member 1400 can be positioned within the housing 1100 spaced apart from the medicament container 1200. Moreover, in some embodiments, the energy storage member 1400 can be positioned such that a longitudinal axis of the energy storage member 1400 is offset from the medicament container 1200. In other embodiments, the energy storage member 1400 can substantially surround the medicament container 1200.

As shown in FIG. 1, the energy storage member 1400 is operably coupled to the movable member 1300, the medicament container 1200 and/or the medicament therein such that the force $F_1$ delivers the medicament. In some embodiments, for example, the force $F_1$ can be transmitted to the medicament container 1200 and/or the medicament therein via the movable member 1300. The movable member 1300 can be any suitable member, device, assembly or mechanism configured to move within the housing 1100. As shown in FIGS. 1-4, the movable member 1300 includes a piston portion 1330 configured to transmit the force $F_1$ to the plunger 1217 disposed within the medicament container 1200.

The movable member 1300 includes a first shoulder 1335 and a second shoulder 1337. The first shoulder 1335 of the movable member 1300 is configured to exert the force $F_1$, produced by the energy storage member 1400, on the flange 1214 of the medicament container 1200. In this manner, when the medicament delivery device 1000 is actuated to produce the force $F_1$, movable member 1300 moves the medicament container 1200 from the first position (see FIG. 1, which corresponds to the first configuration of the medicament delivery device 1000) to the second position (see FIG. 2, which corresponds to the second configuration of the medicament delivery device 1000). In some embodiments, the movement of the medicament container 1200 within the housing 1100 results in a needle insertion operation. Although the first shoulder 1335 is shown as directly contacting the flange 1214 when the medicament delivery device 1000 is in the second configuration (FIG. 2), in other embodiments, there can be intervening structure (e.g., an o-ring, a damping member, or the like) disposed between the first shoulder 1335 and the flange 1214.

In some embodiments, the first shoulder 1335 of the movable member 1300 can be configured to maintain a distance between the piston portion 1330 of the movable member 1300 and the plunger 1217 when the medicament delivery device 1000 is in the first configuration (FIG. 1). Similarly stated, in some embodiments, the movable member 1300 and the medicament container 1200 are collectively configured such that the piston portion 1330 is spaced apart from the plunger 1217 when the medicament delivery device 1000 is in its storage configuration and/or when the medicament container 1200 is moving between its first position and its second position. In this manner, any preload or residual force produced by the energy storage member 1400 on the movable member 1300 is not transferred to the plunger 1217. Said another way, the plunger 1217 is isolated from the energy storage member 1400 during the storage configuration. Accordingly, this arrangement reduces and/or eliminates medicament leakage from the medicament container 1200.

Figure 3:
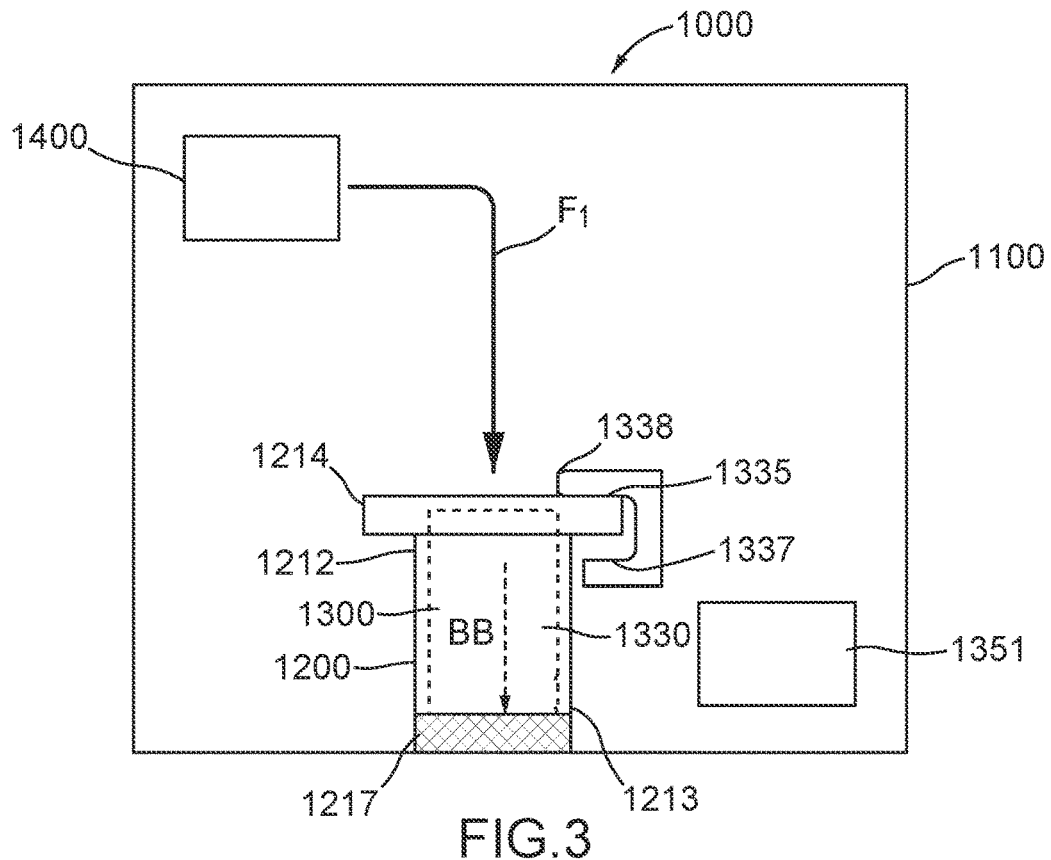

As shown in FIG. 3, the first shoulder 1335 includes a deformable portion 1338 configured to deform when the medicament container 1200 is in the second position such that at least a portion of the force $F_1$ is exerted upon the plunger 1217. In some embodiments, the deformable portion 1338 can be separated from the piston portion 1330 of the movable member 1300. In other embodiments, the deformable portion 1338 is configured to bend, deform, rotate and/or otherwise move relative to the piston portion 1300 such that the piston portion 1330 is placed into contact (directly or indirectly via intervening structure) with the plunger 1217. Similarly stated, in some embodiments, the deformable portion 1338 is configured to bend, deform, rotate and/or otherwise move relative to the piston portion 1300 such that the first shoulder 1335 no longer maintains the distance between the piston portion 1300 and the plunger 1217. In this manner, the piston portion 1330 transmits at least a portion of the force $F_1$ to the plunger 1217, thereby placing the medicament container 1200 into the third configuration (FIG. 3). More specifically, when the deformable portion 1338 deforms, the piston portion 1330 moves within the medicament container 1200 in the direction of the arrow BB (FIG. 3) and moves the plunger 1217 from the proximal end portion 1212 of the medicament container 1200 towards the distal end portion 1213 of the medicament container 1200. This arrangement allows for the delivery of the medicament contained within the medicament container 1200 into a body of a patient.

Figure 2:
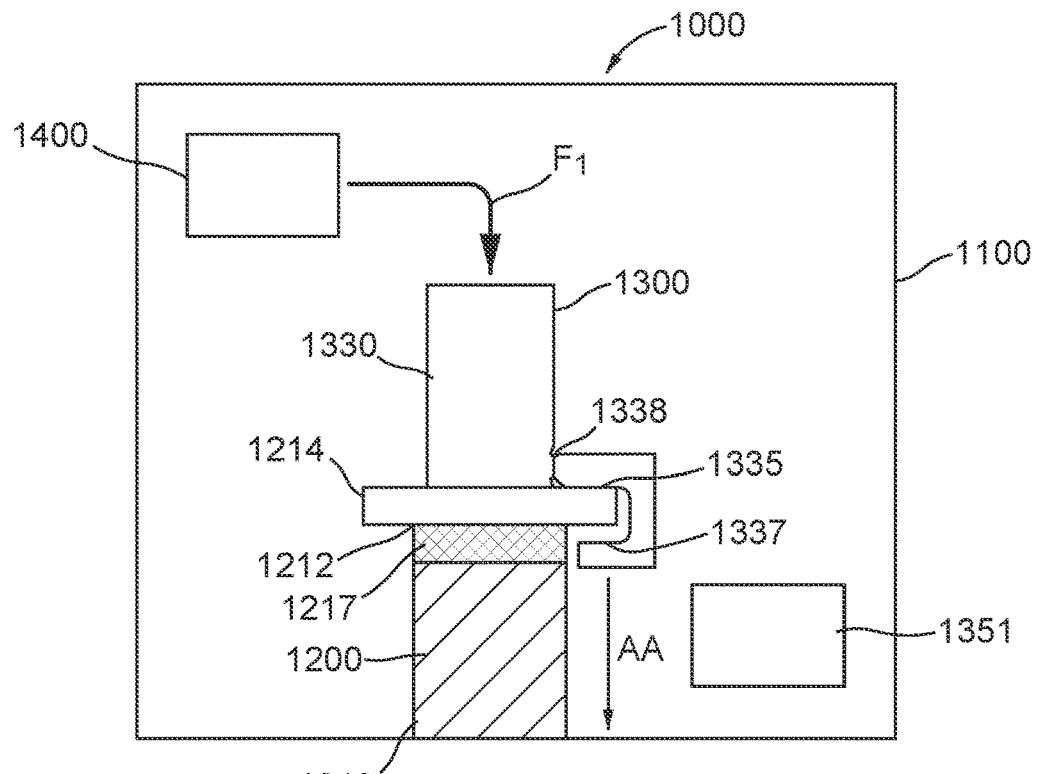

When the medicament is delivered, the retraction member 1351 exerts a retraction force $F_2$ on at least the second shoulder 1337 of the movable member 1300 in a second direction, opposite the first direction. When the retraction force $F_2$ is exerted, the second shoulder 1337 engages a distal surface of the flange 1214 of the medicament container 1200, thereby exerting at least a portion of the retraction force $F_2$ on the flange 1214. Although the second shoulder 1337 is shown as directly contacting the flange 1214 when the medicament delivery device 1000 is in the fourth configuration (FIG. 4), in other embodiments, there can be intervening structure (e.g., an o-ring, a damping member, or the like) disposed between the second shoulder 1337 and the flange 1214. The exertion of the retraction force $F_2$ on the flange 1214 moves the medicament container 1200 from the second position (e.g., the second and third configuration, as shown in FIGS. 2 and 3) in the direction of the arrow CC toward the first position. In this manner, the retraction member 1351 produces the retraction force $F_2$ and moves the distal end portion 1213 of the medicament container 1200 (which can include, for example, a needle) away from the body of the patient and into the housing 1100 of the medicament delivery device 1000.

Figure 4:
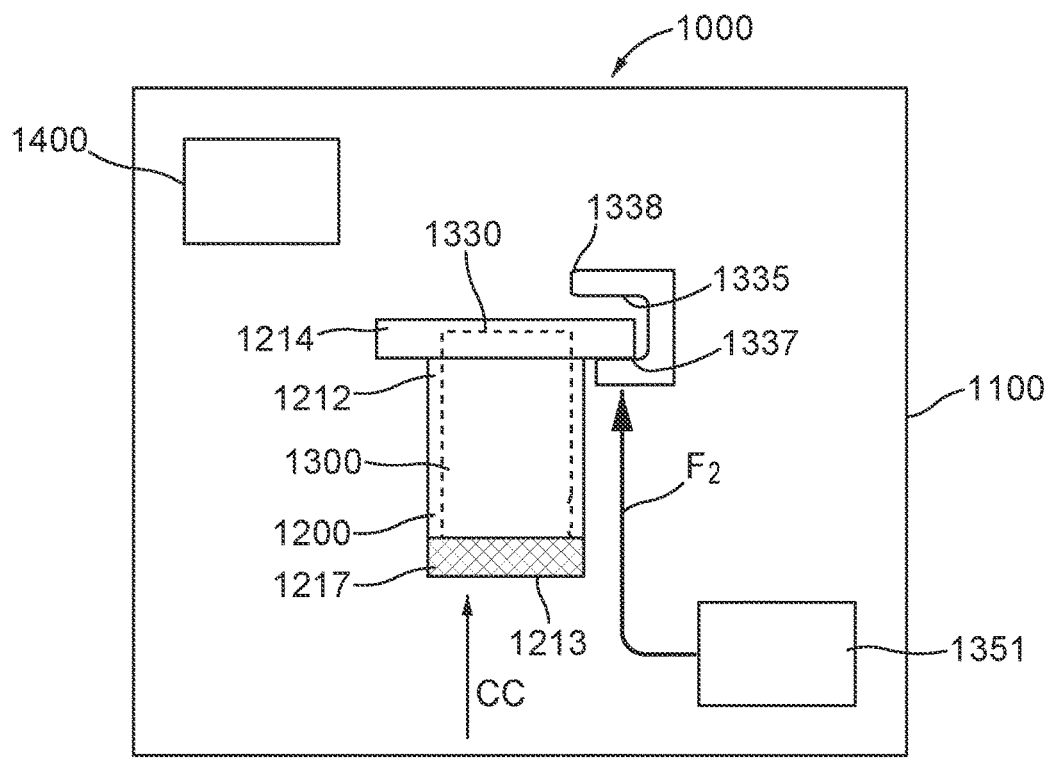

The retraction member 1351 can be any suitable device or mechanism that, when actuated, produces a force $F_2$ to move the medicament container 1200 in the second direction as indicated by the arrow CC in FIG. 4. In some embodiments, the retraction member 1351 can be a mechanical energy storage member, such as a spring, a device containing compressed gas, a device containing a vapor pressure-based propellant or the like. In other embodiments, the retraction member 1351 can be an electrical energy storage member, such as a battery, a capacitor, a magnetic energy storage member or the like. In yet other embodiments, the retraction member 1351 can be a chemical energy storage member, such as a container containing two substances that, when mixed, react to produce energy. Although the retraction member 1351 is shown as being separate and distinct from the energy storage member 1400, in some embodiments, the energy storage member 1400 can be configured to produce the retraction force $F_2$.

The retraction member 1351 can be in any position and/or orientation relative to the medicament container 1200. In some embodiments, for example, the retraction member 1351 can be positioned within the housing 1100 spaced apart from the medicament container 1200. Moreover, in some embodiments, the retraction member 1351 can be positioned such that a longitudinal axis of the retraction member 1351 is offset from the medicament container 1200. In other embodiments, the retraction member 1351 can substantially surround the medicament container 1200. In some embodiments, the retraction member 1351 is coupled to the second shoulder 1337 of the movable member 1300. In other embodiments, the retraction member 1351 is monolithically formed with the movable member 1300.

FIGS. 5-8 are schematic illustrations of a medicament delivery device 2000 according to an embodiment in a first, second, third and fourth configuration, respectively. The medicament delivery device 2000 includes a housing 2100, a medicament container 2200, a first movable member 2300, a second movable member 2345 and an energy storage member 2400. The housing 2100 can be any suitable size, shape, or configuration and can be made of any suitable material. For example, in some embodiments, the housing 2100 is an assembly of multiple parts formed from a plastic material and defines a substantially rectangular shape when assembled.

The medicament container 2200 is disposed within the housing 2100, and contains (i.e., is filled or partially filled with) a medicament. The medicament container 2200 includes a proximal end portion 2212 that has a flange 2214 and a distal end portion 2213 that is coupled to a delivery member, such as a needle, nozzle or the like (not shown in FIGS. 5-8). The medicament container 2200 includes an elastomeric member 2217. The elastomeric member 2217 is formulated to be compatible with the medicament housed within the medicament container 2200. Similarly stated, the elastomeric member 2217 is formulated to minimize any reduction in the efficacy of the medicament that may result from contact (either direct or indirect) between the elastomeric member 2217 and the medicament. For example, in some embodiments, the elastomeric member 2217 can be formulated to minimize any leaching or out-gassing of compositions that may have an undesired effect on the medicament. The elastomeric member 2217 is disposed within the medicament container 2200 to seal the proximal end portion 2212 of the medicament container 2200. In some embodiments, the elastomeric member 2217 can be formulated to maintain its chemical stability, flexibility and/or sealing properties when in contact (either direct or indirect) with a medicament over a long period of time (e.g., for up to six months, one year, two years, five years or longer). The medicament container 2200 can be any container suitable for storing the medicament. In some embodiments, the medicament container 2200 can be, for example, a prefilled syringe having a staked needle at the distal end thereof. In those embodiments in which the medicament container 1200 is a prefilled syringe, the elastomeric member 2217 is disposed within the medicament container 2200 during the fill process (e.g., before the prefilled syringe is placed in the housing 2100).

The energy storage member 2400 can be any suitable device or mechanism that, when actuated, produces a force $F_3$ to deliver the medicament contained within the medicament container 2200. Similarly stated, the energy storage member 2400 can be any suitable device or mechanism that produces the force $F_3$ such that the medicament is conveyed from the medicament container 2200 into a body of a patient. More specifically, the energy storage member 2400 produces the force $F_3$ that moves the medicament container 2200 from a first position to a second position in a first direction indicated by the arrow DD in FIG. 6 and/or that moves the plunger 2217 from a first plunger position to a second plunger position, as shown by the arrow EE in FIG. 7. The medicament can be conveyed into a body via any suitable mechanism, such as, for example, by injection via a needle, nozzle or the like.

In some embodiments, the energy storage member 2400 can be a mechanical energy storage member, such as a spring, a device containing compressed gas, a device containing a vapor pressure-based propellant or the like. In other embodiments, the energy storage member 2400 can be an electrical energy storage member, such as a battery, a capacitor, a magnetic energy storage member or the like. In yet other embodiments, the energy storage member 2400 can be a chemical energy storage member, such as a container containing two substances that, when mixed, react to produce energy.

The energy storage member 2400 can be in any position and/or orientation relative to the medicament container 2200. In some embodiments, for example, the energy storage member 2400 can be positioned within the housing 2100 spaced apart from the medicament container 2200. Moreover, in some embodiments, the energy storage member 2400 can be positioned such that a longitudinal axis of the energy storage member 2400 is offset from the medicament container 2200. In other embodiments, the energy storage member 2400 can substantially surround the medicament container 2200.

Figure 5:
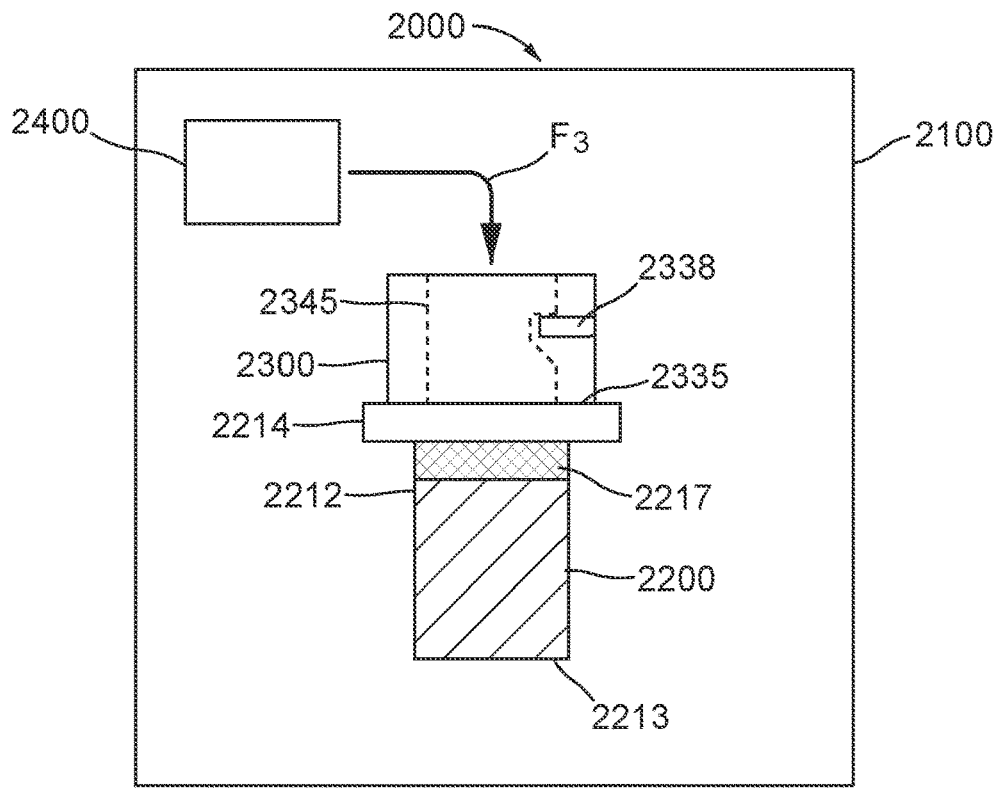
FIGS. 5-8 are schematic illustrations of a medicament delivery device according to an embodiment, in a first, second, third and fourth configuration, respectively.

As shown in FIG. 5, the energy storage member 2400 is operably coupled to the first movable member 2300, the second movable member 2345, the medicament container 2200 and/or the medicament therein such that the force $F_3$ delivers the medicament. In some embodiments, for example, the force $F_3$ can be transmitted to the medicament and/or the medicament container 2200 via the first movable member 2300 and/or the second movable member 2345. As described in more detail herein, the first movable member 2300 and the second movable member 2345 are collectively configured to transmit the force $F_3$ to the plunger 2217 disposed within the medicament container 2200.

The first movable member 2300 includes a first portion 2335 and a second portion 2338. The first portion 2335 of the movable member 2300 is configured to transmit and/or exert at least a portion of the force $F_3$ produced by the energy storage member 2400 on the flange 2214 of the medicament container 2200 to move the medicament container 2200 from the first position (see FIG. 5, which corresponds to the first configuration of the medicament delivery device 2000) to the second position (see FIG. 6, which corresponds to the second configuration of the medicament delivery device 2000). Although the medicament container 2200 is shown as being within the housing 2100 when the medicament container 2200 is in the second position, in some embodiments, the movement of the medicament container 2200 can result in a needle insertion operation in which a needle (not shown in FIGS. 5-8) is extended outside of the housing 2100. The first portion 2335 of the movable member 2300 can be, for example, a first shoulder, protrusion, sleeve or the like. Although the first portion 2335 is shown as directly contacting the flange 2214 when the medicament delivery device 2000 is in the second configuration (FIG. 6), in other embodiments, there can be intervening structure (e.g., an o-ring, a damping member, or the like) disposed between the first portion 2335 and the flange 2214.

Figure 6:
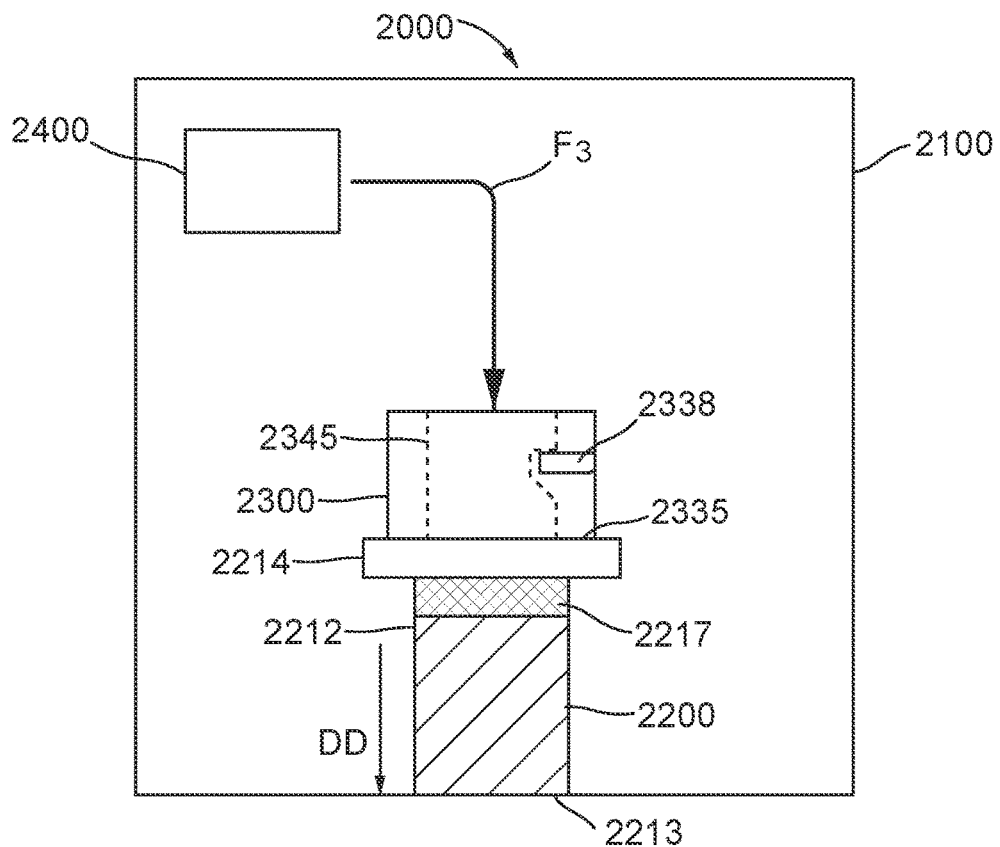

The second portion 2338 of the first movable member 2300 maintains the second movable member 2345 in a first position (FIGS. 5 and 6), relative to the medicament container 2200 and/or the first movable member 2300 when the medicament delivery device 2000 is in the first (i.e., storage) configuration (FIG. 5). In this manner, as shown in FIG. 6, at least a portion of the force $F_3$ can be transferred from the energy storage member 2400 to the first movable member 2300 (and to the flange 2214) via the second movable member 2345. Thus, when the medicament container 2200 is moved from its first position to its second position, the second movable member 2345 moves with the medicament container 2200 and/or the first movable member 2300.

In some embodiments, the second portion 2338 can engage the second movable member 2345 to maintain a distance (e.g., an air gap, space, or void) between the second movable member 2345 and the plunger 2217, when the medicament container 2200 is in the first configuration (FIG. 1) and/or when the medicament container 2200 is moving between its first position and its second position. In this manner, any preload or residual force produced by the energy storage member 1400 on the second movable member 2345 is not transferred to the plunger 2217. Said another way, the plunger 2217 is substantially isolated from the energy storage member 2400 during the storage configuration and/or when the medicament container 2200 is moving. Accordingly, this arrangement reduces and/or eliminates medicament leakage from the medicament container 2200.

Figure 7:
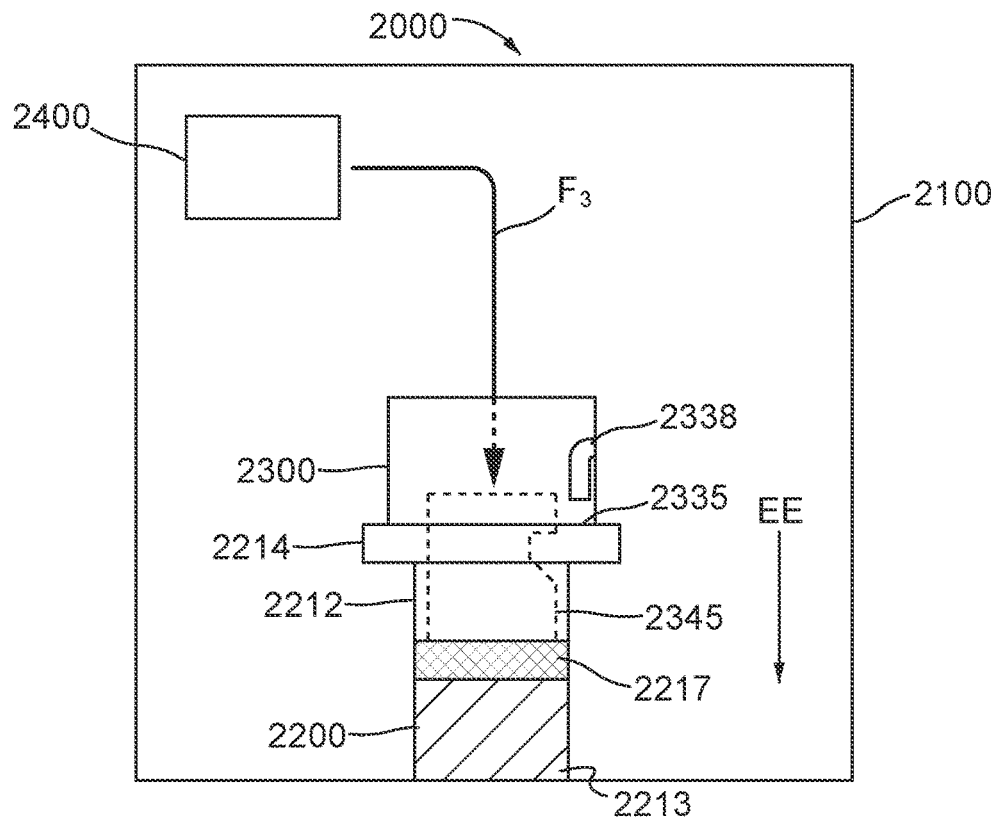
Figure 8:
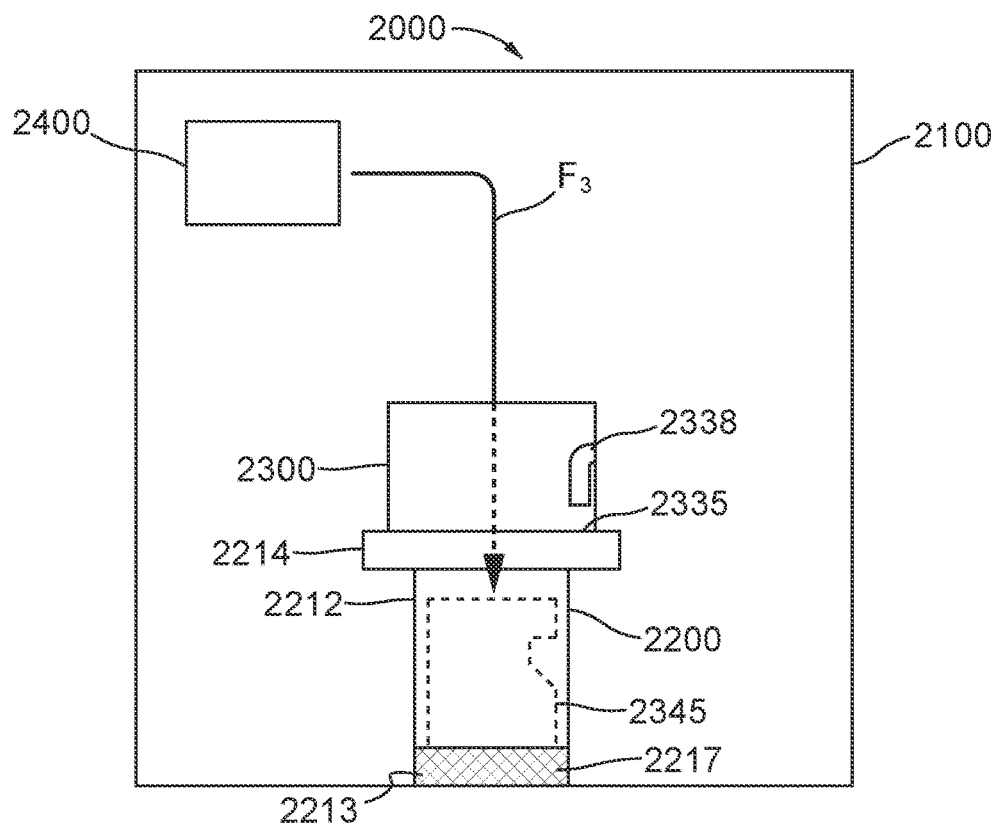

When the medicament container 2200 in the second position (FIGS. 6 and 7), the second portion 2338 of the first movable member 2300 is configured to deform (e.g., by a portion of the force $F_3$), thereby allowing movement of the second movable member 2345 relative to the first movable member 2300 and/or the medicament container 2200. Thus, when the second portion 2338 of the first movable member 2300 deforms, at least a portion of the force $F_3$ is exerted upon the plunger 2217. Similarly stated, when the medicament delivery device 2000 is in the second configuration (FIG. 6), a portion of the force $F_3$ can deform the second portion 2338 of the movable member 2300 (FIG. 7). After the second portion 2338 is deformed, at least a portion of the force $F_3$ is transmitted from the second movable member 2345 to the plunger 2217 to place the medicament container 2200 in the third configuration (FIG. 7). More specifically, when the second portion 2338 deforms, the second movable member 2345 moves in the direction of the arrow EE (FIG. 7) and moves the plunger 2217 from the proximal end portion 2212 of the medicament container 2200 toward the distal end portion 2213 of the medicament container 2200. Similarly stated, when the second portion 2338 deforms, the second movable member 2345 moves relative to the medicament container 2200 to move the plunger 2217 within the medicament container 2200. This arrangement allows for the delivery of the medicament contained within the medicament container 2200 into a body of a patient, as shown in FIG. 8.

In some embodiments, the medicament delivery device 2000 can include a retraction member (not shown in FIGS. 5-8). The retraction member can be any suitable device and/or mechanism configured to move the medicament container 2200 from the second position (e.g., the fourth configuration shown in FIG. 8) toward the first position (e.g. the first configuration shown in FIG. 5). In some embodiments, the retraction member can be substantially similar to the retraction member 1351 described with respect to FIGS. 1-4. In such embodiments, the retraction member can be configured to transmit a force to the flange 2214 of the medicament container 2200 and move the medicament container 2200 in a second direction opposite the first direction indicated by the arrow DD in FIG. 6.

Figure 9:
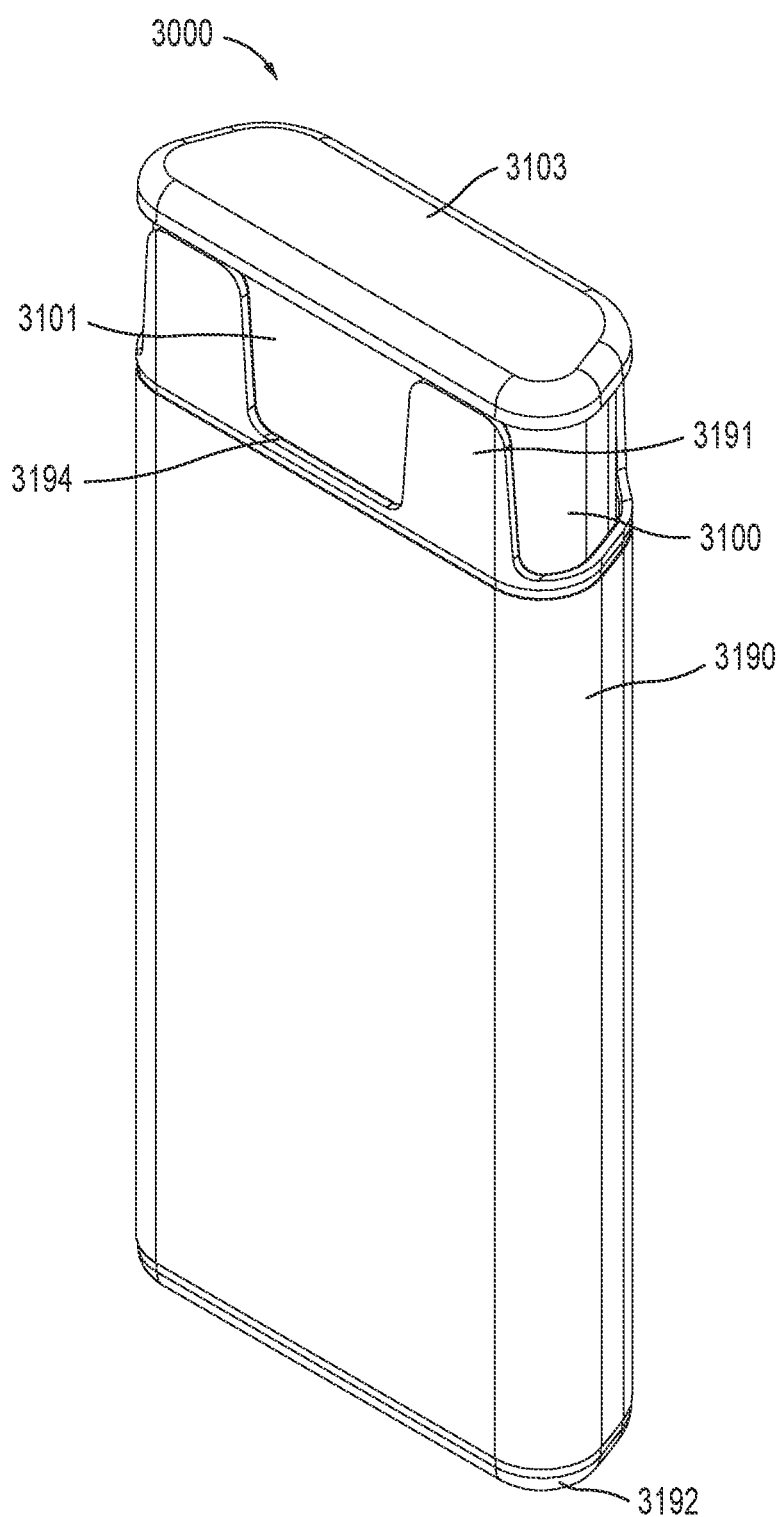
FIGS. 9 and 10 are perspective views of a medical injector according to an embodiment, in a first configuration.
Figure 10:
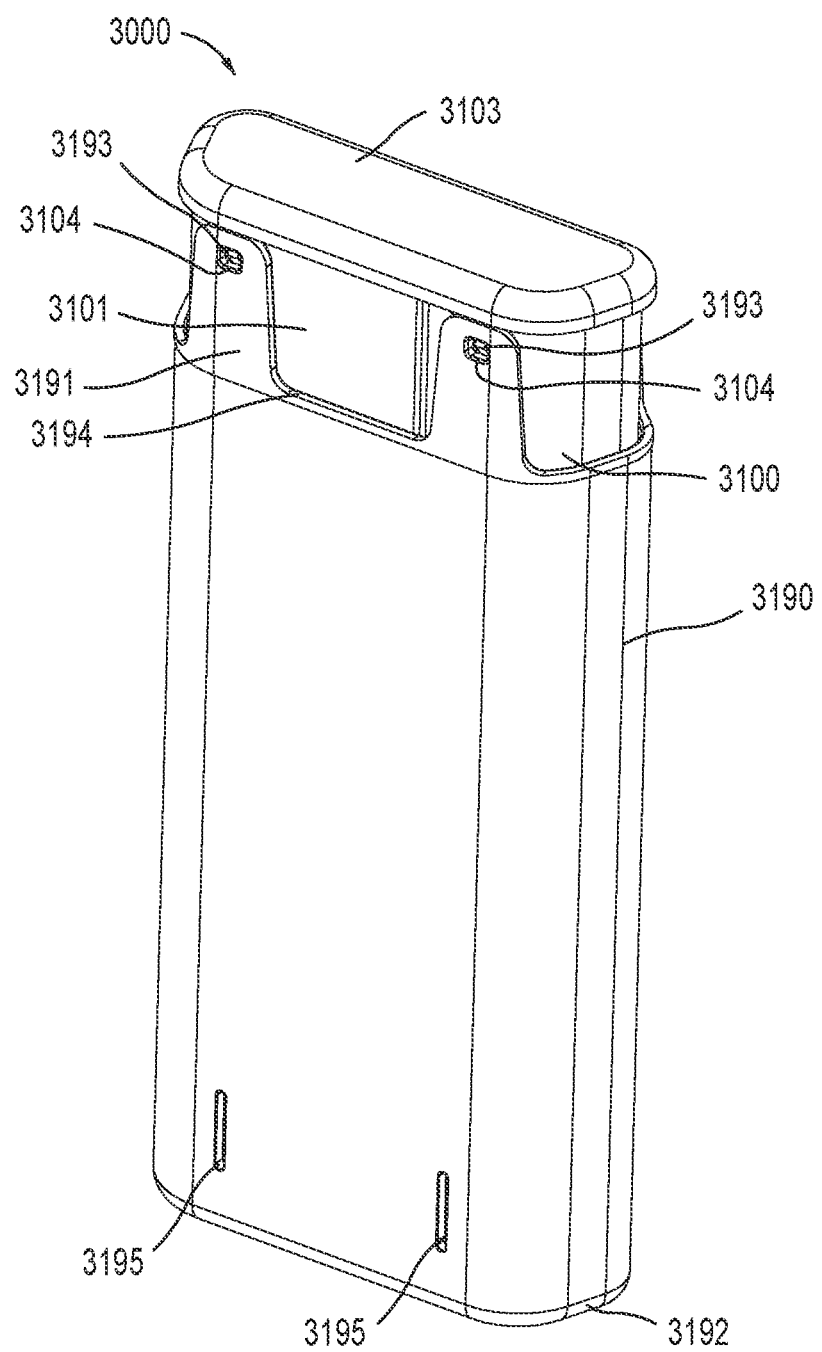
Figure 11:
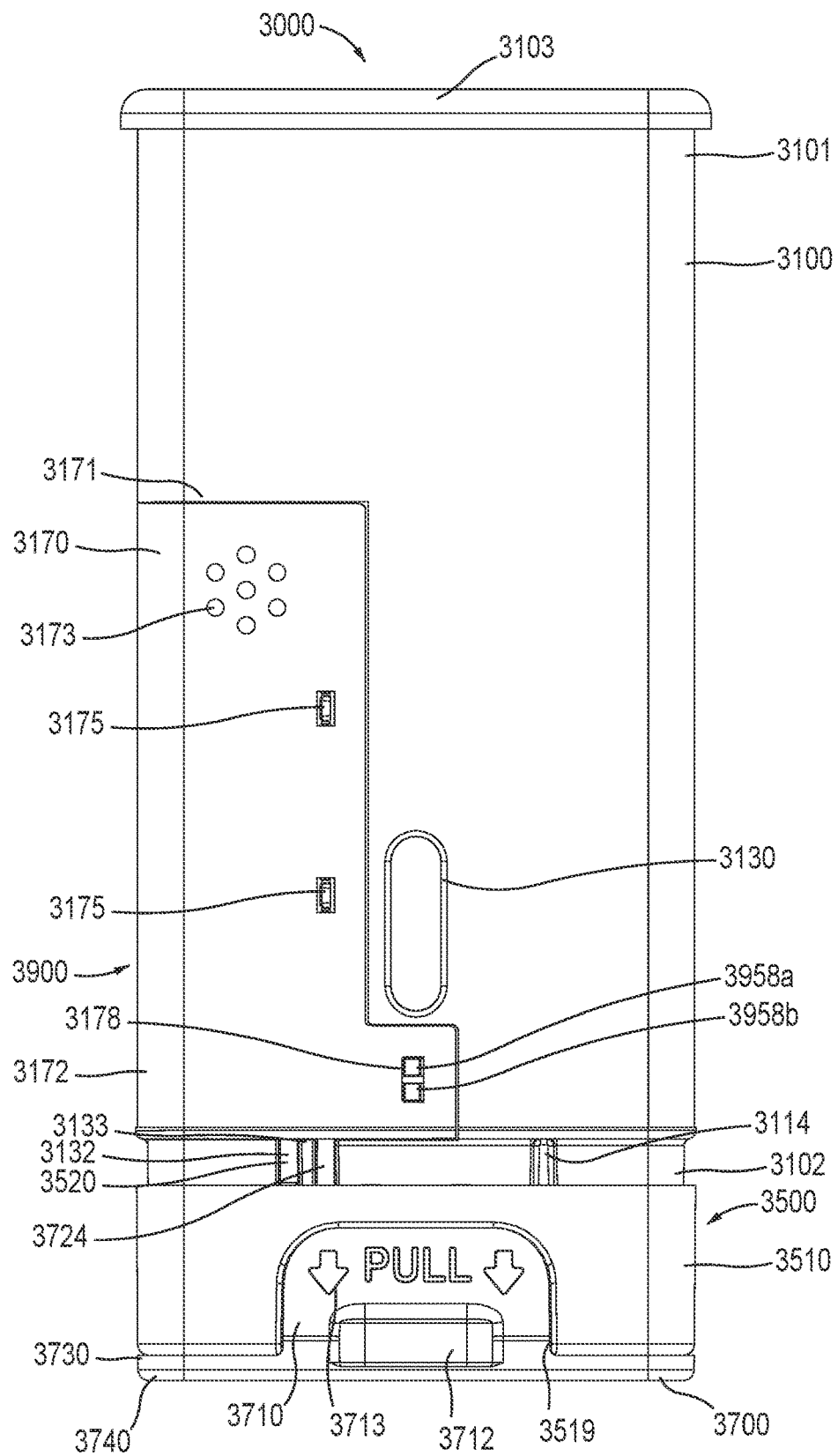
FIG. 11 is a front view of the medical injector illustrated in FIG. 9 with a cover removed.

In some embodiments, the medicament delivery device can be a medical injector configured to automatically deliver a medicament contained within a medicament container, such as, for example a prefilled syringe. For example, FIGS. 9-55 show a medical injector 3000, according to an embodiment. FIGS. 9-10 are perspective views of the medical injector 3000 in a first configuration (i.e., prior to use). The medical injector 3000 includes a housing 3100 (see e.g., FIGS. 11-17), a system actuation assembly 3500 (see e.g., FIGS. 18-21), a medicament container 3200 containing a medicament 3220 (see e.g., FIG. 22), a medicament delivery mechanism 3300 (see e.g., FIG. 26-28), an electronic circuit system 3900 (see e.g., FIGS. 29-39), a cover 3190 (see e.g., FIGS. 40-41), and a safety lock 3700 (see e.g., FIGS. 42-46). A discussion of the components of the medical injector 3000 will be followed by a discussion of the operation of the medical injector 3000.

As shown in FIGS. 11-17, the housing 3100 has a proximal end portion 3101 and a distal end portion 3102. The housing 3100 defines a first status indicator aperture 3130 and a second status indicator aperture 3160. The first status indicator aperture 3130 defined by the housing 3100 is located on a first side of the housing 3100, and the second status indicator aperture 3160 of the housing 3100 is located on a second side of the housing 3100. The status indicator apertures 3130, 3160 can allow a patient to monitor the status and/or contents of the medicament container 3200 contained within the housing 3100. For example, by visually inspecting the status indicator apertures 3130, 3160, a patient can determine whether the medicament container 3200 contains a medicament 3220 and/or whether the medicament 3220 has been dispensed.

Figure 15:
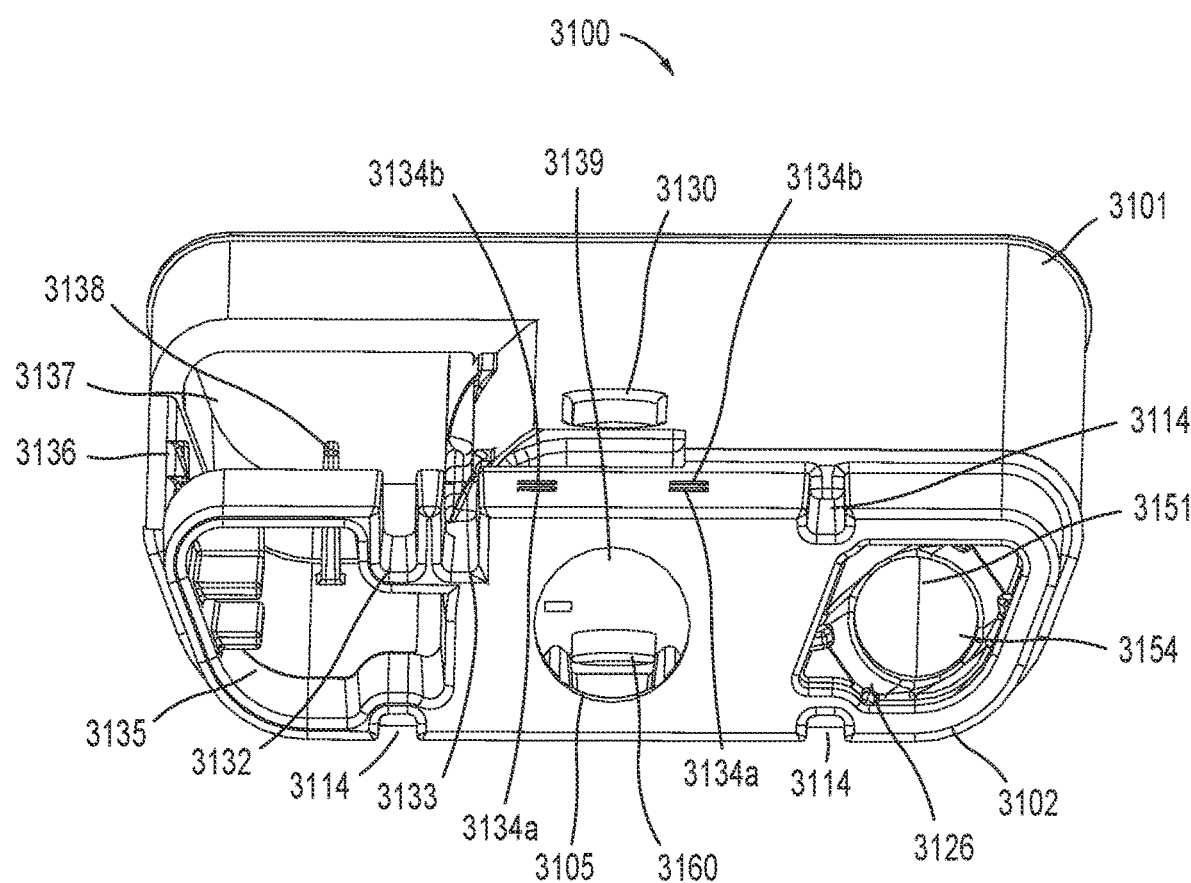
FIG. 15 is a bottom perspective view of a housing of the medical injector illustrated in FIG. 9.
Figure 16:
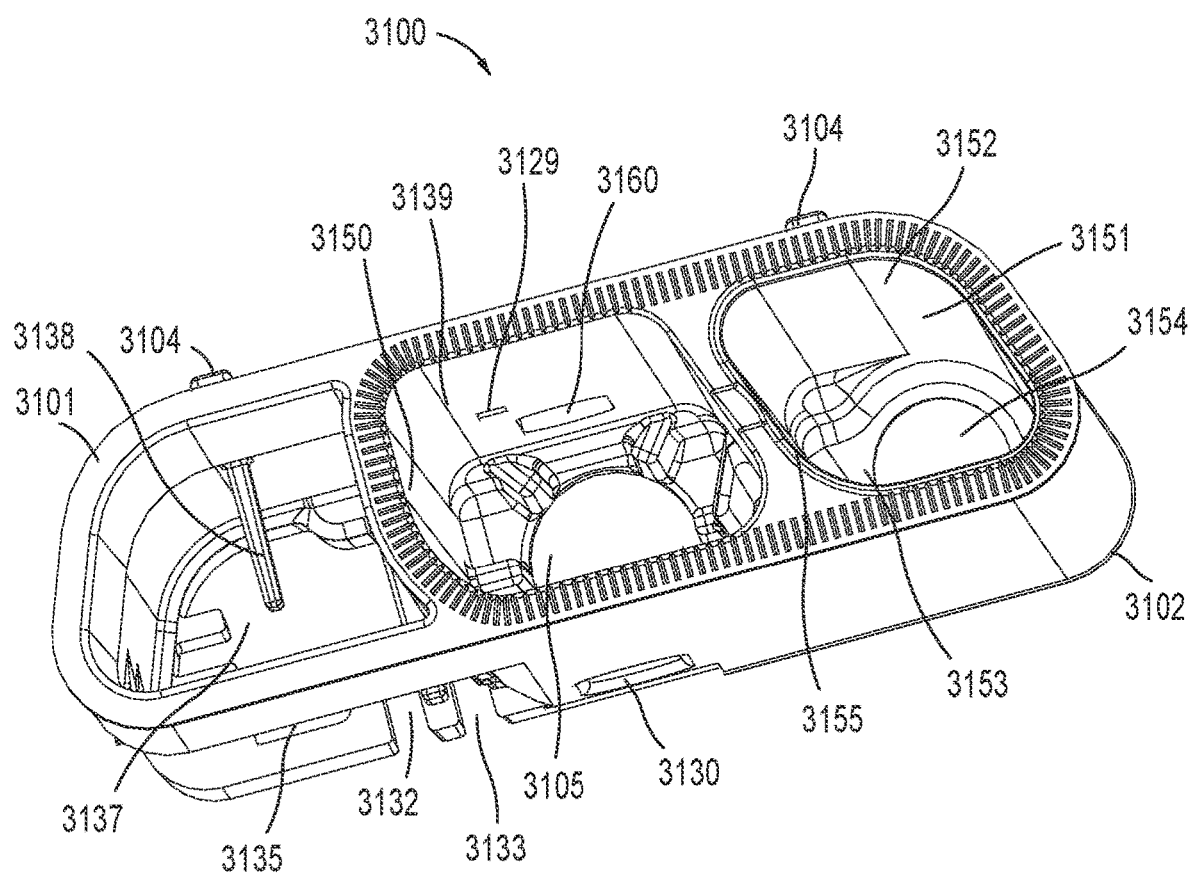
FIG. 16 is a top perspective view of a housing of the medical injector illustrated in FIG. 9.
Figure 18:
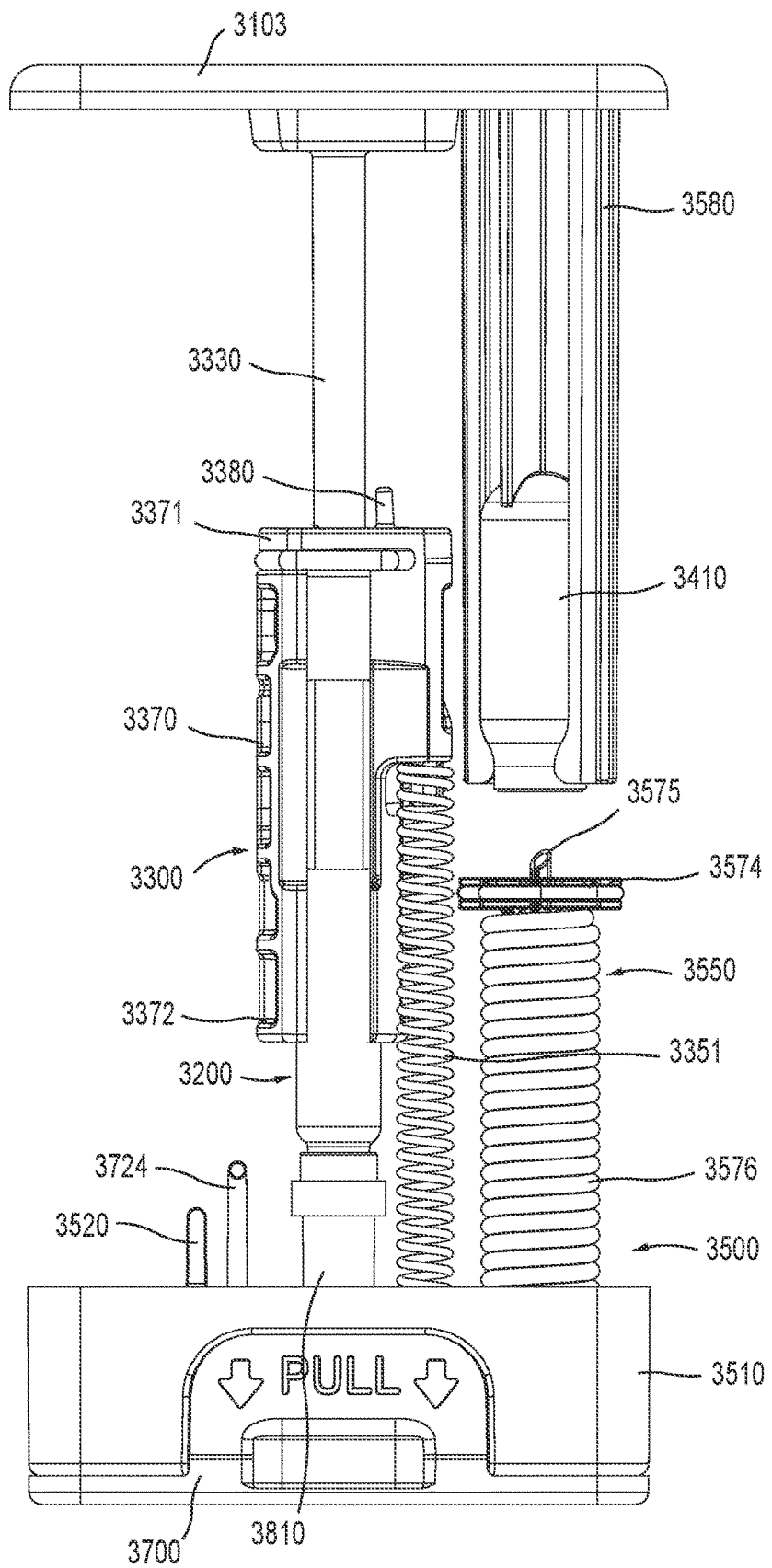
FIGS. 18 and 19 are front views of a medicament delivery mechanism of the medical injector illustrated in FIG. 9.
Figure 19:
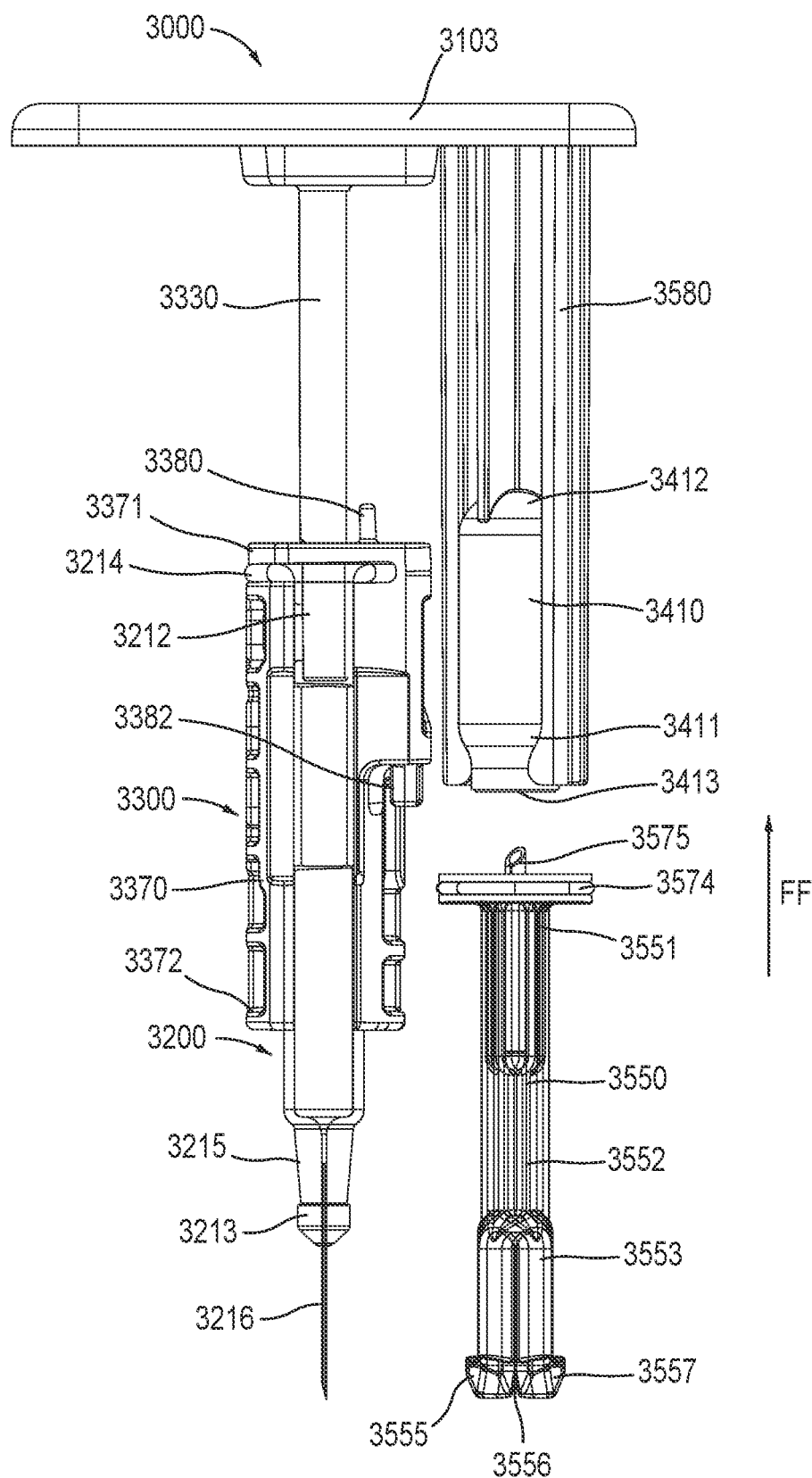
Figure 20:
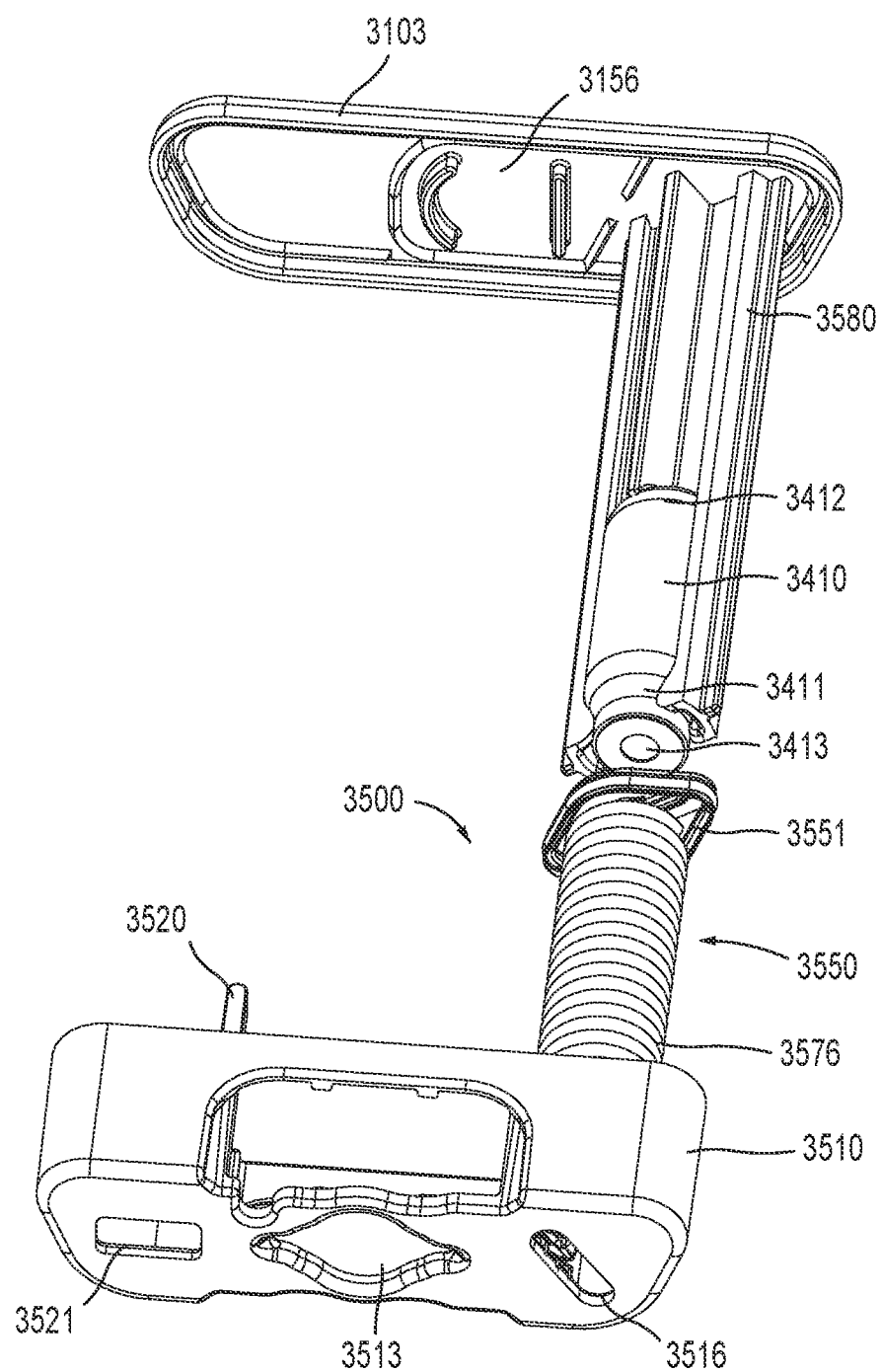
FIG. 20 is a perspective view of a portion of the medical injector illustrated in FIG. 9.

As shown in FIGS. 15 and 16, the housing 3100 defines a gas cavity 3151, a medicament cavity 3139 and an electronic circuit system cavity 3137. The gas cavity 3151 has a proximal end portion 3152 and a distal end portion 3153. The gas cavity 3151 is configured to receive the gas container 3410 and a portion of the system actuator assembly 3500 (e.g., a release member 3550 and the spring 3576, as shown in FIGS. 18 and 19) as described in further detail herein. The proximal end portion 3152 of the gas cavity 3151 is configured to receive the gas container retention member 3580 of a proximal cap 3103 of the housing 3100, as described in further detail herein. The gas cavity 3151 is in fluid communication with the medicament cavity 3139 via a gas passageway 3156 (see e.g., FIG. 17), as described in further detail herein, and the gas cavity 3151 is in fluid communication with a region outside the housing 3100 via a release member aperture 3154 (see e.g., FIGS. 15 and 16).

The medicament cavity 3139 is configured to receive the medicament container 3200 and at least a portion of the medicament delivery mechanism 3300. In particular, as described below, the medicament delivery mechanism 3300 includes a carrier 3370 and piston member 3330 movably disposed in the medicament cavity 3139. The medicament cavity 3139 is in fluid communication with a region outside the housing 3100 via a needle aperture 3105 (see e.g., FIGS. 15 and 16).

The electronic circuit system cavity 3137 is configured to receive the electronic circuit system 3900. The housing 3100 has protrusions 3136 (see e.g., FIG. 14) configured to stabilize the electronic circuit system 3900 when the electronic circuit system 3900 is disposed within the electronic circuit system cavity 3137. The outer surface of the housing 3100 is configured to receive a set of connection protrusions 3174A and connection protrusion 3177B of the electronic circuit system 3900 (see e.g., FIG. 32). In this manner, the electronic circuit system 3900 can be coupled to the housing 3100 within the electronic circuit system cavity 3137. In other embodiments, the electronic circuit system 3900 can be coupled within the electronic circuit system cavity 3137 by other suitable means such as an adhesive, a clip, a label and/or the like.

The electronic circuit system cavity 3137 is fluidically and/or physically isolated from the gas cavity 3151 and/or the medicament cavity 3139 by a sidewall 3150. The sidewall 3150 can be any suitable structure to isolate the electronic circuit system cavity 3137 within the housing 3100 from the gas cavity 3151 and/or the medicament cavity 3139 within the housing 3100. Similarly, the gas cavity 3151 and the medicament cavity 3139 are separated by a sidewall 3155 (see FIG. 16). In some embodiments, sidewall 3155 can be similar to the sidewall 3150, which isolates the gas cavity 3151 and the medicament cavity 3139 from the electronic circuit system cavity 3137. In other embodiments, the gas cavity 3151 can be fluidically and/or physically isolated from the medicament cavity 3139 by any suitable means. In yet other embodiments, the medicament cavity 3139 need not be fluidically and/or physically isolated from the electronic circuit system cavity 3137 and/or the gas cavity 3151.

Figure 12:
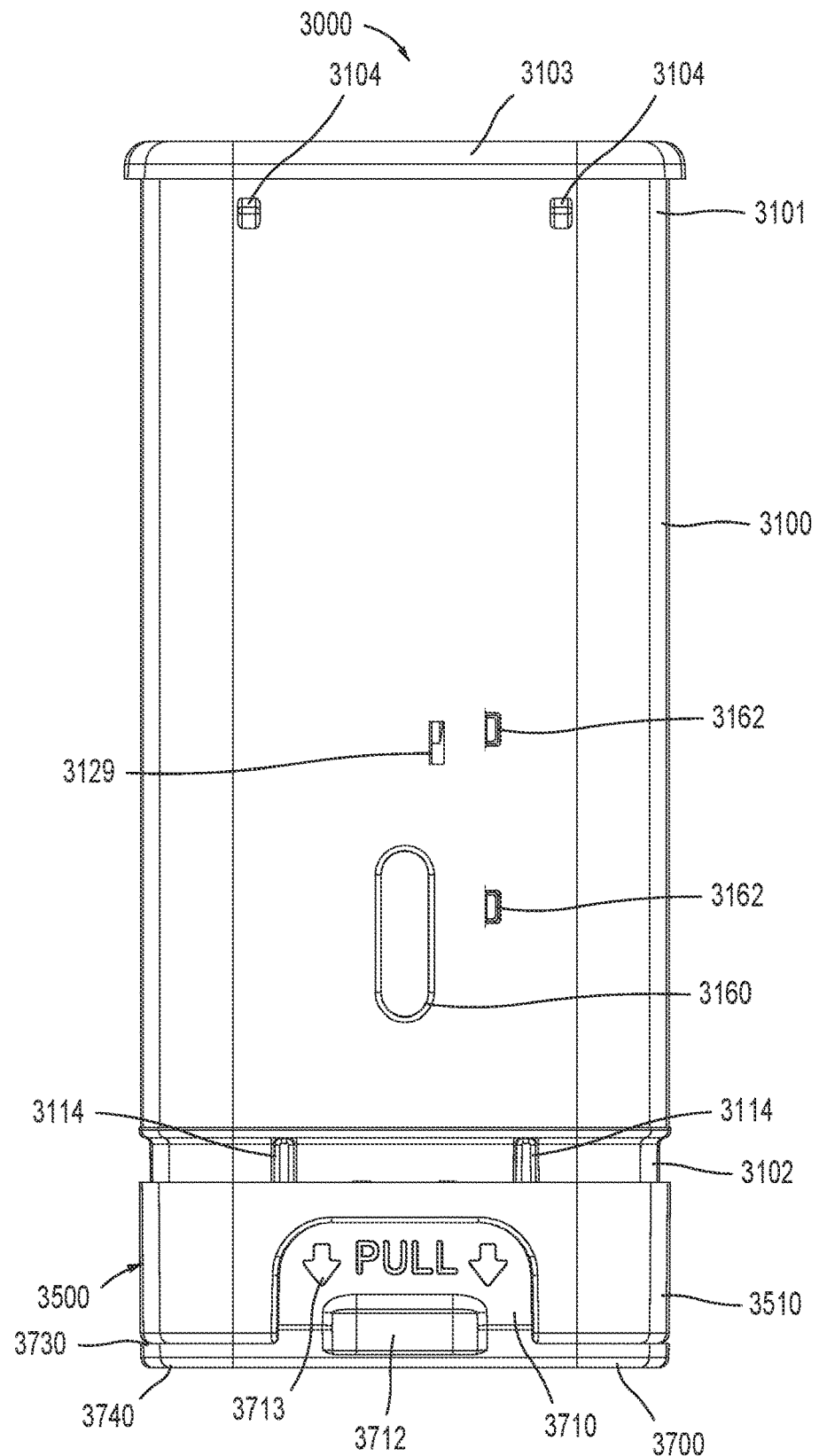
FIG. 12 is a back view of the medical injector illustrated in FIG. 9 with the cover removed.

The proximal end portion 3101 of the housing 3100 includes a proximal cap 3103 (see e.g., FIG. 17), a speaker protrusion 3138 (see e.g., FIGS. 14-16), and cover retention protrusions 3104 (see e.g., FIGS. 10 and 12). The speaker protrusion 3138 is configured to maintain a position of an audio output device 3956 of the electronic circuit system 3900 relative to the housing 3100 when the electronic circuit system 3900 is attached to the housing 3100, as described herein. The cover retention protrusions 3104 are configured to be received within corresponding openings 3193 defined by the cover 3190 (see e.g., FIG. 10) to retain the cover 3190 about the housing 3100. In this manner, as described in more detail herein, the cover 3190 is removably coupled to and disposed about at least a portion of the housing 3100.

Figure 17:
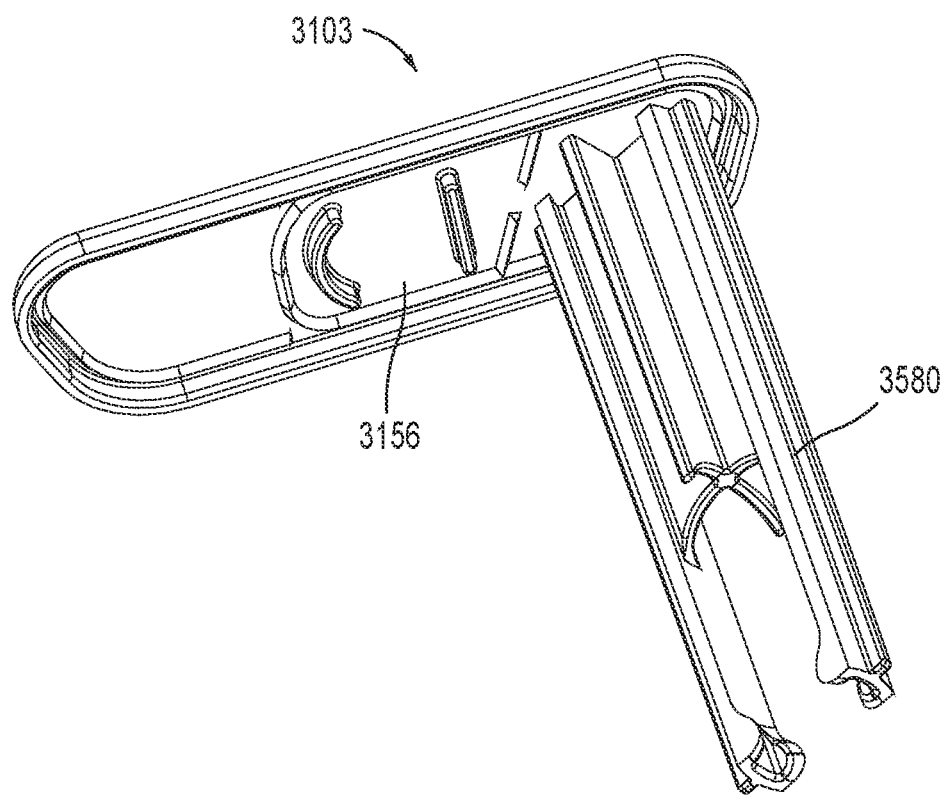
FIG. 17 is a perspective view of a proximal cap of the medical injector illustrated in FIG. 9.

As shown in FIG. 17, the proximal cap 3103 includes a gas container retention member 3580 and defines a gas passageway 3156. The gas container retention member 3580 is configured to receive and/or retain a gas container 3410 that contains a pressurized gas, as shown in FIG. 18. When the medical injector 3000 is actuated, pressurized gas from the gas container 3140 is conveyed from the gas cavity 3151 to the medicament cavity 3139 via the gas passageway 3156, as further described herein. Said another way, the gas passageway 3156 places the gas cavity 3151 in fluid communication with the medicament cavity 3139.

Figure 13:
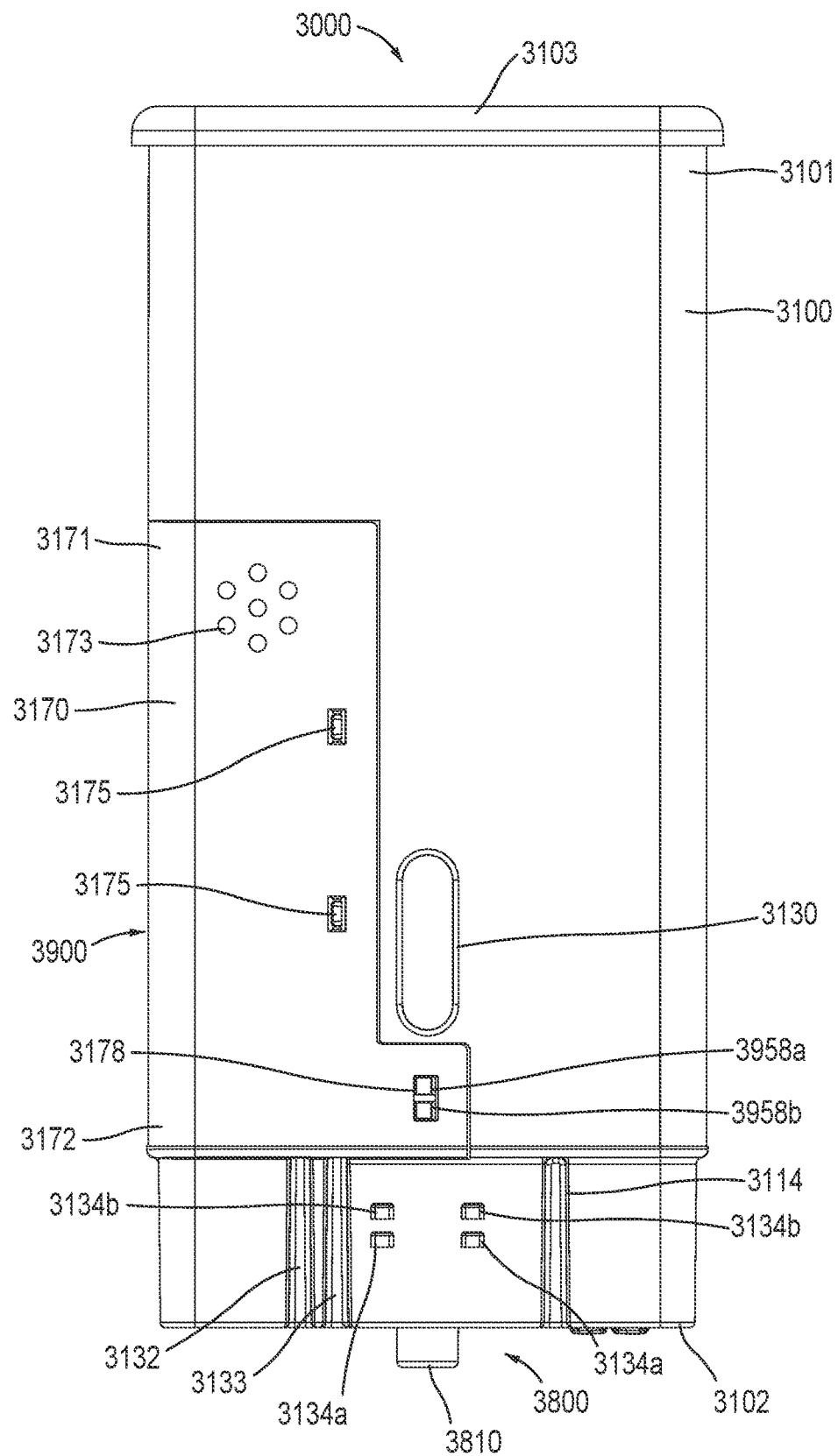
FIG. 13 is a front view of a portion of the medical injector illustrated in FIG. 9.
Figure 14:
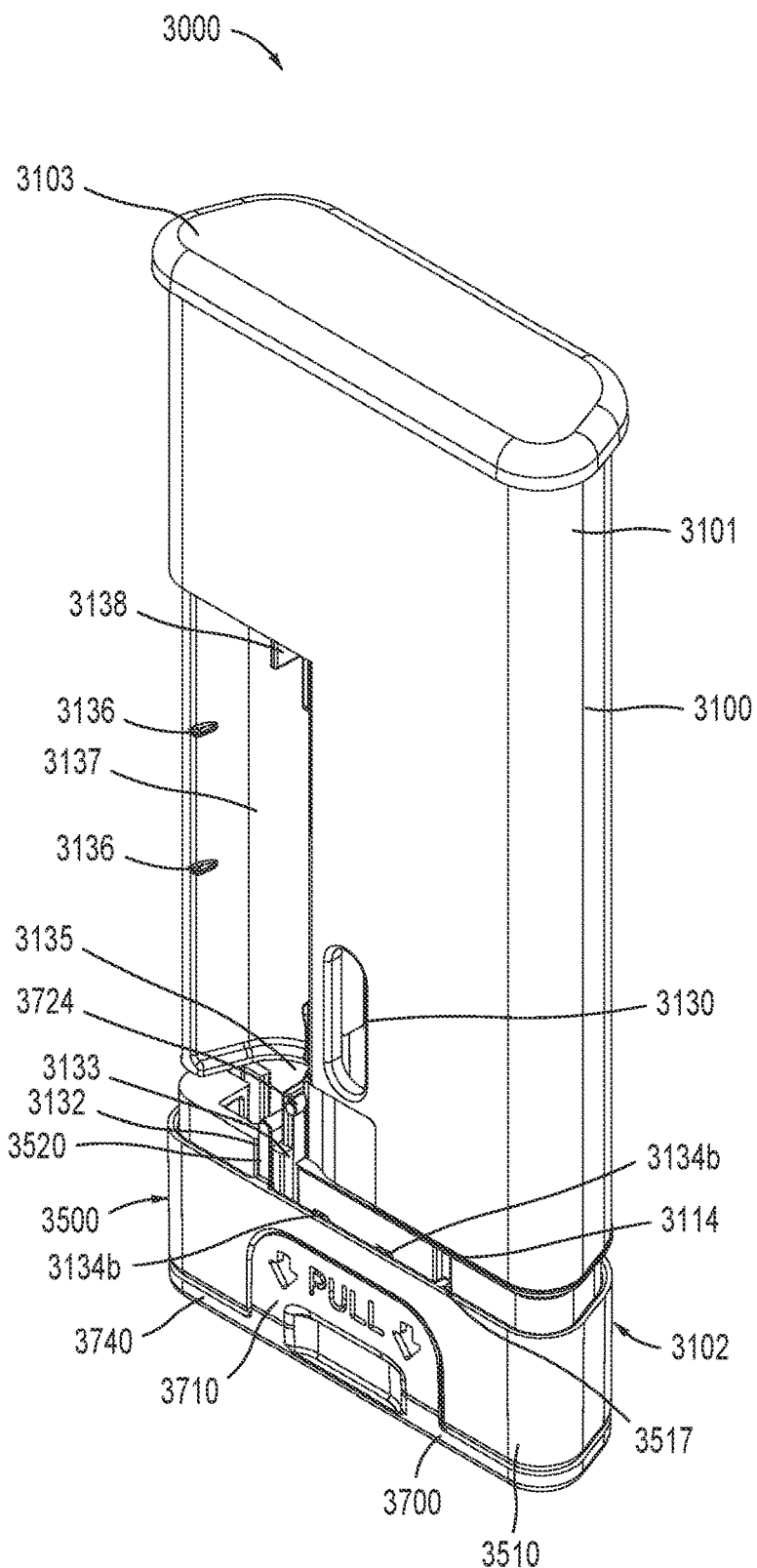
FIG. 14 is a perspective view of a portion of the medical injector illustrated in FIG. 9.

As shown in FIGS. 13 and 15, the distal end portion 3102 of the housing 3100 defines a battery isolation protrusion aperture 3135, a needle aperture 3105, a safety lock actuator groove 3133, a release member contact surface 3126, a release member aperture 3154, a base protrusion groove 3132, base retention recesses 3134A, 3134B, and base rail grooves 3114. The battery isolation protrusion aperture 3135 receives the battery isolation protrusion 3197 of the cover 3190 (see e.g., FIG. 41) when the cover 3190 is disposed about at least a portion of the housing 3100. The needle aperture 3105 is the opening through which the needle 3216 is disposed (see e.g., FIGS. 19, 51 and 52) when the medical injector 3000 is actuated, as described in further detail herein.

Figure 21:
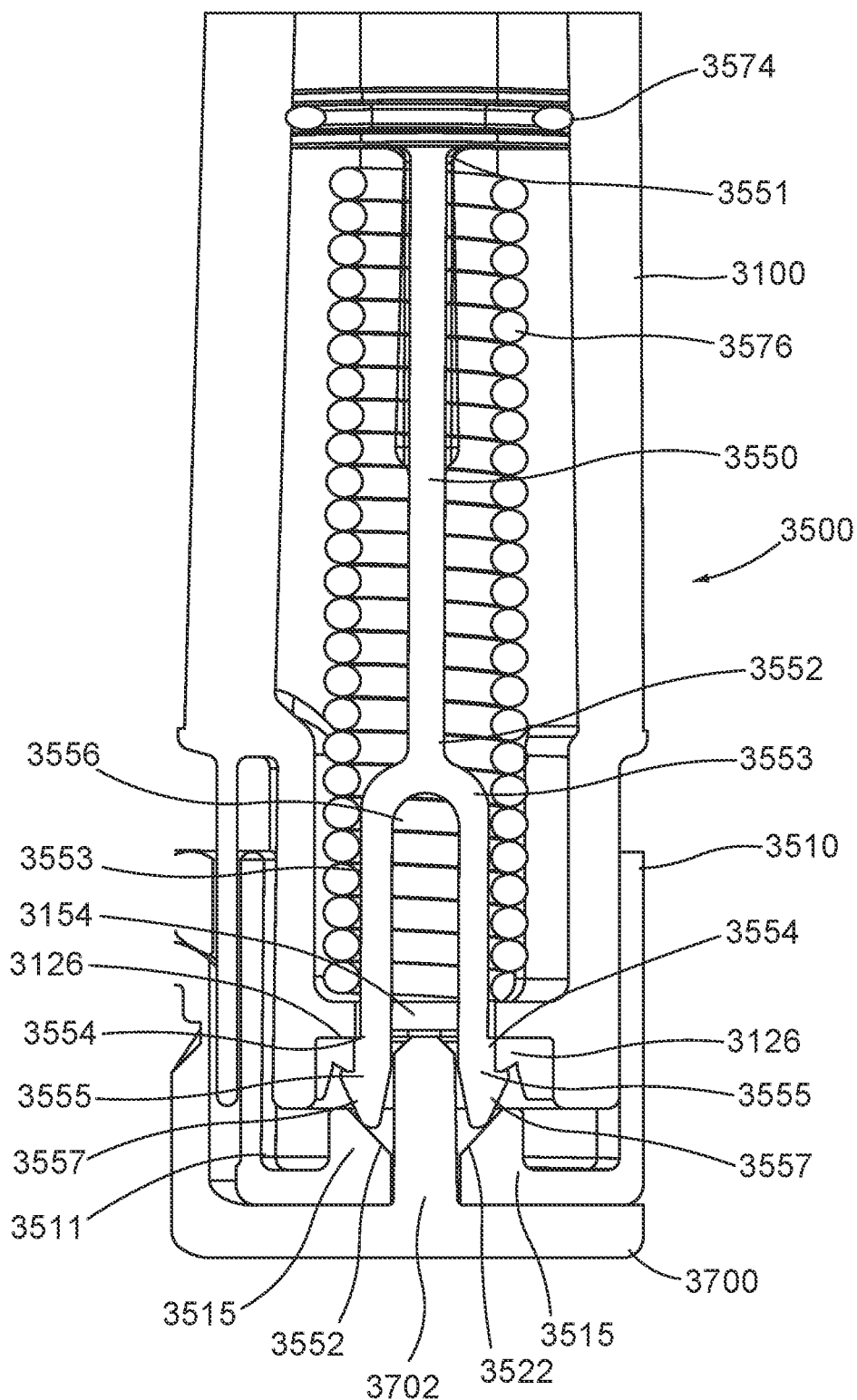
FIG. 21 is an enlarged cross-sectional view of a portion of the medical injector illustrated in FIG. 9.
Figure 43:
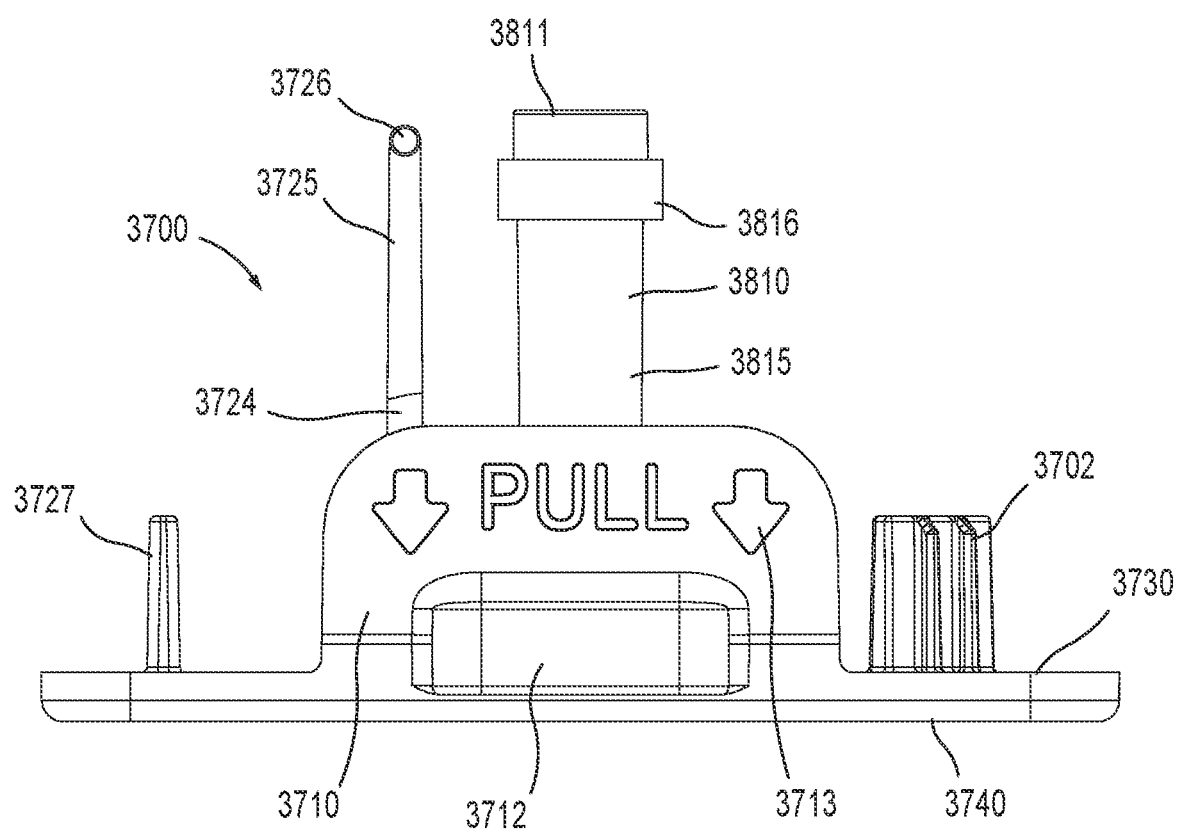
FIG. 43 is a front view of the safety lock of the medical injector illustrated in FIG. 42.
Figure 44:
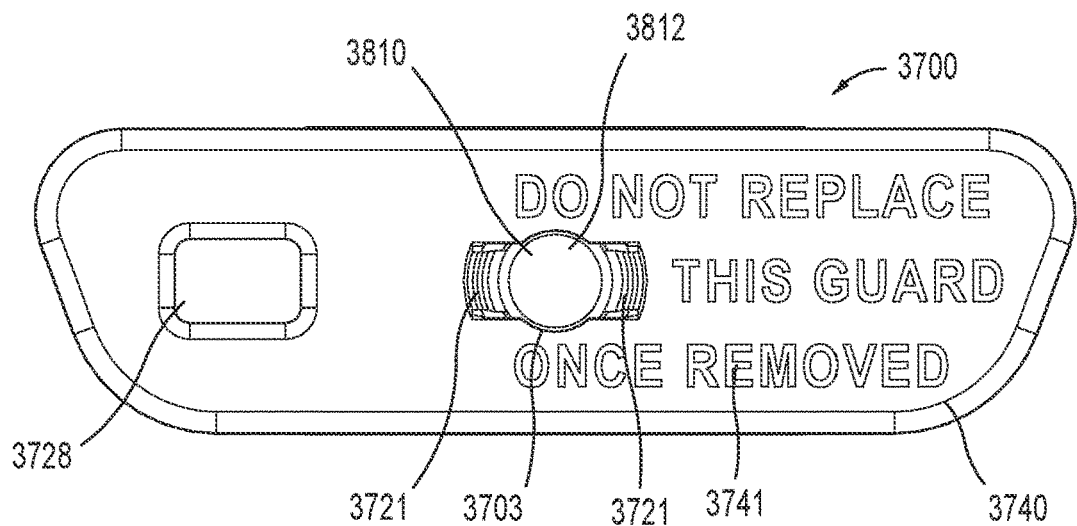
FIG. 44 is a bottom view of the safety lock of the medical injector illustrated in FIG. 42.

The safety lock actuator groove 3133 receives an actuator 3724 of the safety lock 3700 (see e.g., FIG. 43). As described in more detail herein, the actuator 3724 is configured to engage and/or activate the electronic circuit system 3900 when the safety lock 3700 is moved with respect to the housing 3100. The release member contact surface 3126 defines the release member aperture 3154. As shown in FIG. 21 and described in more detail below, the release member aperture 3154 receives a distal end portion 3552 of a release member 3550. As described in more detail below, a safety lock protrusion 3702 (see e.g., FIG. 42) is disposed within an opening 3556 between extensions 3553 of the release member 3550 (see e.g., FIGS. 19 and 21) such that an engagement surface 3554 of the extensions 3553 is engaged with the release member contact surface 3126 to prevent activation of the medical injector 3000. The safety lock 3700, its components and functions are described in more detail below.

The distal base retention recesses 3134A are configured to receive the base connection knobs 3518 of the actuator 3510 (also referred to herein as "base 3510," see e.g., FIG. 47) when the base 3510 is in a first position relative to the housing 3100. The proximal base retention recesses 3134B are configured to receive the base connection knobs 3518 of the base 3510 when the base 3510 is in a second position relative to the housing 3100. The base retention recesses 3134A, 3134B have a tapered proximal sidewall and a non-tapered distal sidewall. This allows the base retention recesses 3134A, 3134B to receive the base connection knobs 3518 such that the base 3510 can move proximally relative to the housing 3100, but cannot move distally relative to the housing 3100. Said another way, the distal base retention recesses 3134A are configured to prevent the base 3510 from moving distally when the base 3510 is in a first position and the proximal base retention recesses 3134B are configured to prevent the base 3510 from moving distally when the base 3510 is in a second position. Similarly stated, the proximal base retention recesses 3134B and the base connection knobs 3518 cooperatively to limit movement of the base to prevent undesirable movement of the base 3510 after the medical injector 3000 is actuated. The proximal base retention recesses 3134B and the base connection knobs 3518 also provide a visual cue to the user that the medical injector 3000 has been used.

The base actuator groove 3132 receives a protrusion 3520 of the base 3510. As described in more detail herein, the protrusion 3520 of the base 3510 is configured to engage the electronic circuit system 3900 when the base 3510 is moved with respect to the housing 3100. The base rail grooves 3114 receive the guide members 3517 of the base 3510 (see FIG. 47). The guide members 3517 of the base 3510 and the base rail grooves 3114 of the housing 3100 engage each other in a way that allows the guide members 3517 of the base 3510 to slide in a proximal and/or distal direction within the base rail grooves 3114 while limiting lateral movement of the guide members 3517. This arrangement allows the base 3510 to move in a proximal and/or distal direction with respect to the housing 3100 but prevents the base 3510 from moving in a lateral direction with respect to the housing 3100.

Figure 25:
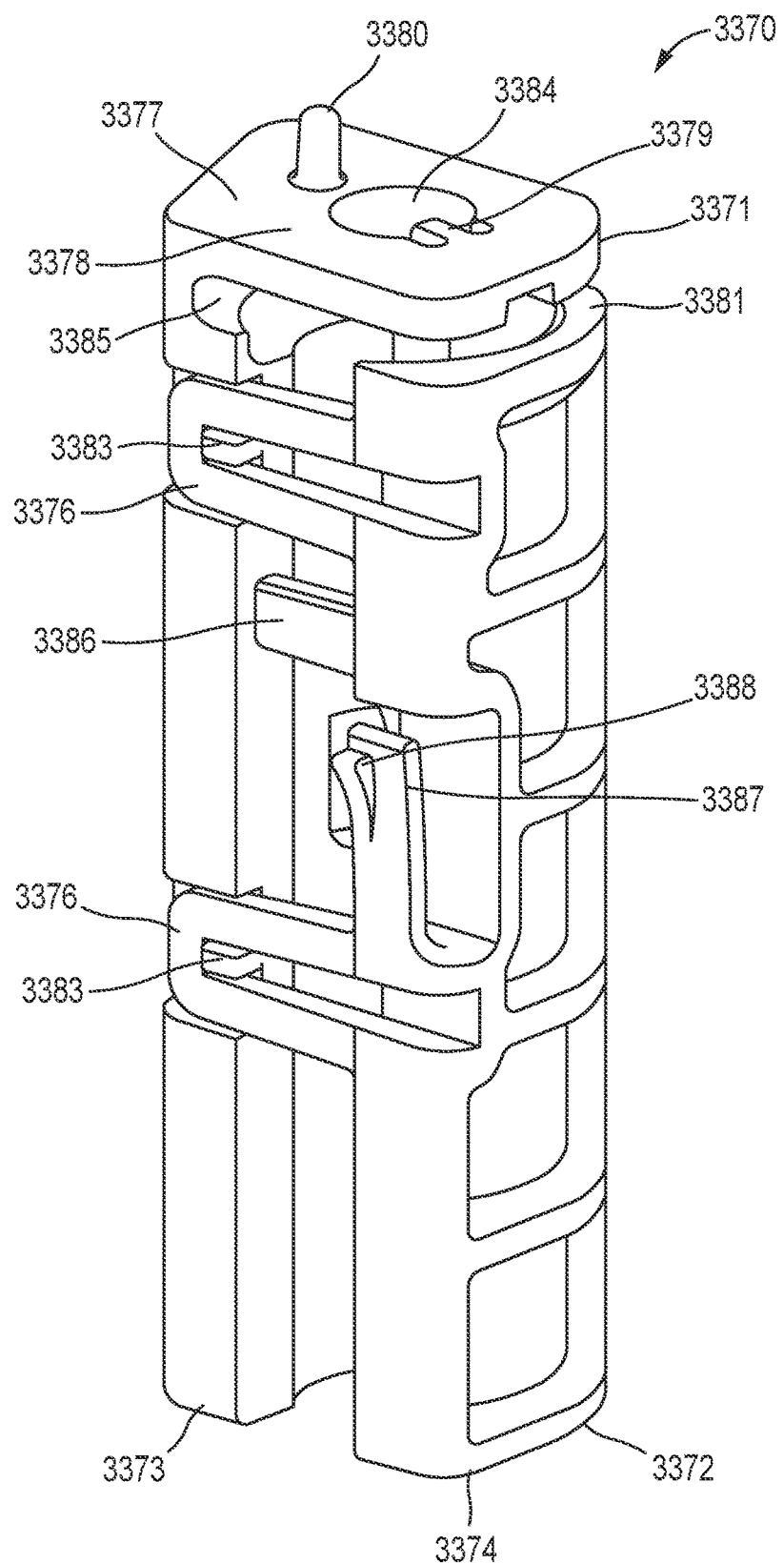
FIG. 25 is a perspective view of the carrier included in the medical injector illustrated in FIG. 9 in a second configuration.
Figure 26:
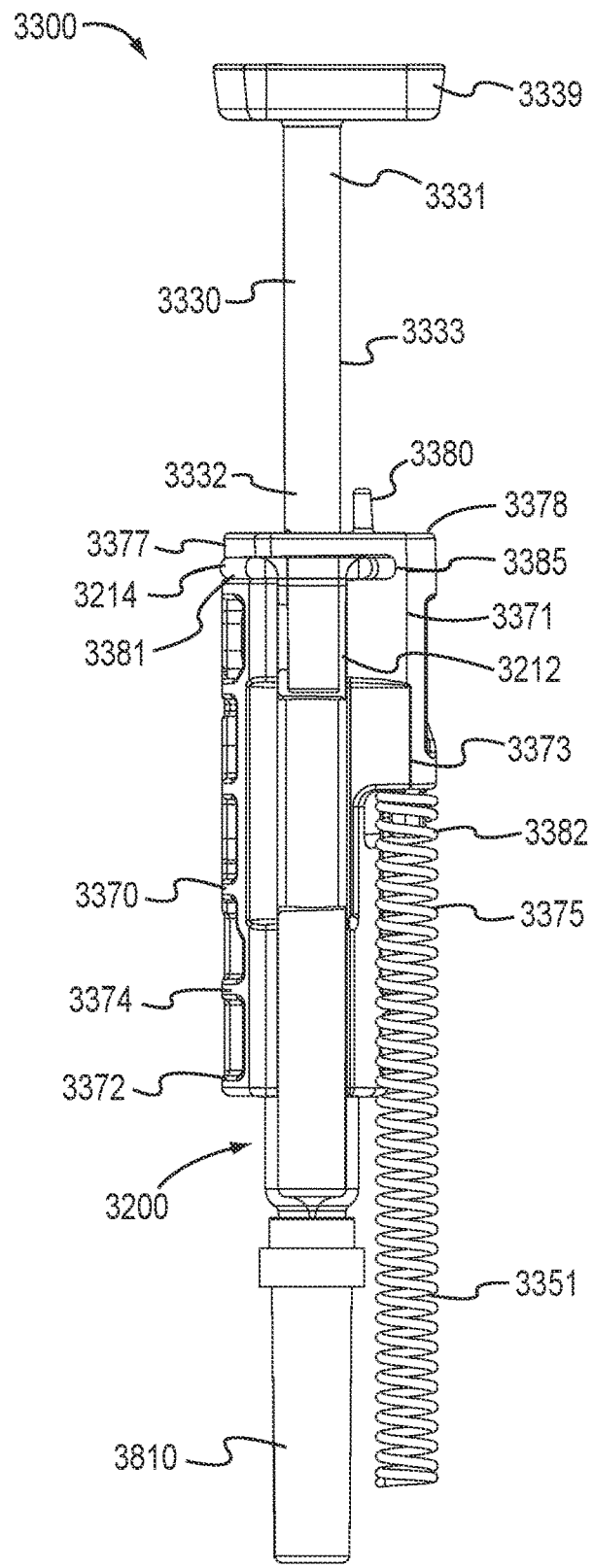
FIG. 26 is a perspective view of a portion of the medical injector illustrated in FIG. 9.
Figure 27:
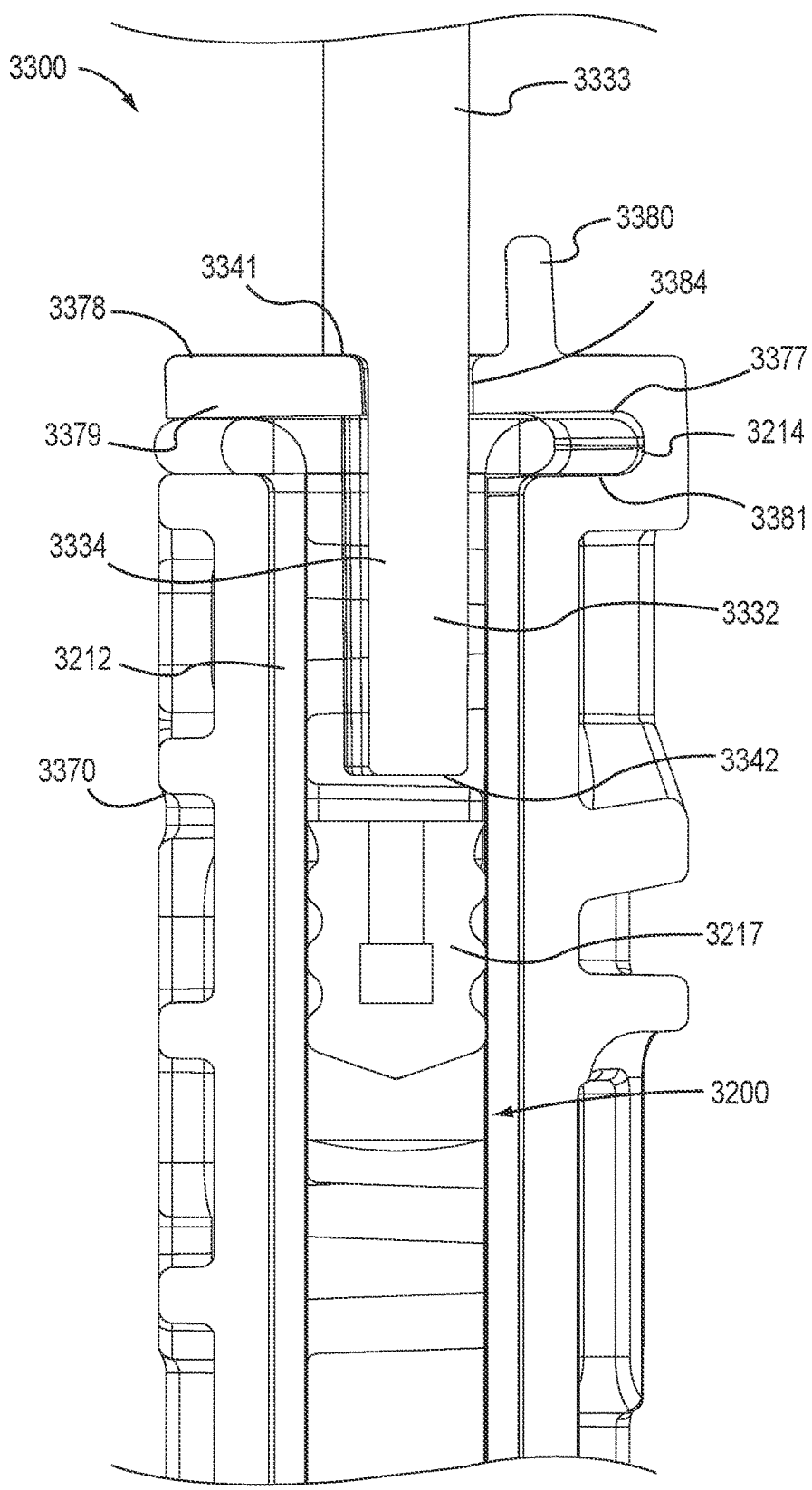
FIG. 27 is an enlarged front cross-sectional view of the portion of the medical injector illustrated in FIG. 26.
Figure 28:
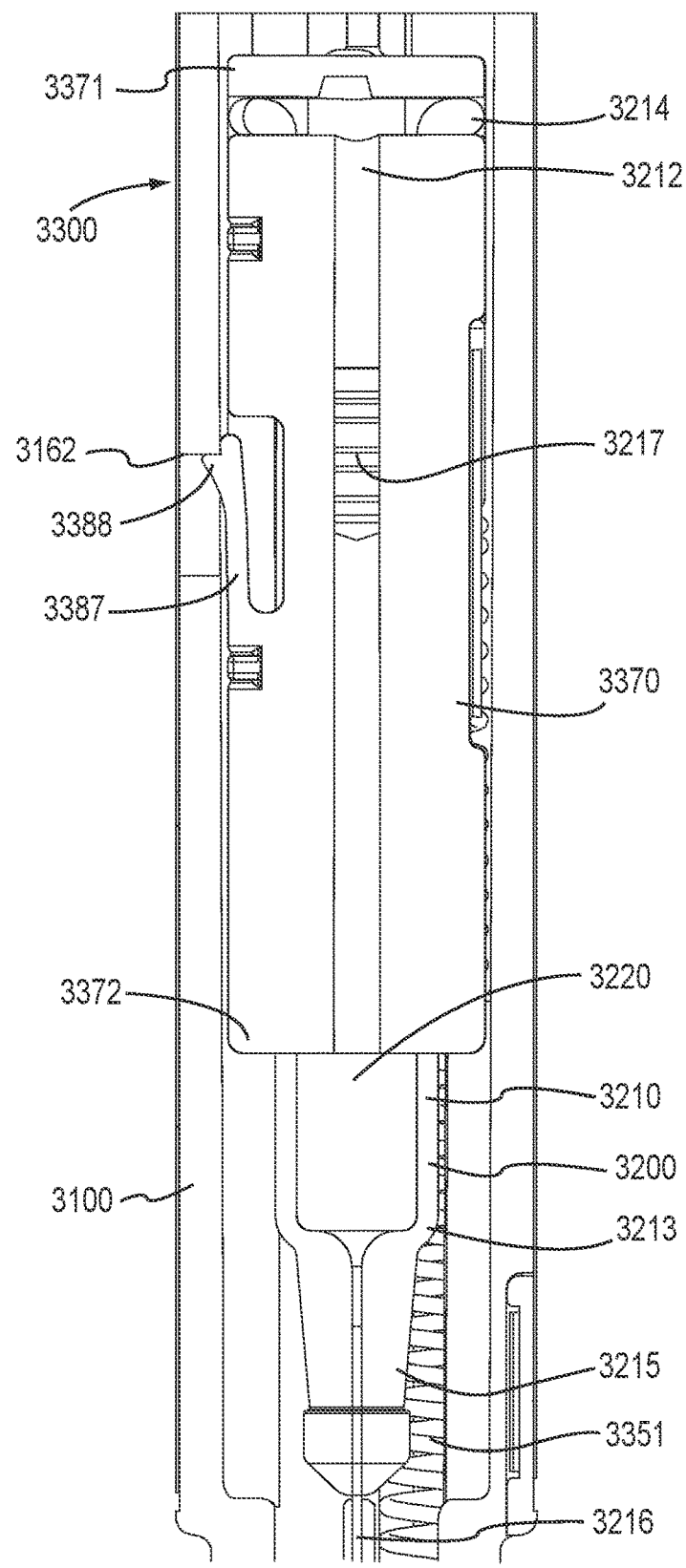
FIG. 28 is an enlarged side cross-sectional view of the portion of the medical injector illustrated in FIG. 26.
Figure 29:
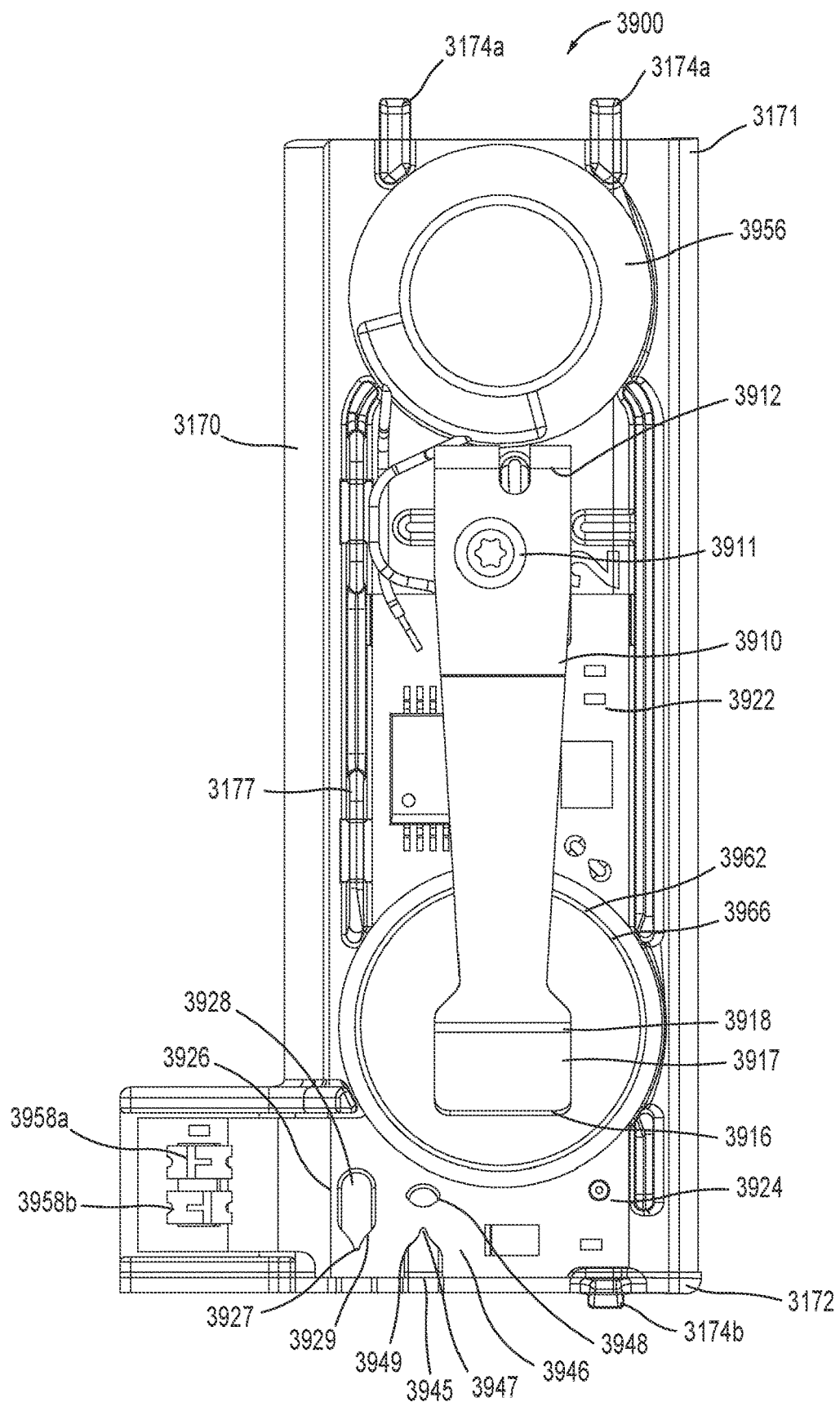
FIG. 29 is a back view of an electronic circuit system of the medical injector illustrated in FIG. 9.
Figure 30:
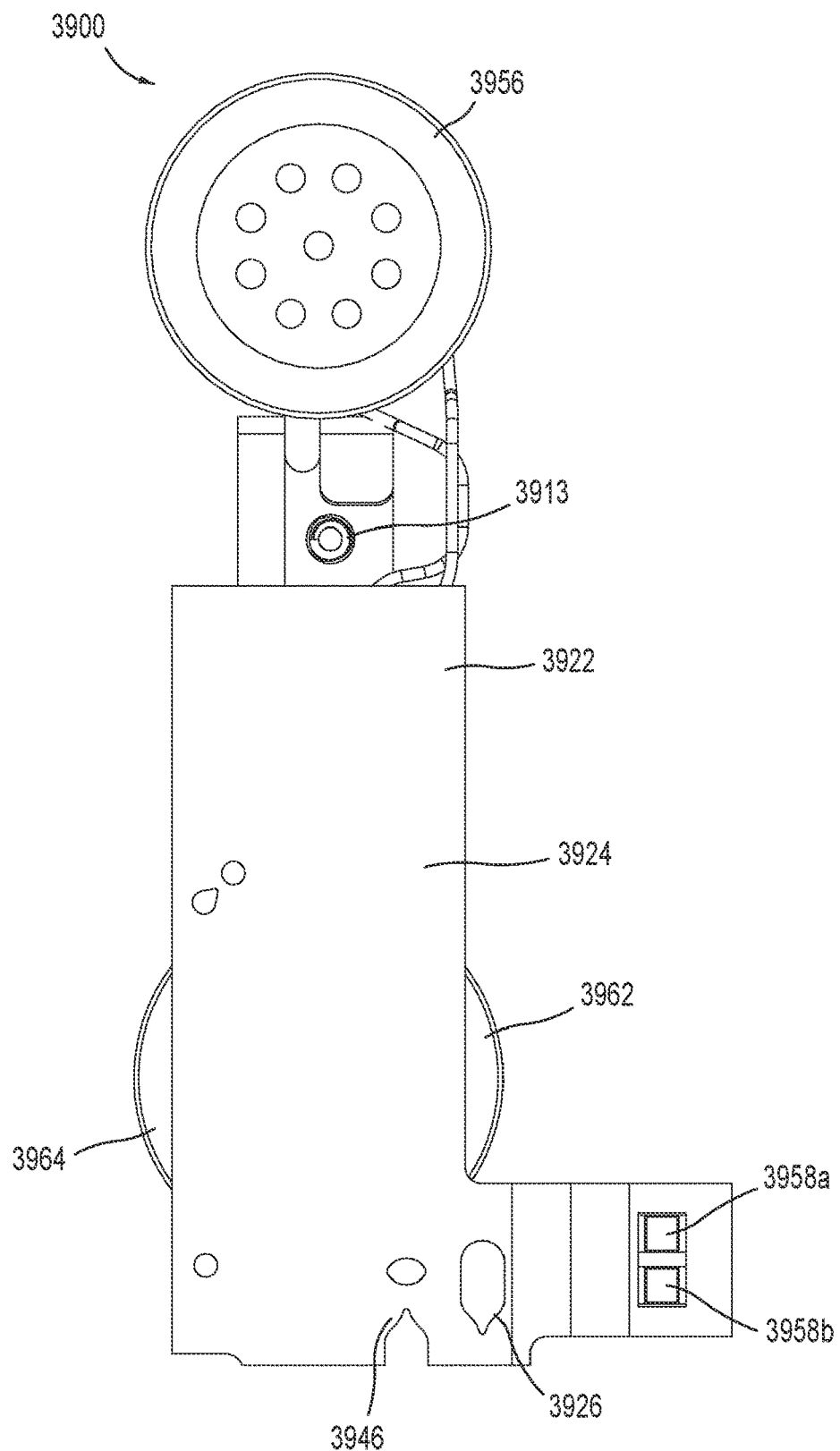
FIG. 30 is a front view of a portion of the electronic circuit system of the medical injector illustrated in FIG. 29.
Figure 31:
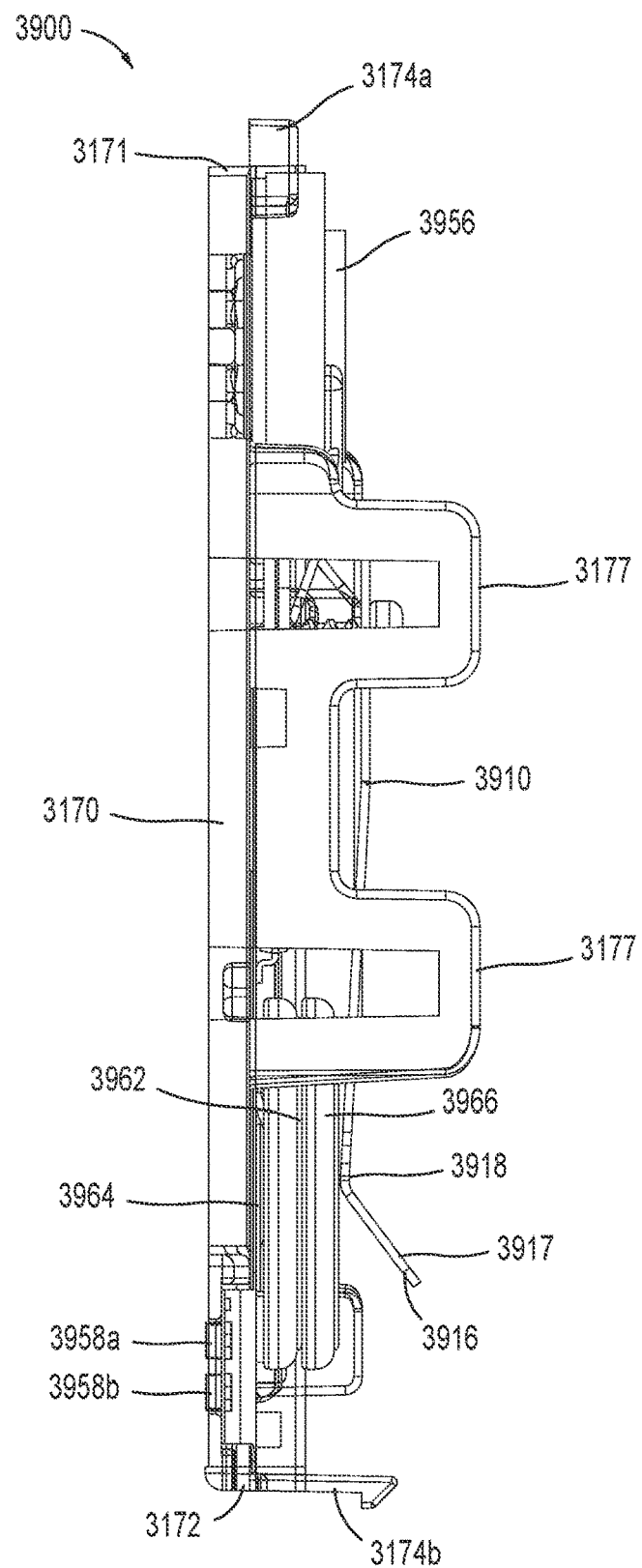
FIG. 31 is a side view of the electronic circuit system of the medical injector illustrated in FIG. 29.

FIGS. 18-28 show the medicament container 3200, the system actuator assembly 3500 and the medicament delivery mechanism 3300 of the medical injector 3000. The medicament container 3200 has a body 3210 with a distal end portion 3213 and a proximal end portion 3212. The body 3210 defines a volume that contains (i.e., is filled with or partially filled with) a medicament 3220 (see, e.g., FIGS. 22 and 28). The distal end portion 3213 of the medicament container 3200 includes a neck 3215 that is coupled to the needle 3216, as described below. The proximal end portion 3212 of the medicament container 3200 includes an elastomeric member 3217 (i.e., a plunger) that seals the medicament 3220 within the body 3210. The elastomeric member 3217 is configured to move within the body to inject the medicament 3220 from the medicament container 3200. More particularly, as shown in FIG. 27, the elastomeric member 3217 is configured to receive and/or contact a piston rod 3333 of a piston member 3330 (also referred to herein as "second movable member 3330") of the medicament delivery mechanism 3300.

The elastomeric member 3217 can be of any design or formulation suitable for contact with the medicament 3220. For example, the elastomeric member 3217 can be formulated to minimize any reduction in the efficacy of the medicament 3220 that may result from contact (either direct or indirect) between the elastomeric member 3217 and the medicament 3220. For example, in some embodiments, the elastomeric member 3217 can be formulated to minimize any leaching or out-gassing of compositions that may have an undesired effect on the medicament 3220. In other embodiments, the elastomeric member 3217 can be formulated to maintain its chemical stability, flexibility and/or sealing properties when in contact (either direct or indirect) with the medicament 3220 over a long period of time (e.g., for up to six months, one year, two years, five years or longer).

In some embodiments, the elastomeric member 3217 can be constructed from multiple different materials. For example, in some embodiments, at least a portion of the elastomeric member 3217 can be coated. Such coatings can include, for example, polydimethylsiloxane. In some embodiments, at least a portion of the elastomeric member 3217 can be coated with polydimethylsiloxane in an amount of between approximately 0.02 mg/cm$^2$ and approximately 0.80 mg/cm$^2$.

The proximal end portion 3212 of the body 3210 includes a flange 3214 configured to be disposed within a portion of the carrier 3370 (also referred to as a first movable member 3370), as described in further detail herein. The flange 3214 can be of any suitable size and/or shape. Although shown as substantially circumscribing the body 3210, in other embodiments, the flange 3214 can only partially circumscribe the body 3210.

Figure 22:
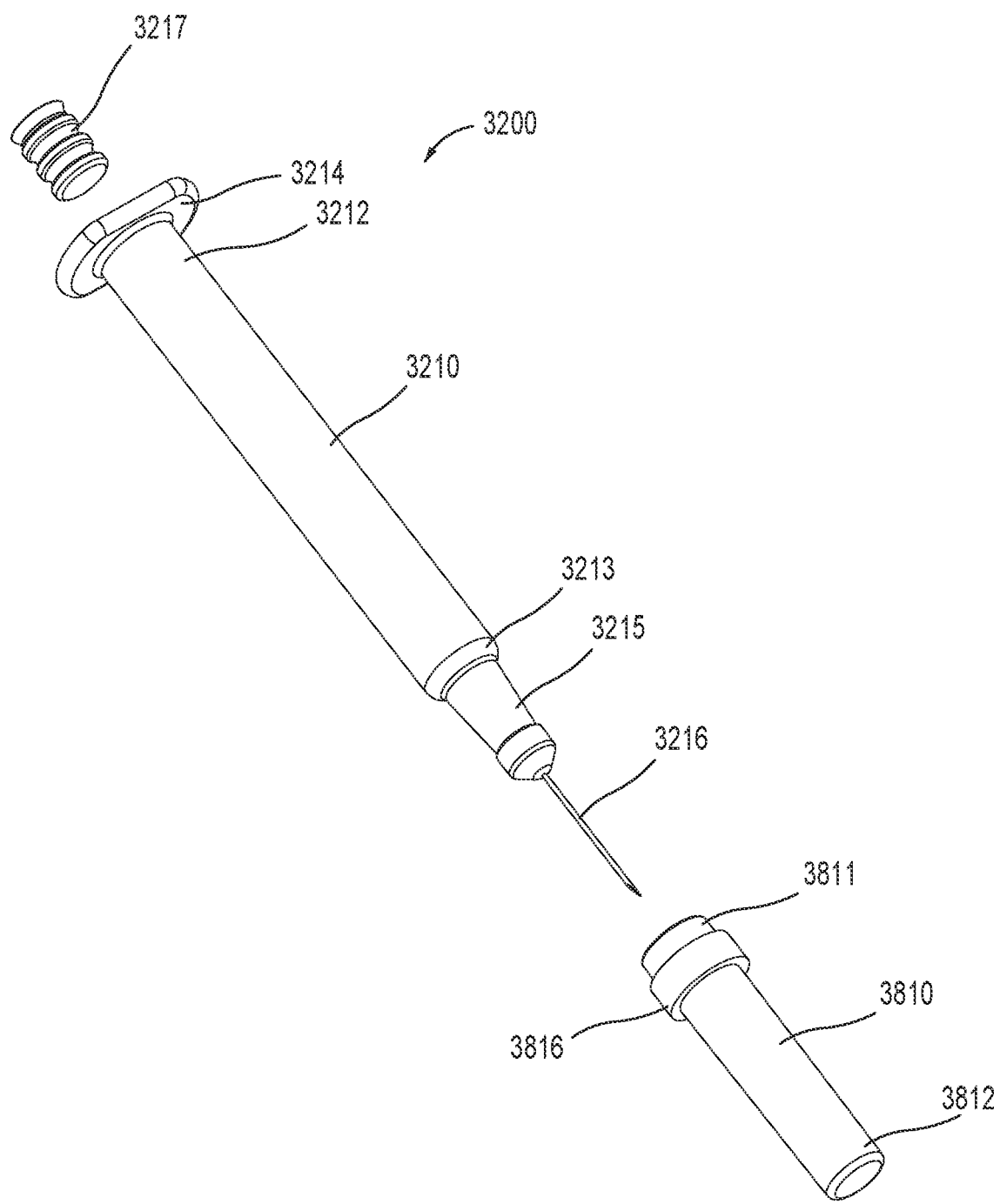
FIG. 22 is an exploded view of a medicament container of the medical injector illustrated in FIG. 9.
Figure 23:
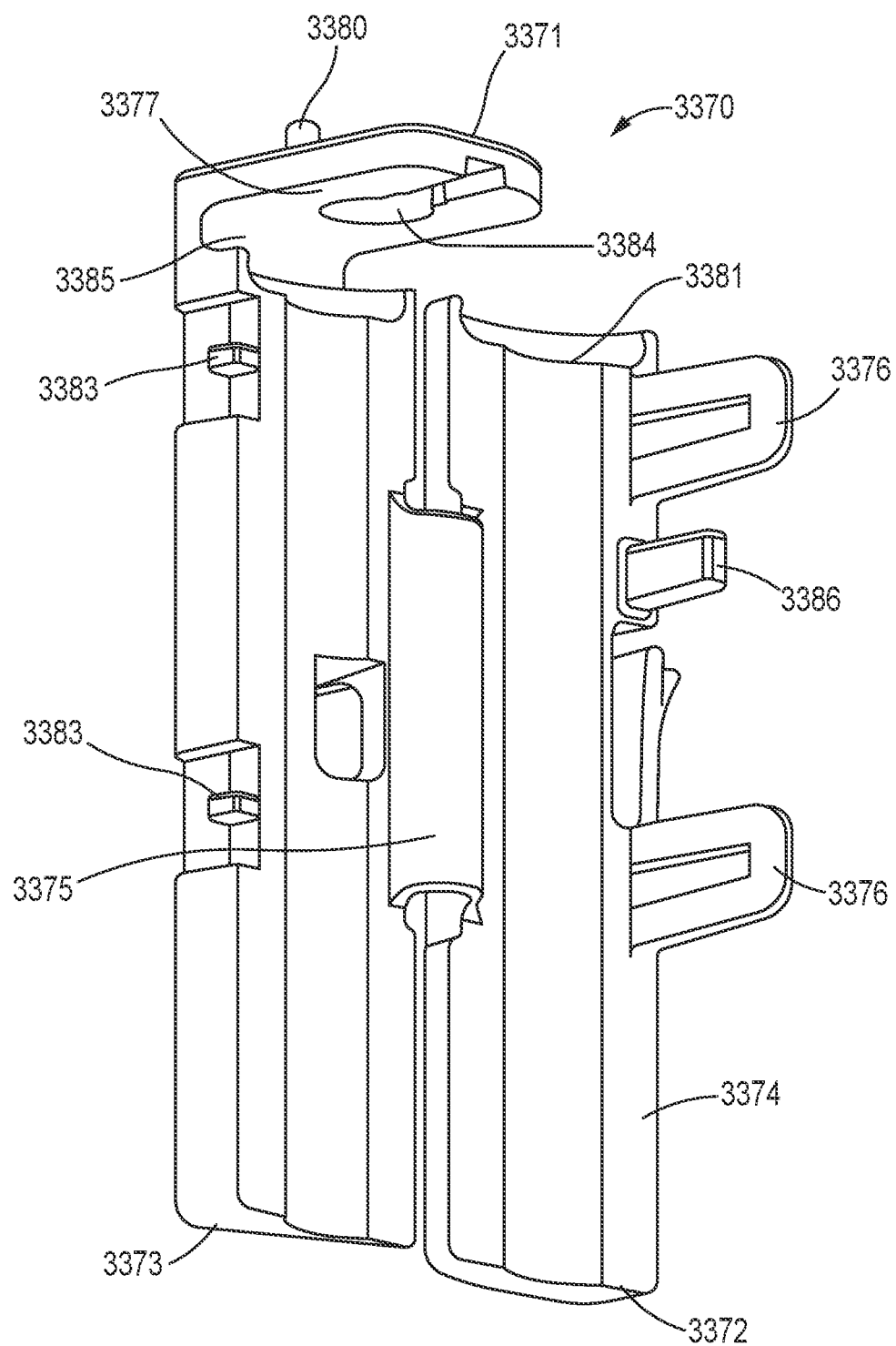
FIGS. 23 and 24 are perspective views of a carrier included in the medical injector illustrated in FIG. 9 in a first configuration.
Figure 24:
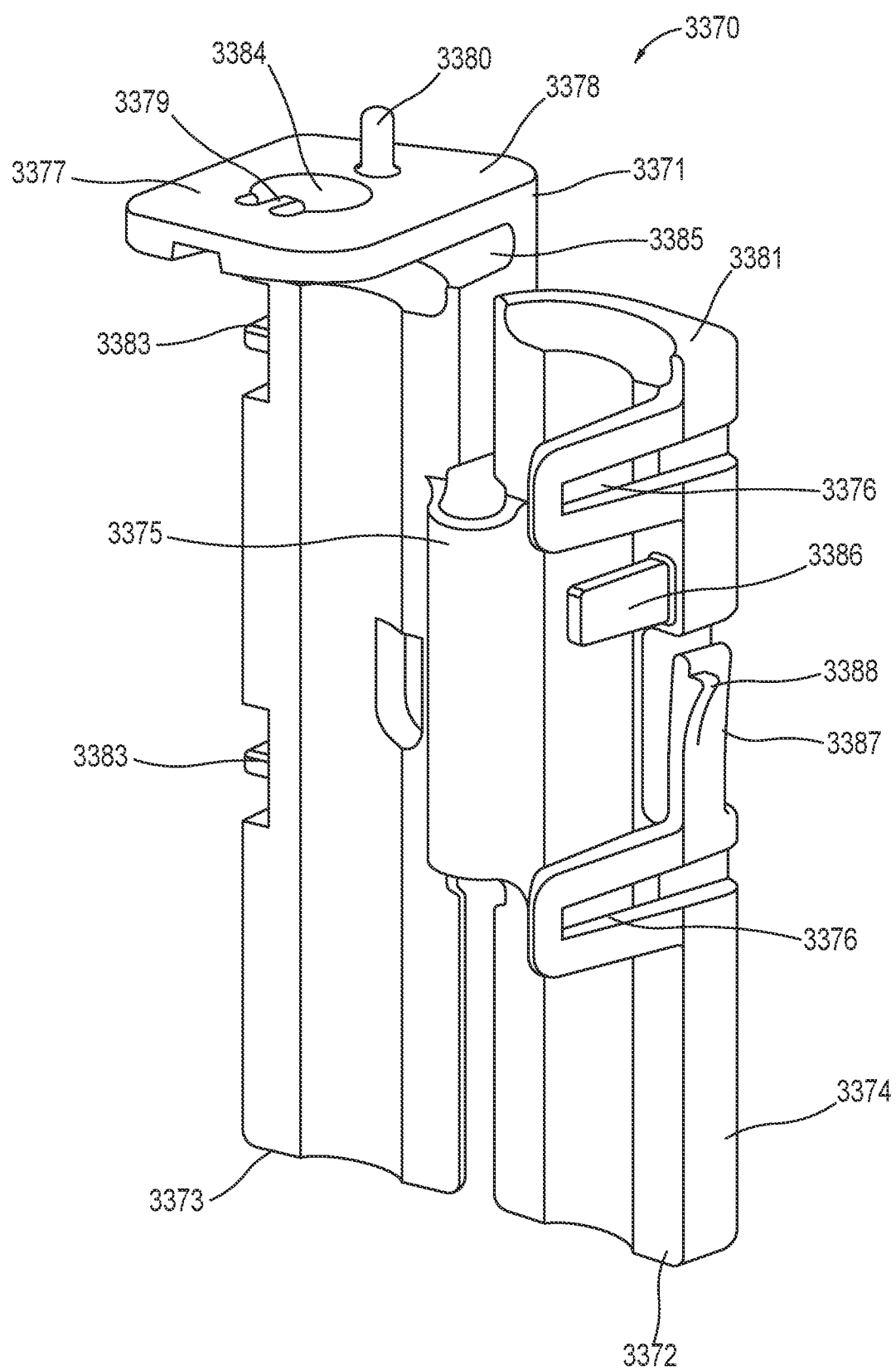

The medicament container 3200 can have any suitable size (e.g., length and/or diameter) and can contain any suitable volume of the medicament 3220. Moreover, the medicament container 3200 and the second movable member 3330 can be collectively configured such that the second movable member 3330 travels a desired distance within the medicament container 3200 (i.e., the "stroke") during an injection event. In this manner, the medicament container 3200, the volume of the medicament 3220 within the medicament container 3200 and the second movable member 3330 can be collectively configured to provide a desired fill volume and delivery volume. For example, the medicament container 3200, as shown in FIG. 22, is a prefilled syringe having a predetermined fill volume. Based on the predetermined fill volume, the second movable member 3330 can be configured to provide a desired delivery volume.

Moreover, the length of the medicament container 3200 and the length of the second movable member 3330 can be configured such that the medicament delivery mechanism 3300 can fit within the same housing 3100 regardless of the fill volume, the delivery volume and/or the ratio of the fill volume to the delivery volume. In this manner, the same housing and production tooling can be used to produce devices having various dosages of the medicament 3220. For example, in a first embodiment (e.g., having a fill volume to delivery volume ratio of 0.4), the medicament container has a first length and the second movable member has a first length. In a second embodiment (e.g., having a fill volume to delivery volume ratio of 0.6), the medicament container has a second length shorter than the first length, and the second movable member has a second length longer than the first length. In this manner, the stroke of the device of the second embodiment is longer than that of the device of the first embodiment, thereby allowing a greater dosage. The medicament container of the device of the second embodiment, however, is shorter than the medicament container of the device of the first embodiment, thereby allowing the components of both embodiments to be disposed within the same housing and/or a housing having the same length.

As shown in FIGS. 18-21, the system actuator assembly 3500 includes the base 3510, a release member 3550 and a spring 3576. FIG. 19 shows certain internal components of the medical injector 3000 without the base 3510 and the spring 3576 so that the release member 3550 can be more clearly shown.

The release member 3550 has a proximal end portion 3551 and a distal end portion 3552, and is movably disposed within the distal end portion 3153 of the gas cavity 3151. The proximal end portion 3551 of the release member 3550 includes a sealing member 3574 and a puncturer 3575. The sealing member 3574 is configured to engage the sidewall of the housing 3100 defining the gas cavity 3151 such that the proximal end portion 3152 of the gas cavity 3151 is fluidically isolated from the distal end portion 3153 of the gas cavity 3151. In this manner, when gas is released from the gas container 3410, the gas contained in the proximal end portion 3152 of the gas cavity 3151 is unable to enter the distal end portion 3153 of the gas cavity 3151. The puncturer 3575 of the proximal end portion 3551 of the release member 3550 is configured to contact and puncture a frangible seal 3413 on the gas container 3410 when the release member 3550 moves proximally within the gas cavity 3151, as shown by the arrow FF in FIG. 19.

The distal end portion 3552 of the release member 3550 includes extensions 3553. The extensions 3553 have projections 3555 that include tapered surfaces 3557 and engagement surfaces 3554. Further, the extensions 3553 define an opening 3556 between the extensions 3553. The engagement surfaces 3554 of the projections 3555 are configured to extend through the release member aperture 3154 of the housing 3100 and contact the release member contact surface 3126 of the housing 3100, as shown in FIG. 21. In this manner, the engagement surfaces 3554 of the projections 3555 limit proximal movement of the release member 3550 when the engagement surfaces 3554 are in contact with the release member contact surface 3126 of the housing 3100.

The opening 3556 defined by the extensions 3553 is configured to receive the safety lock protrusion 3702 of the safety lock 3700 (see e.g., FIGS. 21 and 42) when the safety lock 3700 is coupled to the housing 3100 and/or the base 3510. The safety lock protrusion 3702 is configured to prevent the extensions 3553 from moving closer to each other. Said another way, the safety lock protrusion 3702 is configured to ensure that the extensions 3553 remain spaced apart and the engagement surfaces 3554 of the projections 3555 remain in contact with the release member contact surface 3126 of the housing 3100. In some embodiments, for example, the release member 3550 and/or the extensions 3553 can be constructed from any suitable material configured to withstand deformation that may occur when exposed to a load over an extended period of time. In some embodiments, for example, the release member 3550 and/or the extensions 3553 can be constructed from brass.

The tapered surfaces 3557 of the projections 3555 are configured to contact tapered surfaces 3522 of contact protrusions 3515 on a proximal surface 3511 of the base 3510 (see e.g., FIGS. 21 and 47) when the base 3510 is moved proximally relative to the housing 3100. Accordingly, when the base 3510 is moved proximally relative to the housing 3100, the extensions 3553 are moved together by the tapered surfaces 3522 of the contact protrusions 3515. The inward movement of the extensions 3553 causes the release member 3550 to disengage the release member contact surface 3126 of the housing 3100, thereby allowing the release member 3550 to be moved proximally along its longitudinal axis as the spring 3576 expands.

The medicament delivery mechanism 3300 includes a gas container 3410, the carrier 3370 (also referred to herein as the first movable member 3370), the piston member 3330 (also referred to herein as the second movable member 3330), and a retraction spring 3351. As described above, the carrier 3370 and the piston member 3330 are each movably disposed within the medicament cavity 3139 of the housing 3100. The gas container 3410 is disposed within the gas cavity 3151 of the housing 3100.

The gas container 3410 includes a distal end portion 3411 and a proximal end portion 3412, and is configured to contain a pressurized gas. The distal end portion 3411 of the gas container 3410 contains a frangible seal 3413 configured to break when the puncturer 3575 of the proximal end portion 3551 of the release member 3550 contacts the frangible seal 3413. The gas container retention member 3580 of the proximal cap 3103 of the housing 3100 is configured to receive and/or retain the proximal end portion 3412 of the gas container 3410. Said another way, the position of the gas container 3410 within the gas cavity 3151 is maintained by the gas container retention member 3580. As shown in FIGS. 18 and 19, the length of the gas container retention member 3580 and the length of the release member 3550 collectively determine the distance between the puncturer 3575 and the frangible seal 3413 when the medical injector 3000 is in the storage configuration. Accordingly, this distance, which is the distance through which the puncturer 3575 travels when the medical injector 3000 is actuated, can be adjusted by changing the length of the gas container retention member 3580 and/or the length of the release member 3550. In some embodiments, the actuation time and/or the force exerted by the puncturer 3575 on the frangible seal 3413 can be adjusted by changing the distance between the puncturer 3575 and the frangible seal 3413.

Figure 52:
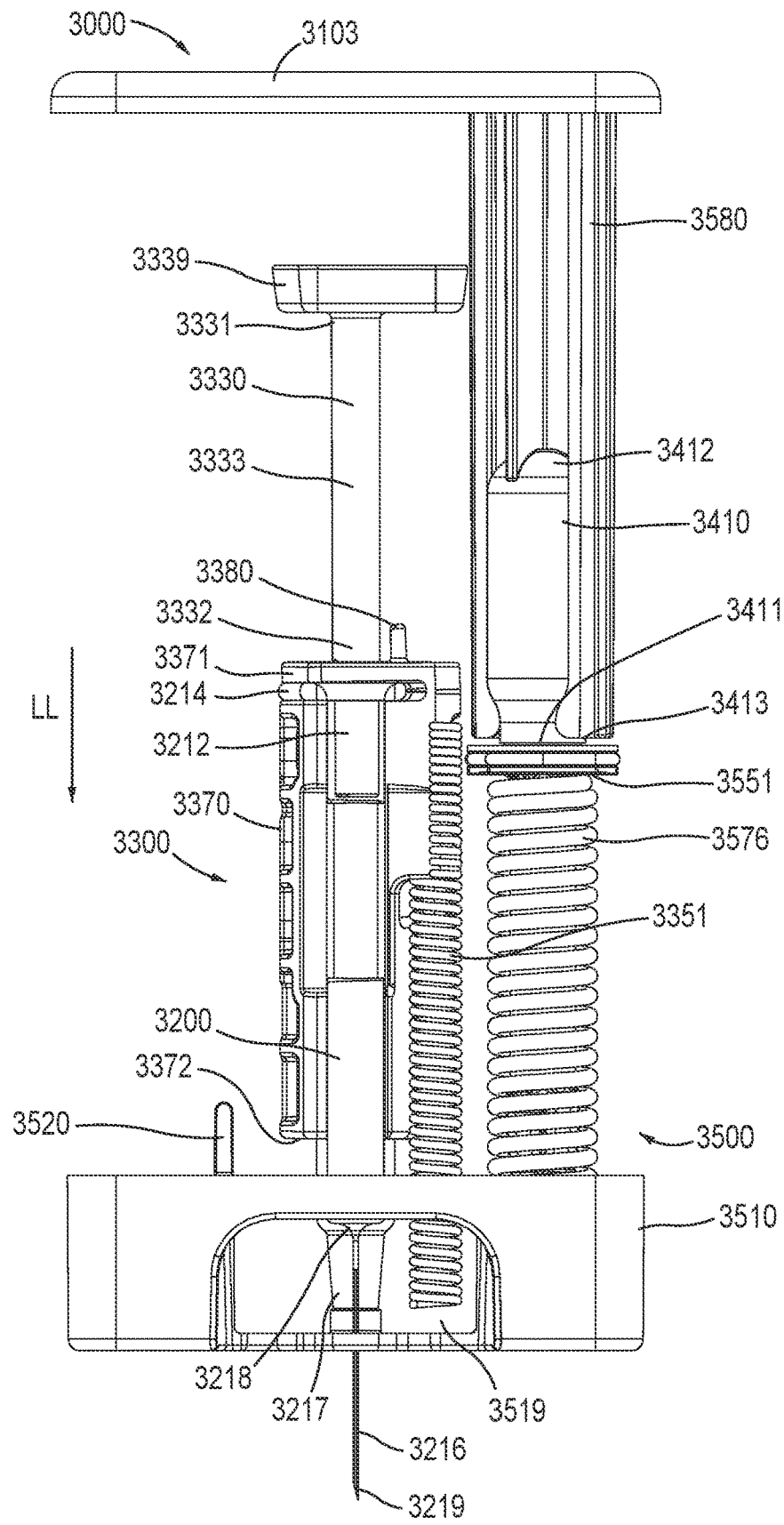
FIG. 52 is a front view of a portion of the medical injector illustrated in FIG. 9 in the fourth configuration (i.e., the needle insertion configuration).
Figure 53:
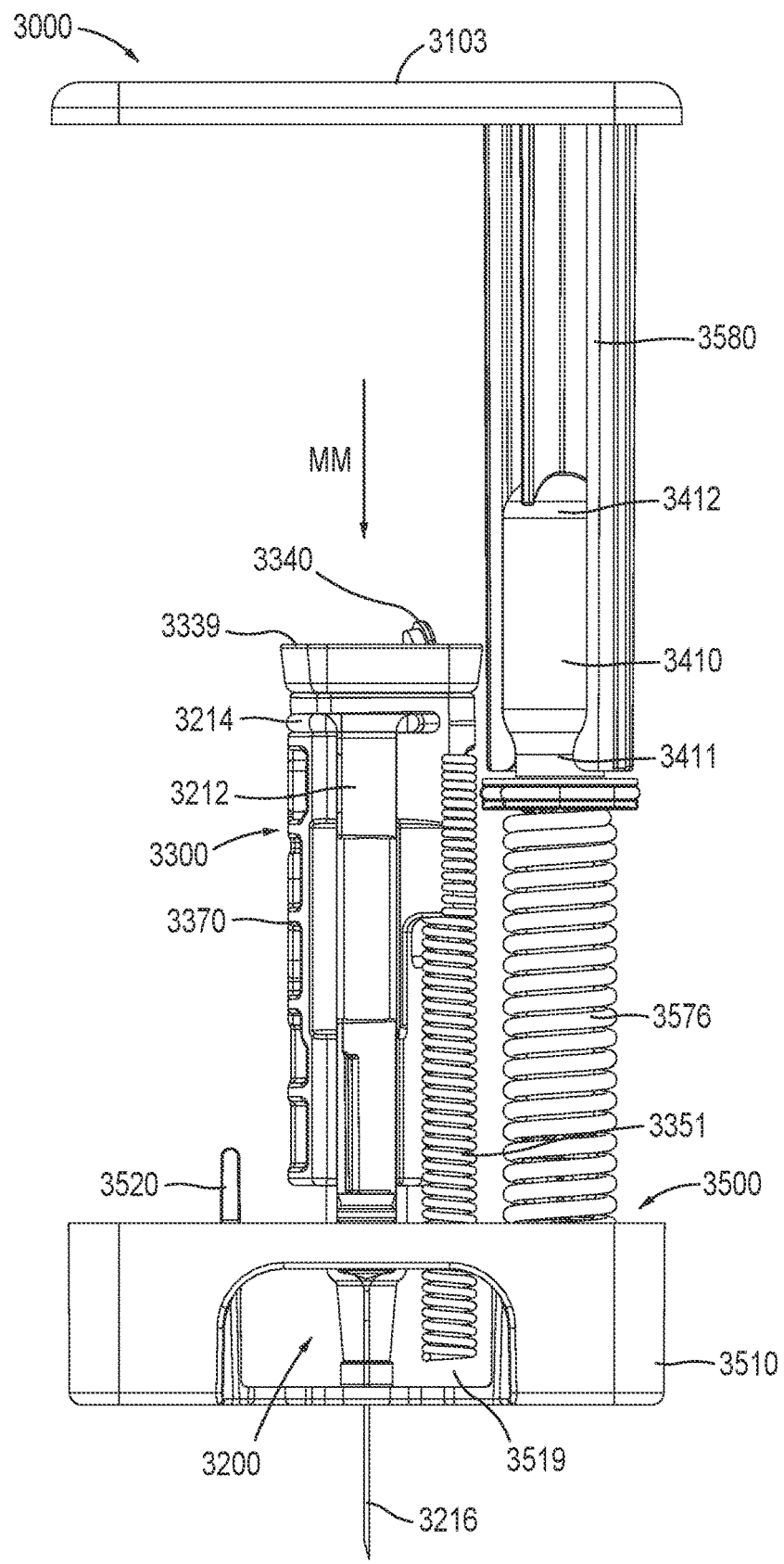
FIG. 53 is a front view of a portion of the medical injector illustrated in FIG. 9 in a fifth configuration (i.e., the injection configuration).

As shown in FIGS. 26 and 52, the piston member 3330 includes a piston rod 3333, and has a proximal end portion 3331 and a distal end portion 3332. The proximal end portion 3331 includes a sealing member 3339. The sealing member 3339 engages the sidewall of the housing 3100 to define a gas chamber (i.e., a volume within the medicament cavity 3139 between the proximal end of the housing 3100 and the proximal end of the piston member 3330) that receives the pressurized gas from the gas container 3410. The sealing member 3339 can be any suitable structure and or component to produce a substantially fluid-tight seal between the sidewall of the housing 3100 and the piston member 3330. The proximal end portion 3331 also includes a gas relief valve 3340 (see e.g., FIGS. 26 and 53-55) configured to be selectively actuated to allow fluid communication between the gas chamber and a volume outside of the gas chamber (e.g., the distal end portion of the medicament cavity 3139). As described in more detail below, the gas relief valve 3340 allows the gas pressure within the gas chamber to be reduced upon completion of the injection event.

Referring to FIG. 27, the distal end portion 3332 includes a first surface 3341 and a second surface 3342. The second surface 3342 is disposed through a piston rod opening 3384 of the carrier 3370 and within the proximal end portion 3212 of the medicament container 3200. The first surface 3341 is configured to contact a proximal surface 3378 of an engagement portion 3379 of the carrier 3370 when the medicament injector 3000 is in a first configuration (i.e., when the medicament container 3200 is in its first position). The distance between the first surface 3341 and the second surface 3342 is such that when the first surface 3341 is in contact with the engagement portion 3379 of the carrier 3370, the second surface 3342 is spaced apart from the elastomeric member 3217 within the medicament container 3200 (see e.g., FIG. 27). This arrangement limits any preload and/or residual force applied to the piston member 3330 (e.g., via the retraction spring 3351 and/or the pressurized gas) from being transferred to the plunger 3217. Said another way, the plunger 3217 is isolated from the piston member 3330 during the storage configuration and/or when the medicament container 3200 is moving distally within the housing 3100. Accordingly, this arrangement reduces and/or eliminates leakage of the medicament 3220 from the medicament container 3200.

As described in more detail herein, the piston member 3330 is configured to move within the medicament container 3200. Because the first surface 3341 is configured to contact the engagement portion 3379, the piston member 3330 applies a force to the proximal surface 3378 of the first shoulder 3377 such that the carrier 3370 and the piston member 3330 move together within the medicament cavity 3139. Moreover, when the medicament container 3200 is in its second position, the piston member 3330 can move relative to the carrier 3370 and/or the medicament container 3200 such that the second surface 3342 engages and/or contacts the elastomeric member 3217 to convey the medicament 3220 contained in the medicament container 3200. The piston member 3330 can be constructed of a resilient, durable and/or sealing material or combination of materials, such as a rubber.

The carrier 3370 of the medicament delivery mechanism 3300 includes a distal end portion 3372, a proximal end portion 3371, a first side portion 3373, a second side portion 3374 and a hinge portion 3375 (see e.g., FIGS. 23-28). The first side portion 3373 includes latch protrusions 3383 configured to be coupled to the corresponding latches 3376 of the second side portion 3374. The second side portion 3374 is configured to move relative to the first side portion 3373 via the hinge portion 3375 between an opened configuration (FIGS. 23 and 24) and a closed configuration (FIG. 25). This arrangement allows at least the proximal end portion 3212 of the medicament container 3200 to be disposed within (and/or removed from) the carrier 3370 when the carrier 3370 is in the opened configuration (see e.g., FIGS. 23 and 24). When the carrier 3370 is in the closed configuration (see e.g., FIGS. 25-28), the latches 3376 of the second side portion 3374 engage the latch protrusions 3383 of the first side portion 3373 to maintain the medicament container 3200 within the carrier 3370.

The proximal end portion 3371 of the carrier 3370 includes a first shoulder 3377 and a second shoulder 3381 that collectively define a flange groove 3385. The flange groove 3385 is configured to receive the flange 3214 of the proximal end portion 3212 of the medicament container 3200 (see e.g., FIG. 26). More particularly, the first shoulder 3377 is defined by the first side portion 3373, and the second shoulder 3381 is defined by portions of both the first side portion 3373 and the second side portion 3374. In this manner, the first shoulder 3377 is configured to contact a proximal surface of the flange 3214, either directly or via intervening structure (e.g., an o-ring, a damping member, or the like). Similarly, the second shoulder 3381 is configured to contact a distal surface of the flange 3214, either directly or via intervening structure (e.g., an o-ring, a damping member, or the like). In this manner, as described in more detail below, the first shoulder 3377 can transfer at least a portion of a distal force (i.e., an insertion force) to the flange 3214 to produce distal movement of the carrier 3370 and/or the medicament container 3200 within the housing 3100. The second shoulder 3381 can transfer at least a portion of a proximal force (i.e., a retraction force) to the flange 3214 to produce proximal movement of the carrier 3370 and/or the medicament container 3200 within the housing 3100.

The second side portion 3374 includes a protrusion 3386 configured to contact a surface of the first side portion 3373 when the carrier 3370 is in the closed configuration (FIG. 25). In this manner, the protrusion 3386 and the corresponding portion of the first side portion 3373 limits the movement of the second side portion 3374 relative to the first side portion 3373 when the carrier 3370 is in the closed configuration. Similarly stated, the protrusion 3386 of the second side portion 3374 contacts the first side portion 3373 to prevent the carrier 3370 from squeezing the medicament container 3200, when the carrier 3370 is in the closed configuration.

The second side portion 3374 includes a latch 3387 having a protrusion 3388. The protrusion 3388 of the latch 3387 is configured to engage a retraction lock protrusion 3162 defined by the sidewall of the housing 3100 defining the medicament cavity 3139 (see e.g., FIG. 28) when the carrier 3370 and the medicament container 3200 are in the first (i.e., storage) position. This arrangement allows the medicament delivery mechanism 3300 (e.g., the carrier 3370, the piston member 3330) and the medicament container 3200 to move in the distal direction within the housing 3100 but limits the movement of the carrier 3370 and the medicament container 3200 in the proximal direction. In this manner, the preload of the retraction spring 3351 is not transferred to the piston member 3330 and/or the engagement portion 3379 of the carrier 3370. Similarly stated, this arrangement prevents the medicament delivery mechanism 3300 from moving in the proximal direction when the medical injector 3000 is in the first configuration. This arrangement also limits proximal motion of the medicament delivery mechanism 3300 during assembly (e.g., when the needle sheath is being pressed about the needle).

As described above, the carrier 3370 includes the engagement portion 3379 configured to engage the first surface 3341 of the piston member 3330. The first shoulder 3377 is in contact with the proximal surface of the flange 3214 and therefore transmits a force from the piston member 3330 to move the medicament container 3200 from a first position to a second position when the medicament injector 3000 is actuated.

As shown in FIG. 26, the carrier 3370 also includes an engagement portion 3382 configured to engage the retraction spring 3351. Although the engagement portion 3382 is shown as including a protrusion about which a portion of the retraction spring 3351 is disposed, in other embodiments, the engagement portion 3382 can include any suitable features for engaging and/or retaining the retraction spring 3351 (e.g., a recess). The second shoulder 3381 is configured to engage the distal end of the flange 3214 and therefore transmits a retraction force produced by the retraction spring 3351 to move the medicament container 3200 from the second position toward the first position.

A proximal surface 3378 of the first shoulder 3377 of the carrier 3370 includes a gas valve actuator 3380. The gas valve actuator 3380 is configured to engage the gas relief valve 3340 (see e.g., FIG. 26) of the piston member 3330 to allow the pressurized gas contained within the gas chamber (i.e., the volume within the medicament cavity 3139 between the proximal end of the housing 3100 and the proximal end of the piston member 3330) to escape when the injection event is complete. Thus, after the gas pressure within the medicament cavity 3139 decreases below a certain level, the force exerted by the retraction spring 3351 on the carrier 3370 is sufficient to cause the carrier 3370 to move proximally within the housing 3100 (i.e., to retract). In addition, this arrangement results in there being substantially no residual force (from the pressurized gas) within the housing, which decreases stress on the components after the injection event.

Figure 36:
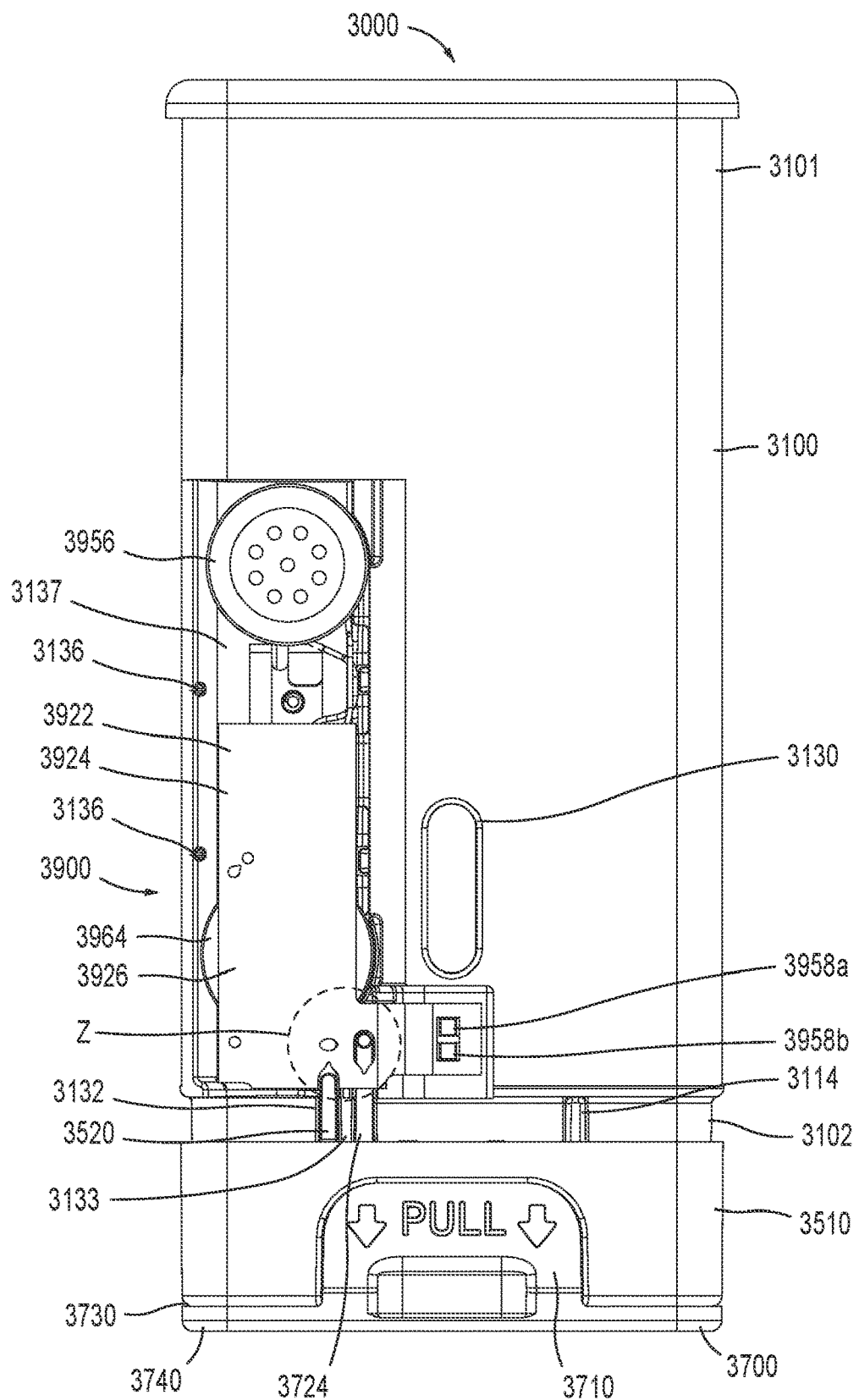
FIG. 36 is a front view of the medical injector illustrated in FIG. 9 in a first configuration showing the electronic circuit system.

FIGS. 29-39 show the electronic circuit system 3900. The electronic circuit system 3900 of the medical injector 3000 includes an electronic circuit system housing 3170, a printed circuit board 3922, a battery assembly 3962, an audio output device 3956, two light emitting diodes (LEDs) 3958A, 3958B and a battery clip 3910. As shown in FIG. 36, the electronic circuit system 3900 is disposed within the electronic circuit system cavity 3137 of the housing 3100. As described herein, the electronic circuit system 3900 is configured to output an electronic output associated with the use of the medical injector 3000.

The electronic circuit system housing 3170 of the electronic circuit system 3900 includes a distal end portion 3172 and a proximal end portion 3171. The proximal end portion 3171 includes connection protrusions 3174A and a battery clip protrusion 3176 (see e.g., FIG. 33). The connection protrusions 3174A are configured to matingly engage a surface of the sidewalls of the housing 3100 that define the electronic cavity 3137, as described above. In this manner, the electronic circuit system 3900 can be coupled to the housing 3100 within the electronic circuit system cavity 3137. In other embodiments, the electronic circuit system 3900 can be coupled to the housing 3100 by other suitable means such as an adhesive, a clip, a label and/or the like. As described in more detail herein, the battery clip protrusion 3176 is configured to hold the battery clip 3910 in place.

The proximal end portion 3171 of the electronic circuit system housing 3170 defines multiple sound apertures 3173. The audible output device 3956 is disposed against the proximal end portion 3171 of the electronic circuit system housing 3170 such that the front face of the audible output device 3956 is disposed adjacent the sound apertures 3173. In this manner, the sound apertures 3173 are configured to allow sound produced by the audio output device 3956 to pass from the audio output device 3956 to a region outside of the housing 3100.

Figure 32:
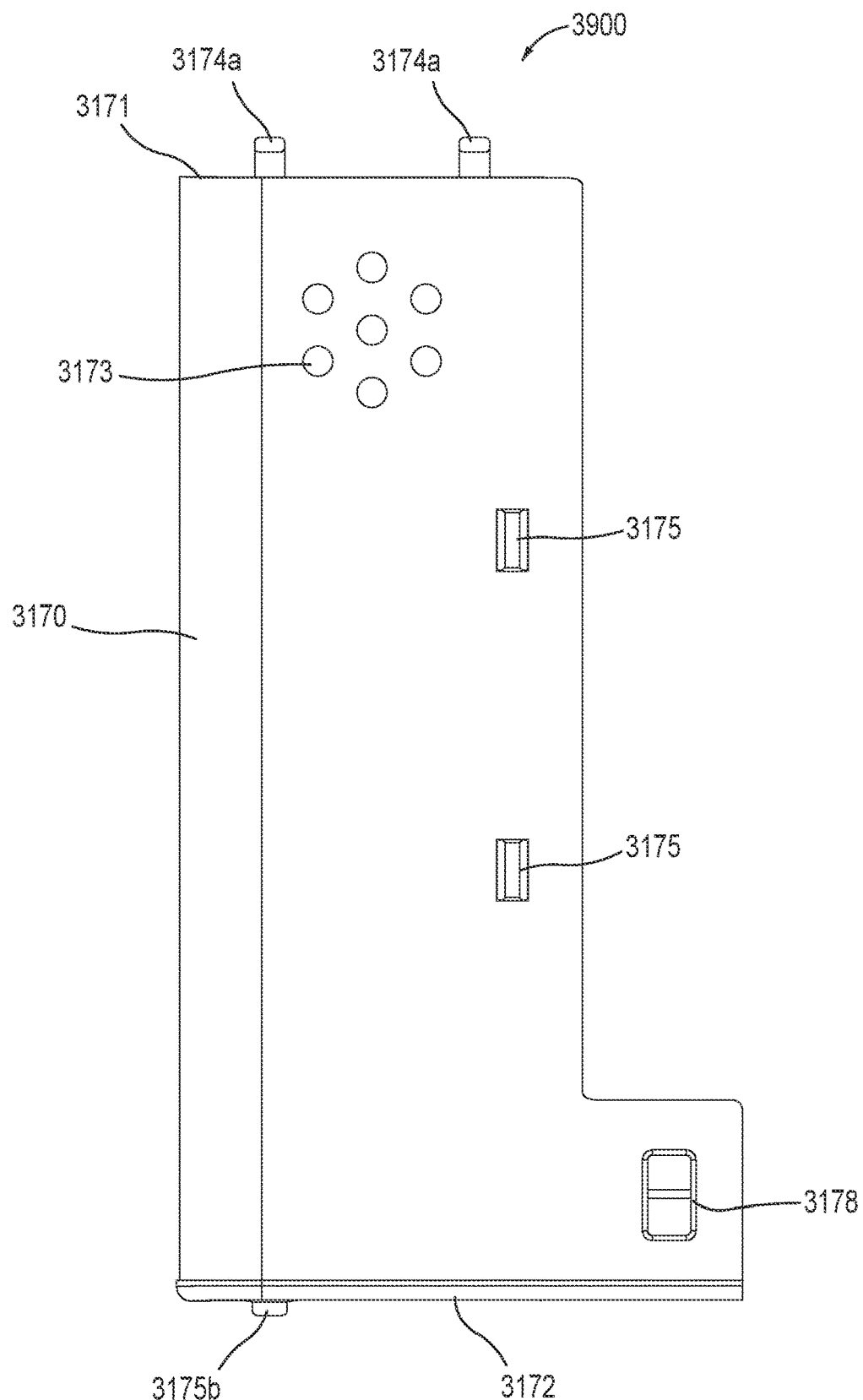
FIG. 32 is a front view of an electronic circuit system housing of the electronic circuit system illustrated in FIG. 29.
Figure 33:
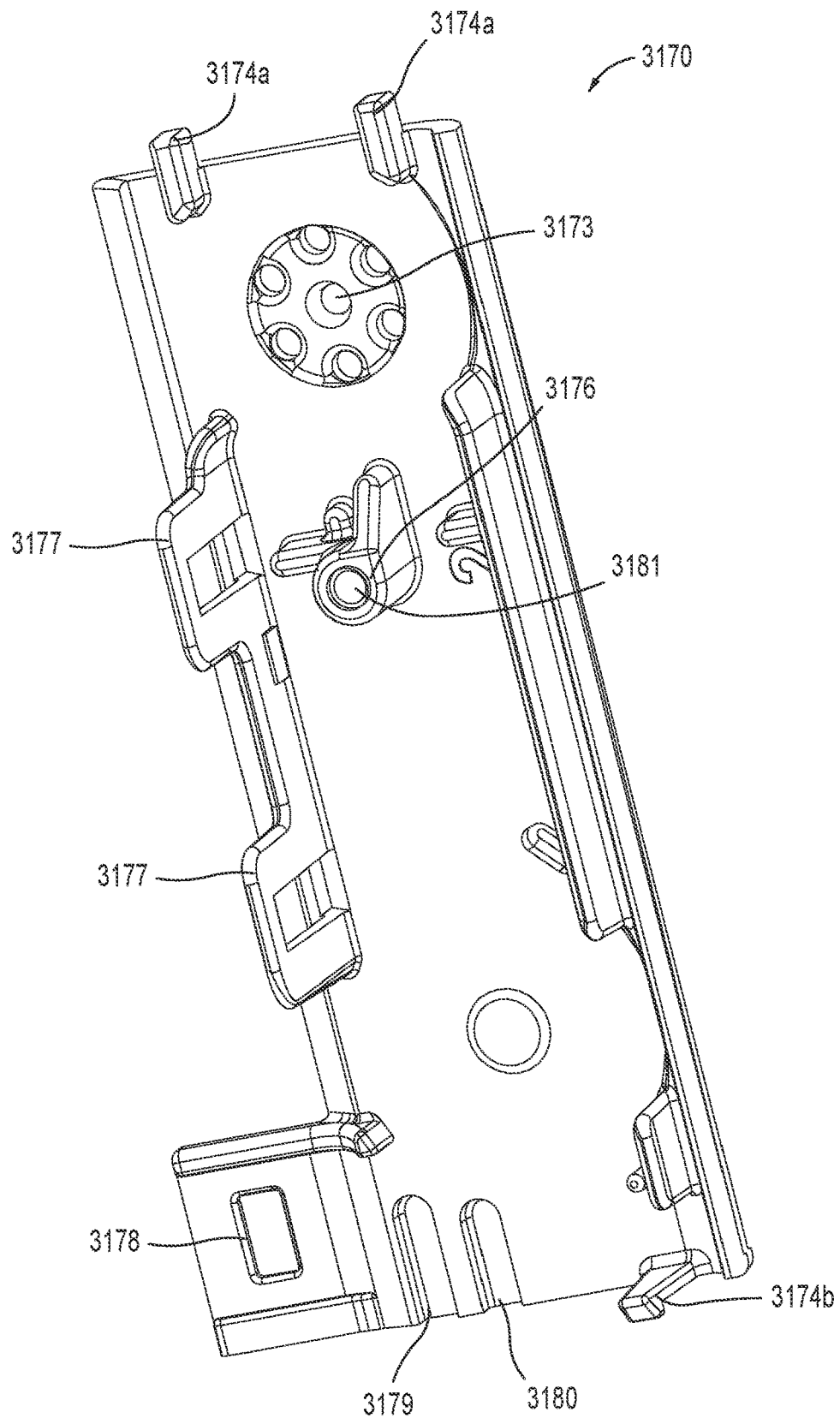
FIG. 33 is a perspective view of the electronic circuit system housing of the electronic circuit system illustrated in FIG. 32.
Figure 34:
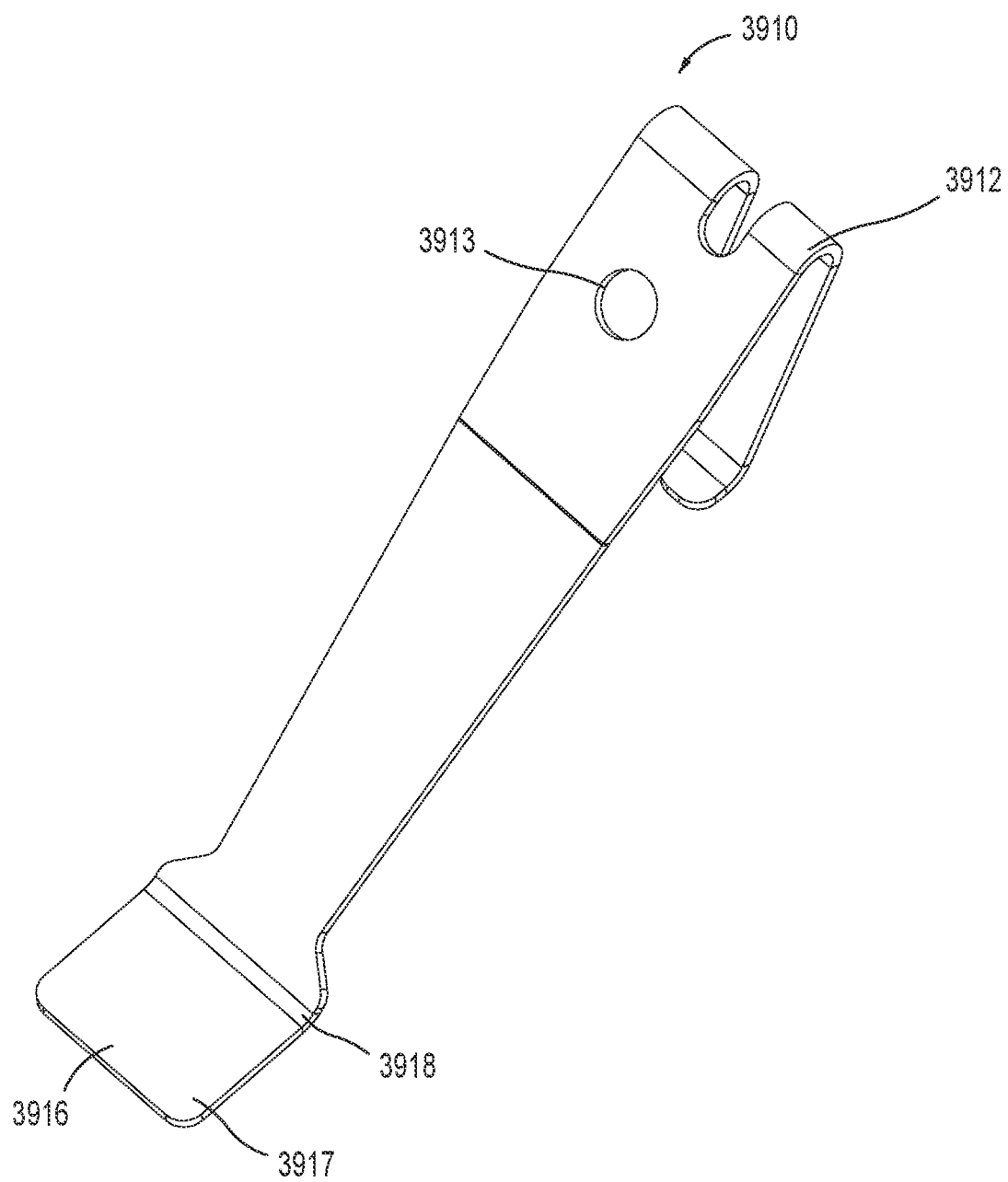
FIG. 34 is a perspective view of a battery clip of the electronic circuit system illustrated in FIG. 29.
Figure 35:
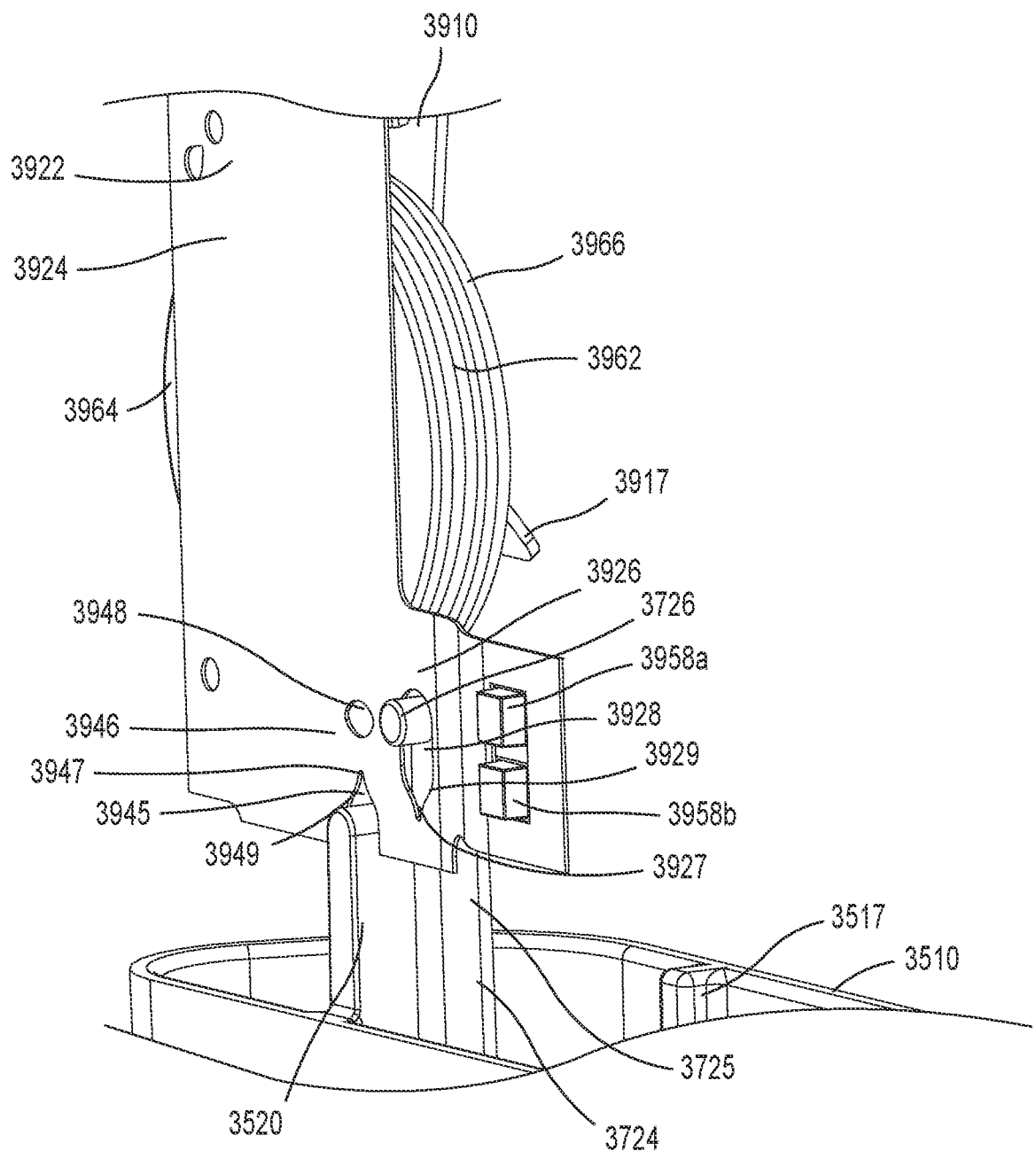
FIG. 35 is a perspective view of a portion of an electronic circuit system of the medical injector illustrated in FIG. 9, in a first configuration.

As shown in FIGS. 32 and 33, the distal end portion 3172 of the electronic circuit system housing 3170 includes the connection protrusion 3174B, a stiffening protrusion 3177 and defines an LED aperture 3178, apertures 3175, a safety lock actuator groove 3179 and a base actuator groove 3180. The LED aperture 3178 is configured to receive the LEDs 3958A, 3958B such that a user can view the LEDs 3958A, 3958B, which are described in more detail herein.

The connection protrusion 3174B extends from the distal end portion 3172 of the electronic circuit system housing 3170, and is configured to attach the electronic circuit system 3900 to the housing 3100, as described above. The stiffening protrusion 3177 is configured to have at least a portion received within and/or accessible via the apertures 3175 defined by the housing 3100 (see e.g., FIG. 11). The stiffening protrusion 3177 is configured to limit the bending (e.g., buckling) of the electronic circuit system housing 3170 when the electronic circuit system housing 3170 is coupled to the housing 3100. Moreover, a user can access the stiffening protrusion 3177 via the apertures 3175. In this manner, for example, the user can disengage the stiffening protrusion 3177 from the apertures 3175.

The safety lock actuator groove 3179 of the electronic circuit system housing 3170 is configured to be disposed adjacent the safety lock actuator groove 3133 of the distal end portion 3102 of the housing 3100. In this manner, the safety lock actuator groove 3179 of the electronic circuit system housing 3170 and the safety lock actuator groove 3133 of the distal end portion 3102 of the housing 3100 collectively receive the actuator 3724 of the safety lock 3700, which is described in more detail herein. Similarly, the base actuator groove 3180 of the electronic circuit system housing 3170 is configured to be disposed adjacent the base actuator groove 3132 of the distal end portion 3102 of the housing 3100. The base actuator groove 3180 of the electronic circuit system housing 3170 and the base actuator groove 3132 of the distal end portion 3102 of the housing 3100 collectively receive the protrusion 3520 of the base 3510, which is described in more detail herein.

The printed circuit board 3922 of the electronic circuit system 3900 includes a substrate 3924, a first actuation portion 3926 and a second actuation portion 3946. The substrate 3924 of the printed circuit board 3922 includes the electrical components for the electronic circuit system 3900 to operate as desired. For example, the electrical components can be resistors, capacitors, inductors, switches, microcontrollers, microprocessors and/or the like. The printed circuit board may also be constructed of materials other than a flexible substrate such as a FR4 standard board (rigid circuit board).

Figure 37:
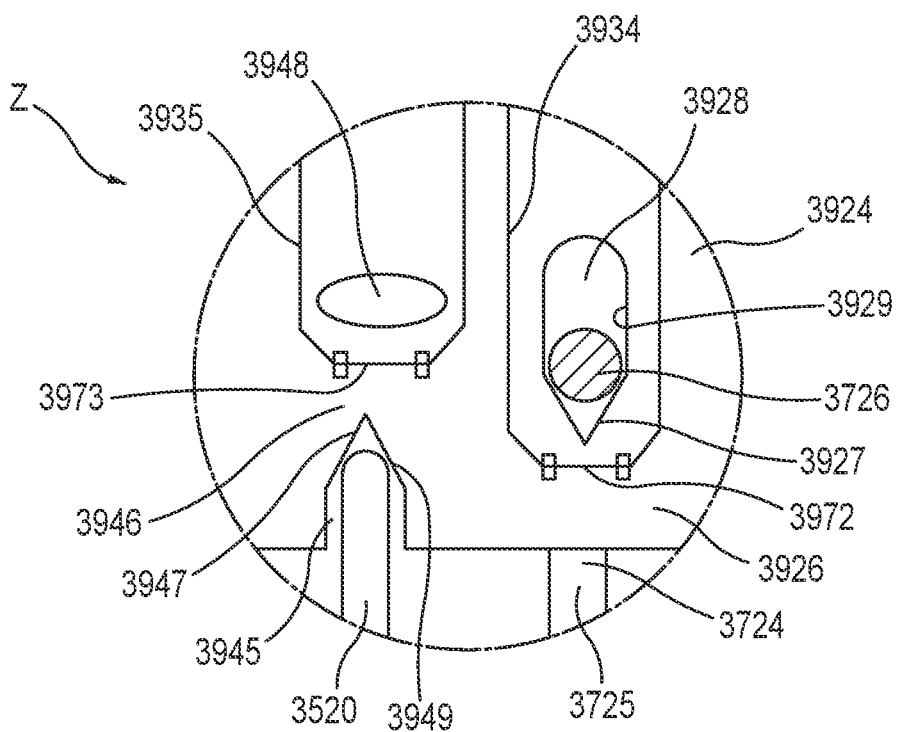
FIGS. 37-39 are front views of a portion of the electronic circuit system of the medical injector labeled as Region Z in FIG. 36 in a first configuration, a second configuration and a third configuration, respectively.
Figure 38:
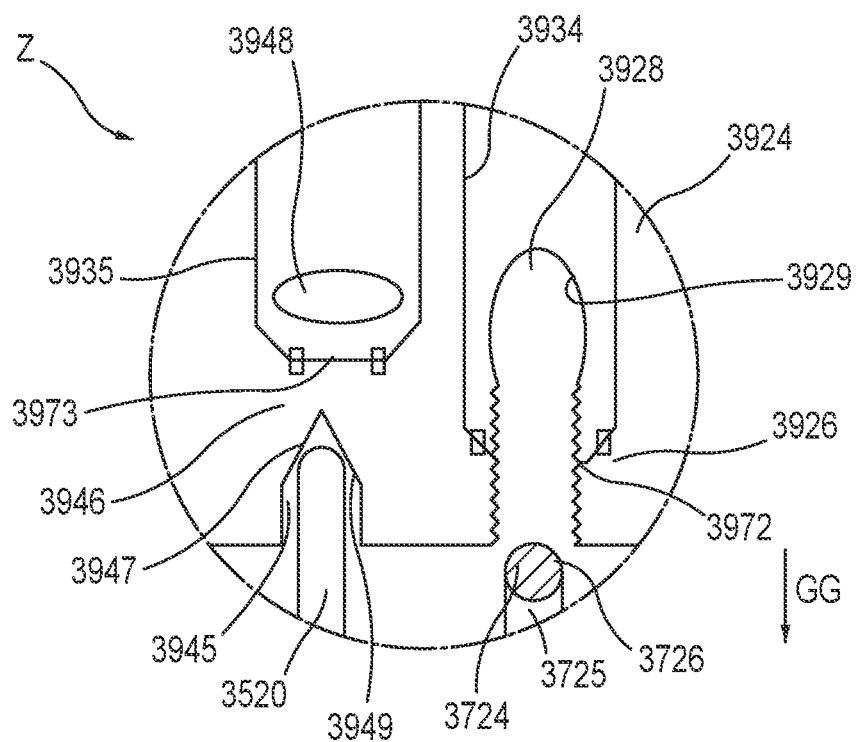
Figure 39:
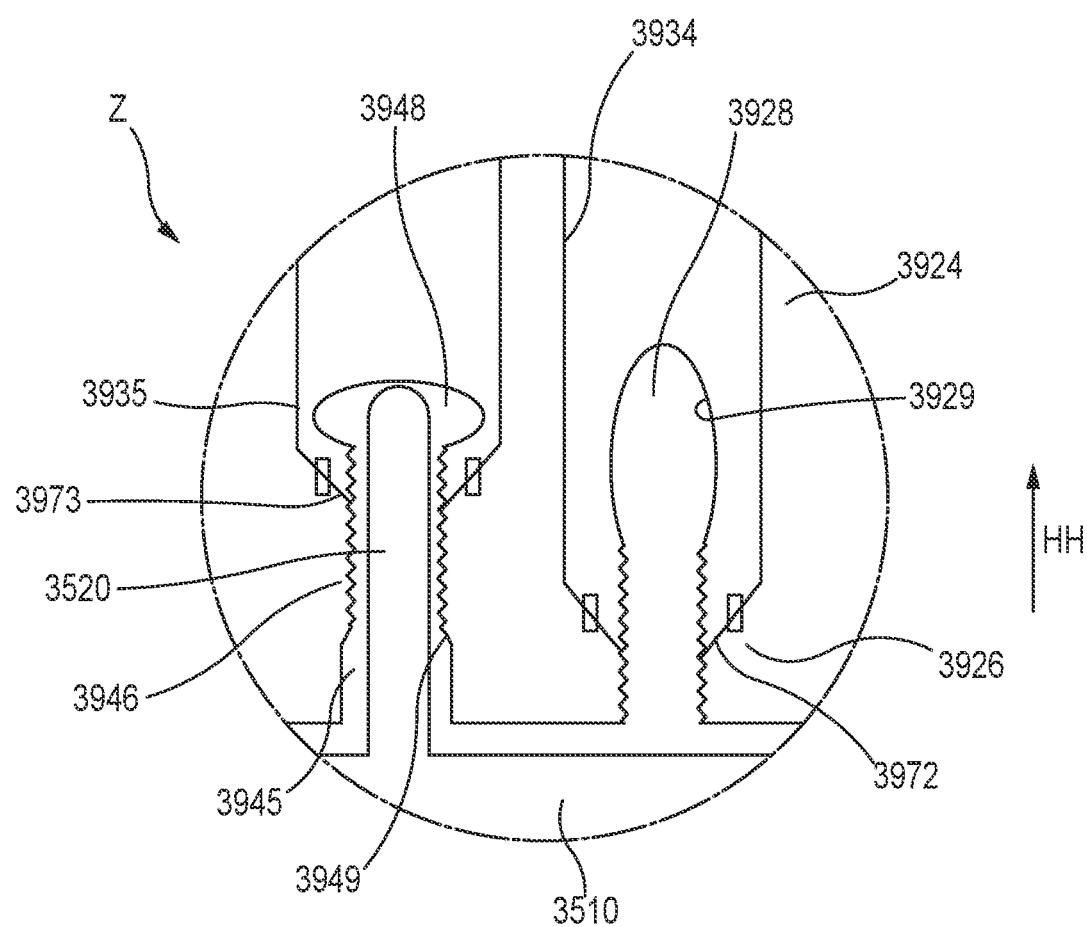

As shown in FIGS. 37-39, the first actuation portion 3926 includes a first electrical conductor 3934 and defines an opening 3928 having a boundary 3929. The opening 3928 of the first actuation portion 3926 is configured to receive a protrusion 3726 of the actuator 3724 of the safety lock 3700. The boundary 3929 of the first opening 3928 has a discontinuous shape, such as, for example, a teardrop shape, that includes a stress concentration riser 3927. The discontinuity and/or the stress concentration riser 3927 of the boundary 3929 can be of any suitable shape to cause the substrate 3924 to deform in a predetermined direction when the protrusion 3726 of the actuator 3724 of the safety lock 3700 is moved relative to the opening 3928, as shown by the arrow GG in FIG. 38.

The opening 3928 is defined adjacent the first electrical conductor 3934 that electronically couples the components included in the electronic circuit system 3900. The first electrical conductor 3934 includes a first switch 3972, which can be, for example a frangible portion of the first electrical conductor 3934. In use, when the safety lock 3700 is moved from a first position (see e.g., FIG. 37) to a second position (see e.g., FIG. 38), the actuator 3724 moves in a direction substantially parallel to a plane defined by a surface of the first actuation portion 3926 of the substrate 3924. The movement of the actuator 3724 causes the protrusion 3726 to move within the first opening 3928, as indicated by the arrow GG in FIG. 38. The movement of the protrusion 3726 tears the first actuation portion 3926 of the substrate 3924, thereby separating the portion of the first electrical conductor 3934 including the first switch 3972. Said another way, when the safety lock 3700 is moved from its first position to its second position (see e.g., FIG. 50), the actuator 3724 moves irreversibly the first switch 3972 from a first state (e.g., a state of electrical continuity) to a second state (e.g., a state of electrical discontinuity). Said yet another way, when the safety lock 3700 is moved from its first position to its second position, the actuator 3724 disrupts the first electrical conductor 3934.

The second actuation portion 3946 includes a second electrical conductor 3935 and defines an opening 3945, having a boundary 3949 and a tear propagation limit aperture 3948. As shown in FIGS. 36-39, the opening 3945 of the second actuation portion 3946 is configured to receive a portion of an actuator 3520 of the base 3510. The boundary 3949 of the opening 3945 has a discontinuous shape that includes a stress concentration riser 3947. The discontinuity and/or the stress concentration riser 3947 of the boundary 3949 can be of any suitable shape to cause the substrate 3924 to deform in a predetermined direction when the actuator 3520 of the base 3510 is moved in a proximal direction relative to the opening 3945, as shown by the arrow HH in FIG. 39.

The second electrical conductor 3935 includes a second switch 3973 disposed between the opening 3945 and the tear propagation limit aperture 3948, which can be, for example, a frangible portion of the second electrical conductor 3935. In use, when the base 3510 is moved from its first position to its second position (see e.g., FIG. 51), the actuator 3520 moves in a proximal direction, substantially parallel to a plane defined by a surface of the second actuation portion 3946 of the substrate 3924. The proximal movement of the actuator 3520 tears the second actuation portion 3946 of the substrate 3924, thereby separating the portion of the second electrical conductor 3935 including the second switch 3973. Said another way, when the base 3510 is moved from its first position to its second position, the actuator 3520 moves irreversibly the second switch 3973 from a first state (e.g., a state of electrical continuity) to a second state (e.g., a state of electrical discontinuity). The tear propagation limit aperture 3948 is configured to limit the propagation of the tear in the substrate 3924 in the proximal direction. Said another way, the tear propagation limit aperture 3948 is configured to ensure that the tear in the substrate 3924 does not extend beyond the tear propagation limit aperture 3948. The tear propagation limit aperture 3948 can be any shape configured to stop the propagation of a tear and/or disruption of the substrate 3924. For example, the tear propagation limit aperture 3948 can be oval shaped. In other embodiments, the proximal boundary of the tear propagation limit aperture 3948 can be reinforced to ensure that the tear in the substrate 3924 does not extend beyond the tear propagation limit aperture 3948.

In some embodiments, the safety lock 3700 and base 3510 can be configured to interact with mechanical and/or optical switches to produce an electronic output in a reversible manner.

The battery assembly 3962 of the electronic circuit system 3900 includes two batteries stacked on top of one another. In other embodiments, the electronic circuit system can include any number of batteries and/or any suitable type of power source. In some embodiments, for example, the battery assembly can include Lithium batteries such as, for example, CR1616, CR2016s, type AAA or the like. The battery assembly 3962 has a first surface 3964 and a second surface 3966. The first surface 3964 of the battery assembly 3962 can contact an electrical contact (not shown) disposed on the substrate 3924. The second surface 3966 of the battery assembly 3962 is configured to contact a contact portion 3918 of a distal end portion 3916 of a battery clip 3910. When both the electrical contact of the substrate 3924 and the contact portion 3918 of the distal end portion 3916 of the battery clip 3910 contact the battery assembly 3962, the batteries of the battery assembly 3962 are placed in electrical communication with the electronic circuit system 3900. Said another way, when the electrical contact of the substrate 3924 and the contact portion 3918 of the distal end portion 3916 of the battery clip 3910 contact the battery assembly 3962, the battery assembly 3962 is configured to supply power to the electronic circuit system 3900.

The battery clip 3910 (shown in FIG. 34) includes a proximal end portion 3912 and a distal end portion 3916. The proximal end portion 3912 defines a retention aperture 3913. The retention aperture 3913 is configured to receive a screw 3911 to couple the battery clip 3910 to the battery clip protrusion 3176 of the electronic circuit system housing 3170. In this manner, the battery clip protrusion 3176 maintains the position of the battery clip 3910 with respect to the electronic circuit system housing 3170 and/or the battery assembly 3962.

The distal end portion 3916 of the battery clip 3910 includes a contact portion 3918 and an angled portion 3917. As described above, the contact portion 3918 is configured to contact the second surface 3966 of the battery assembly 3962 to place the battery assembly 3962 in electrical communication with the electronic circuit system 3900. The angled portion 3917 of the distal end portion 3916 of the battery clip 3910 is configured to allow a proximal end portion 3236 of a battery isolation protrusion 3197 (see e.g., FIG. 41) to be disposed between the second surface 3966 of the battery assembly 3962 and the contact portion 3918 of the distal end portion 3916 of the battery clip 3910. When the battery isolation protrusion 3197 is disposed between the second surface 3966 of the battery assembly 3962 and the contact portion 3918 of the distal end portion 3916 of the battery clip 3910, the electrical path between the battery assembly 3962 and the remainder of the electrical circuit system 3900 is disrupted, thereby removing power from the electronic circuit system 3900. The contact portion 3918 of the distal end portion 3916 of the battery clip 3910 is biased such that when the battery isolation protrusion 3197 is removed, the contact portion 3918 will move into contact the second surface 3966 of the battery assembly 3962, thereby restoring electrical communication between the battery assembly 3962 and the electronic circuit system 3900. In some embodiments, the battery isolation protrusion 3197 can be repeatedly removed from between the second surface 3966 of the battery assembly 3962 and the contact portion 3918 of the distal end portion 3916 of the battery clip 3910 and reinserted. Said another way, the battery isolation protrusion 3197 and the battery clip 3910 collectively form a reversible on/off switch.

The audio output device 3956 of the electronic circuit system 3900 is configured to output audible sound to a user in response to use of the medical injector 3000. In some embodiments, the audible output device 3956 can be a speaker. In some embodiments, the audible sound can be, for example, associated with a recorded message and/or a recorded speech. In other embodiments, the audible instructions can be an audible beep, a series of tones and/or or the like.

In other embodiments, the medical injector 3000 can have a network interface device (not shown) configured to operatively connect the electronic circuit system 3900 to a remote device (not shown) and/or a communications network (not shown). In this manner, the electronic circuit system 3900 can send information to and/or receive information from the remote device. The remote device can be, for example, a remote communications network, a computer, a compliance monitoring device, a cell phone, a personal digital assistant (PDA) or the like. Such an arrangement can be used, for example, to download replacement processor-readable code from a central network to the electronic circuit system 3900. In some embodiments, for example, the electronic circuit system 3900 can download information associated with a medical injector 3000, such as an expiration date, a recall notice, updated use instructions or the like. Similarly, in some embodiments, the electronic circuit system 3900 can upload information associated with the use of the medical injector 3000 via the network interface device (e.g., compliance information or the like).

Figure 40:
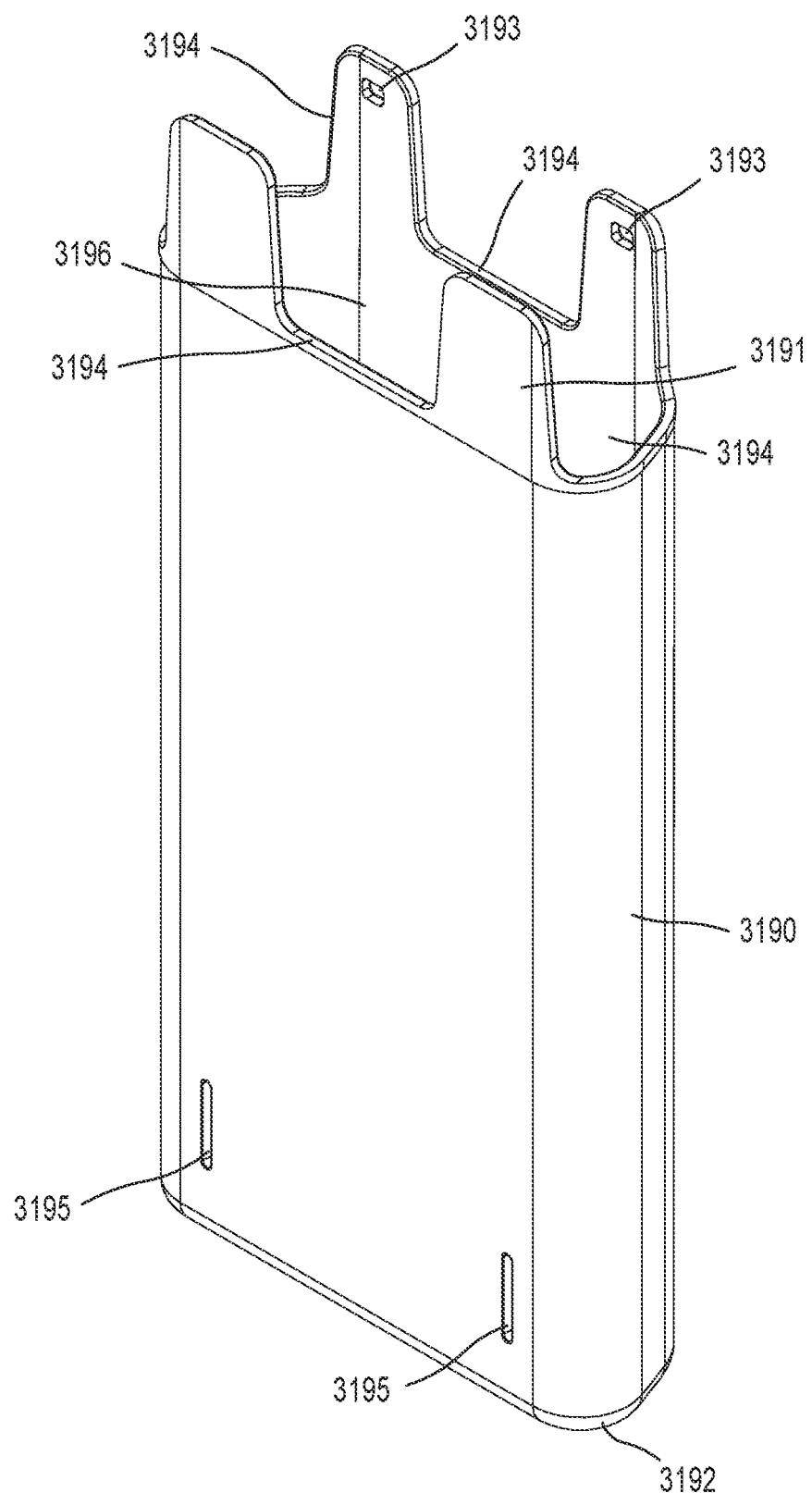
FIGS. 40 and 41 are perspective views of a cover of the medical injector illustrated in FIG. 9.
Figure 41:
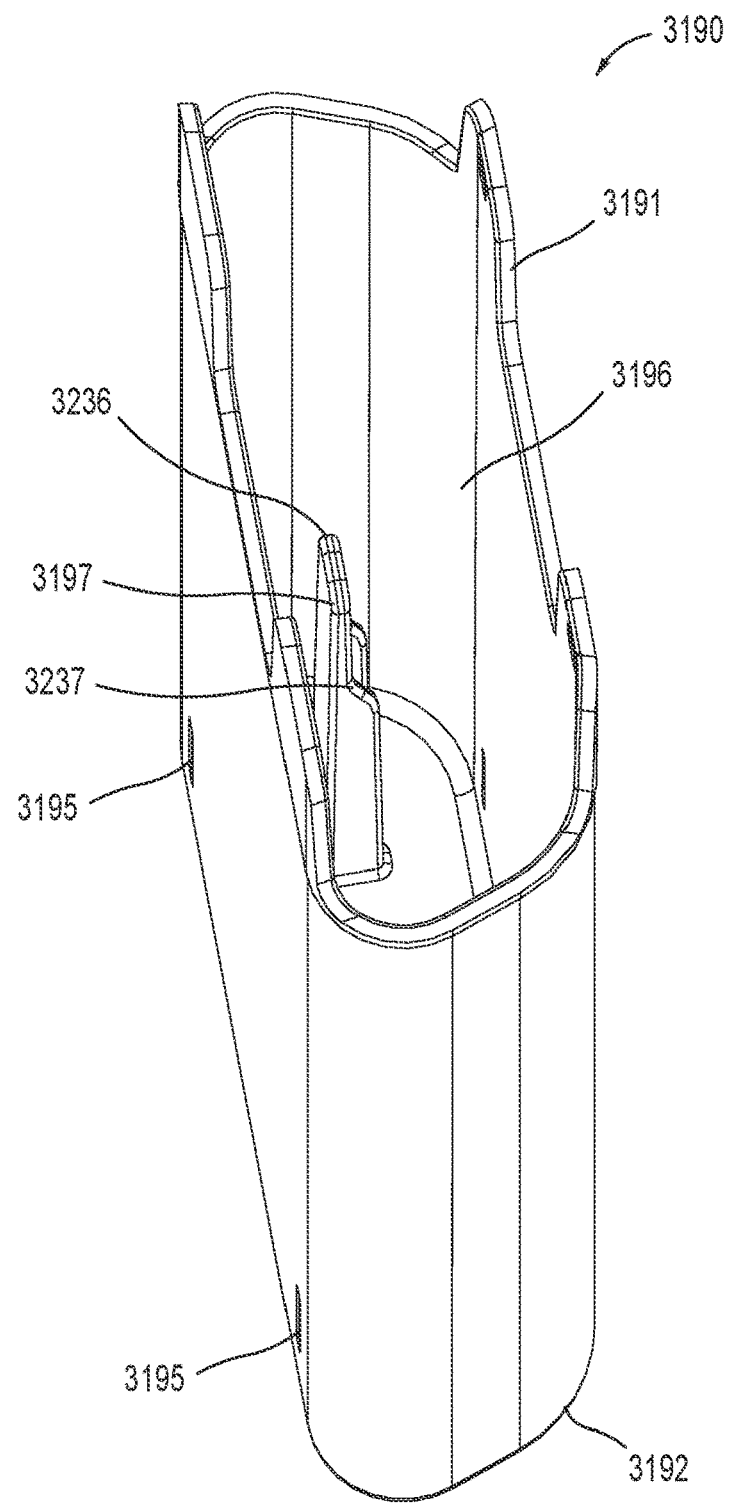
Figure 42:
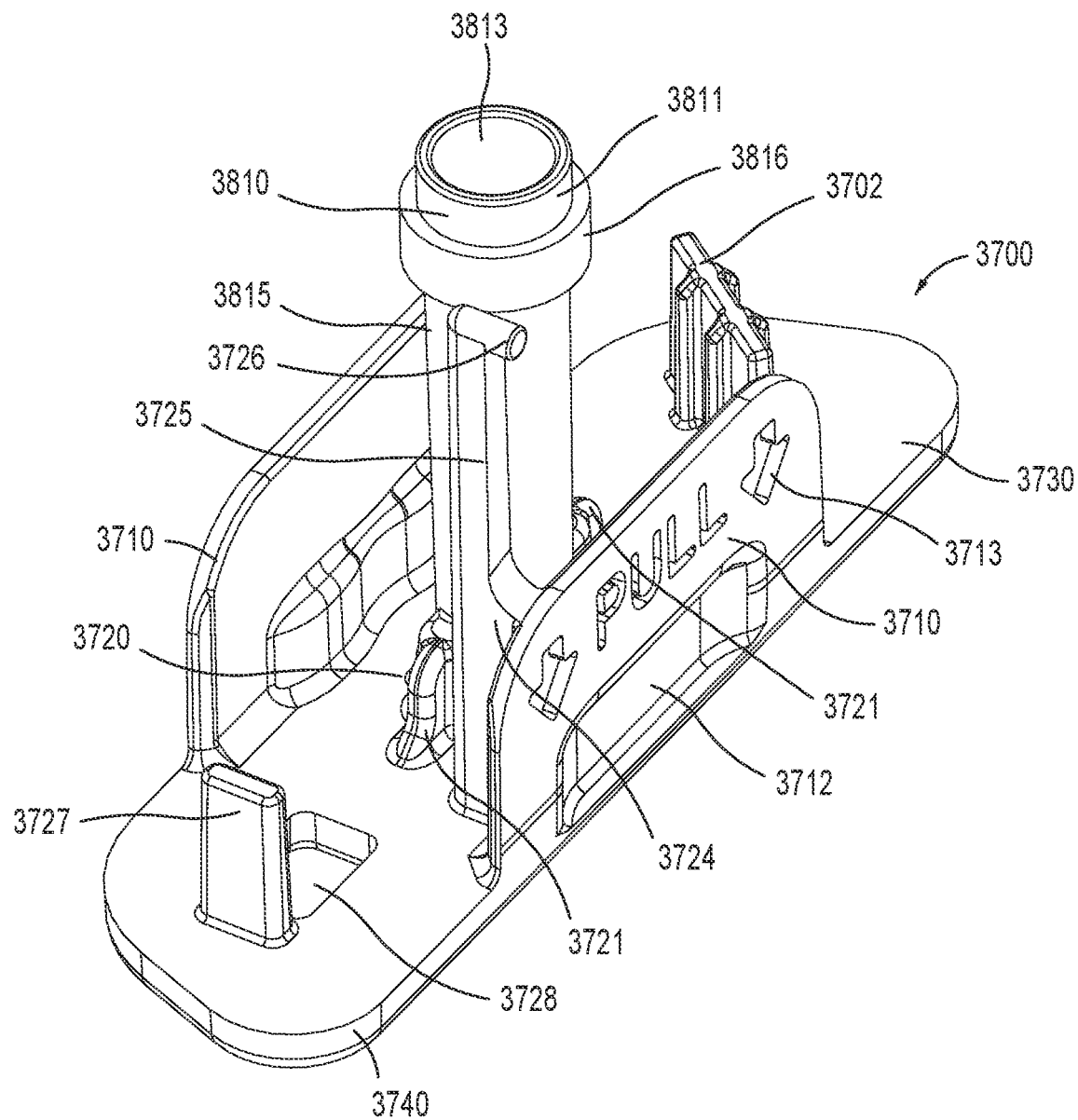
FIG. 42 is a perspective view of a safety lock of the medical injector illustrated in FIG. 9.

FIGS. 40 and 41 show the cover 3190 of the medical injector 3000. The cover 3190 includes a proximal end portion 3191 and a distal end portion 3192, and defines a cavity 3196. The cavity 3196 of the cover 3190 is configured to receive at least a portion of the housing 3100. Thus, when the portion of the housing 3100 is disposed within the cover 3190, the cover 3190 blocks an optical pathway between the medicament container 3200 and a region outside of the housing 3100. Similarly stated, when the portion of the housing 3100 is disposed within the cover 3190, the cover 3190 obstructs the first status indicator aperture 3130 and/or the second status indicator aperture 3160 of the housing 3100 to reduce the amount of light transmitted to the medicament 3220 within the medicament container 3200. In this manner, the life of the medicament 3220 can be extended by the prevention and/or reduction of degradation to the medicament 3220 that may be caused by ultra-violet radiation. In other embodiments, however, such those containing a medicament that is not sensitive to ultraviolet (UV) radiation, the cover 3190 can include viewing windows and/or openings that substantially correspond to the aperture 3130 and/or the aperture 3160.

The proximal end portion 3191 of the cover 3190 defines apertures 3193 configured to receive the cover retention protrusions 3104 of the housing 3100 (shown in FIGS. 10 and 12). In this manner, the apertures 3193 and the cover retention protrusions 3104 of the housing 3100 removably retain the cover 3190 about at least a portion of the housing 3100. Said another way, the apertures 3193 and the cover retention protrusions 3104 of the housing 3100 are configured such that the cover 3190 can be removed from a portion of the housing 3100 and then replaced about the portion of the housing 3100.

As described above, the electronic circuit system 3900 can be actuated when the housing 3100 is at least partially removed from the cover 3190. More particularly, the distal end portion 3192 of the cover 3190 includes the battery isolation protrusion 3197. The battery isolation protrusion 3197 includes a proximal end portion 3236 and a tapered portion 3237. The proximal end portion 3236 of the battery isolation protrusion 3197 is configured to be removably disposed between the second surface 3966 of the battery assembly 3962 and the contact portion 3918 of the distal end portion 3916 of the battery clip 3910, as described above.

The cover 3190 can be any suitable configuration and can include any suitable feature. For example, the cover 3190 includes openings 3195 and notches 3194. In some embodiments, the openings 3195 can receive inserts (not shown). The inserts can be flexible inserts and can increase friction between the cover 3190 and a surface. For example, the inserts can increase the friction between the cover 3190 and a surface on which the medical injector 3000 is placed, to prevent sliding. The notches 3194 are disposed at the proximal end of the cover 3190. In some embodiments, the notches 3194 can be used to reduce the material needed to manufacture the cover 3190.

FIGS. 42-46 show the safety lock 3700 of the medical injector 3000. The safety lock 3700 of the medical injector 3000 includes a proximal surface 3730, a distal surface 3740 opposite the proximal surface 3730 and a needle sheath 3810. The safety lock 3700 defines a needle sheath aperture 3703 and a battery isolation protrusion aperture 3728. The battery isolation protrusion aperture 3728 is configured to receive the battery isolation protrusion 3197 of the cover 3190 such that the battery isolation protrusion 3197 can be disposed within the electronic circuit system cavity 3137 and/or in engagement with the electronic circuit system 3900, as described above. Similarly stated, the battery isolation protrusion aperture 3728 of the safety lock 3700 is aligned with the battery isolation protrusion aperture 3135 of the housing 3100, such that the battery isolation protrusion 3197 can be disposed within the electronic circuit system cavity 3137 when the cover 3190 is disposed about a portion of the housing 3100.

The proximal surface 3730 of the safety lock 3700 includes a safety lock protrusion 3702, a stopper 3727, an actuator 3724, two opposing pull-tabs 3710 and an engagement portion 3720. As described above, when the safety lock 3700 is in a first (locked) position, the safety lock protrusion 3702 is configured to be disposed in the opening 3556 defined by the extensions 3553 of the distal end portion 3552 of the release member 3550 (see e.g., FIG. 21). Accordingly, the safety lock protrusion 3702 is configured to prevent the extensions 3553 from moving closer to each other, thereby preventing proximal movement of the release member 3550 and/or delivery of the medicament 3220. The stopper 3727 of the safety lock 3700 is a protrusion extending from the proximal surface 3730 of the safety lock 3700. The stopper 3727 is configured to contact a portion of the housing 3100 to limit the proximal movement of the safety lock 3700 relative to the housing 3100. In other embodiments, the stopper 3727 can be any structure configured to limit the proximal movement of the safety lock 3700.

The actuator 3724 of the safety lock 3700 has an elongated portion 3725 and a protrusion 3726. The elongated portion 3725 extends in a proximal direction from the proximal surface 3730. In this manner, the elongated portion 3725 can extend through a safety lock actuator opening 3524 of the base 3510 (see e.g., FIG. 47) and within the safety lock actuator groove 3133 of the housing 3100 and the safety lock actuator groove 3179 of the electronic circuit system housing 3170. The protrusion 3726 extends in a direction substantially transverse to the elongated portion 3725 and/or substantially parallel to the proximal surface 3730 of the safety lock 3700. As described above, the opening 3928 of the first actuation portion 3926 of the printed circuit board 3922 is configured to receive the protrusion 3726 of the actuator 3724 of the safety lock 3700.

The pull-tabs 3710 of the safety lock 3700 include a grip portion 3712 and indicia 3713. The grip portion 3712 of the pull-tabs 3710 provides an area for the user to grip and/or remove the safety lock 3700 from the rest of the medicament delivery system 3700. The indicia 3713 provide instruction on how to remove the safety lock 3700. The distal end surface 3740 also includes indicia 3741 (see e.g., FIG. 44). In some embodiments, for example, indicia can indicate the direction the user should pull the safety lock 3700 to remove the safety lock 3700.

The engagement portion 3720 of the safety lock 3700 includes engagement members 3721. The engagement members 3721 extend in a proximal direction from the proximal surface 3730. The engagement members 3721 have tabs 3722 that extend from a surface of the engagement members 3721. The tabs 3722 are configured to engage an outer surface 3815 of a distal end portion 3812 of the needle sheath 3810.

Figure 45:
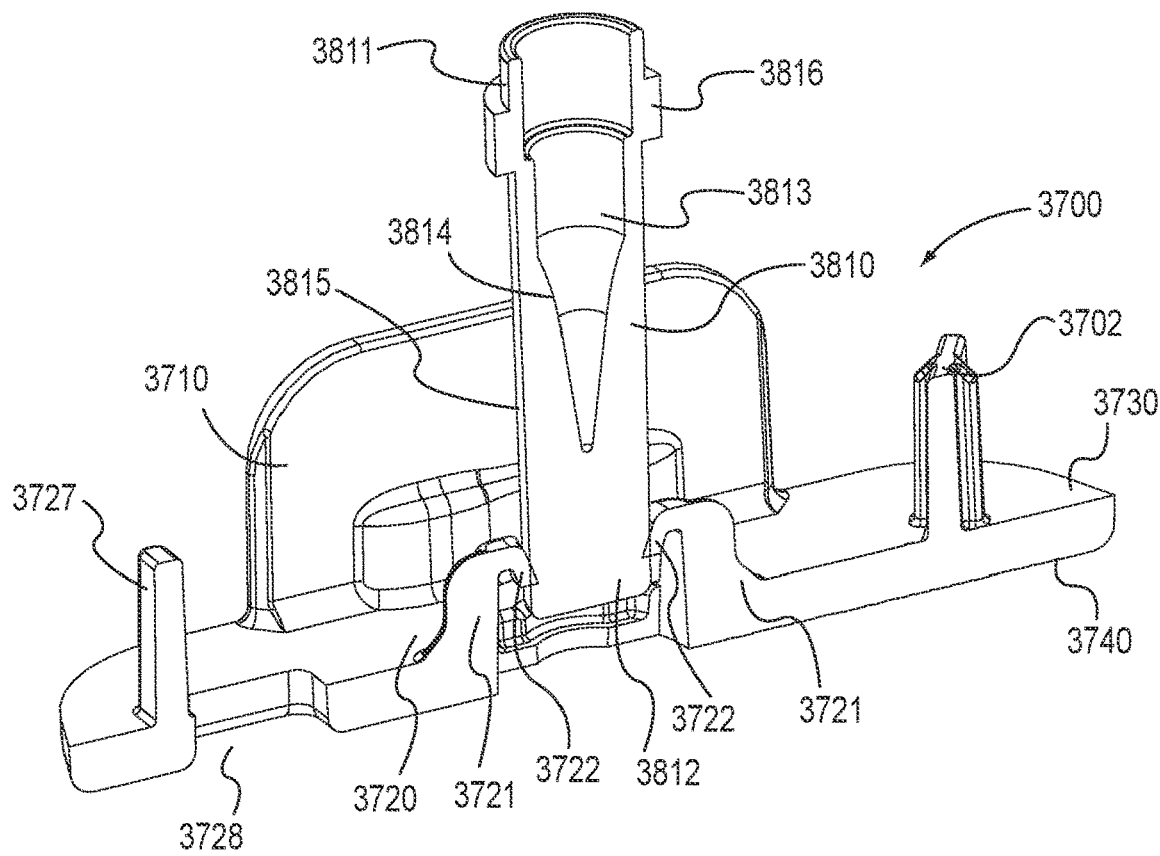
FIG. 45 is a cross-sectional view of the safety lock of the medical injector illustrated in FIG. 42.
Figure 46:
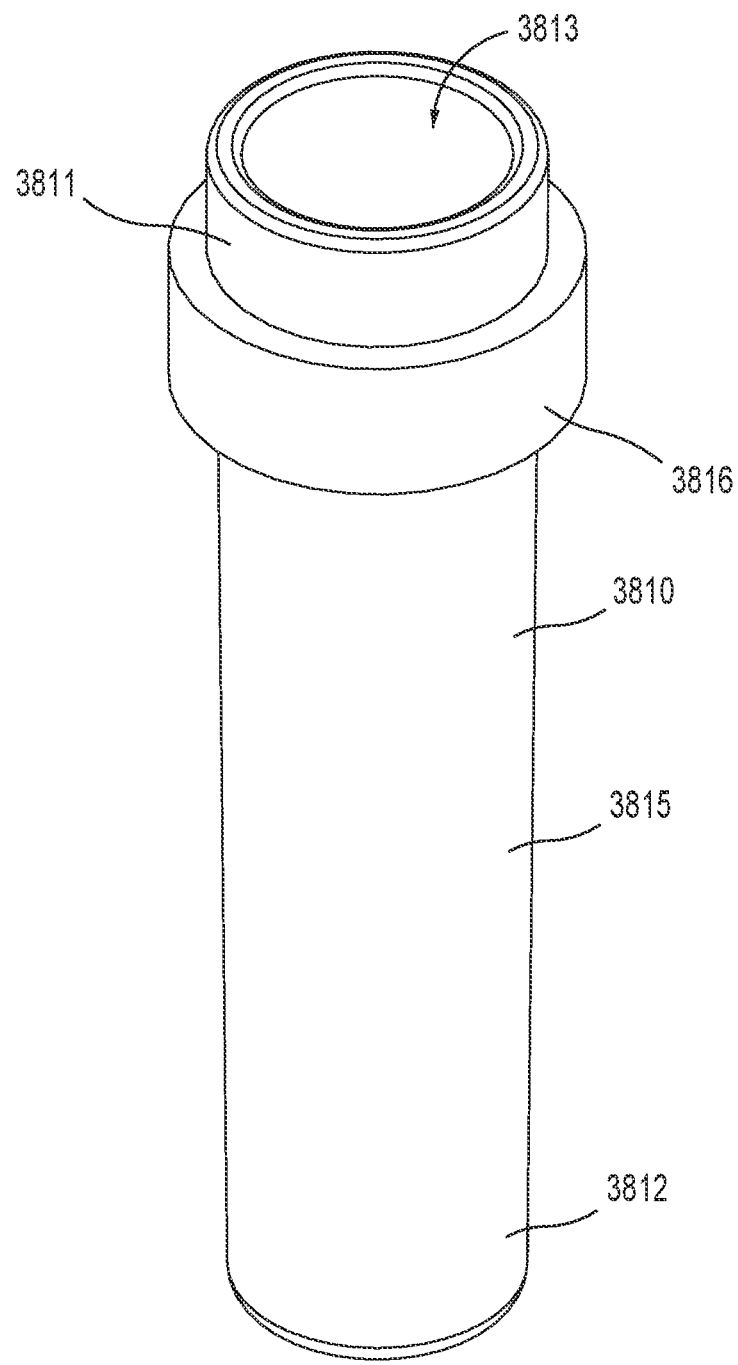
FIG. 46 is a perspective view of a needle sheath of the safety lock of the medical injector illustrated in FIG. 42.

As shown in FIGS. 45 and 46, the needle sheath 3810 includes the distal end portion 3812, a proximal end portion 3811 and a rib 3816. The needle sheath 3810 also defines a bore 3813. The bore 3813 is defined by a contoured portion 3814 of the needle sheath 3810, and is configured to receive the needle 3216 and/or a distal end portion of the 3213 of the medicament container 3200. The inner portion of the needle sheath 3810 defines a friction fit with the distal end portion 3213 of the medicament container 3200. In this manner, the needle sheath 3810 can protect the user from the needle 3216 and/or can keep the needle 3216 sterile before the user actuates the medical injector 3000. The proximal end portion 3811 of the needle sheath is configured to contact the body 3210 of the medicament container 3200.

The distal end portion 3812 of the needle sheath 3810 is configured to be inserted into a space defined between the tabs 3722 of the engagement members 3721 of the safety lock 3700. The tabs 3722 are angled and/or bent towards the distal direction to allow the distal end portion 3812 of the needle sheath 3810 to move between the engagement members 3721 in a distal direction, but not in a proximal direction. Similarly stated, the tabs 3722 include an edge that contacts the outer surface 3815 of the needle sheath 3810 to prevent the safety lock 3700 from moving in a distal direction relative to the needle sheath 3810. In this manner, the needle sheath 3810 is removed from the needle 3216 when the safety lock 3700 is moved in a distal direction with respect to the housing 3100 (see e.g., FIG. 50).

Figure 47:
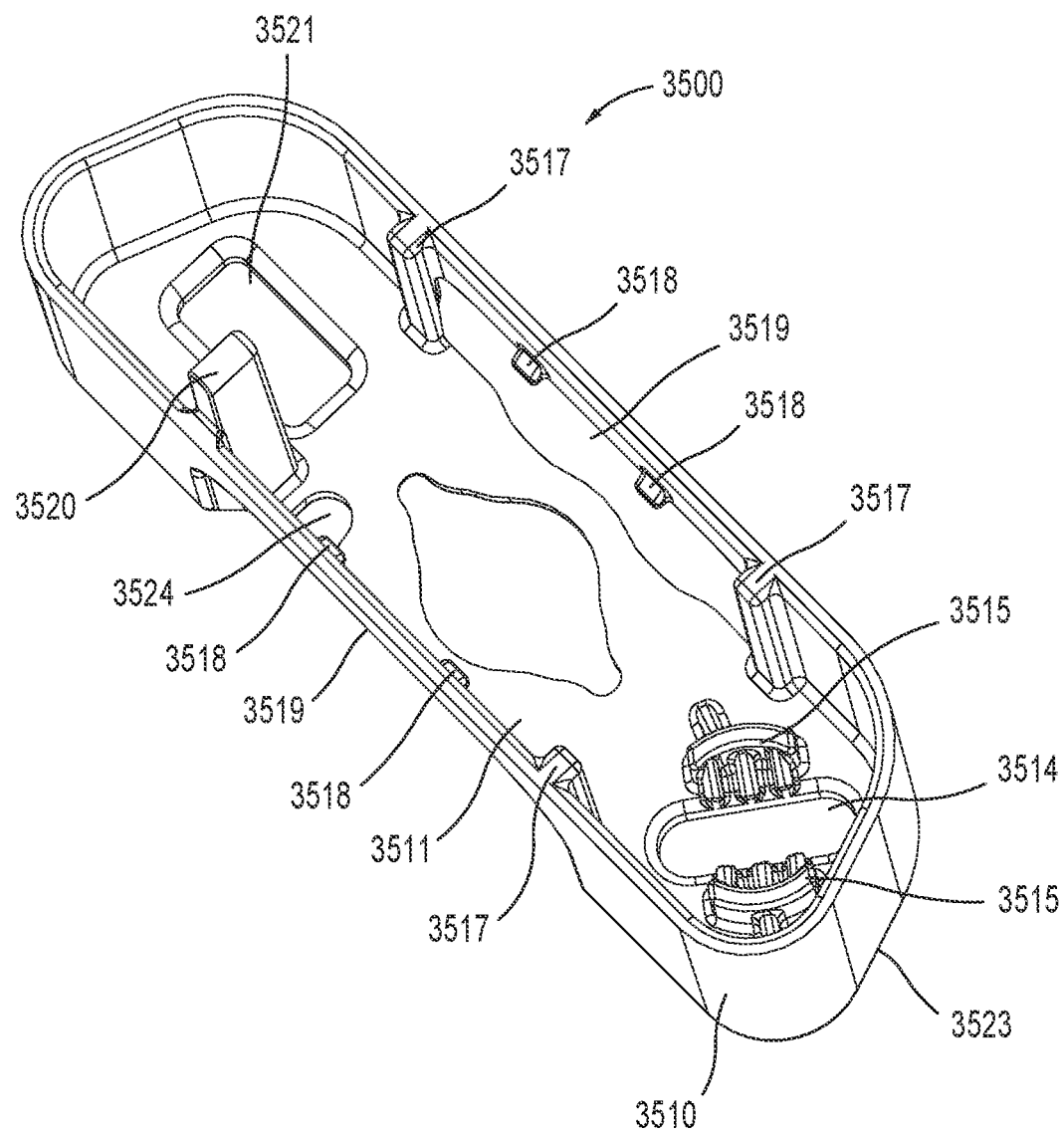
FIG. 47 is a perspective view of a base of the medical injector illustrated in FIG. 9.
Figure 48:
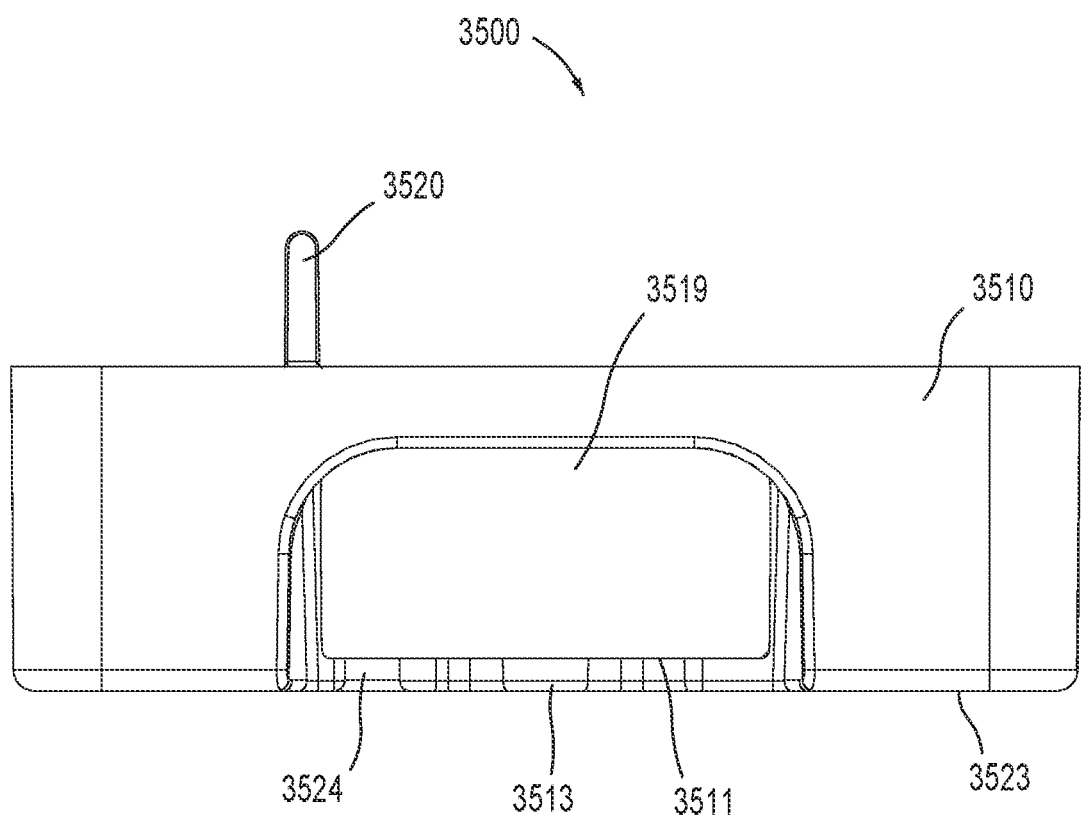
FIG. 48 is a front view of the base of the medical injector illustrated in FIG. 47.

FIGS. 47 and 48 show the base (or actuator) 3510 of the medical injector 3000. The base 3510 includes a proximal surface 3511, a distal surface 3523 and base connection knobs 3518. The base 3510 defines a needle aperture 3513, a safety lock protrusion aperture 3514, a battery isolation protrusion aperture 3521, a safety lock actuator opening 3524 and pull-tab openings 3519. The needle aperture 3513 is configured to receive the needle 3216 when the medical injector 3000 is actuated. The safety lock protrusion aperture 3514 of the base 3510 receives the safety lock protrusion 3702 of the safety lock 3700 when the safety lock 3700 is coupled to the housing 3100 and/or the base 3510. The battery isolation protrusion aperture 3521 of the base 3510 receives the battery isolation protrusion 3197 of the cover 3190 and the stopper 3727 of the safety lock 3700. The safety lock actuator opening 3524 receives the safety lock actuator 3724 of the safety lock 3700. The pull-tab openings 3519 are configured to receive the pull-tabs 3710 of the safety lock 3700.

The proximal surface 3511 of the base 3510 includes a protrusion 3520, guide members 3517 and protrusions 3515. The protrusion 3520 is configured to engage the substrate 3924 of the electronic circuit system 3900. As described above, the opening 3945 of the second actuation portion 3946 of the printed circuit board 3922 is configured to receive the actuator 3520 of the base 3510. The guide members 3517 of the base 3510 engage and/or slide within the base rail grooves 3114 of the housing 3100, as described above. The protrusions 3515 of the base 3510 engage the tapered surfaces 3557 of the extensions 3553 of the release member 3550. As described in further detail herein, when the safety lock 3700 is removed and the base 3510 is moved in a proximal direction with respect to the housing 3100, the protrusions 3515 of the base 3510 are configured to move the extensions 3553 of the release member 3550 closer to each other, actuating the medicament delivery mechanism 3300. As described above, the base connection knobs 3518 engage the base retention recesses 3134A, 3134B in a way that allows proximal movement of the base 3510 but limits distal movement of the base 3510.

Figure 49:
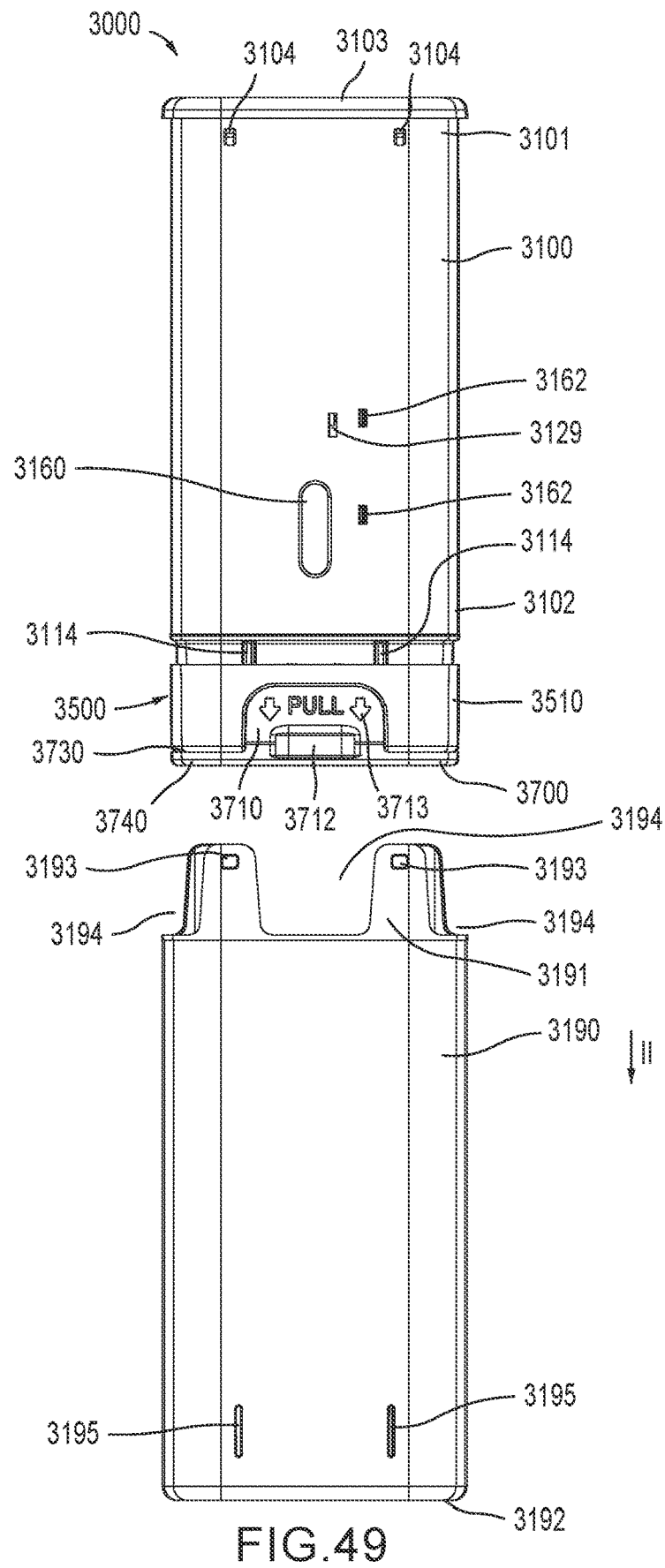
FIG. 49 is a back view of the medical injector illustrated in FIG. 9 in a second configuration.
Figure 50:
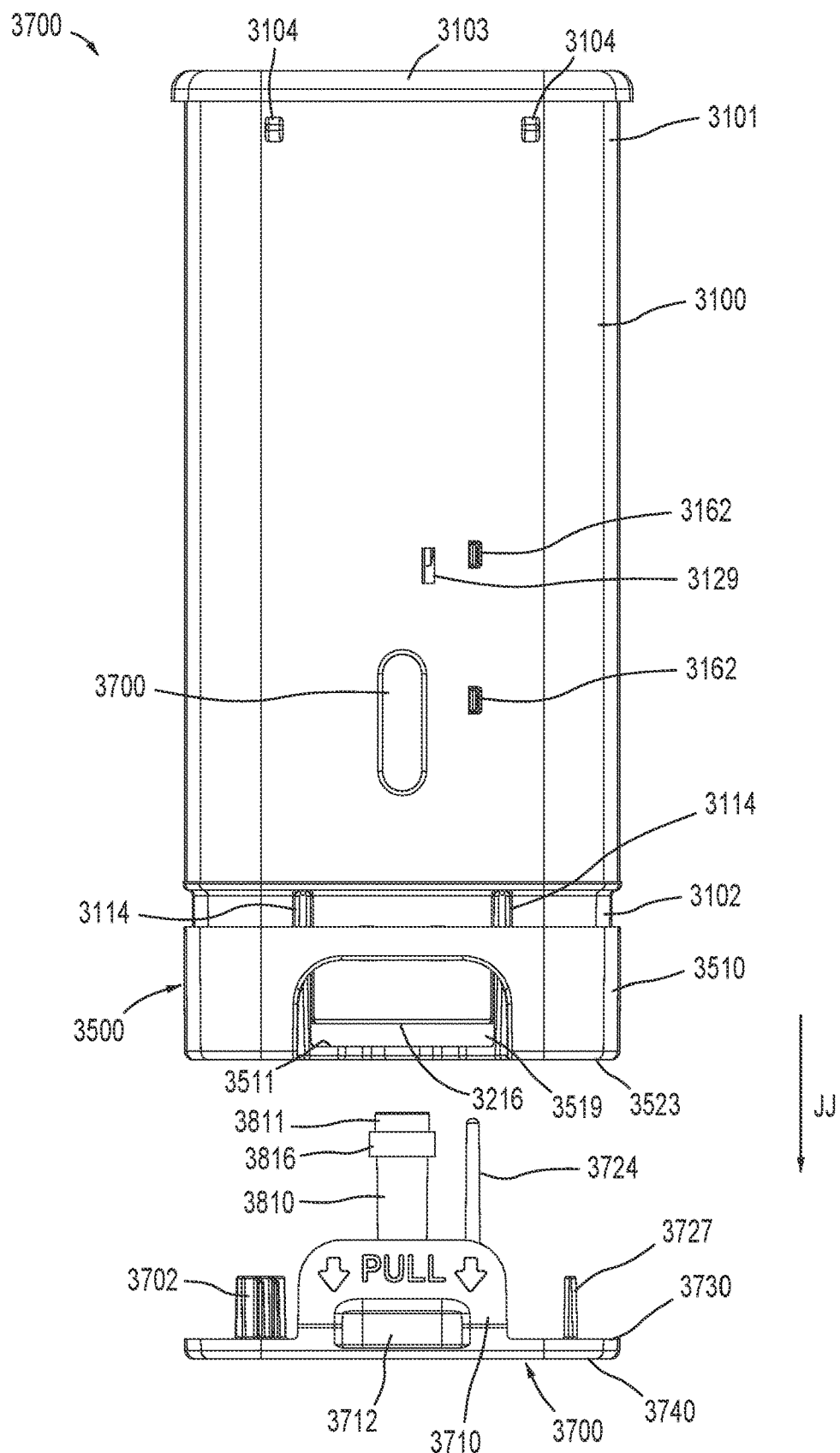
FIG. 50 is a back view of the medical injector illustrated in FIG. 9 in a third configuration.

As shown in FIG. 49, the medical injector 3000 is first enabled by moving the medicament delivery device 3000 from a first configuration to a second configuration by moving the cover 3190 from a first position to a second position. The cover 3190 is moved from the first position to the second position by moving it with respect to the housing 3100 in the direction shown by the arrow II in FIG. 49. When the cover 3190 is moved with respect to the housing 3100 in the direction II, the battery isolation protrusion 3197 is removed from the area between the battery clip 3910 and the second surface 3966 of the battery assembly 3962. In this manner, the battery assembly 3962 is operatively coupled to the electronic circuit system 3900 when the cover 3190 is removed, thereby providing power to the electronic circuit system 3900. Similarly stated, this arrangement allows the electronic circuit system 3900 to be actuated when the cover 3190 is removed.

When power is provided, as described above, the electronic circuit system 3900 can output one or more predetermined electronic outputs. For example, in some embodiments, the electronic circuit system 3900 can output an electronic signal associated with recorded speech to the audible output device 3956. Such an electronic signal can be, for example, associated with a .WAV file that contains a recorded instruction, instructing the user in the operation of the medical injector 3000. Such an instruction can state, for example, "Remove the safety tab near the base of the auto-injector." The electronic circuit system 3900 can simultaneously output an electronic signal to one and/or both of the LEDs 3958A, 3958B thereby causing one and/or both of the LEDs 3958A, 3958B to flash a particular color. In this manner, the electronic circuit system 3900 can provide both audible and visual instructions to assist the user in the initial operation of the medical injector 3000.

In other embodiments, the electronic circuit system 3900 can output an electronic output associated with a description and/or status of the medical injector 3000 and/or the medicament 3220 contained therein. For example, in some embodiments, the electronic circuit system 3900 can output an audible message indicating the symptoms for which the medicament 3220 should be administered, the expiration date of the medicament 3220, the dosage of the medicament 3220 or the like.

As described above, the medical injector 3000 can be repeatedly moved between the first configuration and the second configuration when the cover 3190 is moved repeatedly between the first position and the second position respectively. Said another way, the cover 3190 can be removed and replaced about the housing 3100 any number of times. When the cover 3190 is moved from the second position to the first position, the battery isolation protrusion 3197 is inserted between the battery clip 3910 and the second surface 3966 of the battery assembly 3962, deactivating the electronic circuit system 3900. When the cover is moved from the first position to the second position a second time, the electronic circuit system 3900 is once again activated. In this manner, the cover 3190 can be removed and the electronic circuit system 3900 can output an electronic output without compromising the sterility of the needle 3216.

After the cover 3190 is removed from the housing 3100, the medical injector 3000 can be moved from the second configuration (FIG. 49) to a third configuration (FIG. 50) by moving the safety lock 3700 from a first position to a second position. The safety lock 3700 is moved from a first position to a second position by moving the safety lock 3700 with respect to the housing 3100 in the direction shown by the arrow JJ in FIG. 50. When the safety lock 3700 is moved from the first position to the second position, the safety lock protrusion 3702 is removed from between the extensions 3553 of the release member 3550, thereby enabling the medicament delivery mechanism 3300. Moreover, as shown in FIGS. 37 and 38, when the safety lock 3700 is moved from the housing 3100, the actuator 3724 of the safety lock 3700 moves in the direction GG as shown in FIG. 38, irreversibly moving the first switch 3972 from a first state (e.g., a state of electrical continuity) to a second state (e.g., a state of electrical discontinuity). When the actuator 3724 of the safety lock 3700 moves irreversibly the first switch 3972 of the electronic circuit system 3900 to the second state, the electronic circuit system 3900 can output one or more predetermined electronic outputs. For example, in some embodiments, a processor (not shown) can output an electronic signal associated with recorded speech to the audible output device 3956. Such an electronic signal can be, for example, associated with a recorded message notifying the user of the status of the medical injector 3000. Such a status message can state, for example, "If ready to use the medical injector, pull off the red safety guard." The electronic circuit system 3900 can also simultaneously output an electronic signal to one and/or both of the LEDs 3958A, 3958B, thereby causing one and/or both of the LEDs 3958A, 3958B to stop flashing, change color or the like.

In some embodiments, the first actuation portion 3926 and the actuator 3724 can be configured such that the actuator 3724 must move a predetermined distance before the actuator 3724 engages the boundary 3929 of the opening 3928. For example, in some embodiments, the actuator 3724 must move approximately 0.200 inches before the actuator 3724 engages the boundary 3929 of the opening 3928. In this manner, the safety lock 3700 can be moved slightly without irreversibly moving the first switch 3972 of the electronic circuit system 3900 to the second state. Accordingly, this arrangement will permit the user to inadvertently and/or accidentally move the safety lock 3700 without actuating the electronic circuit system 3900.

In some embodiments, the electronic circuit system 3900 can be configured to output the status message for a predetermined time period, such as, for example, five seconds. After the predetermined time period has elapsed, the electronic circuit system 3900 can output an audible message further instructing the user in the operation of the medical injector 3000. Such an instruction can state, for example, "Place the base of the auto-injector against the patient's thigh. To complete the injection, press the base firmly against the patient's thigh." In some embodiments, the electronic circuit system 3900 can simultaneously output an electronic signal to one and/or both of the LEDs 3958A, 3958B, thereby causing one and/or both of the LEDs 3958A, 3958B to flash a particular color. In this manner, the electronic circuit system 3900 can provide both audible and/or visual instructions to assist the user in the placement and actuation of the medical injector 3000. In some embodiments, the electronic circuit system 3900 can be configured to repeat the instructions after a predetermined time period has elapsed.

As described above, in other embodiments, the medical injector 3000 can have a network interface device (not shown) configured to operatively connect the electronic circuit system 3900 to a remote device (not shown) and/or a communications network (not shown). In this manner, the electronic circuit system 3900 can send a wireless signal notifying a remote device that the safety lock 3700 of the medical injector 3000 has been removed and that the medical injector 3000 has been armed. In other embodiments, the electronic circuit system 3900 can send a wireless signal (e.g., a wireless 911 call) notifying an emergency responder that the medical injector 3000 has been armed, for example, via removal of the safety lock 3700.

After the safety lock 3700 is moved from the first position to the second position, the medical injector 3000 can be moved from the third configuration (FIG. 50) to a fourth configuration (FIG. 51) by moving the base 3510 from a first position to a second position. Similarly stated, the medical injector 3000 can be actuated by the system actuator assembly 3500 by moving the base 3510 proximally relative to the housing 3100. The base 3510 is moved from its first position to its second position by placing the medical injector 3000 against the body of the patient and moving the base 3510 with respect to the housing 3100 in the direction shown by the arrow KK in FIG. 51. Moving the base 3510 from the first position to the second position causes the protrusions 3515 on the proximal surface 3511 of the base 3510 to engage the tapered surfaces 3557 of the extensions 3553 of the release member 3550, thereby moving the extensions 3313 together. The inward movement of the extensions 3553 causes engagement surface 3554 of the release member 3550 to become disengaged from the base release surface 3126 of the housing 3100, thereby allowing the release member 3550 to be moved proximally along its longitudinal axis as the spring 3576 expands.

Figure 51:
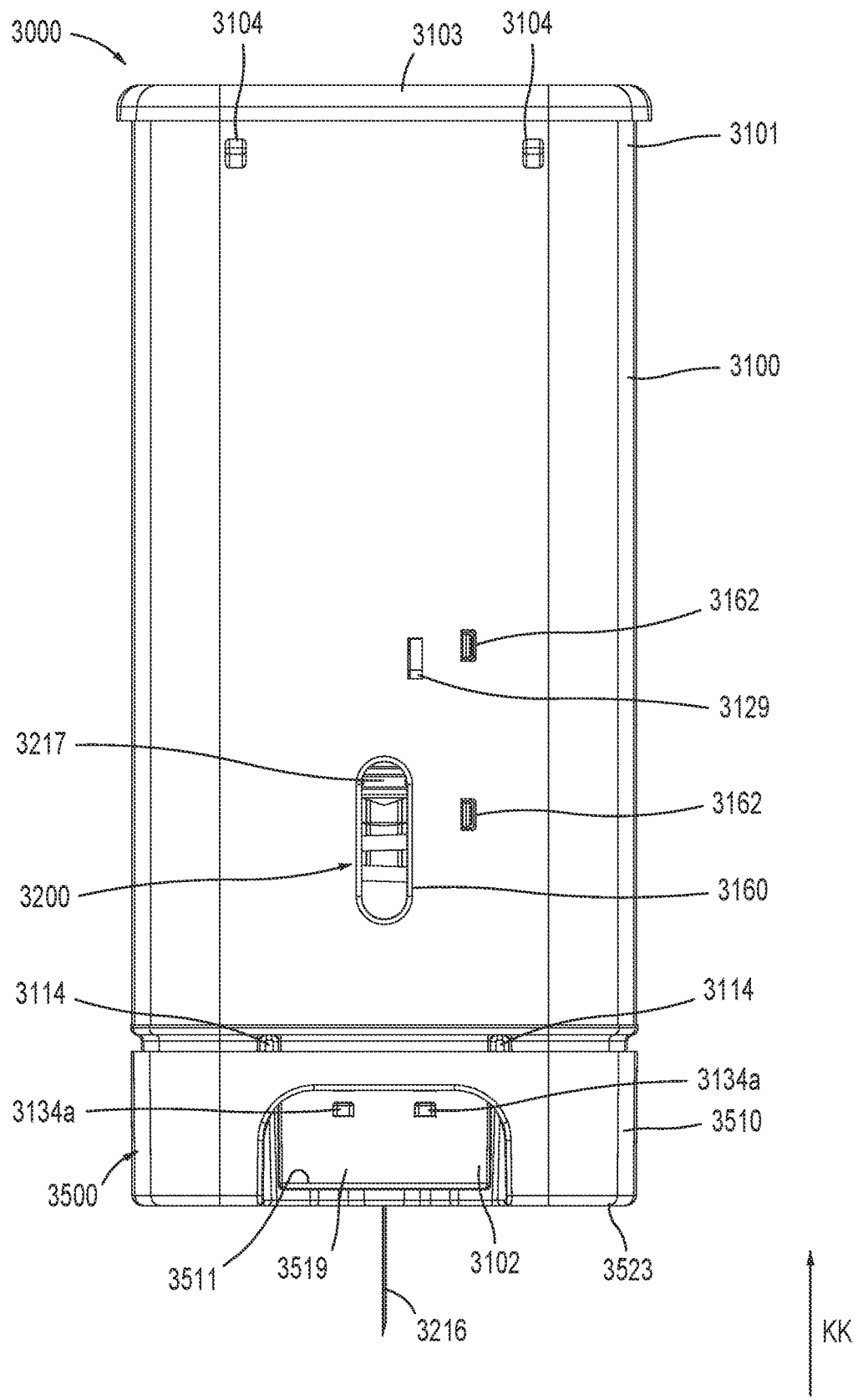
FIG. 51 is a back view of the medical injector illustrated in FIG. 9 in a fourth configuration (i.e., the needle insertion configuration).

When the base 3510 is moved from the first position to the second position, the system actuator assembly 3500 actuates the medicament delivery mechanism 3300, thereby placing the medical injector 3000 in its fourth configuration (i.e., the needle insertion configuration), as shown in FIGS. 51 and 52. More particularly, when the medical injector 3000 is in its fourth configuration, the puncturer 3575 of the release member 3550 is in contact with and/or disposed through the frangible seal 3413 of the gas container 3410.

After the frangible seal 3413 has been punctured, an actuating portion of a compressed gas flows from the gas container 3410, via the gas passageway 3156 and into the medicament cavity 3139. The gas applies gas pressure to the piston member 3330 causing the piston member 3330 and the carrier 3370 to move in a distal direction within the medicament cavity 3139, as shown by the arrow LL in FIG. 52. When the carrier 3370 moves distally within the medicament cavity 3139, the carrier 3370 and the medicament container 3200 are in a first configuration and collectively move toward a second position. In this manner, the medicament container 3200 and the needle 3216 contemporaneously move with piston member 3330 and/or the carrier 3370 in a distal direction. The movement of the needle 3216 in a distal direction causes the distal end portion of the needle 3216 to exit the housing 3100 and enter the body of a patient prior to administering the medicament 3220.

As described above, at least a portion of the force exerted by the compressed gas within the gas chamber upon the piston member 3330 is transferred to the first shoulder 3377 of the carrier 3370 by the contact between the first surface 3341 of the piston member 3330 and the engagement portion 3379 of the carrier 3370. This arrangement further allows at least a portion of the force to be transferred to the flange 3214 of the medicament container 3200. In this manner, the application of the force on the piston member 3330 results in the distal movement of the carrier 3370 and the medicament container 3200. Moreover, because the distal end portion 3332 of the piston member 3330 is configured such that the second surface 3342 is spaced apart from the elastomeric member 3217 within the medicament container 3200 (see e.g., FIG. 27), the force is not transferred to the elastomeric member 3217. In this manner, the elastomeric member 3217 is isolated from the piston member 3330 when the medicament container 3200 is moving distally within the housing 3100, which reduces and/or eliminates injection or leakage of the medicament 3220 from the medicament container 3200 during the needle insertion operation.

After the carrier 3370 and/or the needle 3216 have moved within the medicament cavity 3139 a predetermined distance, the carrier 3370 and the medicament container 3200 are moved from the first configuration to a second configuration. For example, in some embodiments, the retraction spring 3351 can be fully compressed and prevent the carrier 3370 from moving further in the distal direction. In other embodiments, a portion of the medicament container 3200 and/or a portion of the carrier 3370 can contact the housing 3100 when the needle insertion operation is completed, thereby limiting further distal movement of the carrier 3370, medicament container 3200 and/or the needle 3216. When the distal movement of the carrier 3370 is prevented, the gas within the gas chamber continues to apply gas pressure to the piston member 3330 causing the first surface 3341 of the piston member 3330 to deform a portion of the engagement portion 3379. Similarly stated, when the distal movement of the carrier 3370 is complete, the force applied by the pressurized gas exceeds a threshold value, thereby causing the piston member 3330 to deform the engagement portion 3379. In this manner, the engagement portion 3379 deforms (see e.g., FIG. 55) to place the carrier 3370 in its second configuration, in which the first surface 3341 of the piston member 3330 is no longer in contact with the engagement portion 3379 and/or the first shoulder 3377.

When the carrier 3370 is in the second configuration, the piston member 3330 continues to move in the distal direction relative to the carrier 3370 and/or the medicament container 3200. Similarly stated, the piston member 3330 moves with the carrier 3370 during the insertion operation (i.e., when the carrier 3370 is in its first configuration) and the piston member 3330 moves relative to the carrier 3370 (and the medicament container 3200) during the injection operation (i.e., when the carrier 3370 is in its second configuration). More particularly, after the engagement portion 3379 deforms, the piston rod 3333 of the piston member 3330 moves within the piston rod opening 3384 of the carrier 3370 and within the medicament container 3200, as shown by the arrow MM in FIG. 53. As the piston rod 3333 of the piston member 3330 moves within the carrier 3370 and medicament container 3200, the second surface 3342 of the piston rod 3333 contacts the elastomeric member 3217 and generates a pressure upon the medicament 3220 contained within the medicament container 3200, thereby allowing at least a portion of the medicament 3220 to flow out of the medicament container 3200 via the needle 3216. The medicament 3220 is delivered to a body of a user via the medicament delivery path defined by the medicament container 3200 and the needle 3216.

Figure 54:
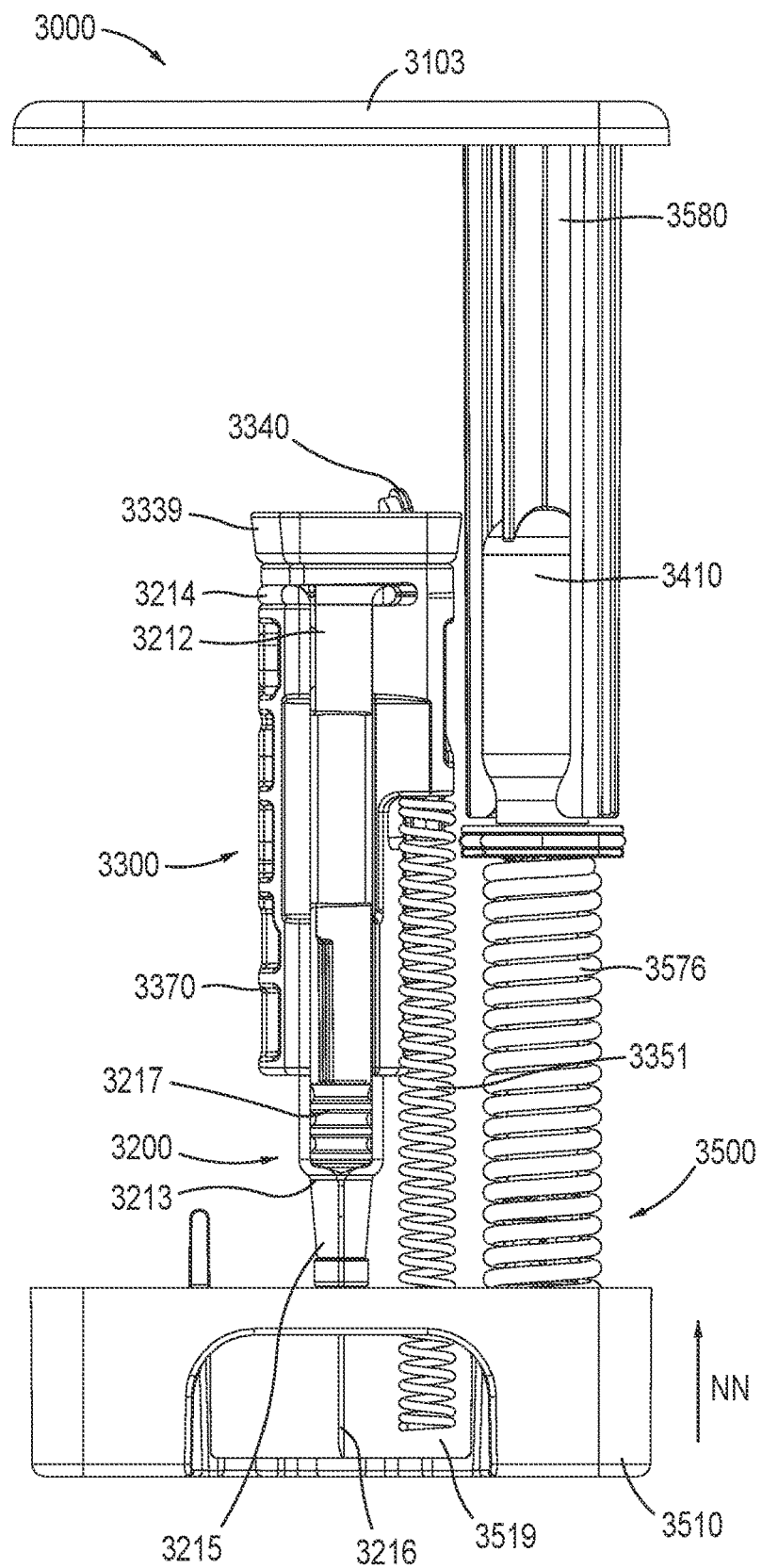
FIG. 54 is a front view of the medical injector illustrated in FIG. 9 in a sixth configuration (i.e., the retraction configuration).
Figure 55:
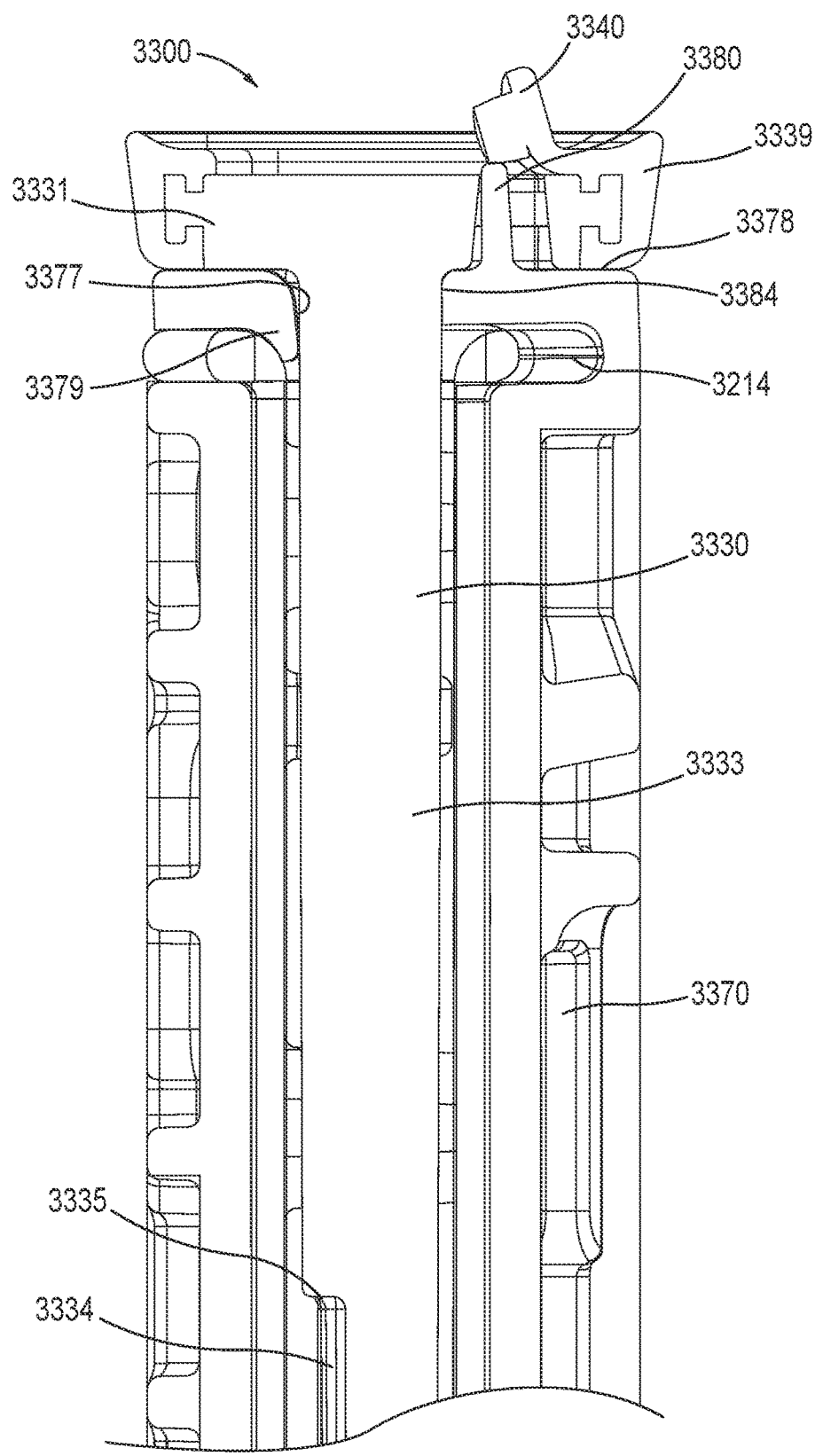
FIG. 55 is an enlarged front cross-sectional view of a portion the medical injector illustrated in FIG. 9 in the sixth configuration (i.e., the retraction configuration).

As shown in FIGS. 54 and 55, after the piston member 3330 moves a predetermined distance within the medicament container 3200, the gas valve actuator 3380 of the carrier 3370 engages the gas relief valve 3340 (see e.g., FIG. 55) of the piston member 3330 thereby allowing the pressurized gas contained within the gas chamber (i.e., the volume within the medicament cavity 3139 between the proximal end of the housing 3100 and the proximal end of the piston member 3330) to escape. Similarly stated, as the gas valve actuator 3380 of the carrier 3370 engages the gas relief valve 3340 of the piston member 3330, the pressure within the housing 3100 is reduced, thereby ending the injection event. In this manner, the pre-injection distance between the proximal end portion 3331 of the piston member 3330 and the gas valve actuator 3380 of the carrier 3370 can be adjusted to control the amount of the medicament 3220 to be injected. After the gas pressure within the medicament cavity 3139 decreases below a certain level, the force exerted by the retraction spring 3351 on the engagement portion 3382 of the carrier 3370 is sufficient to cause the carrier 3370 to move proximally within the housing 3100 (i.e., to retract). Additionally, the second shoulder 3381 engages the distal surface of the flange 3214 of the medicament container 3200 to move the medicament container 3200 proximally within the housing 3100, as shown by the arrow NN in FIG. 54.

As described above, the protrusion 3520 of the base 3510 actuates the electronic circuit 3900 to trigger a predetermined output or sequence of outputs when the base 3510 is moved from its first position to its second position (see, e.g., FIGS. 35-39). When the protrusion 3520 is moved in a proximal direction relative to the opening 3945, as shown by the arrow HH in FIG. 39, the electronic circuit system 3900 is actuated to output one or more predetermined electronic outputs. For example, in some embodiments, the electronic circuit system 3900 can output an electronic signal associated with recorded speech to the audible output device 3956. Such an electronic signal can be, for example, associated with an audible countdown timer, instructing the user on the duration of the injection procedure. Said another way, if it takes, for example, ten seconds to complete an injection, an audible countdown timer can count from ten to zero ensuring that the user maintains the medical injector 3000 in place for the full ten seconds. In other embodiments, the electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The electronic circuit system 3900 can also simultaneously output an electronic signal to one and/or both LEDs 3958A, 3958B, thereby causing one and/or both LEDs 3958A, 3958B to stop flashing, change color or the like, to provide a visual indication that the injection is complete. In other embodiments, the electronic circuit system 3900 can send a wireless signal notifying a remote device that the injection is complete. In this manner, a patient's compliance and/or adherence with the use of the system can be monitored.

In some embodiments, the second actuation portion 3946 and the protrusion 3520 of the base 3510 can be configured such that the base 3510 and/or the actuator 3520 must move a predetermined distance before the protrusion 3520 engages the boundary 3949 of the opening 3945. For example, in some embodiments, the protrusion 3520 must move approximately 0.200 inches before the actuator 3520 engages the boundary 3949 of the opening 3945. In this manner, the base 3510 can be moved slightly without irreversibly moving the second switch 3973 of the electronic circuit system 3900 to the second state. Accordingly, this arrangement will permit the user to inadvertently and/or accidentally move the base 3510 without actuating the electronic circuit system 3900.

While specific components are discussed with respect to the medical injector 3000, in other embodiments, some components can be modified and/or removed without substantially changing the medicament injection event. For example, FIGS. 56-59 show a portion of a medical injector 4000. That does not include an electronic circuit system (e.g., an electronic circuit system substantially similar to the electronic circuit system 3900 included in the medical injector 3000). In some embodiments, the electronic circuit system can be removed to limit the cost of the medical injector 4000. In those embodiments devoid of an electronic circuit system, for example the medical injector 4000 shown in FIGS. 56 and 57, the medical injector 4000 can still include components and/or portions configured to engage and/or interact with an electronic circuit system. For example, the medical injector 4000 includes a battery isolation protrusion 4197 of a cover 4190. In this manner, the cost of production and tooling can be reduced by reducing the number of component variations. Additionally, an electronic circuit system (e.g., similar to the electronic circuit system 3900 included in the medical injector 3000) can be easily added to the medical injector 4000 and disposed within an electronic circuit system cavity 4137 defined by the housing 4100.

Figure 56:
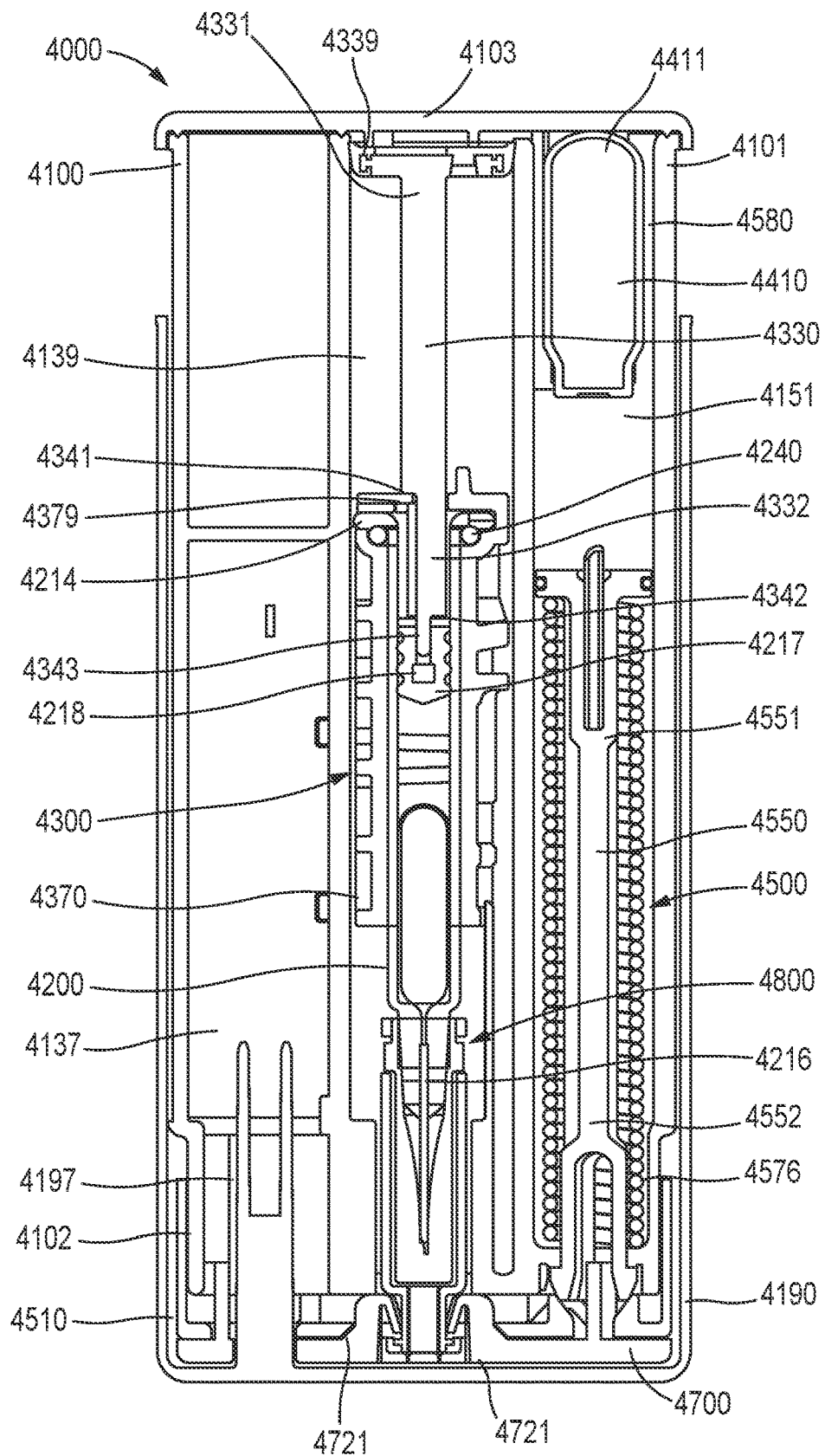
FIG. 56 is a cross-sectional front view of a medical injector according to an embodiment, in a first configuration.
Figure 57:
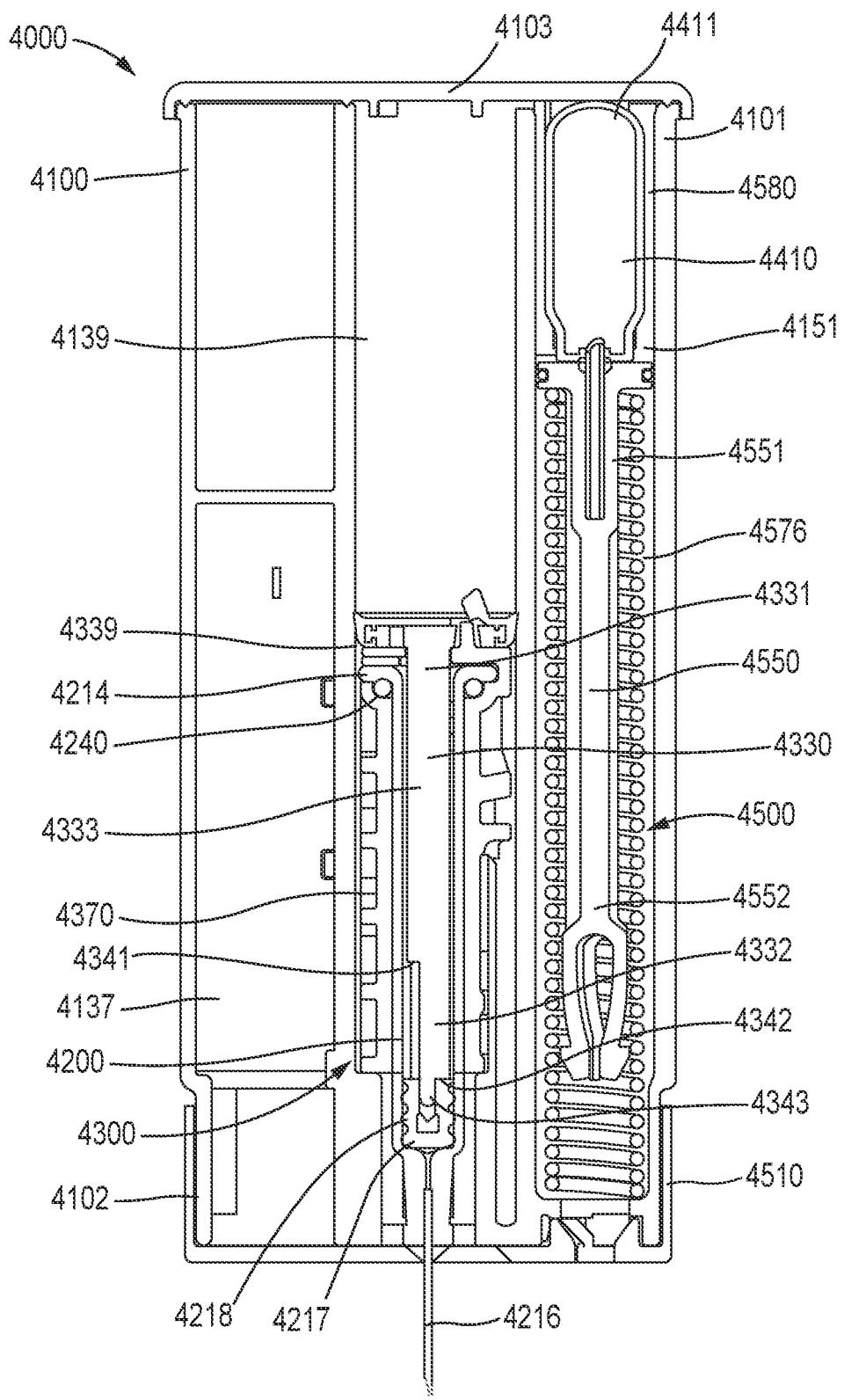
FIG. 57 is a cross-sectional front view of the medical injector illustrated in FIG. 56, in a second configuration.

The medical injector 4000 is similar to the medical injector 3000 described above. As shown in FIGS. 56 and 57, the medical injector 4000 includes a housing 4100, the cover 4190 (FIG. 56), a safety lock 4700 (FIG. 56), a base 4510, a system actuator assembly 4500, a delivery mechanism 4300, a medicament container 4200 and a needle guard assembly 4800. The structure and operation of the cover 4190, the safety lock 4700 and the base 4510 are similar to the structure and operation of the cover 3190, the safety lock 3700 and the base 3510, respectively. Accordingly, only the delivery mechanism 4300, the system actuator assembly 4500 and the needle guard assembly 4800 are described in detail below.

As shown in FIG. 56, the housing 4100 has a proximal end portion 4101 and a distal end portion 4102. The housing 4100 defines a gas cavity 4151, a medicament cavity 4139 and the electronic circuit system cavity 4137. The gas cavity 4151, medicament cavity 4139 and the electronic circuit system cavity 4137 of the housing 4100 of the medical injector 4000 are similar to the gas cavity 3151, the medicament cavity 3139 and the electronic circuit system cavity 3137, shown and described above with reference to FIGS. 15 and 16.

The distal end portion 4102 of the housing 4100 is similar to the distal end portion 3102 of the housing 3100, described above in reference to FIG. 15. The proximal end portion 4101 includes a proximal cap 4103. The proximal cap 4103 includes a gas container retention member 4580 and defines a gas passageway (not shown in FIGS. 56 and 57). The gas container retention member 4580 is configured to receive a gas container 4410. The gas container retention member 4580 extends from a distal surface of the proximal cap 4103 and is configured to place a proximal end 4411 of the gas container adjacent to the proximal cap 4103. Similarly stated, the gas container retention member 4580 extends a given distance from the proximal cap 4103 such that the gas container 4410 is disposed adjacent to the proximal cap 4103 within a proximal end of the gas cavity 4151. In this manner, the gas container retention member 4580 differs from the gas container retention member 3580, which positions the gas container 3410 apart from the proximal cap 3103.

The system actuator assembly 4500 includes the base 4510, a release member 4550 and a spring 4576. The release member 4550 has a proximal end portion 4551 and a distal end portion 4552, and is movably disposed within the gas cavity 4151. The proximal end portion 4551 and the distal end portion 4552 of the release member 4550 are similar to the corresponding structure of the release member 3550 of the medical injector 3000, described above with reference to FIGS. 18-21. The release member 4550 differs from the release member 3550, however, in that the release member 4550 is substantially longer than the length of the release member 3550 of the medical injector 3000. In this manner, the release member 4550 is able to engage the gas container 4410 disposed at the proximal end of the gas cavity 4151. Similarly stated, with the gas container 4410 disposed at the proximal end of the gas cavity 4151, the length of the release member 4550 is increased, compared to the release member 3550 of the medical injector 3000, so that the release member 4550 can engage the gas container 4410. Consequently, the length of the spring 4576 (in the compressed state) is longer than the length of the spring 3576 included in the medical injector 3000, described above with reference to FIGS. 18-21.

The arrangement of the system actuator assembly 4500, the gas container 4410 and the gas container retention member 4580 function similar to the system actuator assembly 3500, the gas container 3410 and the gas container retention member 3580, respectively, to activate the delivery mechanism 4300. In some embodiments, the gas container retention member 4580 can be configured to place the gas container 4410 at any suitable position within the gas cavity 4151. In this manner, the length of the release member 4550 and the spring 4576 can be any given length such that the proximal end portion 4551 of the release member can engage the gas container 4410, as shown in FIG. 57.

The medicament delivery mechanism 4300 includes a carrier 4370 (also referred to herein as the "first movable member" 4370) and a piston member 4330 (also referred to herein as the "second movable member" 4330). The carrier 4370 is similar to the carrier 3370 included in the medical injector 3000 and is movably disposed within the medicament cavity 4139. Therefore, the carrier 4370 is not described in detail herein.

The piston member 4330 includes a proximal end portion 4331, a distal end portion 4332 and a piston rod 4333. The piston portion 4330 is movably disposed within the medicament cavity 4139. The proximal end portion 4331 includes a sealing member 4339 and is similar in form and function to the proximal end portion 3331 of piston member 3330 of the medical injector 3000 described above. The distal end portion 4332 includes a first surface 4341, a second surface 4342 and an elongate protrusion 4343. The second surface 4342 and the elongate protrusion 4343 are disposed within a portion of the carrier 4370 and within the medicament container 4200. The first surface 4341 is configured to contact an engagement portion 4379 of the carrier 4370 when the medicament container 4200 is in a first configuration to maintain a given distance between the second surface 4342 and an elastomeric member 4217 of the medicament container 4200 (see e.g., FIG. 56), in a similar manner as described above. The elongate protrusion 4343 is configured to be disposed within a channel 4218 defined by the elastomeric member 4217. Similarly stated, the piston portion 4330 includes a portion and/or surface in contact with the elastomeric member 4217 and a portion and/or surface not in contact with the elastomeric member 4217, when the carrier 4370 is in the first configuration. In some embodiments, the elongate protrusion 4343 can be used to align the piston rod 4333 with the elastomeric member 4217 disposed within the medicament container 4200.

The piston member 4330 is configured to move within the housing 4100 (e.g., in response to the release of a pressurized gas). When the piston member 4330 moves, the first surface 4341 of the piston portion 4330 can apply a force to a portion of the carrier 4370 such that the carrier 4370 and the piston portion 4330 move together within the medicament cavity 4139. As described above, after the carrier 4370 is placed in its second (or deformed) configuration, the piston rod 4333 can move relative to the carrier 4370 and the elongate 4343 and the second surface 4342 can engage the elastomeric member 4217 to convey the medicament 4220 contained in the medicament container 4200 (see e.g., FIG. 57).

Figure 58:
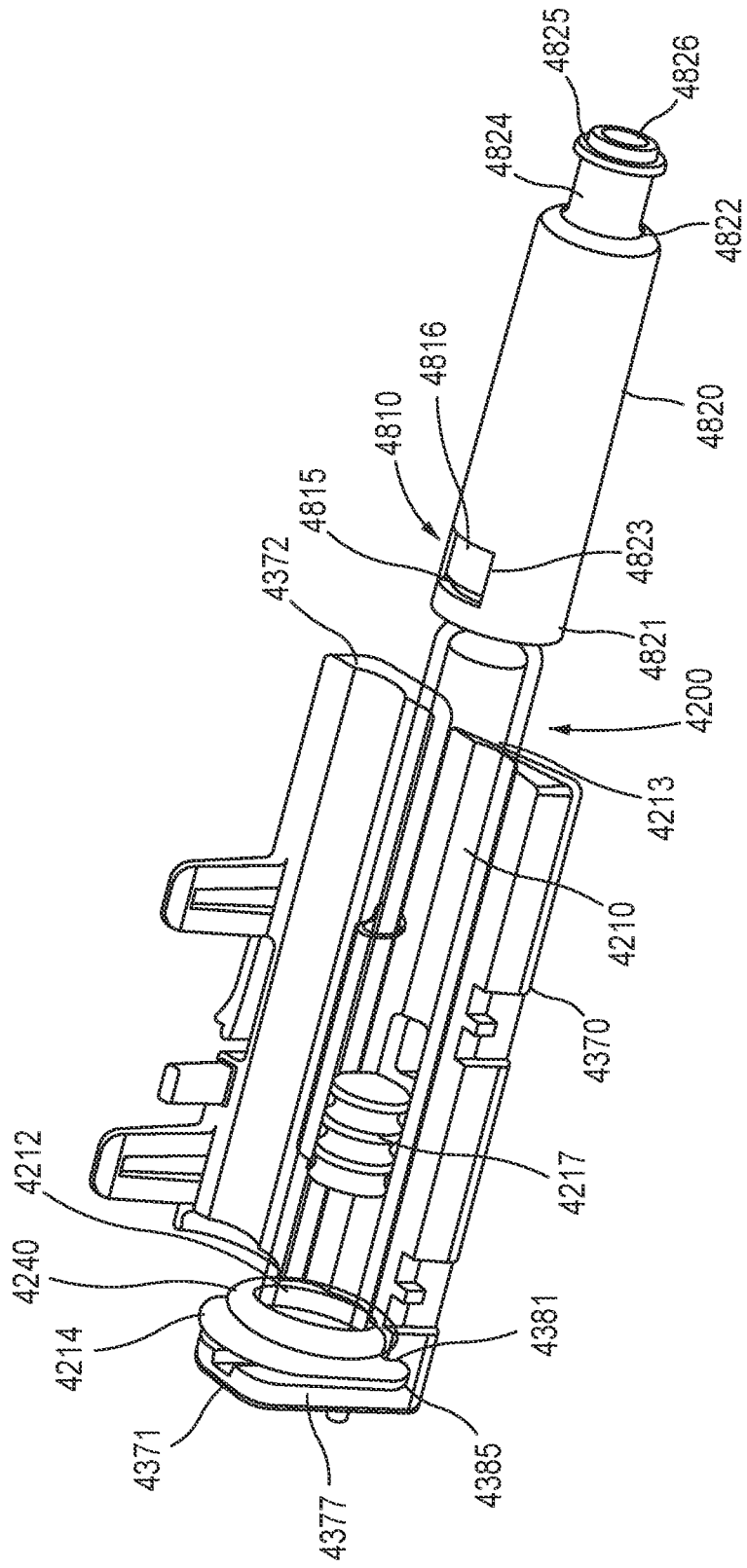
FIG. 58 is a perspective view of a portion of the medical injector illustrated in FIG. 56, in a first configuration.
Figure 59:
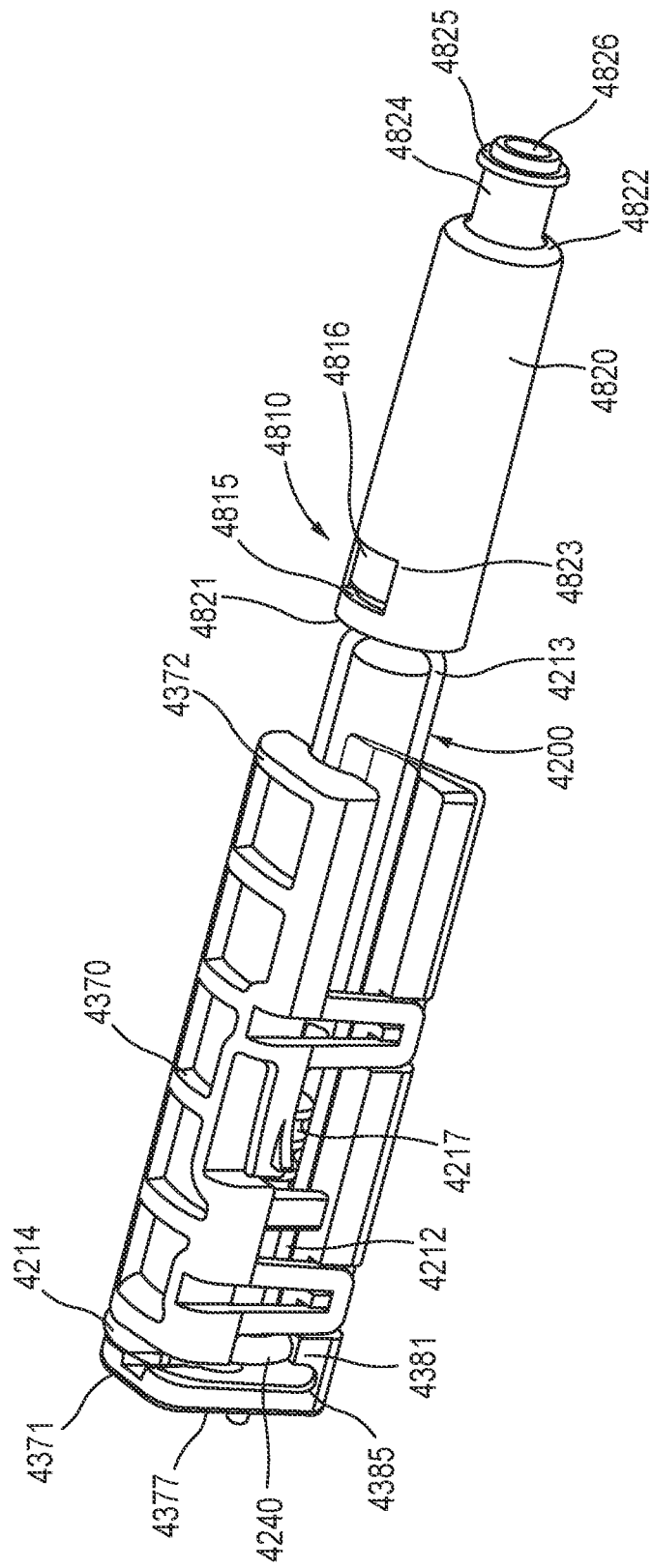
FIG. 59 is a perspective view of a portion of the medical injector illustrated in FIG. 56, in a second configuration.

As shown in FIGS. 58 and 59, the medicament container 4200 is configured to be disposed within the carrier 4370. The medicament container 4200 includes a proximal end portion 4212 and a distal end portion 4213. The proximal end portion 4212 includes a flange 4214. The distal end portion 4213 is in fluid communication with a needle 4216 (see e.g., FIG. 59). The form and function of the medicament container 4200 is similar to the form and function of the medicament container 3200 of the medical injector 3000. The medicament container 4200 also includes a damping member 4240 disposed at a distal surface of the flange 4214.

The flange 4214 of the medicament container 4200 is disposed with in a flange groove 4385 defined by a first shoulder 4377 and a second shoulder 4381 of the carrier 4370. The flange groove 4385 includes a portion configured to receive the damping member 4240. In this manner, the damping member 4240 is configured to dampen a portion of a retraction force applied to the flange 4214 of the medicament container 4200 by the second shoulder 4381. The arrangement of the damping member 4240 within the flange groove 4381 reduces the likelihood of the flange 4214 breaking under the force applied by the second shoulder 4381, which can prevent the retraction of the medicament container 4200.

The needle guard assembly 4800 includes an inner needle sheath 4810 and an outer needle sheath 4820. The inner needle sheath 4810 includes an outer surface 4815 that has a ring 4816. The inner needle sheath 4810 is disposed within the outer needle sheath 4820 (see e.g., FIGS. 58 and 59). The inner needle sheath 4810 is similar to the needle sheath 3810 of the medical injector 3000, described above with reference to FIG. 46. Therefore, details of the inner needle sheath 4810 are not described in detail herein.

The outer needle sheath 4820 includes a proximal end portion 4821 and a distal end portion 4822, and defines a lumen 4826 therebetween. The lumen 4826 is configured to receive the inner needle sheath 4810. The proximal end portion 4821 includes an inner sheath aperture 4823 configured to receive the ring 4816 of the inner needle sheath 4810. The ring 4816 extends from the outer surface 4815 of the inner needle sheath 4810 and a portion of the ring is disposed within the inner sheath aperture 4823. The arrangement of the ring 4816 of the inner needle sheath 4810 and the inner sheath aperture 4823 prevent the movement of the inner needle sheath 4810 within the outer needle sheath 4810.

The distal end portion 4822 includes a neck 4824 that has a rib 4825. The neck 4824 of the distal end portion 4822 is configured to contact engagement members 4721 of the safety lock 4700. Similarly stated, the neck 4824 of the distal end portion 4822 is disposed within a space defined between the engagement members 4721 of the safety lock 4700. The engagement members 4721 allow the distal end portion 4822 of the outer needle sheath 4820 to move between the engagement members 4721 in a distal direction, but not in a proximal direction. Similarly stated, the engagement members 4721 include an edge that contacts the rib 4825 of the outer needle sheath 4820 such as to prevent the safety lock 4700 from moving in a distal direction relative to the outer needle sheath 4820. Said another way, the needle guard assembly 4800 is removed from the needle 4216 when the safety lock 4700 is moved in a distal direction with respect to the housing 4100 (similar to the result as shown for the medical injector 3000 in FIG. 50).

The function of the medical injector 4000 is substantially similar to the function of the medical injector 3000, described with reference to FIGS. 9-55. In this manner, the user of the medical injector 4000 can actuate the medical injector 4000 to inject a medicament, disposed within the medicament container 4200, into an injection site of a patient.

Figure 60:
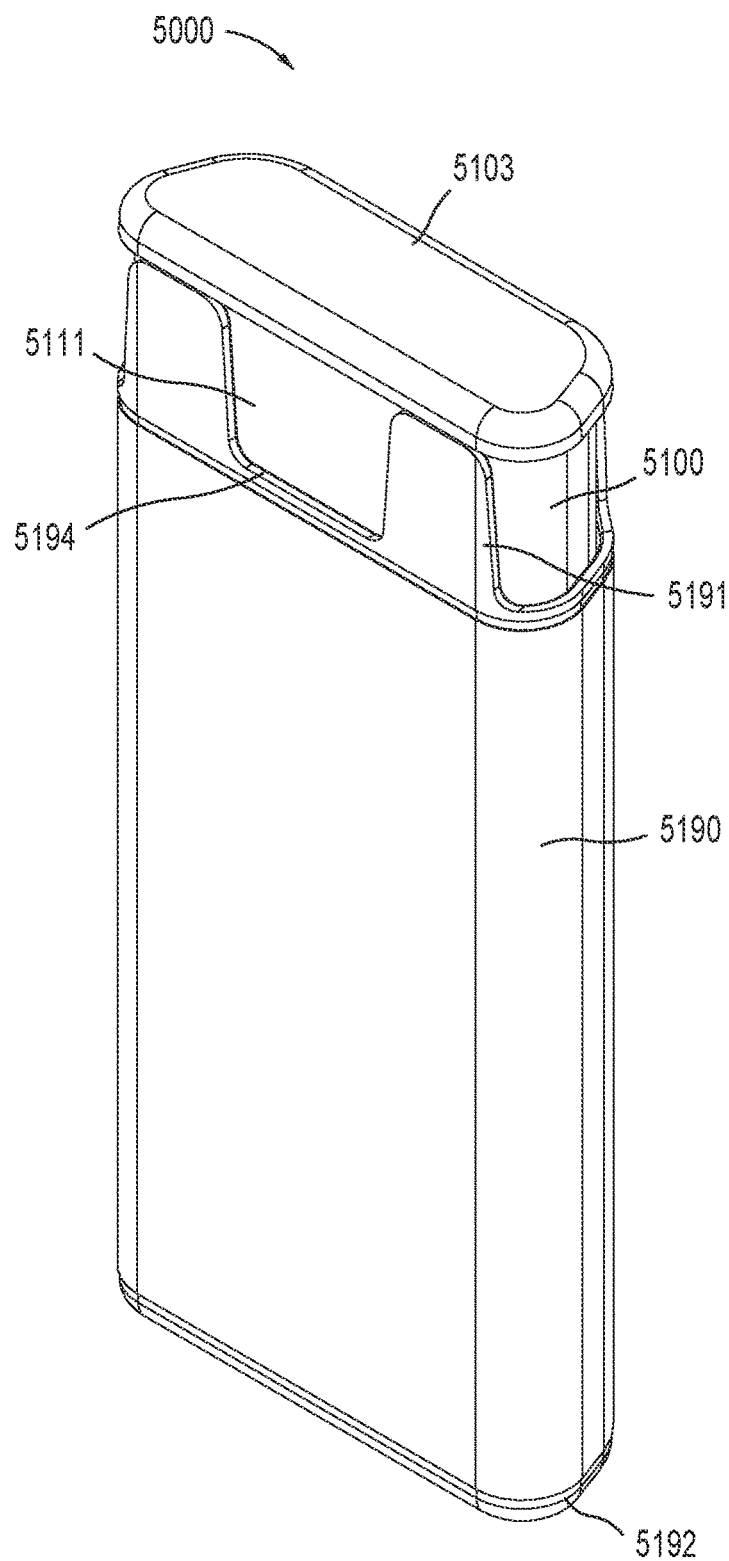
FIGS. 60 and 61 are perspective views of a medical injector according to an embodiment, in a first configuration.
Figure 61:
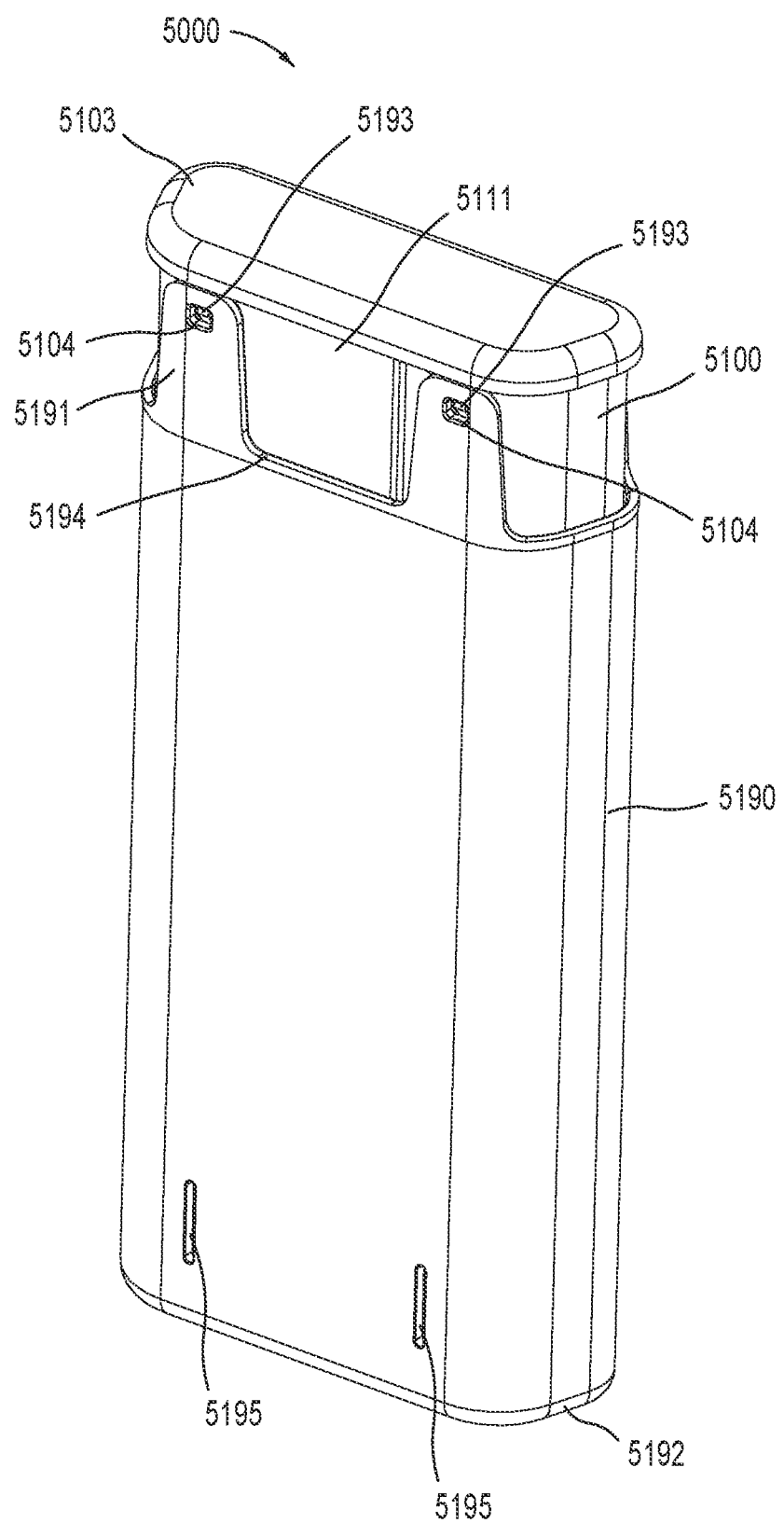
Figure 62:
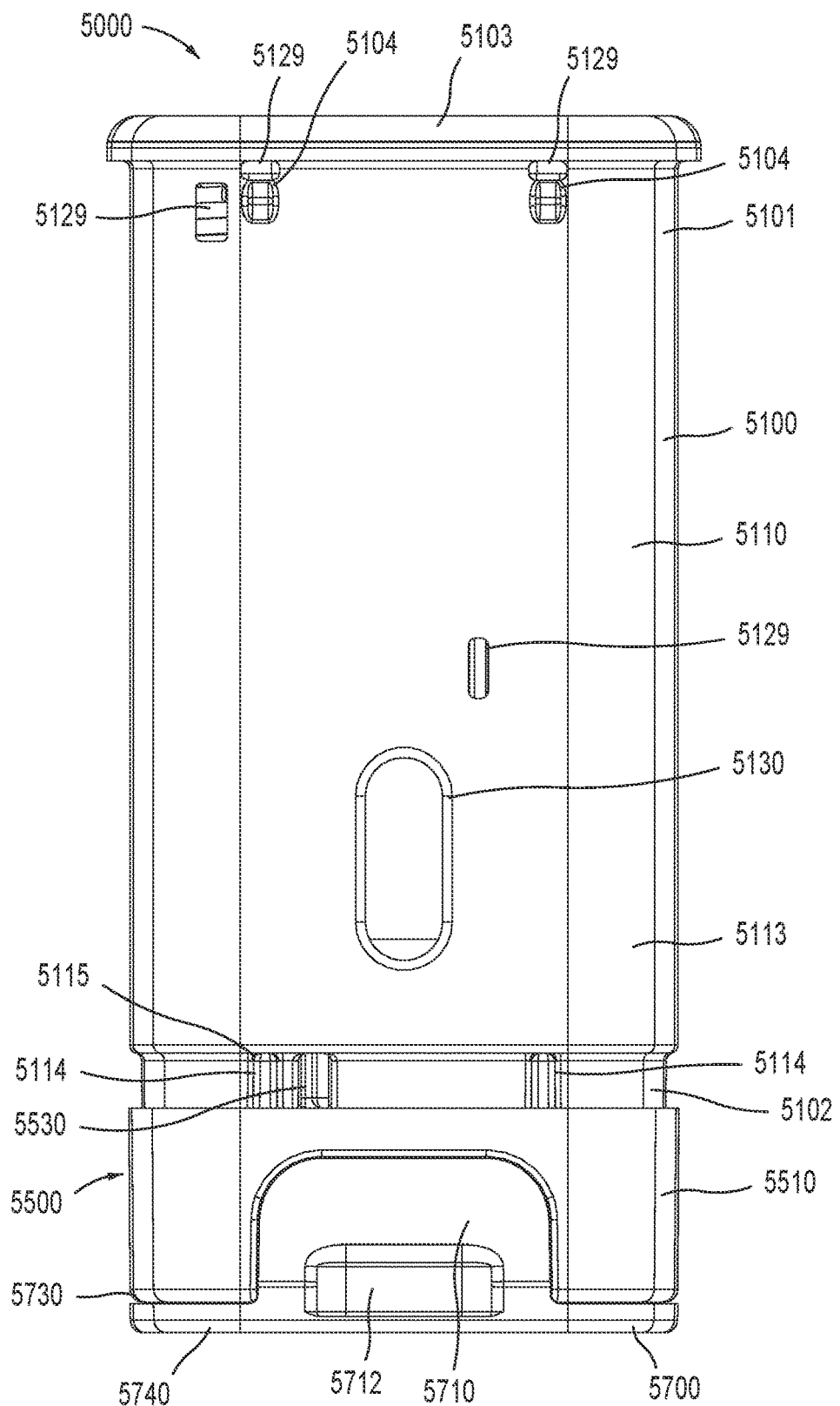
FIG. 62 is a front view of the medical injector illustrated in FIG. 60 with a cover removed.
Figure 63:
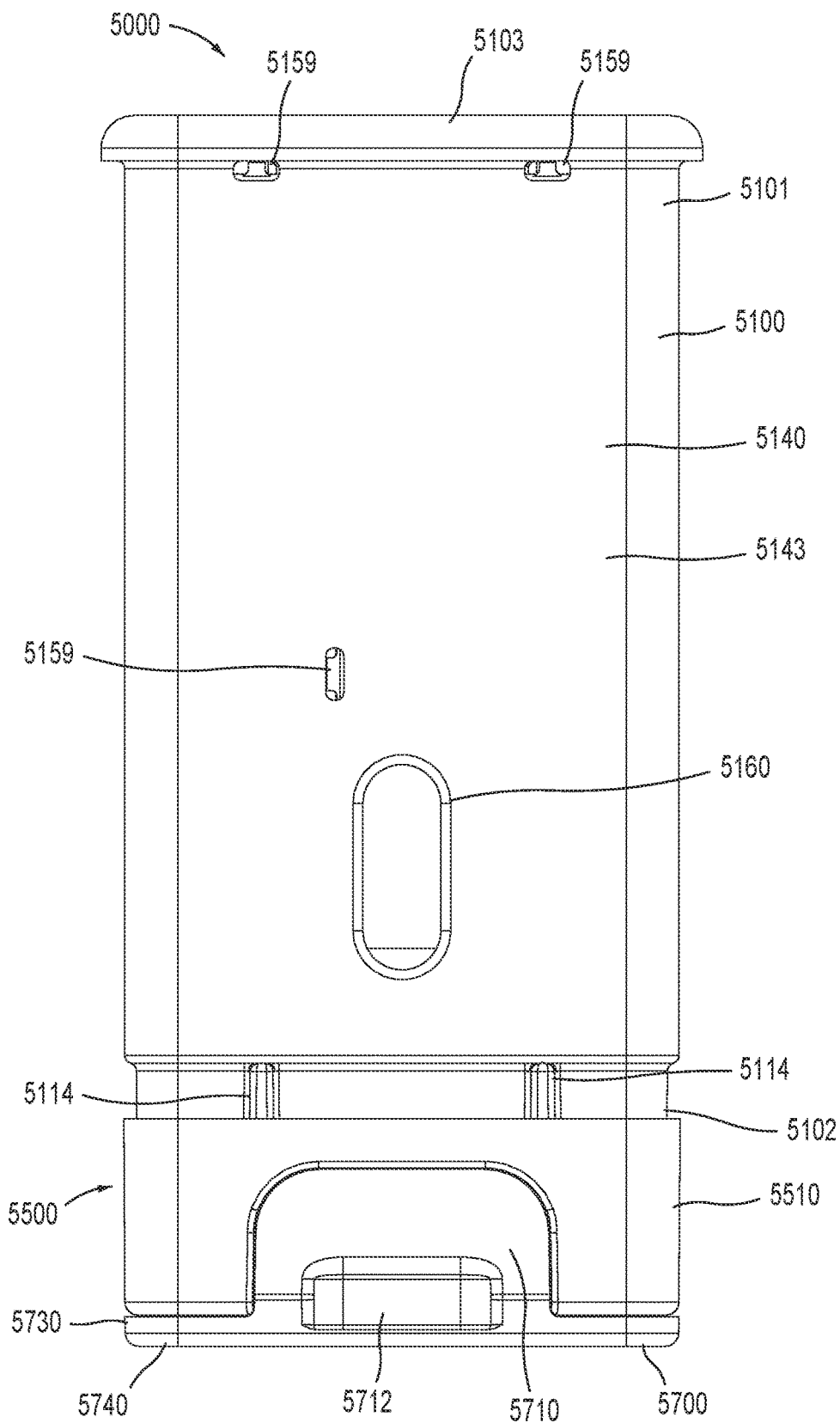
FIG. 63 is a back view of the medical injector illustrated in FIG. 60 with the cover removed.
Figure 64:
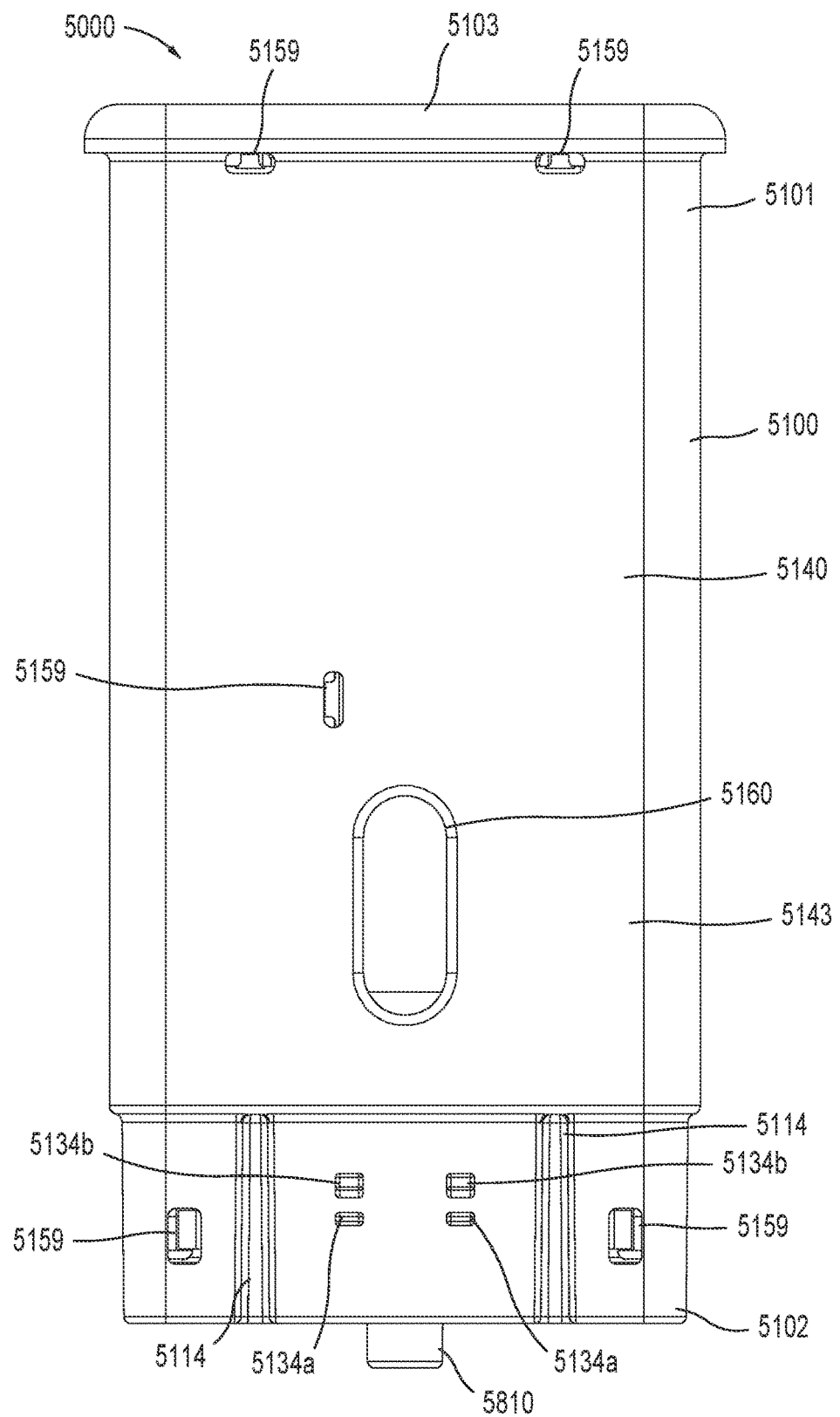
FIG. 64 is a back view of a portion of the medical injector illustrated in FIG. 60.

Although the medicament injector 3000 and the medical injector 4000 are shown and described above as including a system actuation including the release of a pressurized gas, in other embodiments, a medicament delivery device can include any suitable method of delivery of a medicament disposed within. For example, FIGS. 60-98 show a medical injector 5000, according to an embodiment that includes a mechanical energy storage member, rather than a compressed gas container. FIGS. 60-61 are perspective views of the medical injector 5000 in a first configuration (i.e., prior to use). The medical injector 5000 includes a housing 5100 (see e.g., FIGS. 62-70), a system actuator 5500 (see e.g., FIGS. 71-73), a medicament container 5200 containing a medicament 5220 (see e.g., FIG. 74), a medicament delivery mechanism 5300, a transfer member 5600 (see e.g., FIG. 75-80), a cover 5190 (see e.g., FIGS. 81-82), and a safety lock 5700 (see e.g., FIGS. 83-87). A discussion of the components of the medical injector 5000 will be followed by a discussion of the operation of the medical injector 5000.

As shown in FIGS. 62-70, the housing 5100 includes a first housing member 5110 (FIGS. 66 and 67) and a second housing member 5140 (FIGS. 68 and 69) that can couple to form the housing 5100. The housing 5100 has a proximal end portion 5101 and a distal end portion 5102. The housing 5100 defines a first status indicator aperture 5130 (defined by the first housing member 5110) and a second status indicator aperture 5160 (defined by the second housing member 5140). The status indicator apertures 5130, 5160 can allow a patient to monitor the status and/or contents of the medicament container 5200 contained within the housing 5100. For example, by visually inspecting the status indicator aperture 5130 and/or 5160, a patient can determine whether the medicament container 5200 contains a medicament 5220 and/or whether the medicament 5220 has been dispensed.

Figure 66:
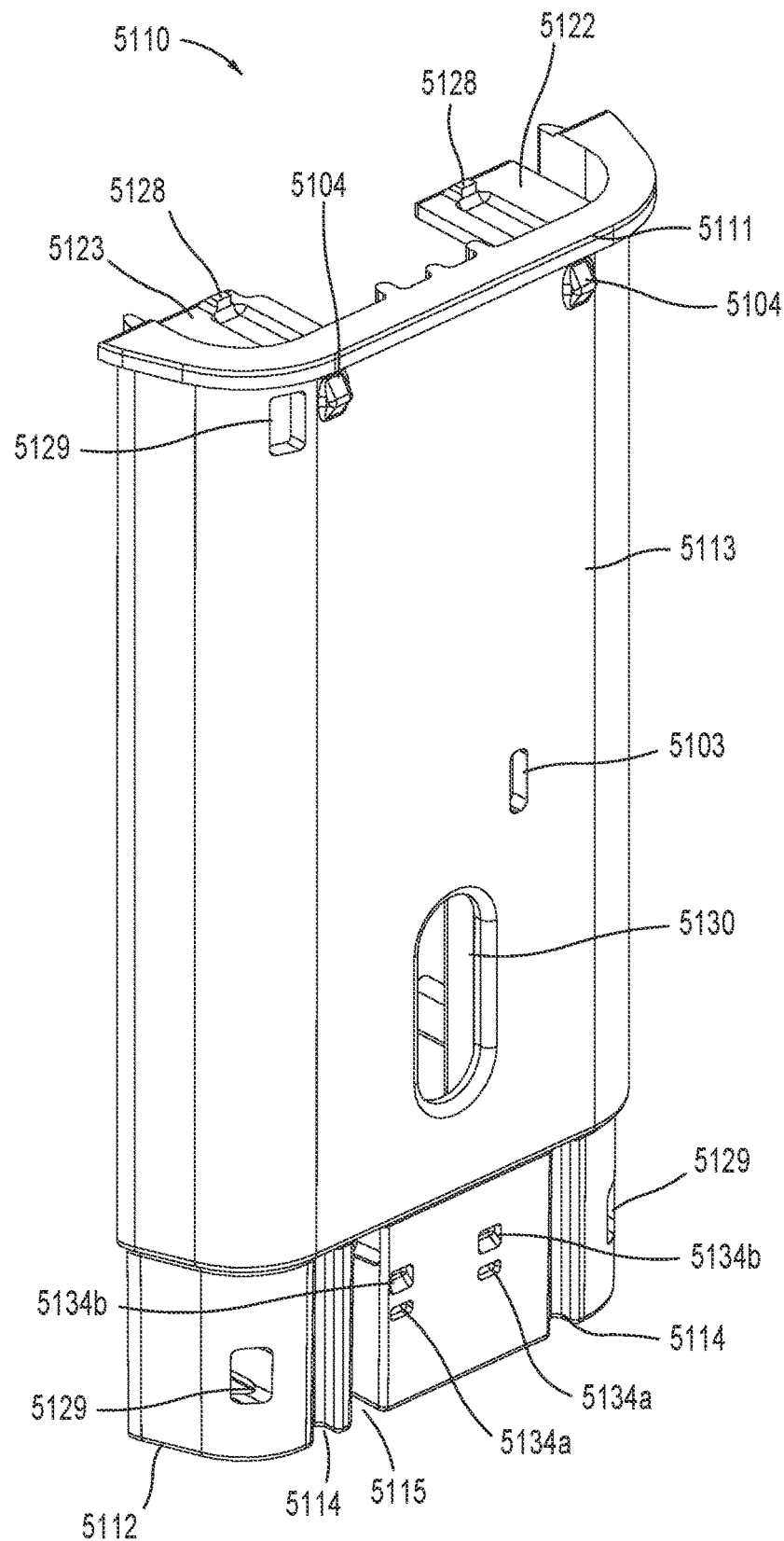
FIG. 66 is a front perspective views of a first portion of the housing of the medical injector illustrated in FIGS. 62 and 63.
Figure 67:
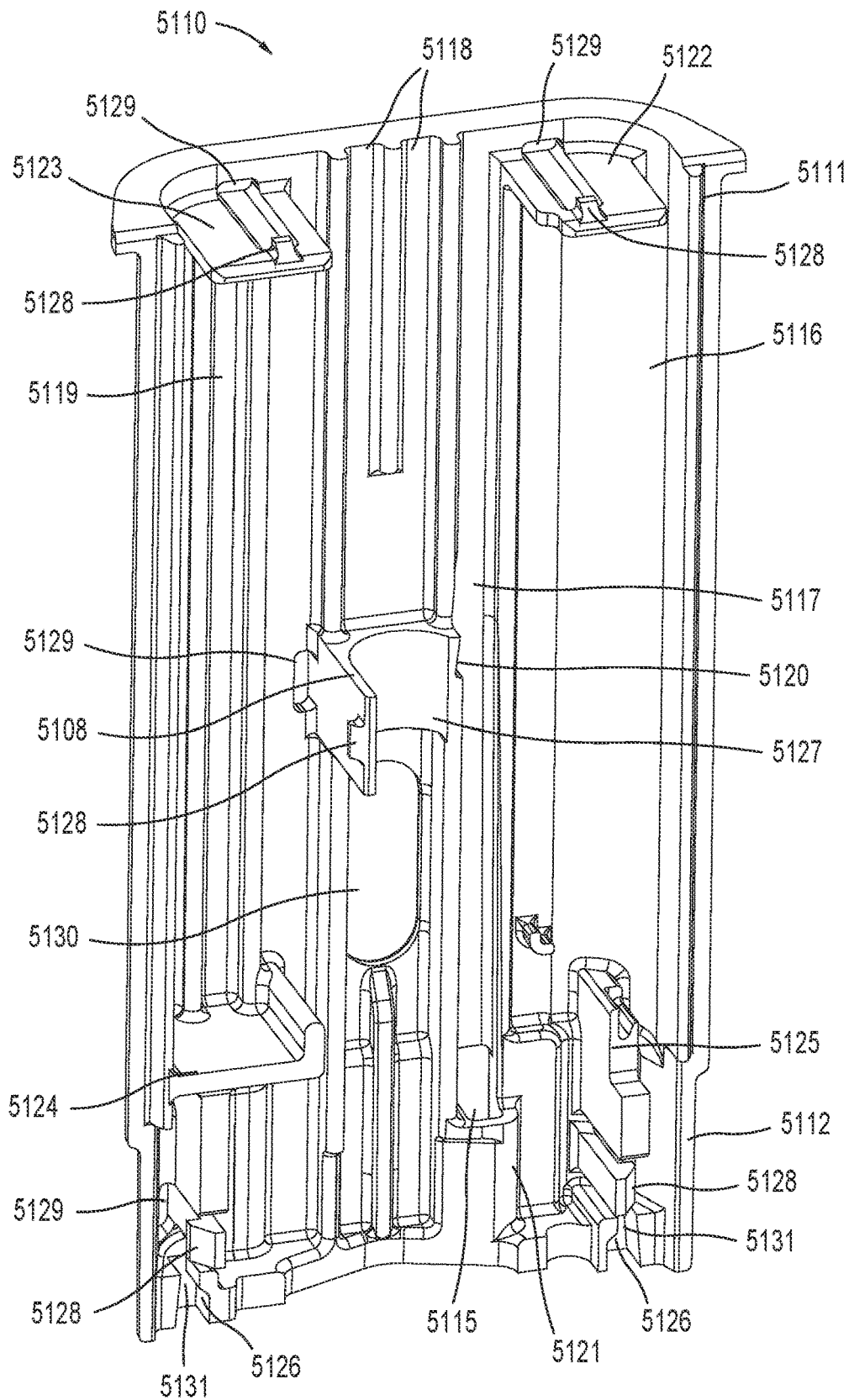
FIG. 67 is a rear perspective views of the first portion of the housing of the medical injector illustrated in FIG. 66.

As shown in FIGS. 66-67, the first housing member 5110 includes an outer surface 5113 and an inner surface 5116, and a proximal end portion 5111 and a distal end portion 5112. The outer surface 5113 includes cover retention protrusions 5104 at the proximal end portion 5111 of the first housing member 5110 (see e.g., FIGS. 61, 62 and 66). The cover retention protrusions 5104 are configured to be received within corresponding openings 5193 defined by the cover 5190 to retain the cover 5190 about the housing 5100. In this manner, as described in more detail herein, the cover 5190 is removably coupled to and disposed about at least a portion of the housing 5100.

The outer surface 5113 defines base retention recesses 5134A and 5134B, an activation rod groove 5115, and base rail grooves 5114, at the distal end portion 5112 of the first housing member 5110. The distal base retention recesses 5134A are configured to receive base connection knobs 5518 of an actuator 5510 (also referred to herein as "base 5510," see e.g., FIG. 88) when the base 5510 is in a first position relative to the housing 5100. The proximal base retention recesses 5134B are configured to receive the base connection knobs 5518 of the base 5510 when the base 5510 is in a second position relative to the housing 5100. The base retention recesses 5134A, 5134B have a tapered proximal sidewall and a non-tapered distal sidewall. This allows the base retention recesses 5134A, 5134B to receive the base connection knobs 5518 such that the base 5510 can move proximally relative to the housing 5100, but cannot move distally relative to the housing 5100. Said another way, the distal base retention recesses 5134A are configured to prevent the base 5510 from moving distally when the base 5510 is in a first position and the proximal base retention recesses 5134B are configured to prevent the base 5510 from moving distally when the base 5510 is in a second position. Similarly stated, the proximal base retention recesses 5134B and the base connection knobs 5518 cooperatively to limit movement of the base 5510 to prevent undesirable movement of the base 5510 after the medical injector 5000 is actuated. The proximal base retention recesses 5134B and the base connection knobs 5518 also provide a visual cue to the user that the medical injector 5000 has been used.

The activation rod groove 5115 is configured to receive an activator 5530 (also referred to herein as "release member 5530," see e.g., FIG. 88) of the base 5510. As described in more detail herein, the release member 5530 of the base 5510 is configured to engage a portion of the medicament delivery mechanism 5300 when the base 5510 is moved with respect to the housing 5100. The base rail grooves 5114 are configured to receive guide members 5517 of the base 5510. The guide members 5517 of the base 5510 and the base rail grooves 5114 of the housing 5100 engage each other in a way that allows the guide members 5517 of the base 5510 to slide in a proximal and/or distal direction within the base rail grooves 5114 while limiting lateral movement of the guide members 5517. This arrangement allows the base 5510 to move in a proximal and/or distal direction with respect to the housing 5100 but prevents the base 5510 from moving in a lateral direction with respect to the housing 5100.

The inner surface 5116 of the first housing member 5110 includes a medicament container holder 5127, an upper spring plate 5122 and an upper bias member plate 5123. The inner surface 5166 also includes a series of protrusions that define a transfer member groove 5117, piston portion grooves 5118 and a bias portion groove 5119 (see e.g., FIG. 67). The medicament container holder 5127 is configured to receive a body 5210 of the medicament container 5200 (e.g., a prefilled syringe). The medicament container holder 5127 defines a latch member notch 5120 that includes an engagement surface 5109 (see e.g. FIG. 72) configured to engage a latch protrusion 5315 of a latch portion 5310 of the medicament delivery mechanism 5300. The medicament container holder 5127 includes a proximal end surface 5108. The proximal end surface 5108 is configured to contact a portion of the medicament container 5200 (either directly or via intervening structure, such as an o-ring or damping member) when the medicament container 5200 is in a second position, as described in further detail herein.

The upper spring plate 5122 is disposed at the proximal end portion 5111 of the first housing member 5110. The upper spring plate 5122 extends from the inner surface 5116 and is configured to contact a proximal end portion 5421 of a spring 5420 (see FIG. 91). In this manner, when activated, the upper spring plate 5122 limits proximal movement of the spring 5420 such that the spring expands distally to move the medicament delivery mechanism 5300 in a distal direction (see e.g., FIG. 93). Similarly stated, the upper spring plate 5122 receives a force from the spring 5420 and applies an equal and opposite reaction force to the proximal end portion 5421 of the spring 5420 such that a distal end portion 5422 of the spring 5420 expands in a distal direction, as described in further detail herein.

The upper bias plate 5123 is disposed at the proximal end portion 5111 of the first housing member 5110 and extends from the inner surface 5116. The upper bias plate 5123 is configured to selectively engage a bias portion 5350 of the medicament delivery mechanism 5300 (see FIG. 91). In this manner, the upper bias plate 5123 is configured to limit the proximal movement of the bias portion 5350 of the medicament delivery mechanism 5300, as described in further detail herein.

As described above, the inner surface 5116 includes protrusions that define the transfer member groove 5117, the piston portion grooves 5118 and the bias portion groove 5119. The transfer member groove 5117 is configured to receive a guide protrusion 5619 of the transfer member 5600 (see FIG. 80). The guide protrusion 5619 of the transfer member 5600 and the transfer member groove 5117 defined by the inner surface 5116 of the first housing member 5110 engage each other in a way that allows the guide protrusion 5619 of the transfer member 5600 to slide in a proximal and/or distal direction within the transfer member groove 5117 while limiting lateral movement of the guide protrusion 5619. This arrangement allows the transfer member 5600 to move in a proximal and/or distal direction with respect to the housing 5100 but prevents the transfer member 5600 from moving in a lateral direction with respect to the housing 5100. Similarly, the piston portion grooves 5118 are configured to receive the guide protrusions 5302 of the piston portion 5330 of the medicament delivery mechanism 5300 (see FIG. 76). The bias portion groove 5119 is configured to receive the guide protrusion 5354 of the bias portion 5350 of the medicament delivery mechanism 5300 (see FIG. 76). In this manner, the piston portion grooves 5118 and the bias member groove 5119 engage the guide protrusions 5302 of the piston portion 5330 and the guide protrusion 5354 of the bias portion 5350, respectively, to prevent the medicament delivery mechanism 5300 from moving in a lateral direction with respect to the housing 5100 and/or rotating within the housing 5100.

The inner surface 5116 of the first housing member 5110 further includes a transfer member release protrusion 5121, a transfer member release support protrusion 5125, a lower bias plate 5124, and base lock protrusions 5126. The transfer member release protrusion 5121 is configured to engage a latch arm 5618 of the transfer member 5600 to place the transfer member 5600 in a second configuration when the transfer member 5600 moves to a second position (see e.g., FIG. 97). Contemporaneously, the transfer member release support protrusion 5125 supports the latch arm 5618 of the transfer member 5600 as the transfer member is placed in the second configuration, as described in further detail herein.

The lower bias plate 5124 engages a distal end portion 5353 of the bias portion 5350 of the delivery mechanism 5300 (see e.g., FIG. 95), as described in further detail herein. The base lock protrusions 5126 are configured to engage base locks 5515 of the base 5510 when the safety lock 5700 is in contact with the medical injector 5000 (see FIG. 73). Similarly stated, the safety lock 5700, the base lock protrusions 5126, and the base locks 5515 collectively prevent the base 5510 from moving in a proximal direction relative to the housing 5100 when the base locks 5515 of the base 5510 are in contact with the base lock protrusions 5126 of the first housing portion 5110, as described in further detail herein.

The first housing member 5110 further includes a set of tabs 5128 and a set of openings 5129. The tabs 5128 extend from portions of the inner surface 5116 of the first housing member 5110. The first housing member 5110 can include any number of tabs 5128 that can have any suitable shape or size. For example, in some embodiments, the tabs 5128 vary in size. The tabs 5128 are configured to engage portions of the second housing member 5140 to couple the first housing member 5110 to the second housing member 5140, as described in further detail herein.

Figure 68:
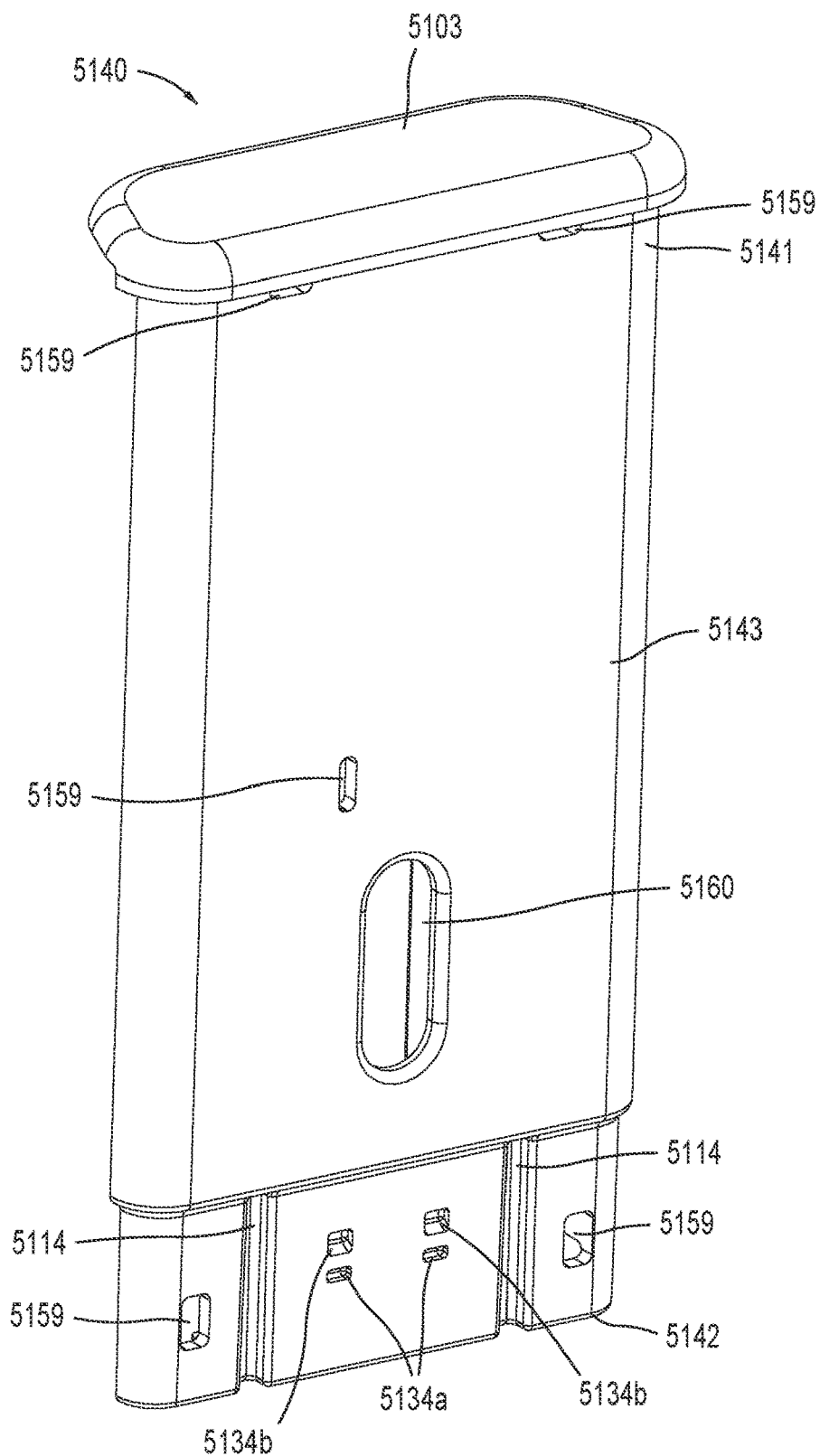
FIG. 68 is a front perspective views of a second portion of the housing of the medical injector illustrated in FIGS. 62 and 63.
Figure 69:
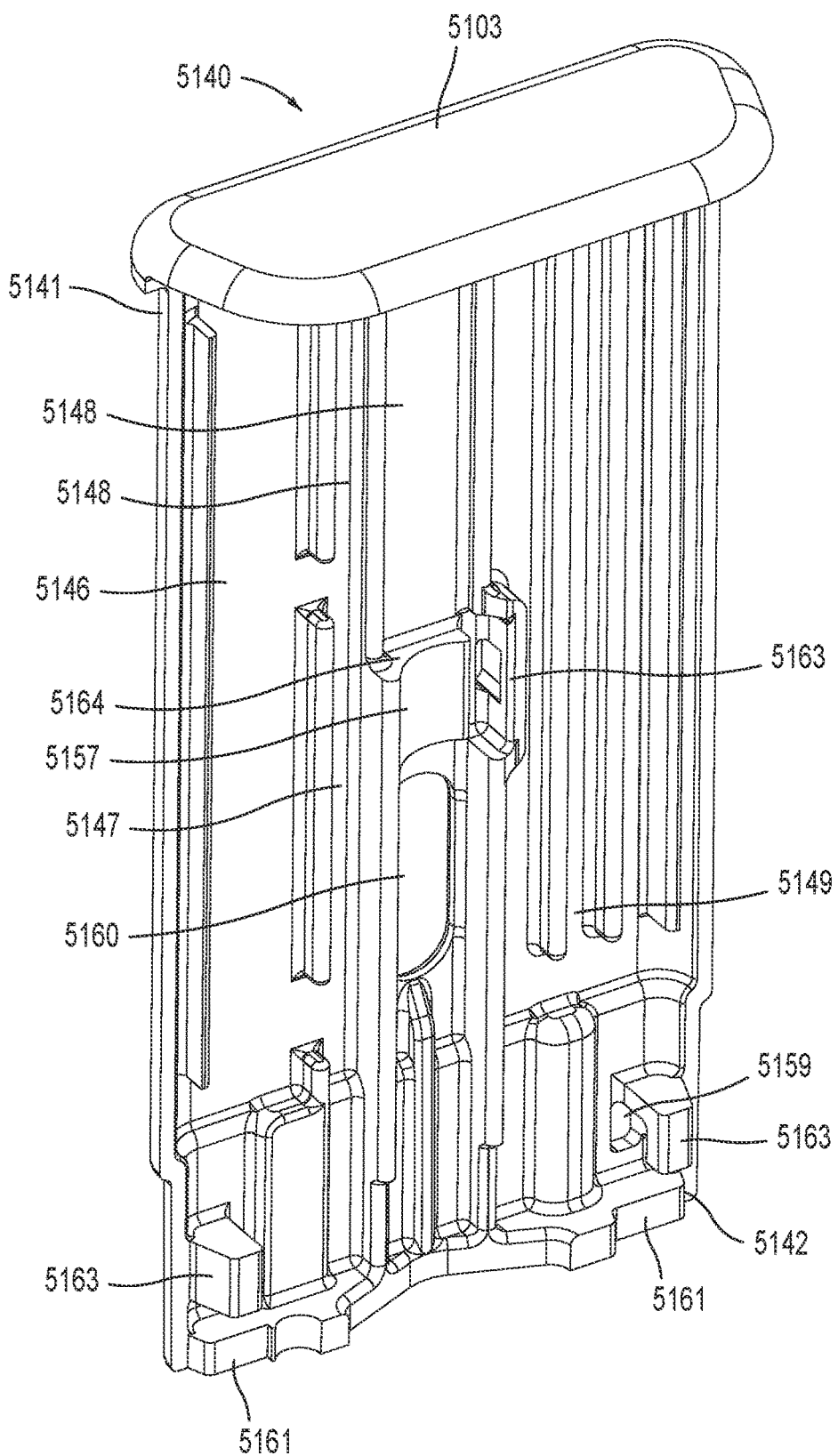
FIG. 69 is a rear perspective views of the second portion of the housing of the medical injector illustrated in FIG. 68.
Figure 70:
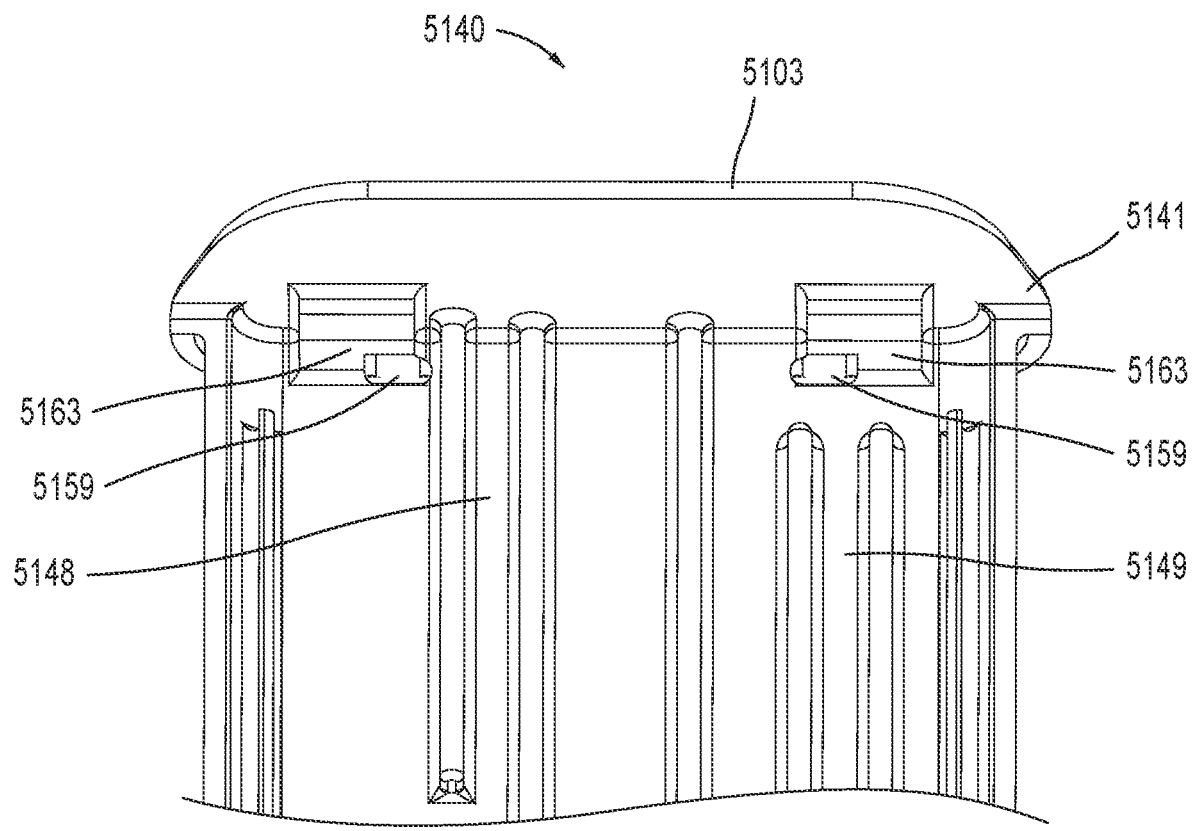
FIG. 70 is an enlarged view of a portion of the second portion of housing of the medical injector illustrated in FIG. 69.

As shown in FIGS. 68-70, the second housing member 5140 includes an outer surface 5143 and an inner surface 5146. The second housing member 5140 also includes a proximal end portion 5141, a proximal cap 5103, and a distal end portion 5142. The outer surface 5143 defines base retention recesses 5134A and 5134B and base rail grooves 5114, at the distal end portion 5142 of the second housing member 5140. The distal base retention recesses 5134A are configured to receive base connection knobs 5518 of the base 5510 when the base 5510 is in a first position relative to the housing 5100. The proximal base retention recesses 5134B are configured to receive the base connection knobs 5518 of the base 5510 when the base 5510 is in a second position relative to the housing 5100. The base retention recesses 5134A, 5134B have a tapered proximal sidewall and a non-tapered distal sidewall. This allows the base retention recesses 5134A, 5134B to receive the base connection knobs 5518 such that the base 5510 can move proximally relative to the housing 5100, but cannot move distally relative to the housing 5100. Said another way, the distal base retention recesses 5134A are configured to prevent the base 5510 from moving distally when the base 5510 is in a first position and the proximal base retention recesses 5134B are configured to prevent the base 5510 from moving distally when the base 5510 is in a second position. Similarly stated, the proximal base retention recesses 5134B and the base connection knobs 5518 cooperatively limit movement of the base 5510 to prevent undesirable movement of the base 5510 after the medical injector 5000 is actuated. The proximal base retention recesses 5134B and the base connection knobs 5518 also provide a visual cue to the user that the medical injector 5000 has been used.

The base rail grooves 5114 are configured to receive guide members 5517 of the base 5510. The guide members 5517 of the base 5510 and the base rail grooves 5114 of the second housing member 5140 engage each other in a way that allows the guide members 5517 of the base 5510 to slide in a proximal and/or distal direction within the base rail grooves 5114 while limiting lateral movement of the guide members 5517. This arrangement allows the base 5510 to move in a proximal and/or distal direction with respect to the housing 5100 but prevents the base 5510 from moving in a lateral direction with respect to the housing 5100.

The proximal cap 5103 extends from the proximal end portion 5141 of the second housing member 5140 and encloses the proximal end portion 5101 of the housing 5100 when the first housing member 5110 is coupled to the second housing member 5140.

The inner surface 5146 of the second housing member 5140 includes a medicament container holder 5157. The inner surface further includes protrusions that define a transfer member groove 5147, piston portion grooves 5148, and a bias portion groove 5149. The medicament container holder 5157 is configured to receive a body 5210 of the medicament container 5200 (e.g., a prefilled syringe). Moreover, the medicament container holder 5157 is configured to be coupled to a portion of the medicament container holder 5127 of the first housing member 5110 to define a space in which the medicament container 5200 is disposed. The medicament container holder 5157 includes a proximal end surface 5164. The proximal end surface 5164 is configured to contact a portion of the medicament container 5200 (either directly or via intervening structure) when the medicament container 5200 is in the second position, as described in further detail herein.

Figure 80:
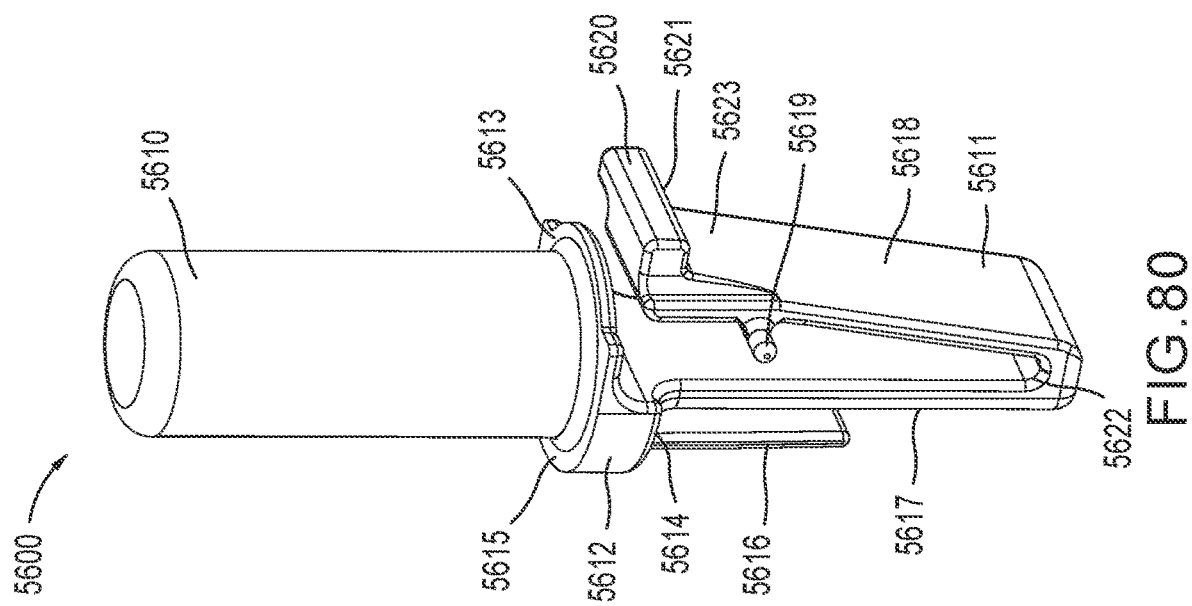
FIG. 80 is a rear perspective view of the second movable member of the medical injector illustrated in FIG. 79 in a first configuration.
Figure 79:
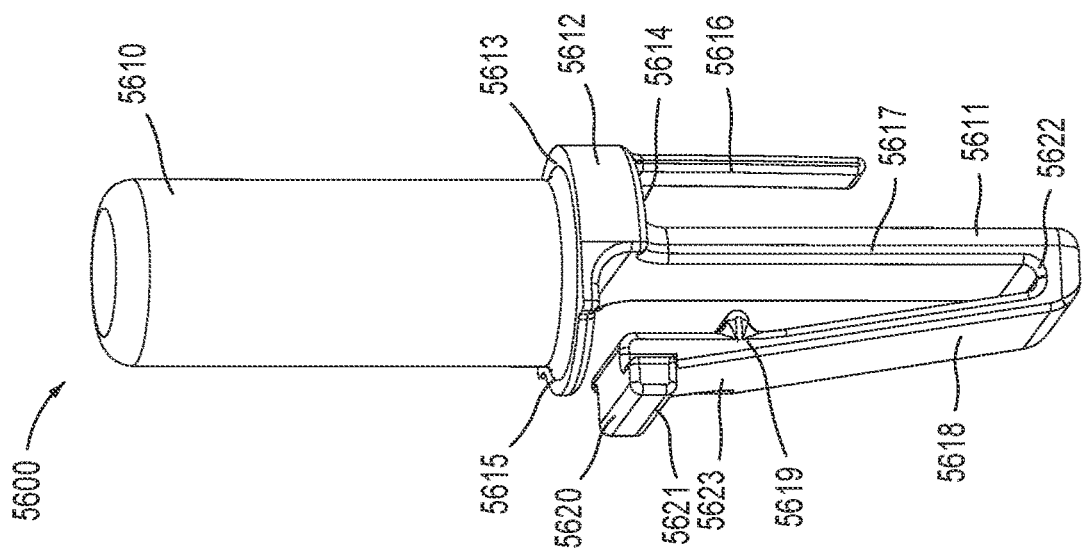
FIG. 79 is a front perspective view of a second movable member of the medical injector illustrated in FIG. 60, in a first configuration.

The transfer member groove 5147 receives a latch 5620 of the transfer member 5600 (see FIGS. 79 and 80). The latch 5620 of the transfer member 5600 and the transfer member groove 5147 defined by the inner surface 5146 of the second housing member 5140 engage each other in a way that allows the latch 5620 of the transfer member 5600 to slide in a proximal and/or distal direction within the transfer member groove 5147 while limiting lateral movement of the guide protrusion 5619. Similarly, the piston portion grooves 5148 are configured to receive the guide protrusions 5302 of the piston portion 5330 of the medicament delivery mechanism 5300. The bias portion groove 5149 is configured to receive the guide protrusion 5354 of the bias portion 5350 of the medicament delivery mechanism 5300. In this manner, the piston portion grooves 5148 and the bias member groove 5149 engage the guide protrusions 5302 of the piston portion 5330 and the guide protrusion 5354 of the bias portion 5350, respectively, to prevent the medicament delivery mechanism 5300 from moving in a lateral direction with respect to the housing 5100 and/or rotating within the housing 5100.

The second housing member 5140 further includes a set of tab latches 5163 and defines a set of openings 5159. The second housing member 5140 can include any number of tab latches 5163 such that the number of tab latches 5163 correspond to the number of tabs 5128 of the first housing member 5110. Collectively, the tabs 5128 of the first housing member 5110 and the tab latches 5163 of the second housing member 5140 couple the first housing member 5110 to the second housing member 5140. Similarly stated, the tabs 5128 are configured to engage the tab latches 5163 to define a lock fit. Moreover, a surface of the tabs 5128 is in contact with a surface of the tab latches 5163 to define a lock fit such that the first housing member 5110 and the second housing member 5140 couple together to define the housing 5100. The openings 5129 of the first housing member 5110 and the openings 5159 of the second housing member 5140 allow access to the tabs 5128 of the first housing member 5110 and the tab latches 5163 of the second housing member 5140, respectively. In this manner, the first housing member 5110 can be decoupled from the second housing member 5140.

Figure 65:
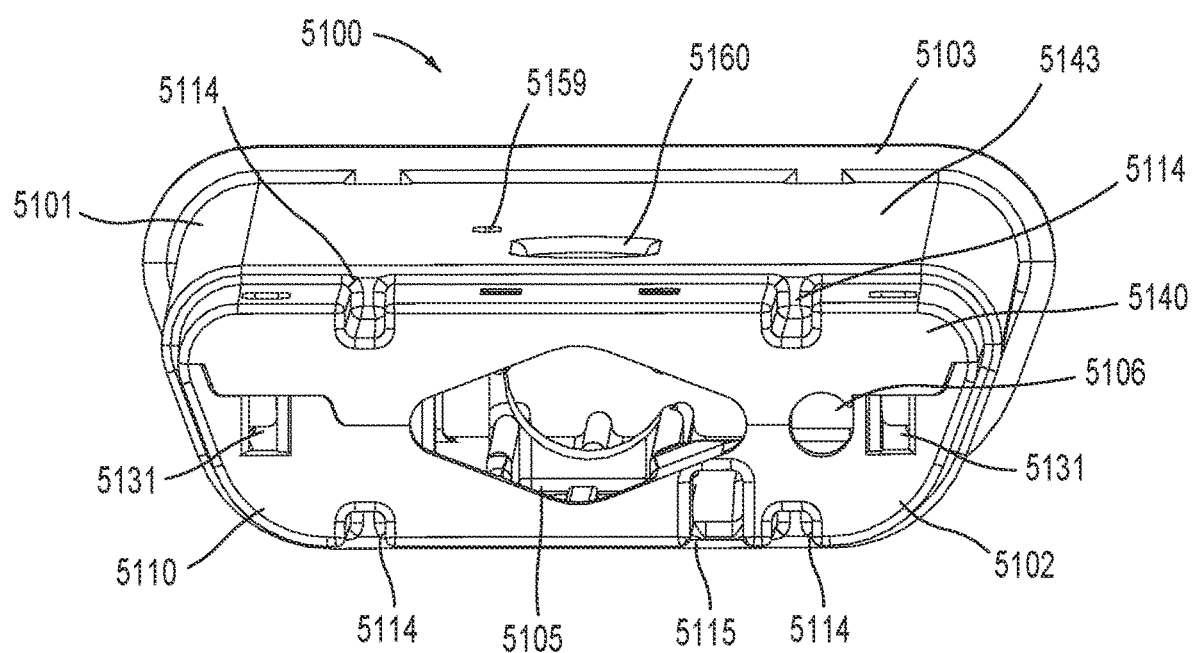
FIG. 65 is a bottom perspective view of a housing of the medical injector illustrated in FIG. 64.

As shown in FIG. 65, when the first housing member 5110 and the second housing member 5140 are assembled, the distal end portion 5102 of the housing 5100 defines a needle aperture 5105, a transfer member access opening 5106 and base lock openings 5131. Similarly stated, the first housing member 5110 and the second housing member 5140 collectively define the needle aperture 5105, the transfer member access opening 5106 and the base lock openings 5131. The needle aperture 5105 is configured to allow the needle 5216 (see e.g., FIGS. 74, 92 and 93) to exit the housing 5100 when the medical injector 5000 is actuated, as described in further detail herein.

The transfer member access opening 5106 is configured to provide access to the transfer member 5600 when the transfer member 5600 is disposed within the housing 5100. For example, in some embodiments, the transfer member 5600 can be disengaged from the medicament delivery mechanism 5300 without moving the medicament delivery mechanism 5300 in the distal direction. In this manner, the medical injector 5000 can be disabled such that the medicament delivery mechanism 5300 cannot engage the medicament container 5200 to convey a medicament 5220. For example, in some embodiments, a user, manufacturer and/or operator can disengage the transfer member 5600 from the medicament delivery mechanism 5300, via the transfer member access opening 5106, to safely dispose of an unused medical injector 5000 whose medicament 5220 expired. In other embodiments, an operator can manipulate the transfer member within the housing 5100 via the transfer member access opening 5106 during the assembly of the medical injector 5000.

Figure 73:
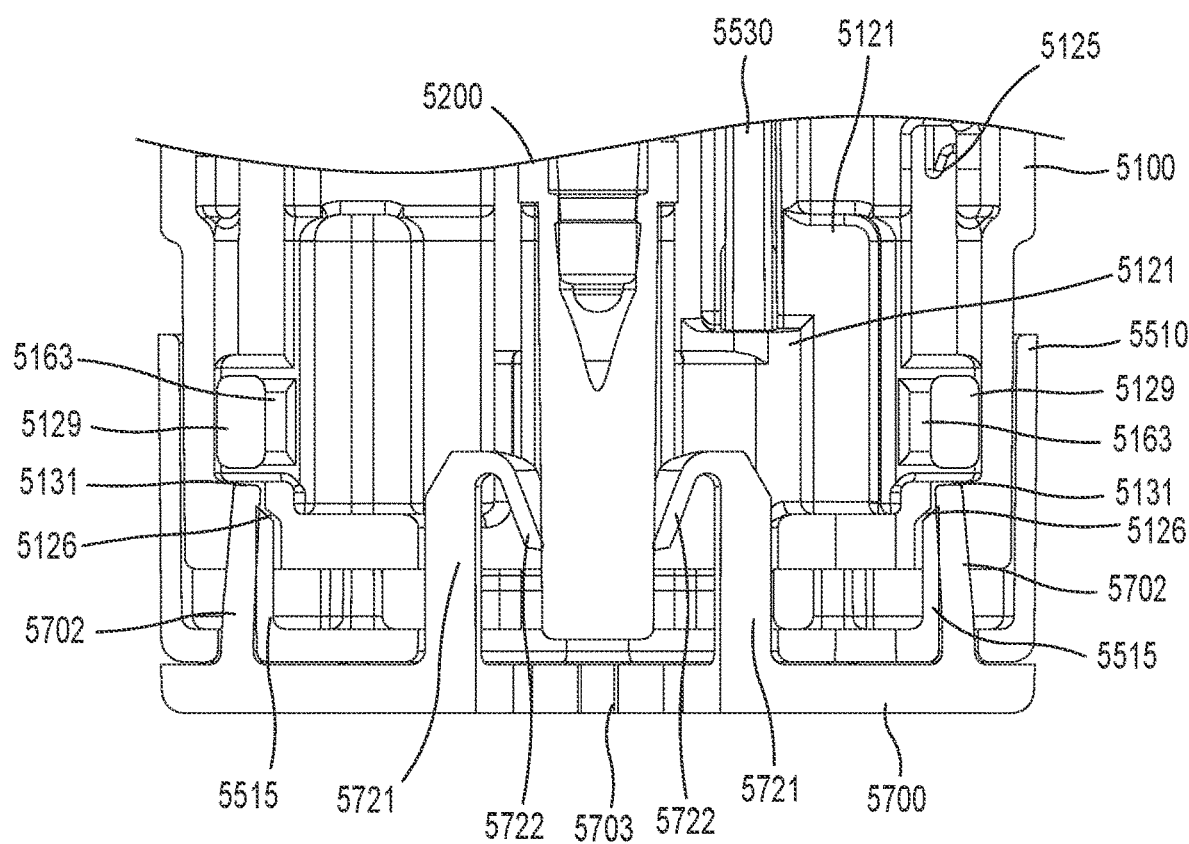
FIG. 73 is an enlarged view of a portion of the medicament delivery mechanism on the medical injector illustrated in FIG. 71.

The base lock openings 5131 are configured to receive the base locks 5515 and the safety lock protrusions 5702, as shown in the cross-sectional view of FIG. 73. The base lock openings 5131 receive the base locks 5515 and the safety lock protrusions 5702 such that the base locks 5515 of the base 5510 are in contact with the base lock protrusions 5126 of the first housing member 5110 when the safety lock protrusions 5702 are disposed within the base lock openings 5131. In this manner, the safety lock protrusions 5702 and the base lock protrusion 5126 prevent the base from moving in a proximal direction by placing the a proximal surface of the base locks 5515 in contact with a distal surface of the base lock protrusions 5126. When the safety lock protrusions 5702 are removed from the base lock openings 5131, the proximal surface of the tapered surface of the base locks 5515 allow movement in a proximal direction past the corresponding tapered surfaces of the base lock protrusions 5126 when the base 5510 is moved in the proximal direction.

Figure 78:
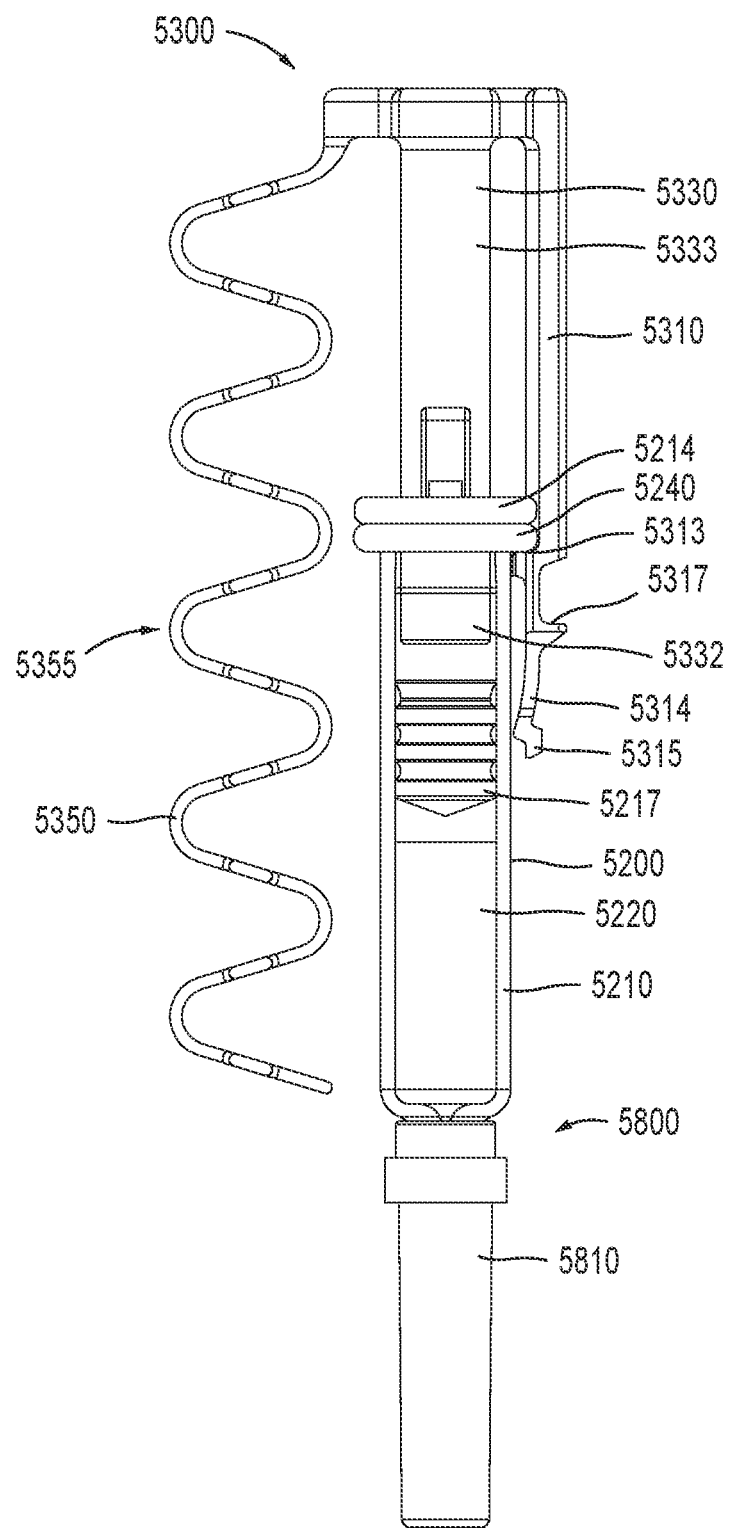
FIG. 78 is a front view of a portion of the medical injector illustrated in FIG. 60.

FIGS. 71-80 show the medicament container 5200, the system actuator 5500, the transfer member 5600 and the medicament delivery mechanism 5300 of the medical injector 5000. The medicament container 5200 has a body 5210 with a distal end portion 5213 and a proximal end portion 5212. The body 5210 defines a volume 5211 that contains (i.e., is filled with or partially filled with) a medicament 5220 (see, e.g., FIG. 74). The distal end portion 5213 of the medicament container 5200 includes a neck 5215 that is coupled to the needle 5216, as described below. The proximal end portion 5212 of the medicament container 5200 includes an elastomeric member 5217 (i.e., a plunger) that seals the medicament 5220 within the body 5210. The elastomeric member 5217 is configured to move within the body 5210 to inject the medicament 5220 from the medicament container 5200. More particularly, as shown in FIG. 78, the elastomeric member 5217 receives a piston rod 5333 of a piston portion 5330 included in the medicament delivery mechanism 5300. The proximal end portion 5212 includes a flange 5214 and a damping member 5240 (see FIG. 78) configured to engage the piston portion 5330 and the latch portion 5310 of the medicament delivery mechanism 5300. The flange 5214 and the damping member 5240 are also configured to engage and/or contact the medicament container holders 5127 and 5157 of the housing 5100.

The elastomeric member 5217 can be of any design or formulation suitable for contact with the medicament 5220. For example, the elastomeric member 5217 can be formulated to minimize any reduction in the efficacy of the medicament 5220 that may result from contact (either direct or indirect) between the elastomeric member 5217 and the medicament 5220. For example, in some embodiments, the elastomeric member 5217 can be formulated to minimize any leaching or out-gassing of compositions that may have an undesired effect on the medicament 5220. In other embodiments, the elastomeric member 5217 can be formulated to maintain its chemical stability, flexibility and/or sealing properties when in contact (either direct or indirect) with the medicament 5220 over a long period of time (e.g., for up to six months, one year, two years, five years or longer). In some embodiments, the elastomeric member 5217 is similar to the elastomeric member 3217 of the medical injector 3000, described with reference to FIG. 22.

Figure 74:
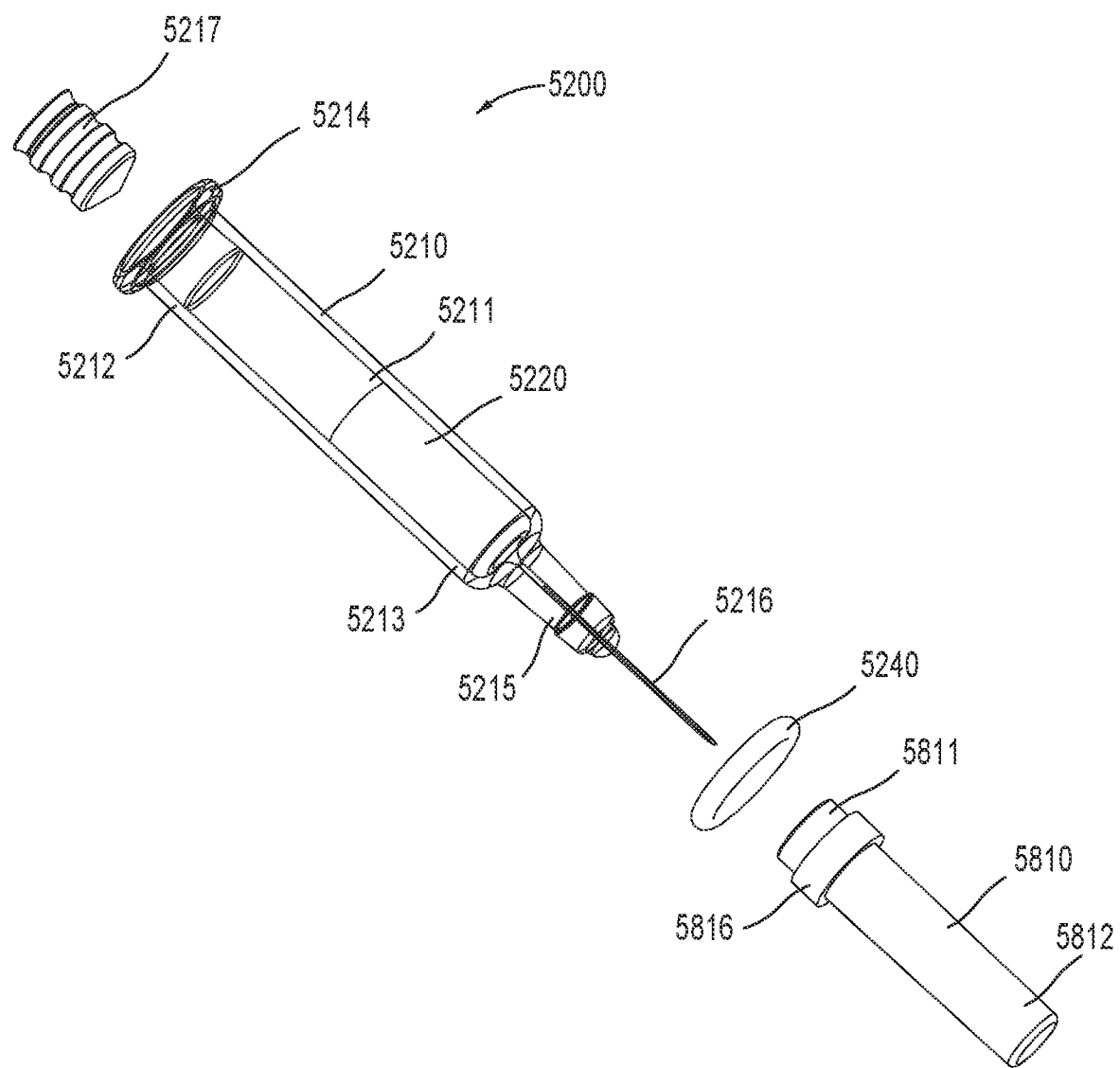
FIG. 74 is an exploded view of a medicament container of the medical injector illustrated in FIG. 60.
Figure 75:
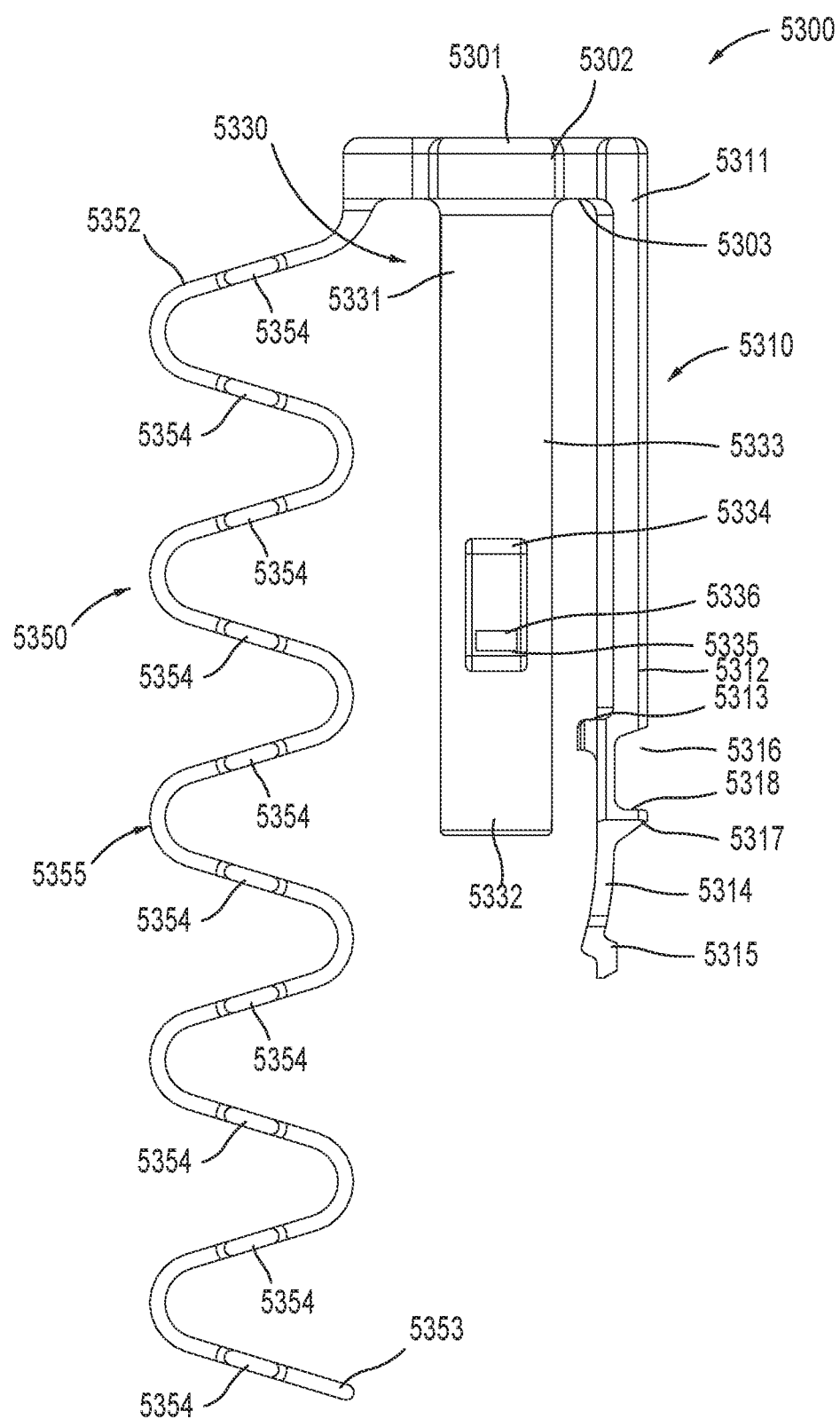
FIG. 75 is a front view of a first movable member of the medical injector illustrated in FIG. 60, in a first configuration.
Figure 76:
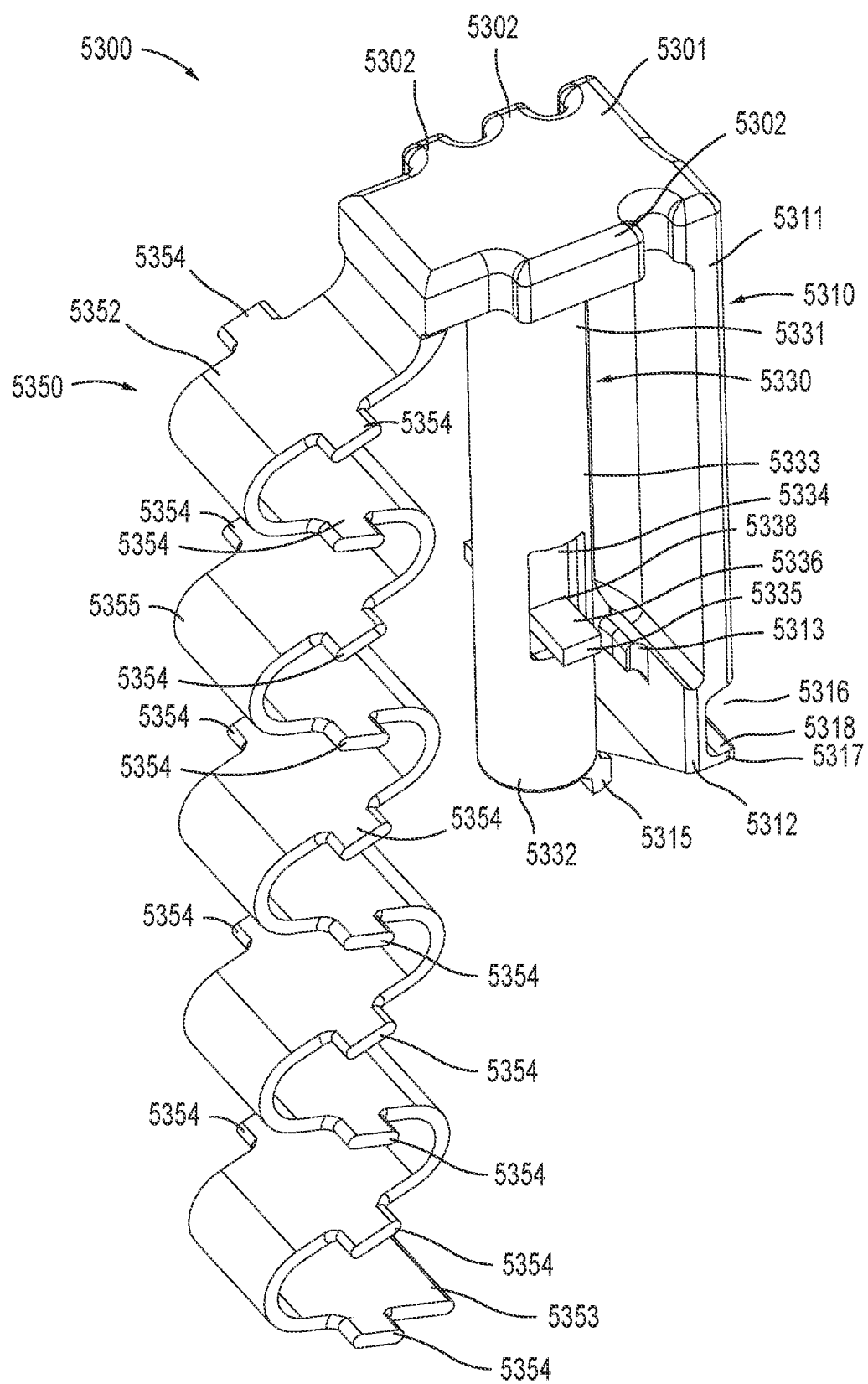
FIG. 76 is a front perspective view of the first movable member of the medical injector illustrated in FIG. 75, in a first configuration.
Figure 77:
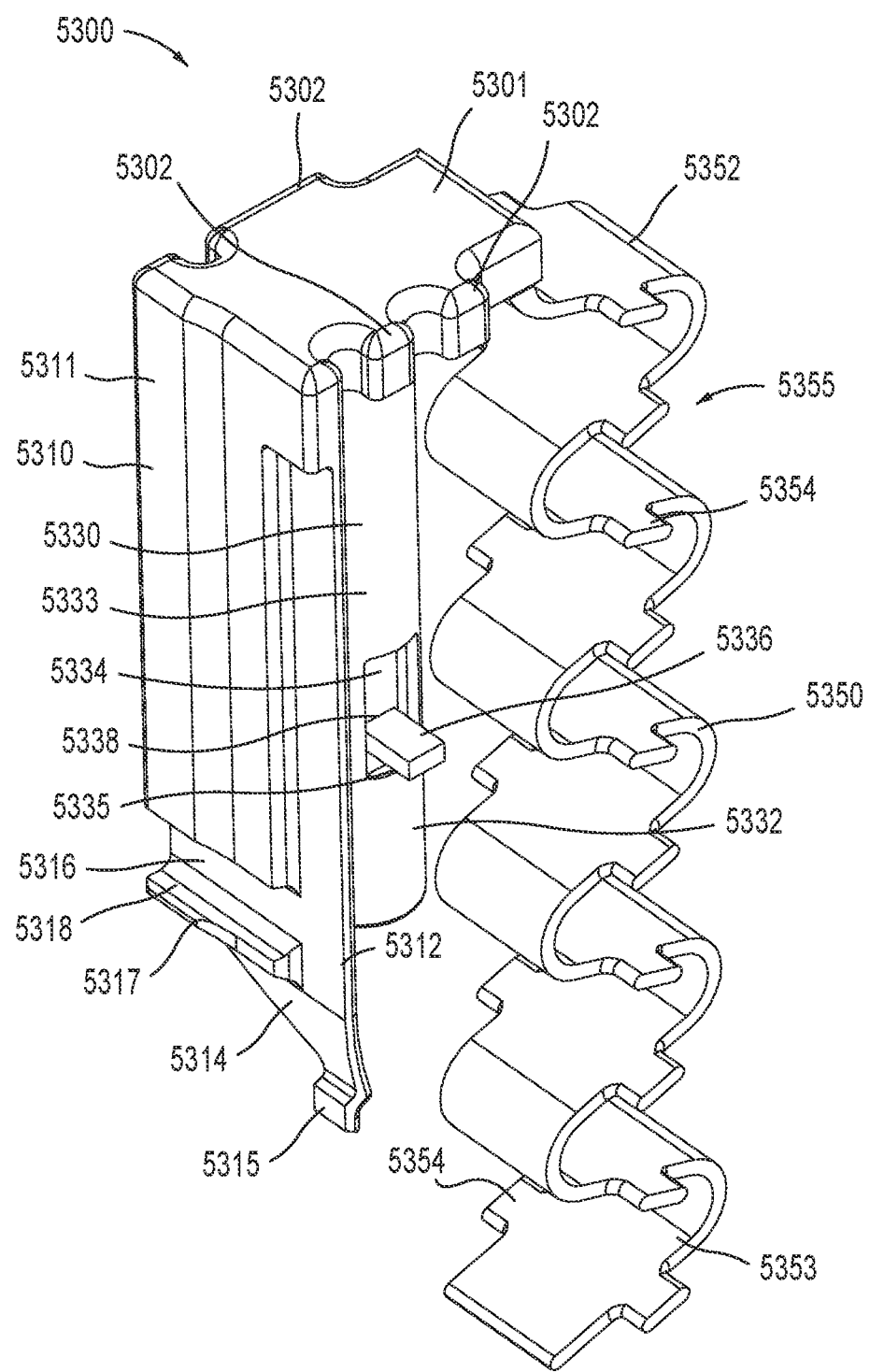
FIG. 77 is a rear perspective view of the first movable member of the medical injector illustrated in FIG. 75, in a first configuration.

The medicament container 5200 can have any suitable size (e.g., length and/or diameter) and can contain any suitable volume of the medicament 5220. Moreover, the medicament container 5200 and the piston portion 5330 can be collectively configured such that the piston portion 5330 travels a desired distance within the medicament container 5200 (i.e., the "stroke") during an injection event. In this manner, the medicament container 5200, the volume of the medicament 5220 within the medicament container 5200 and the piston portion 5330 can be collectively configured to provide a desired fill volume and delivery volume. For example, the medicament container 5200, as shown in FIG. 74, is a prefilled syringe and can be purchased and/or acquired with a given fill volume. In this manner, the piston portion 5330 can be configured to provide a desired delivery volume.

Moreover, the length of the medicament container 5200 and the length of the piston portion 5330 can be configured such that the medicament delivery mechanism 5300 can fit in the same housing 5100 regardless of the fill volume, the delivery volume and/or the ratio of the fill volume to the delivery volume. In this manner, the same housing and production tooling can be used to produce devices having various dosages of the medicament 5220. For example, in a first embodiment (e.g., having a fill volume to delivery volume ratio of 0.4), the medicament container has a first length and the second movable member has a first length. In a second embodiment (e.g., having a fill volume to delivery volume ratio of 0.6), the medicament container has a second length shorter than the first length, and the second movable member has a second length longer than the first length. In this manner, the stroke of the device of the second embodiment is longer than that of the device of the first embodiment, thereby allowing a greater dosage. The medicament container of the device of the second embodiment, however, is shorter than the medicament container of the device of the first embodiment, thereby allowing the components of both embodiments to be disposed within the same housing and/or a housing having the same length.

As shown in FIGS. 71-74, the system actuator 5500 includes the base 5510 and a release member 5530, and is configured to move in the proximal and distal direction relative to the housing 5100. Although the base 5510 and the release member 5530 are shown as being monolithically constructed to form the system actuator 5500, in other embodiments the system actuator 5500 can include a base that is constructed separately from (and later joined to) a release member. As described above, when the medical injector 5000 is in its first configuration (i.e., the storage configuration), the base locks 5515 and the safety lock protrusions 5702 are disposed within the base lock opening 5131 such that the base locks 5515 are urged by the safety lock protrusions 5702 into contact with the base lock protrusions 5126. Therefore, the system actuator 5500 and/or the base 5510 cannot move in the proximal direction to actuate the medicament delivery mechanism 5300. Similarly stated, as shown in FIG. 73, when the medical injector 5000 is in its first configuration (i.e., the storage configuration), the safety lock protrusions 5702 and the base lock protrusions 5126 cooperatively limit the proximal movement of the base 5510.

Figure 72:
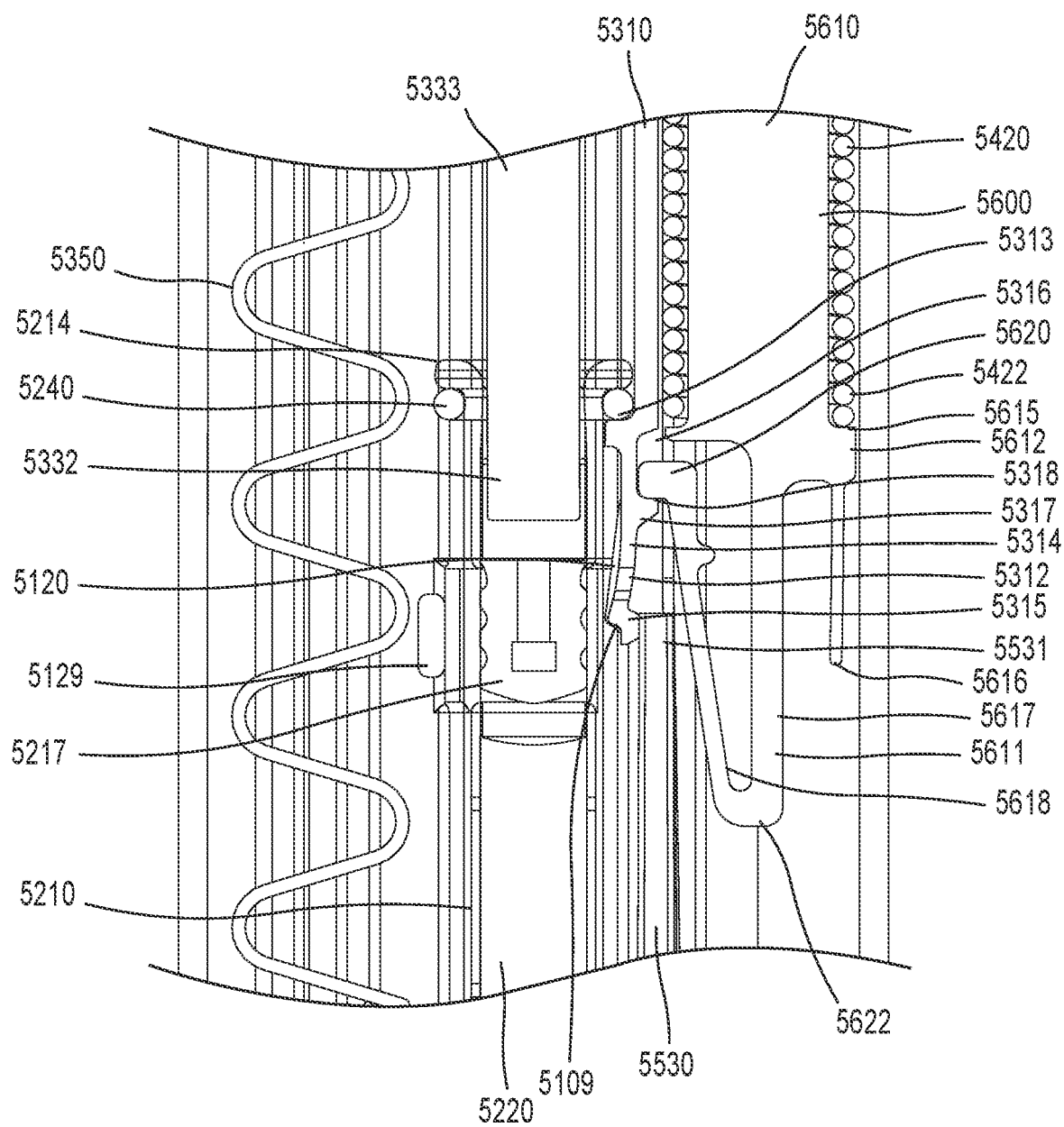
FIG. 72 is an enlarged view of a portion of the medicament delivery mechanism on the medical injector illustrated in FIG. 71.

The release member 5530 has a proximal end portion 5531 and a distal end portion 5532. The release member 5530 extends from a proximal surface 5511 of the base 5510. The proximal end portion 5531 of the release member 5530 is configured to engage that latch portion 5310 of the medicament delivery mechanism 5300 when the medical injector is in its first (or storage) configuration. More particularly, as shown in FIG. 72, the proximal end portion 5531 of the release member 5530 maintains a first latch protrusion 5315 of the latch portion 5310 in contact with the engagement surface 5109 of the latch member notch 5120 of the housing 5100. When the engagement surface 5109 is in contact with the first latch protrusion 5315, the engagement surface 5109 applies a reaction force to the first latch protrusion 5315 in response to the force applied by the spring 5420, which urges the transfer member 5600 and the medicament delivery mechanism 5300 in a distal direction. Similarly stated, when the first latch protrusion 5315 is in contact with the engagement surface 5109, the engagement surface 5109 limits distal movement of the first latch protrusion 5315, and thus, the medicament delivery mechanism 5300. In this manner, when the system actuator 5500 is in a first position (i.e., coupled to the distal end portion of the housing 5100), the release member 5530 maintains the first latch protrusion 5315 within the latch member notch 5120 and maintains the medical injector 5000 in the first configuration (e.g., non-actuated configuration).

The medicament delivery mechanism 5300 (all or portions of which can also be referred to as a "first movable member") includes the latch portion 5310, the piston portion 5330 and the bias portion 5350 (see e.g., FIGS. 75-78). The latch portion 5310 is operably coupled to the spring 5420 via the transfer member 5600 (i.e., the second movable member 5600). The medicament delivery mechanism 5300 includes a proximal end portion 5301. The proximal end portion 5301 includes the guide protrusions 5302, described above with reference to FIGS. 67-70.

The latch portion 5310 includes a proximal end portion 5311 and a distal end portion 5312. The proximal end portion 5311 is disposed at and/or joined with the proximal end portion 5301 of the medicament delivery mechanism 5300. Similarly stated, the latch portion 5310 is configured to extend from the proximal end portion 5301 of the medicament delivery mechanism 5300 in the distal direction. The distal end portion 5312 of the latch portion 5310 includes a latch arm 5314 having a first latch protrusion 5315, a second latch protrusion 5317, and a second shoulder 5313, and defines a channel 5316. As described above, the first latch protrusion 5315 is configured to engage the release member 5530 and the engagement surface 5109 of the latch member notch 5120. In particular, as shown in FIG. 72, the release member 5530 urges, bends and/or deforms the latch arm 5314 to maintain the first latch protrusion 5315 within the latch member notch 5120. Thus, the latch arm 5314 can be constructed from a flexible material such that the release member 5530 can urge, bend and/or deform the latch arm 5314 to engage the first latch protrusion 5315 with the latch member notch 5120.

The channel 5316 of the latch portion 5310 is defined between a surface of the distal end portion 5312 of the latch portion 5310 and a proximal surface 5318 of the second latch protrusion 5317. The channel 5316 is configured to receive the latch 5620 of the transfer member 5600. More particularly, when the medical injector 5000 is in the first configuration, the proximal surface 5318 of the second latch protrusion 5317 is in contact with a distal surface 5621 of the latch 5620 of the transfer member 5600. In this manner, the transfer member 5600 can transfer a force produced by the actuation of the spring 5420 to the latch portion 5310 of the medicament delivery mechanism 5300 to move the medicament delivery mechanism 5300 in the distal direction. Similarly stated, this arrangement allows the medicament delivery mechanism 5300 to move with and/or remain coupled to the transfer member 5600 (which can be referred to as a "second movable member") during the insertion and/or injection operation.

The piston portion 5330 includes a proximal end portion 5331 and a distal end portion 5332 and defines a piston rod 5333 therebetween. The proximal end portion 5331 is disposed at and/or joined with the proximal end portion 5301 of the medicament delivery mechanism 5300. Similarly stated, the piston portion 5330 is configured to extend from the proximal end portion 5301 of the medicament delivery mechanism 5300 in the distal direction. The distal end portion 5332 is configured to be disposed at least partially within the proximal end portion 5212 of the medicament container 5200. The piston rod 5333 defines recesses 5334.

The piston portion 5330 includes two engagement members 5336 that have a first shoulder 5335 and a deformable portion 5338. The engagement members 5336 are at least partially disposed within the recesses 5334 defined by the piston rod 5333, and extend in a lateral direction relative to the piston portion 5330. Similarly stated, the engagement members 5336 extend from the corresponding recess 5334 and are substantially perpendicular to a longitudinal axis defined by the piston portion 5330 between the proximal end portion 5331 and the distal end portion 5332. In this manner, as described in more detail herein, when the engagement members 5336 are deformed (e.g., at the deformable portion 5338), the engagement members 5336 fold into and/or are contained within the recesses 5334. The engagement members 5336 can be any suitable size or shape. In some embodiments, the engagement members 5336 can be monolithically formed with the piston portion 5330. In other embodiments, the engagement members 5336 can be formed separately from a brittle material and later coupled to the piston portion 5330. In still other embodiments, the engagement members 5336 can be formed separately from a flexible material and coupled to the piston portion 5330. In some embodiments, for example, the engagement members 5336 can be a single pin that is disposed through an opening within the piston portion 5330 such that the ends of the pins protrude from the recesses 5334.

Figure 91:
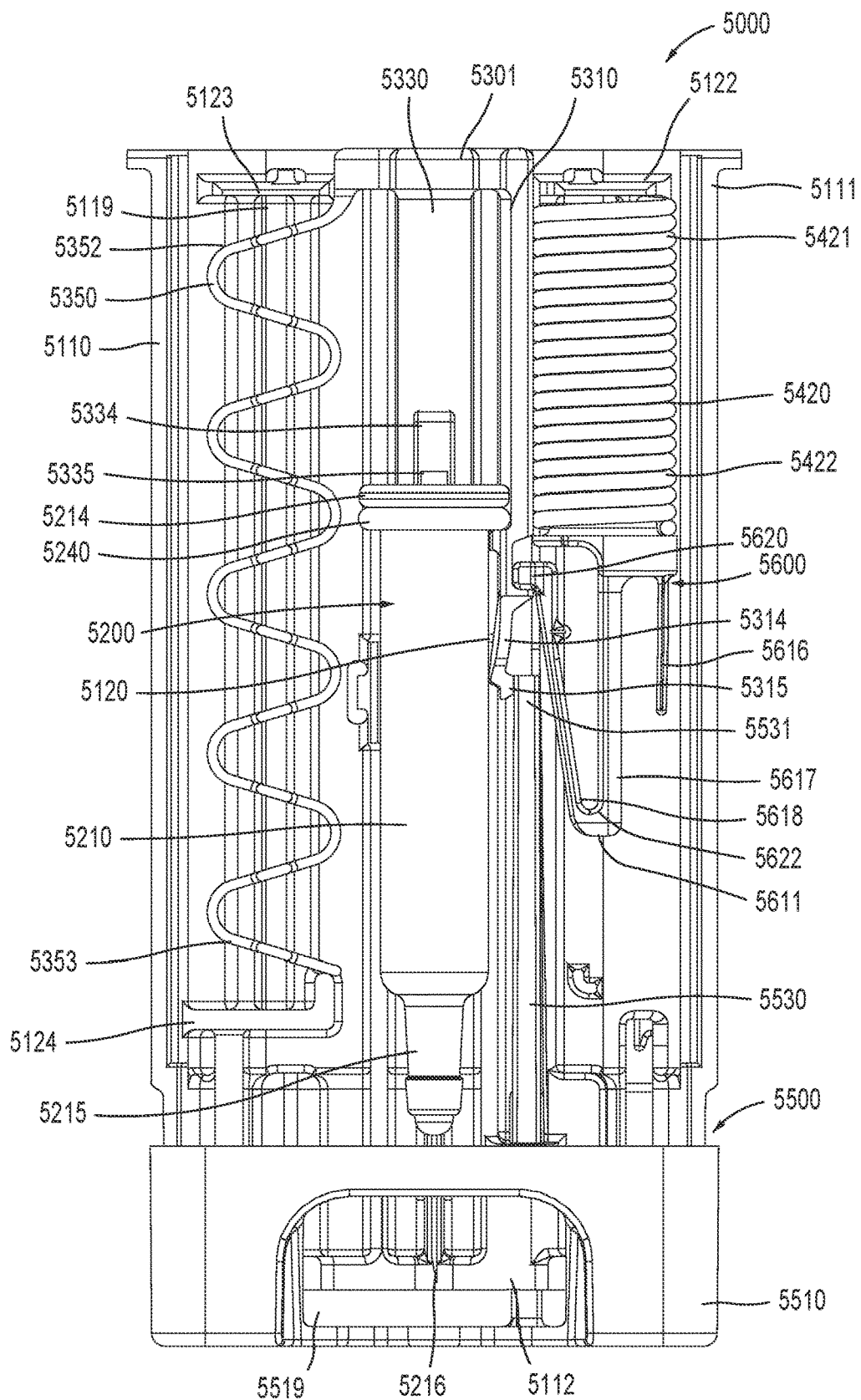
FIG. 91 is a front view of a portion of the medical injector illustrated in FIG. 60 in the third configuration.

The first shoulder 5335 of the engagement member 5336 is disposed at a distal surface of the engagement member 5336. As shown in FIG. 91, the first shoulder 5335 is configured to engage a proximal surface of the flange 5214 of the medicament container 5200. In this manner, the piston portion 5330 of the medicament delivery mechanism 5300 is configured to move the medicament container 5200 in response to a force applied by the spring 5420 when the medical injected 5000 is actuated. Similarly stated, when the release member 5530 actuates the medical injector 5000, the transfer member 5600 transfers a force from the spring 5420 to the medicament delivery mechanism 5300 such that the first shoulder 5335 of the piston portion 5330 moves the medicament container 5200 from the first position to the second position.

The deformable portion 5338 of the engagement member 5336 is configured to deform during and/or to initiate an injection event. The deformable portion 5338 can be any suitable structure that deforms (e.g., either plastically or elastically, including bending, breaking, stretching or the like) when the force applied thereto exceeds a value. For example, in some embodiments, the deformable portion 5338 can include a fillet configured to act as a stress concentration riser configured to deform under a given force. In use within the medical injector 5000, the deformable portion 5338 is configured to deform during and/or to initiate an injection event when the medicament container 5200 is in the second position. After deformation of the deformable portion 5338 and/or movement of the engagement members 5336, the first shoulder 5335 is no longer in contact with the flange 5214 of the medicament container 5200 and the piston portion 5330 is allowed to move in a distal direction, relative to the medicament container 5200.

The bias portion 5350 includes a proximal end portion 5352 and a distal end portion 5353. The proximal end portion 5352 is disposed at and/or joined with the proximal end portion 5301 of the medicament delivery mechanism 5300. Similarly stated, the bias portion 5350 is configured to extend from the proximal end portion 5301 of the medicament delivery mechanism 5300 in the distal direction.

Figure 95:
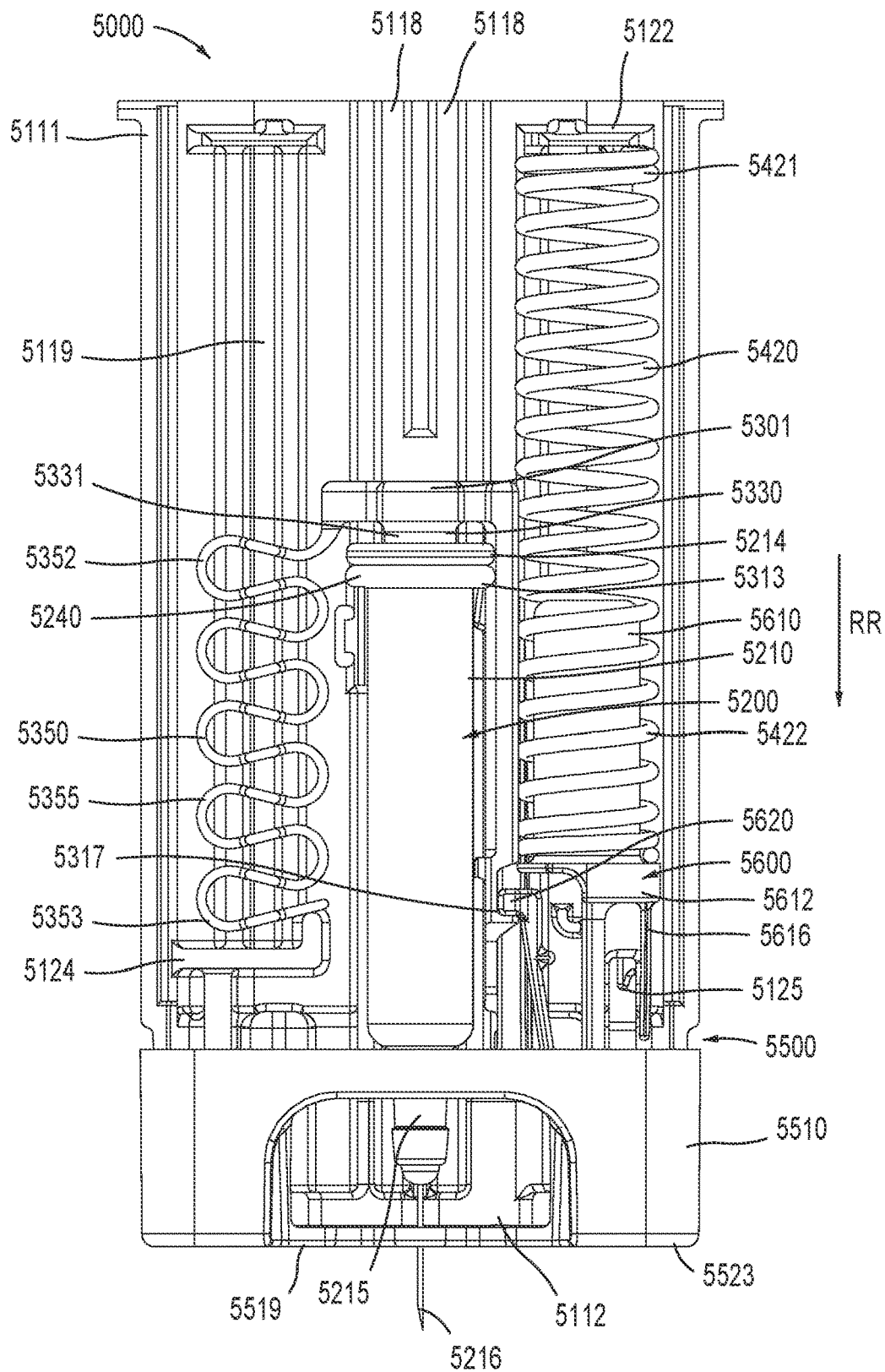
FIG. 95 is a front view of the medical injector illustrated in FIG. 60 in a fifth configuration (i.e., the injection configuration).
Figure 96:
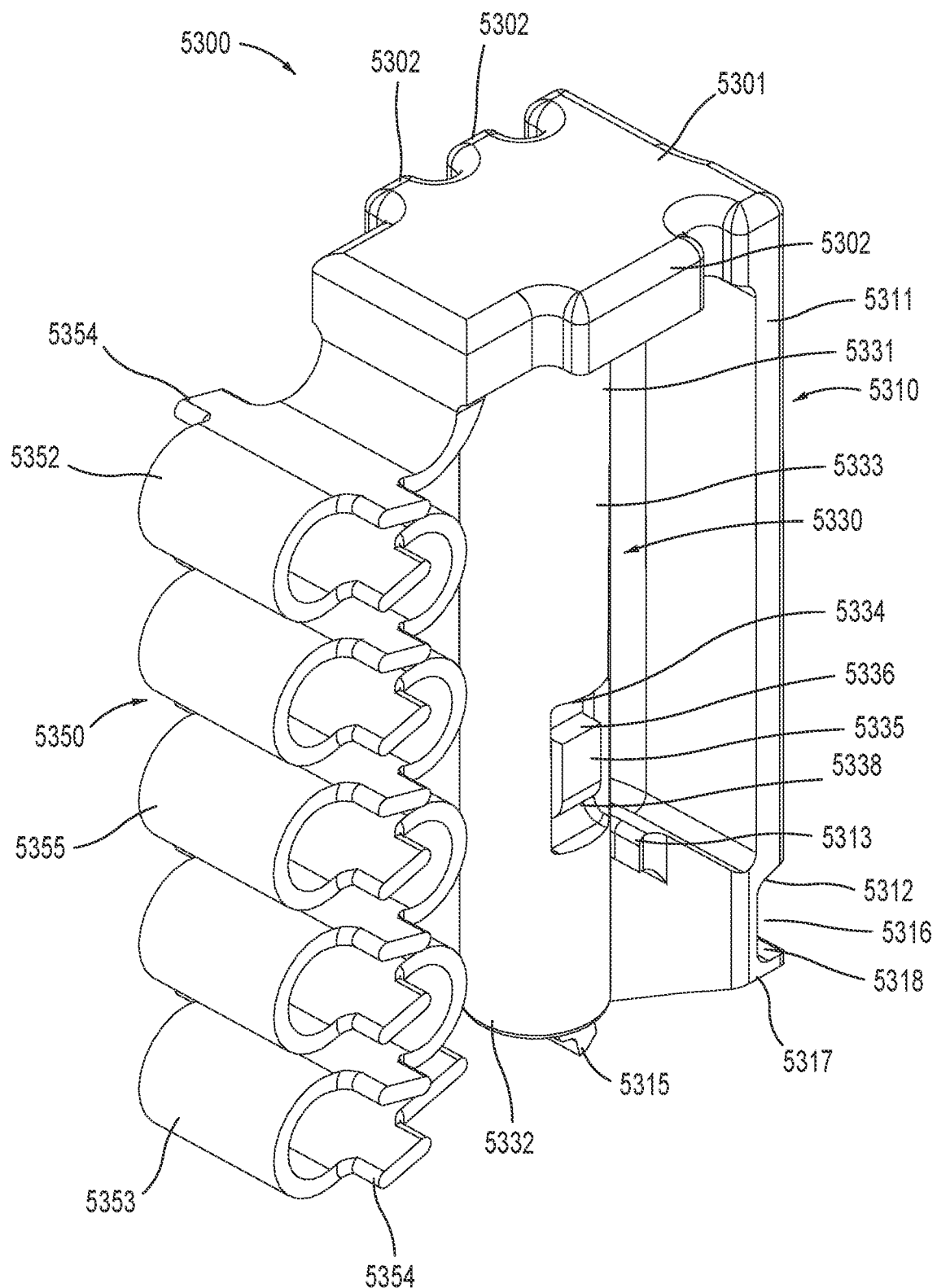
FIG. 96 is a perspective view of a first movable member of the medical injector illustrated in FIG. 60 in a second configuration.

The bias portion 5350 includes a serpentine portion 5355 constructed from any suitable material and having suitable dimensions such that the bias portion 5350 and/or the serpentine portion 5355 produce a force when the serpentine portion 5355 is compressed (see e.g., FIG. 95). As described above, the bias portion 5350 includes guide protrusions 5354 (see e.g., FIG. 76) configured to engage the bias member grooves 5119 defined by the first housing member 5110 and the bias member grooves 5149 defined by the second housing member 5140 to prevent the bias portion 5350 from moving in a lateral direction with respect to the housing 5100 and/or rotating within the housing 5100. The distal end portion 5353 of the bias portion 5350 is configured to engage the lower bias plate 5124. In this manner, a proximal surface of the lower bias plate 5124 prevents the distal end portion 5353 of the bias portion 5350 from moving in the distal direction as the medicament delivery device 5300 moves in the distal direction in response to the distal force applied by the spring 5420 when the medical injector 5000 is actuated. Therefore, the serpentine portion 5355 of the bias portion 5350 is compressed between the proximal end portion 5352 and the distal end portion 5353.

Figure 97:
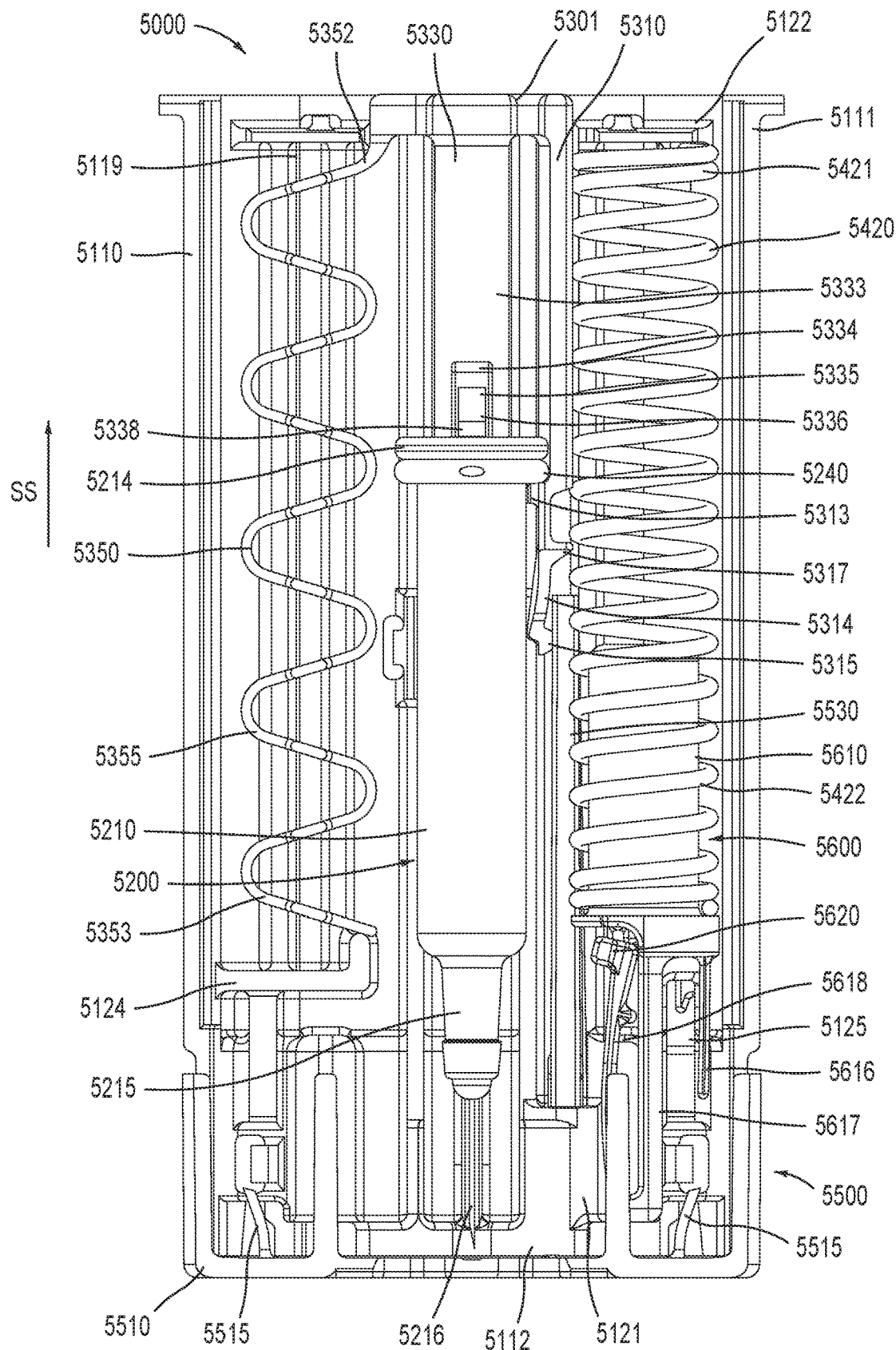
FIG. 97 is a front view of the medical injector illustrated in FIG. 60 in a sixth configuration (i.e., the retraction configuration).
Figure 98:
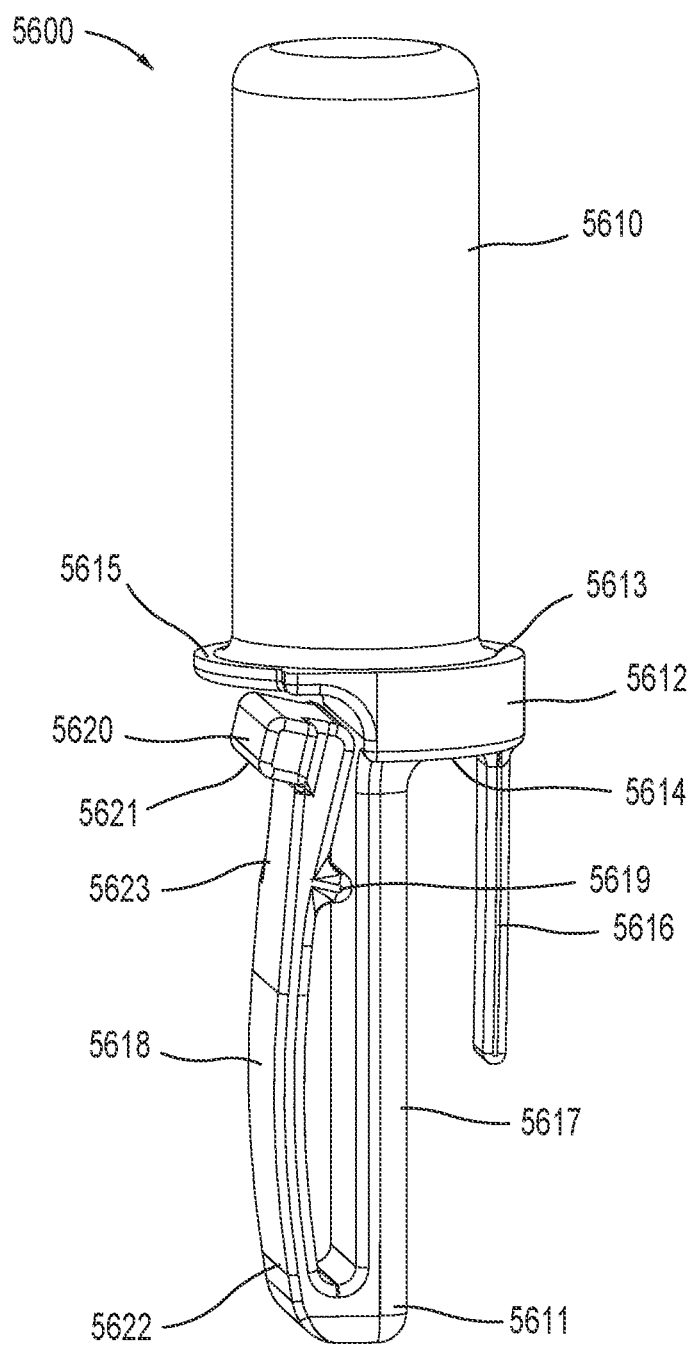
FIG. 98 is a front perspective view of a second movable member of the medical injector illustrated in FIG. 60 in a second configuration.

The transfer member 5600 (also referred to as the "second movable member") includes a proximal end portion 5610 and a distal end portion 5611, and is configured to move between a first configuration (see e.g., FIGS. 79 and 80) and a second configuration (see e.g., FIGS. 97 and 98). The proximal end portion 5610 is substantially cylindrical and is configured to engage and/or contact the spring 5420. Moreover, the transfer member 5600 includes a ring protrusion 5612 that includes a proximal surface 5613 defining a spring seat 5615. As shown in FIG. 72, the distal end portion 5422 of the spring 5420 is disposed about the proximal end portion 5610 of the transfer member 5600, and is configured to engage the spring seat 5615 defined by the ring protrusion 5612.

The transfer member 5600 further includes a guide arm 5616 and the latch extension 5617 that extends from a distal surface 5614 of the ring protrusion 5612. The guide arm 5616 is configured to guide the transfer member 5600 as it moves in the distal direction and provide support to the latch extension 5617 when the transfer member 5600 is placed in the second configuration, as described in further detail herein.

The latch extension 5617 includes the latch arm 5618 and a bendable portion 5622. The latch arm 5618 includes the guide protrusion 5619 and the latch 5620. As described above, the latch extension 5617 extends in a distal direction from the ring protrusion 5612 of the transfer member 5600. The latch arm 5618 is configured to extend from the distal end portion 5611 of the transfer member 5610. Similarly stated, the latch arm 5618 extends from a distal end portion of the latch extension 5617. Moreover, the latch arm 5618 extends from the distal end portion of the latch extension 5617 at a suitable angle such that the latch 5620 is received within the channel 5316 (see e.g., FIG. 72). For example, in some embodiments, the latch arm 5618 extends from the distal end portion of the latch extension 5617 at an acute angle. The guide protrusion 5619 is configured to engage the transfer member groove 5117, as described above.

The latch 5620 extends from a proximal end portion 5623 of the latch arm 5618. The latch 5620 is configured to engage the second latch protrusion 5317 of the latch portion 5310 of the medicament delivery mechanism 5300. As described above, the distal surface 5621 of the latch 5620 is configured to be in contact with a proximal surface 5318 of the second latch protrusion 5317 when the transfer member 5600 is in the first configuration. In this manner, the transfer member 5600 transfers a force from the actuation of the spring 5420 to the medicament delivery mechanism 5300 via the transfer member 5600 to move the medicament delivery mechanism 5300 in the distal direction within the housing 5100. Therefore, the force produced by the spring 5420 results in both the insertion of the needle 5216 and injection of the medicament 5220 within the medicament container 5200, which occur as separate and distinct operations, as described herein.

Furthermore, when the transfer member 5600 has moved a desired distance in the distal direction, in response to the force produced by the actuation of the spring 5420, the latch arm 5618 engages the transfer member release protrusion 5121 of the housing 5100 (see e.g., FIG. 67) to place the transfer member 5600 in the second configuration. Similarly stated, the latch arm 5618 engages and/or contacts the transfer member release protrusion 5121 when the transfer member 5600 is in the second position. The bendable portion 5622 of the latch extension 5617 is configured to bend, relative to the latch extension 5617. Thus, when the latch arm 5618 engages the transfer member release protrusion 5121, the bendable portion 5622 of the transfer member 5600 bends, thereby placing the transfer member 5600 in its second configuration (see FIGS. 97 and 98). When the transfer member 5600 is in its second configuration, the latch 5620 is disengaged from the second latch protrusion 5317 of the medicament delivery mechanism 5300. Said another way, when the latch arm 5618 engages the transfer member release protrusion 5121, the bendable portion 5622 of the transfer member bends such that the angle between the latch arm 5618 and the latch extension 5617 is reduced, thus disengaging the transfer member 5600 from the medicament delivery mechanism 5300. Said yet another way, when the transfer member 5600 is in its second configuration, the medicament delivery mechanism 5300 is isolated and/or no longer operably coupled to the spring 5420. In this manner, as described below, the retraction force exerted by the biasing portion 5350 moves the medicament delivery mechanism 5300 proximally within the housing 5100 to retract the needle 5216.

Figure 81:
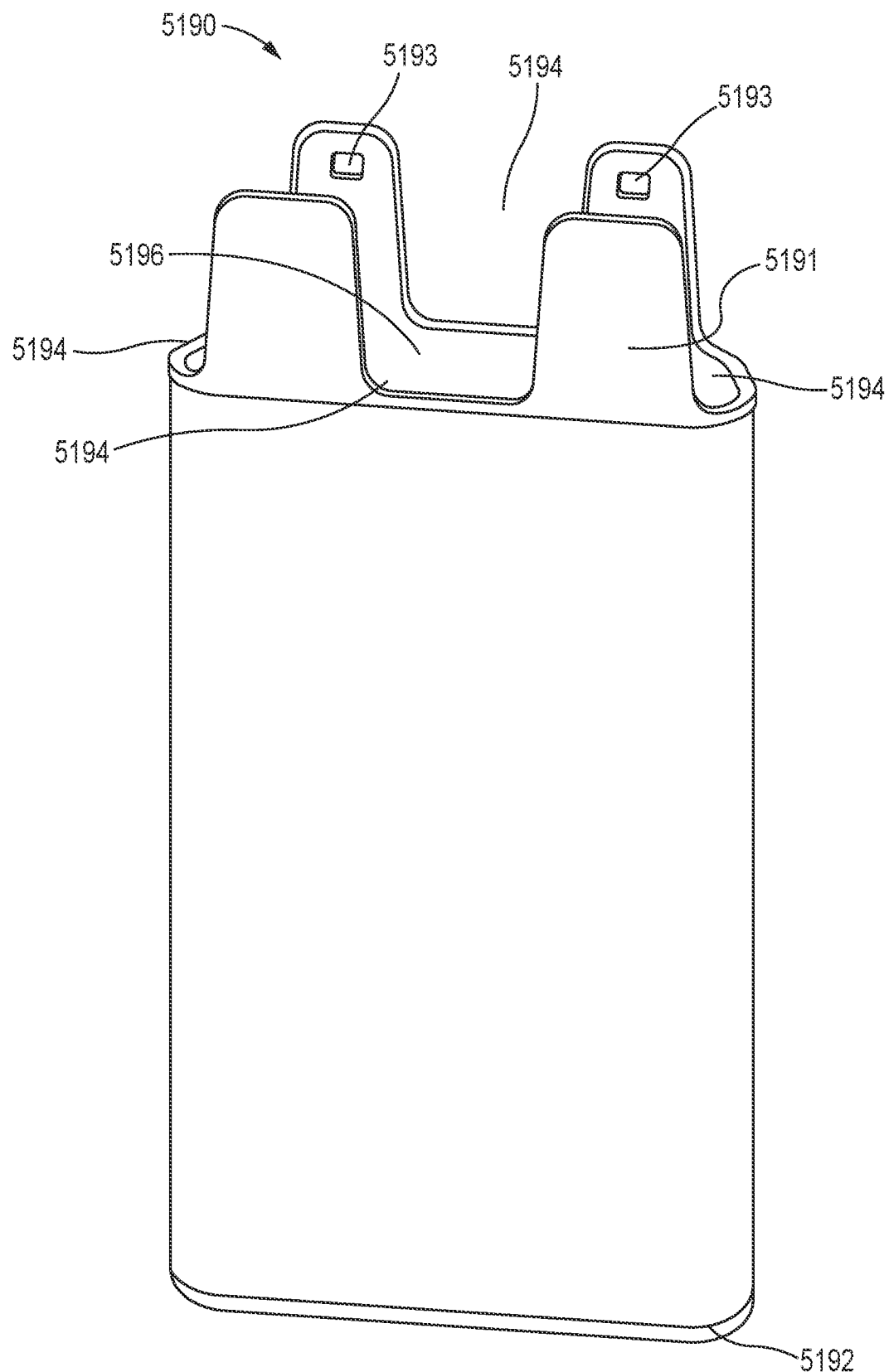
FIGS. 81 and 82 are perspective views of a cover of the medical injector illustrated in FIG. 60.
Figure 82:
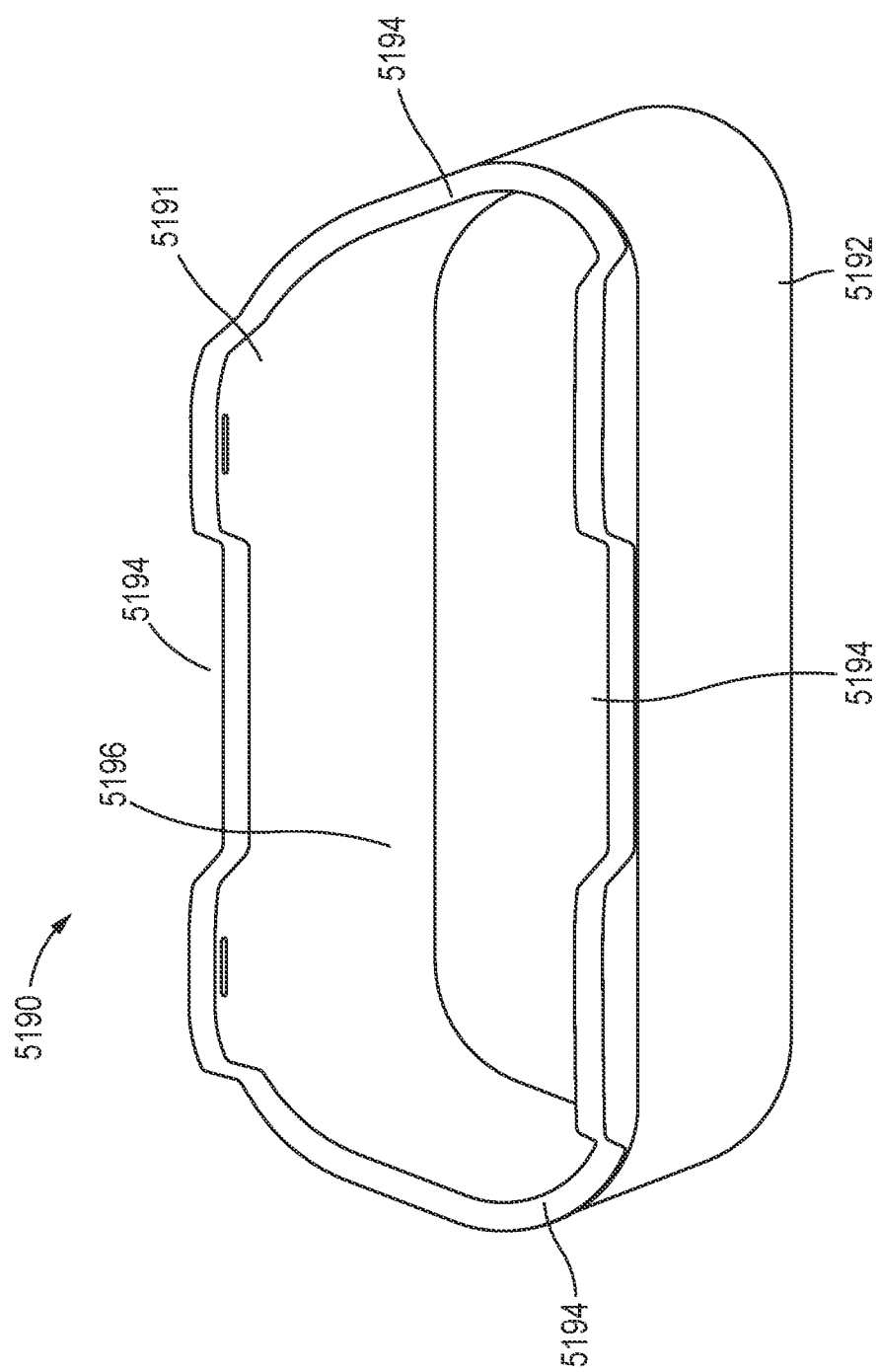
Figure 83:
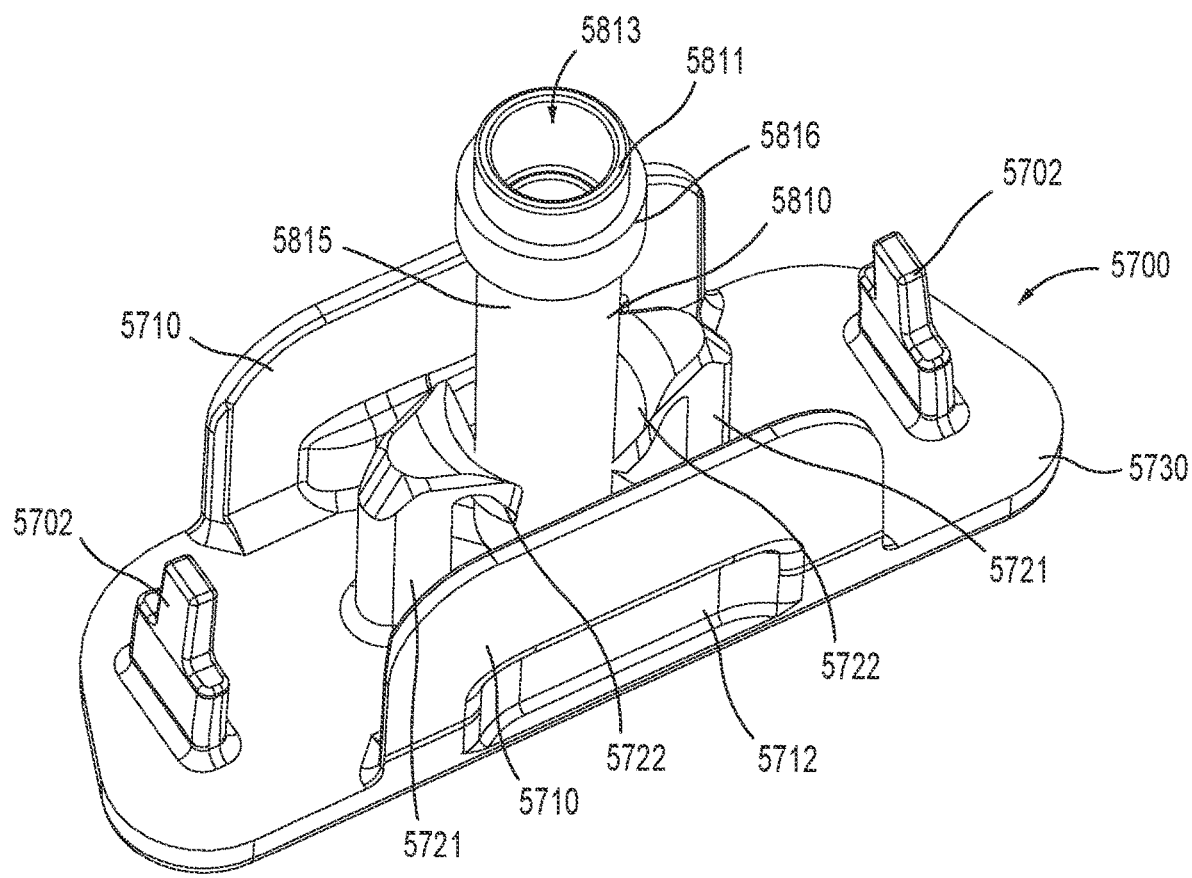
FIG. 83 is a perspective view of a safety lock of the medical injector illustrated in FIG. 60.
Figure 84:
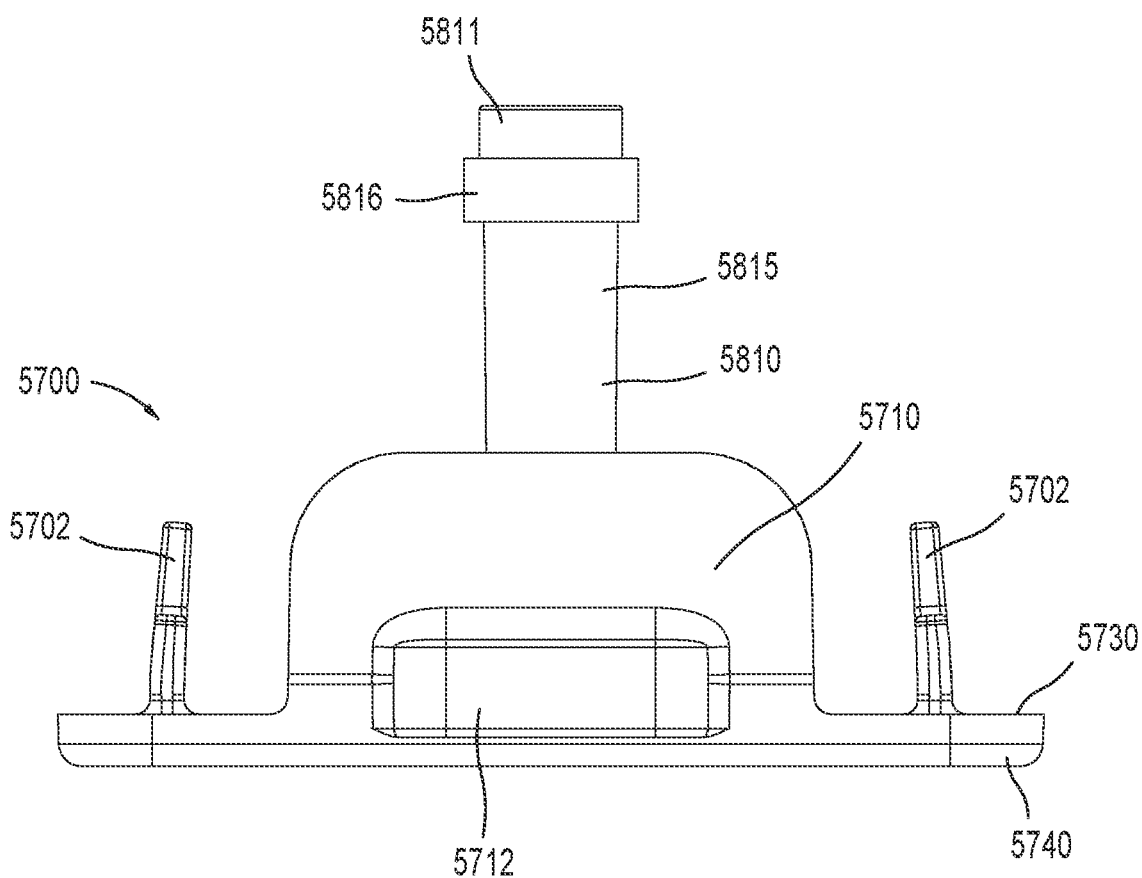
FIG. 84 is a front view of the safety lock of the medical injector illustrated in FIG. 83.
Figure 85:
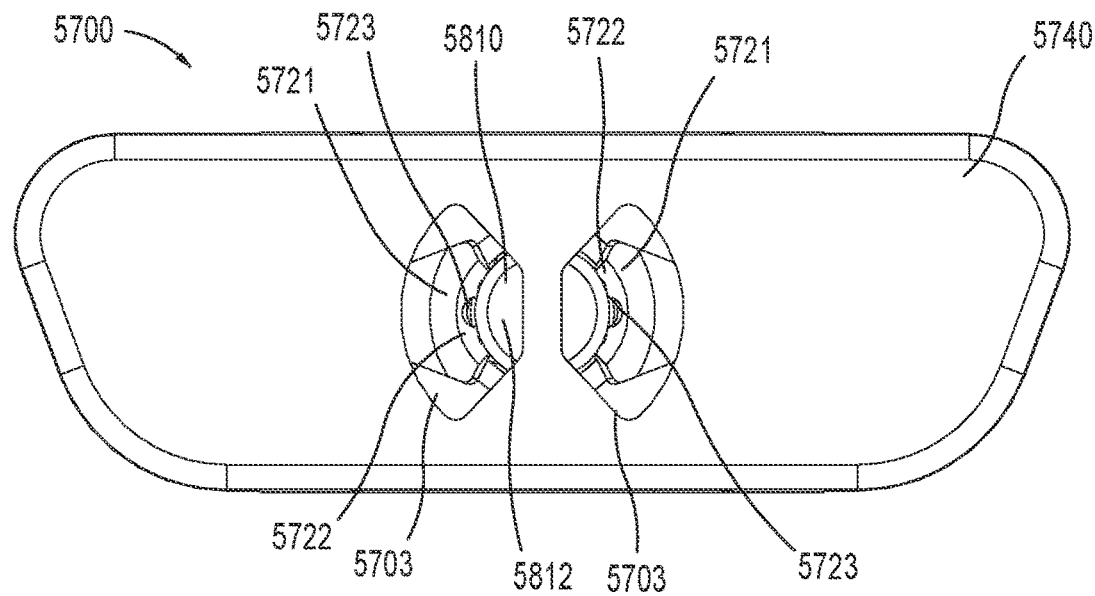
FIG. 85 is a bottom view of the safety lock of the medical injector illustrated in FIG. 83.

FIGS. 81 and 82 show the cover 5190 of the medical injector 5000. The cover 5190 includes a proximal end portion 5191 and a distal end portion 5192, and defines a cavity 5196. The cavity 5196 of the cover 5190 is configured to receive at least a portion of the housing 5100. Thus, when the portion of the housing 5100 is disposed within the cover 5190, the cover 5190 blocks an optical pathway between the medicament container 5200 and a region outside of the housing 5100. Similarly stated, when the portion of the housing 5100 is disposed within the cover 5190, the cover 5190 is obstructs the first status indicator aperture 5130 and/or the second status indicator aperture 5160 of the housing 5100 to reduce the amount of light transmitted to the medicament 5220 within the medicament container 5200. In this manner, the life of the medicament 5220 can be extended by the prevention and/or reduction of degradation to the medicament 5220 that may be caused by ultra-violet radiation.

The proximal end portion 5191 of the cover 5190 defines apertures 5193. The apertures 5193 configured to receive the cover retention protrusions 5104 of the housing 5100 (shown in FIGS. 10 and 12). In this manner, the apertures 5193 and the cover retention protrusions 5104 of the housing 5100 removably retain the cover 5190 about at least a portion of the housing 5100. Said another way, the apertures 5193 and the cover retention protrusions 5104 of the housing 5100 are configured such that the cover 5190 can be removed from a portion of the housing 5100 and then replaced about the portion of the housing 5100.

The cover 5190 can be any suitable configuration and can include any suitable feature. For example, the cover 5190 includes openings 5195 and notches 5194. In some embodiments, the openings 5195 can receive inserts (not shown). The inserts can be a flexible inserts and can be configured to increase friction between the cover 5190 and a surface. For example, the inserts can increase the friction between the cover 5190 and a surface on which the medical injector 5000 is placed, to prevent sliding. The notches 5194 are disposed at the proximal end of the cover 5190. In some embodiments, the notches 5194 can be used to reduce the material needed to manufacture the cover 5190.

FIGS. 83-87 show the safety lock 5700 of the medical injector 5000. The safety lock 5700 of the medical injector 5000 includes a proximal surface 5730, a distal surface 5740 opposite the proximal surface 5730 and a needle sheath 5810. The safety lock 5700 defines a needle sheath aperture 5703. The proximal surface 5730 of the safety lock 5700 includes two safety lock protrusions 5702, two opposing pull-tabs 5710 and an engagement portion 5720. As described above, when the safety lock 5700 is in a first (locked) position, the safety lock protrusions 5702 are configured to be disposed through the safety lock protrusion apertures 5514 defined by the base 5510 (see e.g., FIG. 88) and within the base lock openings 5131 defined by the distal end portion 5102 of the housing 5100 (see e.g., FIG. 73). Accordingly, the safety lock protrusions 5702 are configured to prevent the base locks 5515 of the base 5510 from moving past the base lock protrusion 5126 of the first housing member 5110, thereby preventing proximal movement of the base 5510 and/or delivery of the medicament 5220. Similarly stated, when the medical injector 5000 is in its first configuration (i.e., the storage configuration), the safety lock protrusions 5702 are disposed adjacent and/or in contact with the base lock protrusions 5126, thereby preventing lateral deformation (e.g., a outward flexing motion) of the base lock protrusions 5126. Thus, the arrangement of the safety lock protrusions 5702 prevents the system actuator 5500 and/or the base 5510 from moving in the proximal direction to actuate the medicament delivery mechanism 5300.

The pull-tabs 5710 of the safety lock 5700 include a grip portion 5712. The grip portion 5712 of the pull-tabs 5710 provides an area for the user to grip and/or remove the safety lock 5700 from the rest of the medicament delivery system

5700. In some embodiments, the pull-tabs 5710 can include indicia, such as, for example, an indicia similar to that included in the pull tabs 3710 of the safety lock 3700, described with reference to FIG. 43.

The engagement portion 5720 of the safety lock 5700 includes engagement members 5721. The engagement members 5721 extend in a proximal direction from the proximal surface 5730. The engagement members 5721 have tabs 5722 that extend from a surface of the engagement members 5721. The tabs 5722 are configured to engage an outer surface 5815 of a distal end portion 5812 of the needle sheath 5810.

Figure 86:
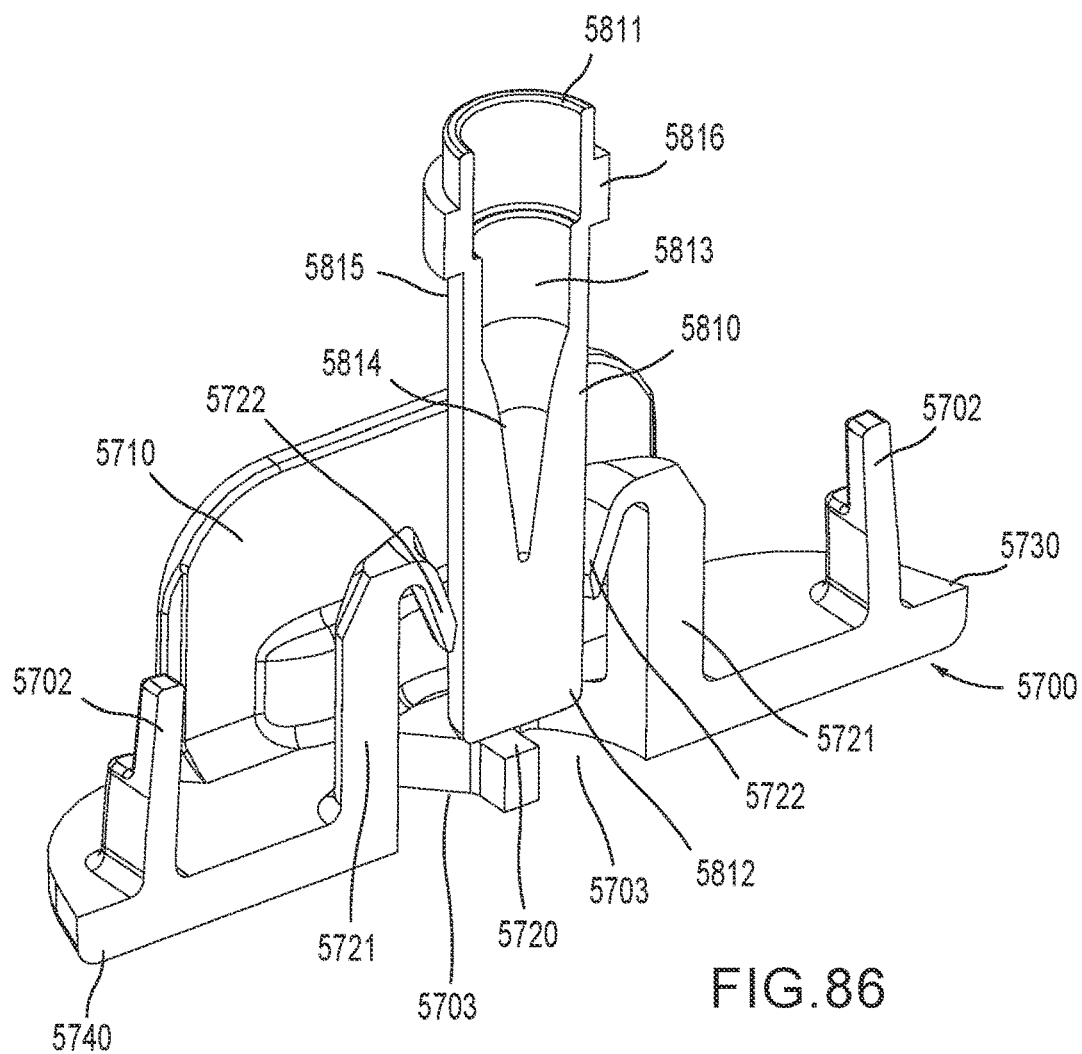
FIG. 86 is a cross-section view of the safety lock of the medical injector illustrated in FIG. 83.
Figure 87:
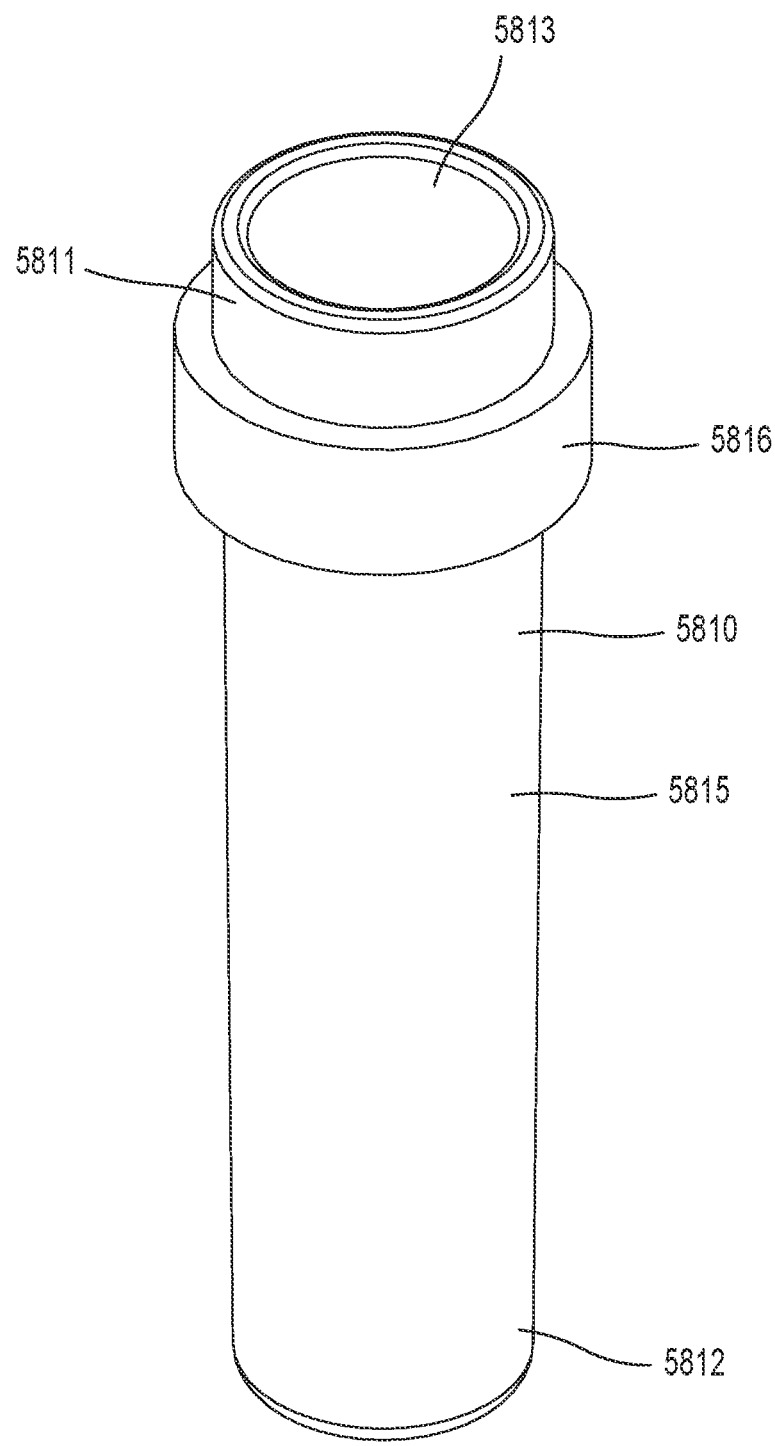
FIG. 87 is a perspective view of a needle sheath of the safety lock of the medical injector illustrated in FIG. 83.

As shown in FIGS. 86 and 87, the needle sheath 5810 includes the distal end portion 5812, a proximal end portion 5811 and a rib 5816. The needle sheath 5810 further includes a contoured portion 5814 that defines a bore 5813. The bore 5813 of the needle sheath 5810 is configured to receive the needle 5216 and/or a distal end portion of the 5213 of the medicament container 5200. The contoured portion 5814 of the needle sheath 5810 defines a friction fit with the distal end portion 5213 of the medicament container 5200. In this manner, the needle sheath 5810 can protect the user from the needle 5216 and/or can keep the needle 5216 sterile before the user actuates the medical injector 5000. The proximal end portion 5811 of the needle sheath is configured to contact the body 5210 of the medicament container 5200.

The distal end portion 5812 of the needle sheath 5810 is configured to be inserted into a space defined between the tabs 5722 of the engagement members 5721 of the safety lock 5700. The tabs 5722 are angled and/or bent towards the distal direction to allow the distal end portion 5812 of the needle sheath 5810 to move between the engagement members 5721 in a distal direction, but not in a proximal direction. Similarly stated, the tabs 5722 include an edge that contacts the outer surface 5815 of the needle sheath 5810 to prevent the safety lock 5700 from moving in a distal direction relative to the needle sheath 5810. Said another way, the needle sheath 5810 is removed from the needle 5216 when the safety lock 5700 is moved in a distal direction with respect to the housing 5100 (see e.g., FIG. 90).

Figure 88:
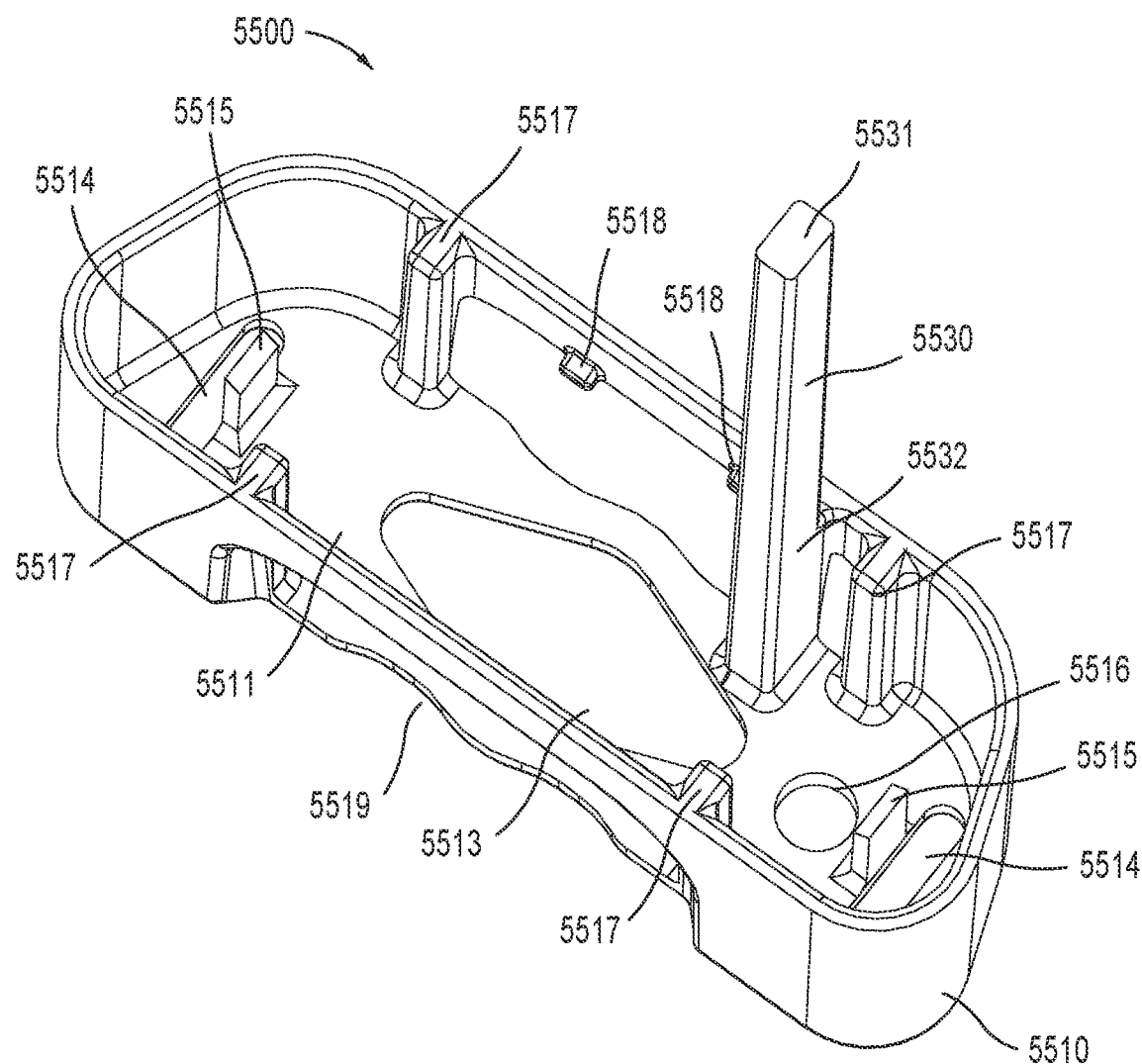
FIG. 88 is a perspective view of a base of the medical injector illustrated in FIG. 60.
Figure 89:
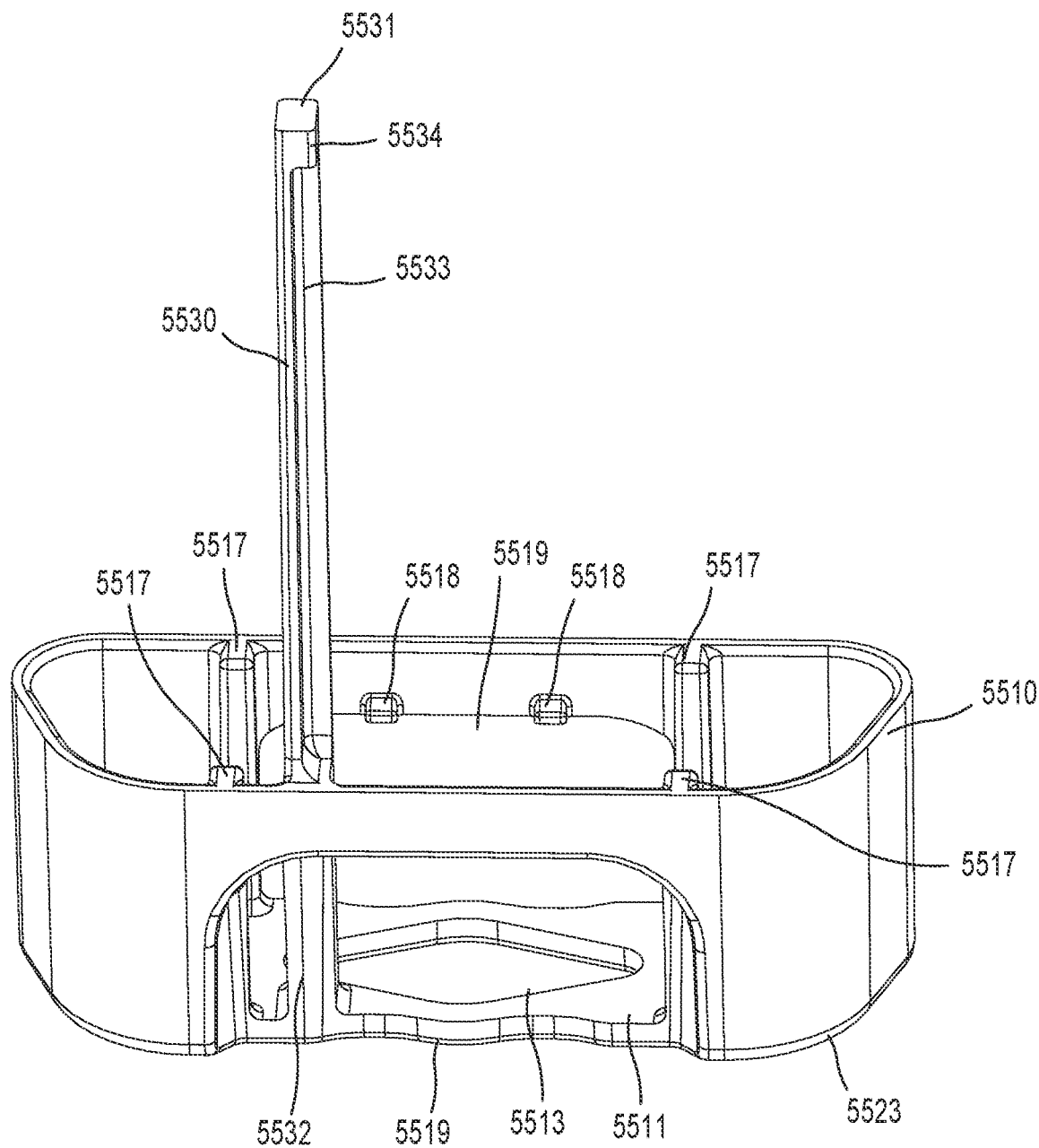
FIG. 89 is a front view of the base of the medical injector illustrated in FIG. 88.
Figure 90:
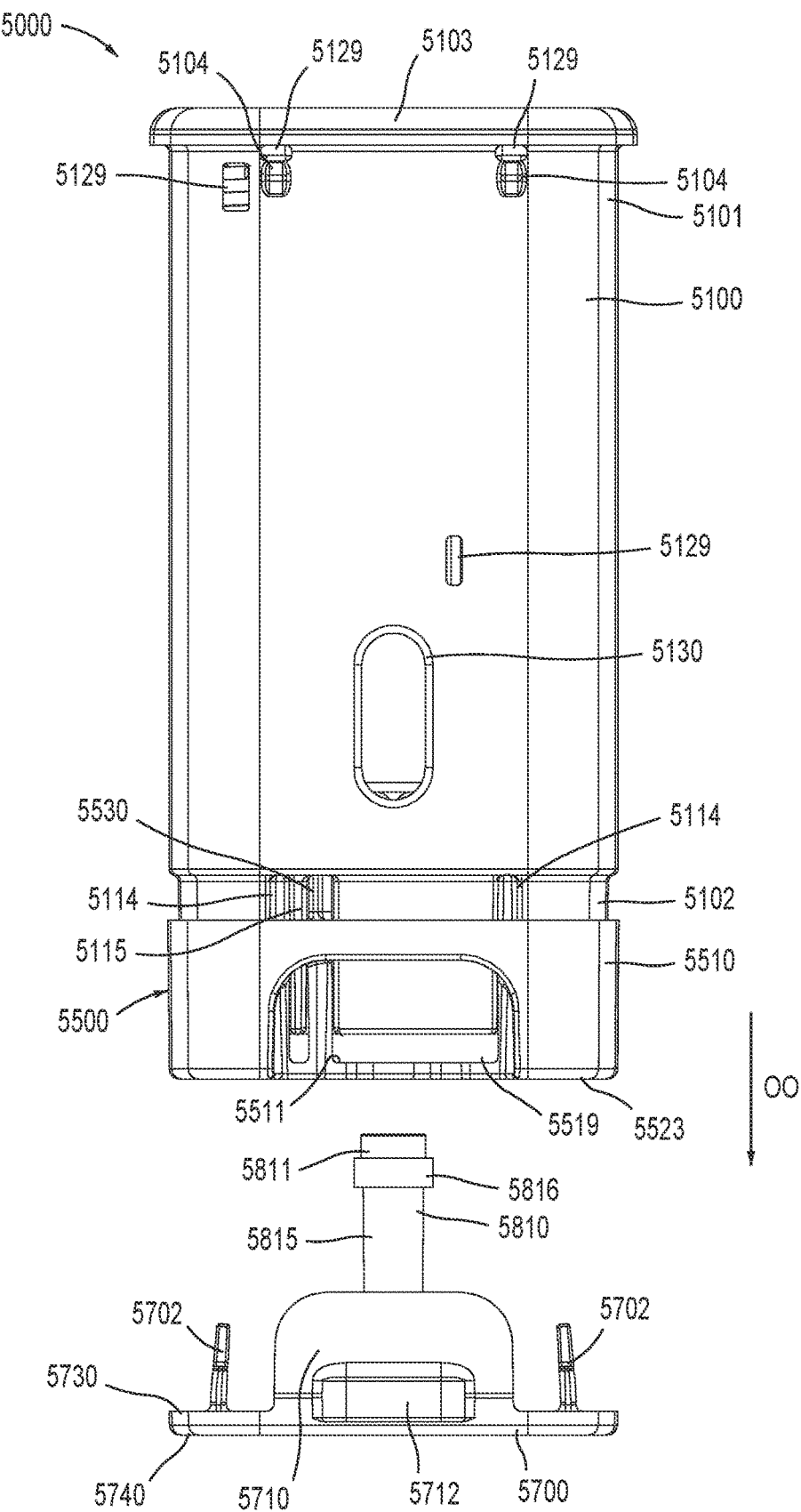
FIG. 90 is a front view of the medical injector illustrated in FIG. 60 in a third configuration.

FIGS. 88 and 89 show the base 5510 (or actuator) of the medical injector 5000. The base 5510 includes the proximal surface 5511, a distal surface 5523 and base connection knobs 5518. The base 5510 defines a needle aperture 5513, safety lock protrusion apertures 5514, transfer member access opening 5516 and pull-tab openings 5519. The needle aperture 5513 is configured to receive the needle 5216 when the medical injector 5000 is actuated. The safety lock protrusion apertures 5514 of the base 5510 receive the safety lock protrusions 5702 of the safety lock 5700 when the medical injector 5000 is in the first configuration, as described above. The transfer member access opening 5516 provides access to the transfer member 5600 when the transfer member 5600 is disposed within the housing 5100. The pull-tab openings 5519 are configured to receive the pull-tabs 5710 of the safety lock 5700 when the medical injector 5000 is in the first configuration.

Figure 71:
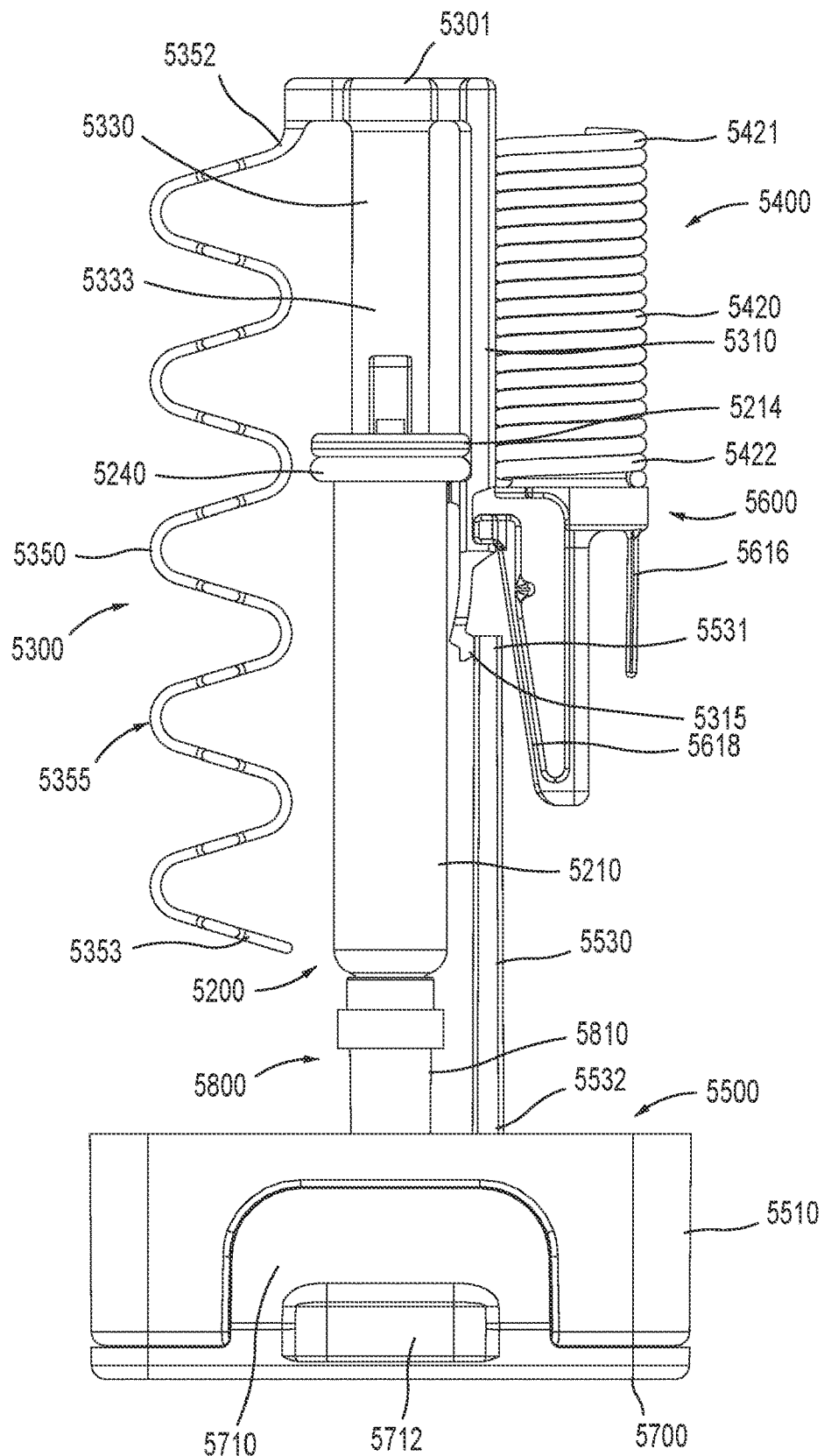
FIG. 71 is a front view of a medicament delivery mechanism of the medical injector illustrated in FIG. 60.

The proximal surface 5511 of the base 5510 includes and/or is coupled to the release member 5530, guide members 5517 and base locks 5515. The release member 5530 includes a proximal end portion 5531 and a distal end portion 5532 and defines a channel 5533 between a system lock surface 5534 and the distal end portion 5532 (see e.g., FIG. 89). As shown in FIG. 71, the system lock surface 5534 is disposed at the proximal end portion 5531 and is configured to engage the first latch protrusion 5315 of the medicament delivery mechanism 5300. Moreover, the system lock surface 5534 engages the first latch protrusion 5315 such that the system lock surface 5534 maintains the engagement of the first latch protrusion 5315 and the latch member notch 5120, as described above and shown in FIG. 72. Similarly stated, the system lock surface 5534 of the release member 5530 applies a force to the first latch protrusion 5315 to maintain the first latch protrusion 5315 within the latch member notch 5120. When the system actuator 5500 is moved in a proximal direction, as described in further detail herein, the system lock surface 5534 moves in the proximal direction to disengage the first latch protrusion 5315. In response, the first latch protrusion 5315 moves within the channel 5533 of the release member 5530 in a distal direction, as described in further detail herein. Similarly stated, upon actuation of the medicament injector 5000, a portion of the medicament delivery mechanism 5300 moves within the release member 5530.

The guide members 5517 of the base 5510 are configured to engage and/or slide within the base rail grooves 5114 of the housing 5100, as described above. The base locks 5515 of the base 5510 are configured to engage the base lock protrusions 5126 of the first housing member 5110. As described in further detail herein, when the safety lock 5700 is removed and the base 5510 is moved in a proximal direction with respect to the housing 5100, the base locks 5515 of the base 5510 are configured to disengage from the base lock protrusions 5126 and move in the proximal direction, relative to the base lock protrusions 5126. As described above, the base connection knobs 5518 are configured to engage the base retention recesses 5134A, 5134B in a way that allows proximal movement of the base 5510 but limits distal movement of the base 5510.

The medical injector 5000 is first enabled by moving the medicament delivery device 5000 from a first configuration to a second configuration by moving the cover 5190 from a first position to a second position. The cover 5190 is moved from the first position to the second position by moving it with respect to the housing 5100 in the distal direction. For example, the cover 5190 can be moved similarly to the cover 3190 of the medical injector 3000 described with reference to FIG. 49.

After the cover 5190 is removed from the housing 5100, the medical injector 5000 can be moved from the second configuration to a third configuration by moving the safety lock 5700 from a first position to a second position. The safety lock 5700 is moved from a first position to a second position by moving the safety lock 5700 with respect to the housing 5100 in the direction shown by the arrow OO in FIG. 90. Similarly stated, the medical injector 5000 can be moved from the second configuration to a third configuration by removing the safety lock 5700 from the distal end portion 5102 of the housing 5100. When the safety lock 5700 is moved from the first position to the second position, the safety lock protrusions 5702 are removed from within the base lock openings 5131 of the first housing member 5110, thereby enabling the system actuator 5500 and/or the base 5510. Similarly stated, when the safety lock 5700 is in the second position, the safety lock protrusions 5702 no longer maintain the engagement of the base locks 5515 with the base lock protrusions 5126 and/or the base locks 5515 can slide proximally relative to the base lock protrusion 5126 of the housing 5100. In this manner, the base 5510 can be moved from a first position to a second position. Moreover, with the safety lock 5700 removed, the needle sheath 5810 is removed from the medicament container 5200, as shown in FIG. 91.

After the safety lock 5700 is moved from the first position to the second position, the medical injector 5000 can be moved from the third configuration to a fourth configuration (i.e., the needle insertion configuration) by moving the base 5510 from the first position to the second position. Similarly stated, the medical injector 5000 can be actuated by the system actuator 5500 by moving the base 5510 proximally relative to the housing 5100. The base 5510 is moved from its first position to its second position by placing the medical injector 5000 against the body of the patient and moving the base 5510 with respect to the housing 5100 in the direction shown by the arrow PP in FIG. 92. With the base locks 5515 disengaged from the base lock protrusions 5126, the system actuator 5500 can move in the proximal direction causing the base locks 5515 move proximally past the base lock protrusions 5126.

Figure 92:
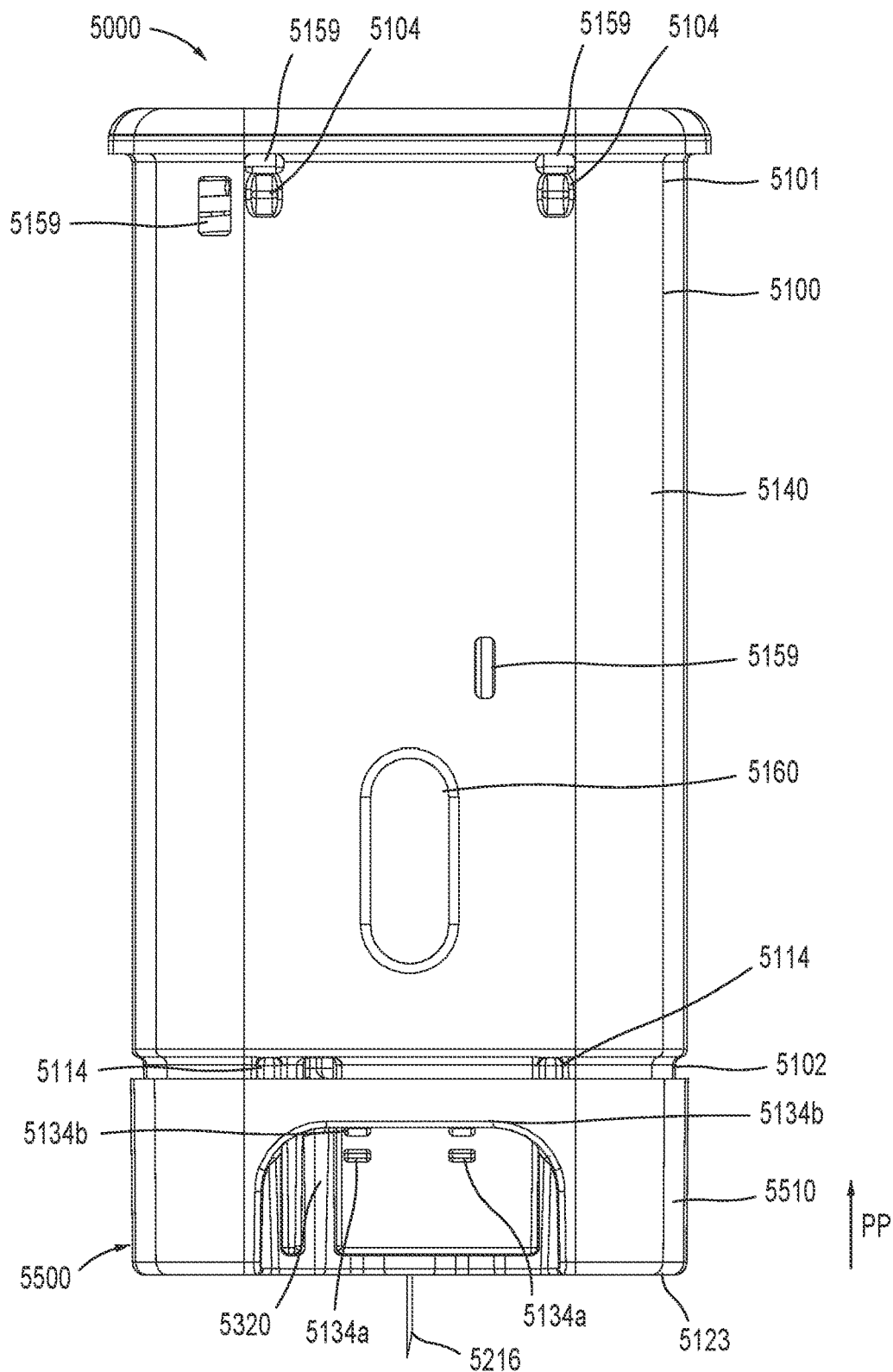
FIG. 92 is a front view of the medical injector illustrated in FIG. 60 in a fourth configuration (i.e., the needle insertion configuration).
Figure 93:
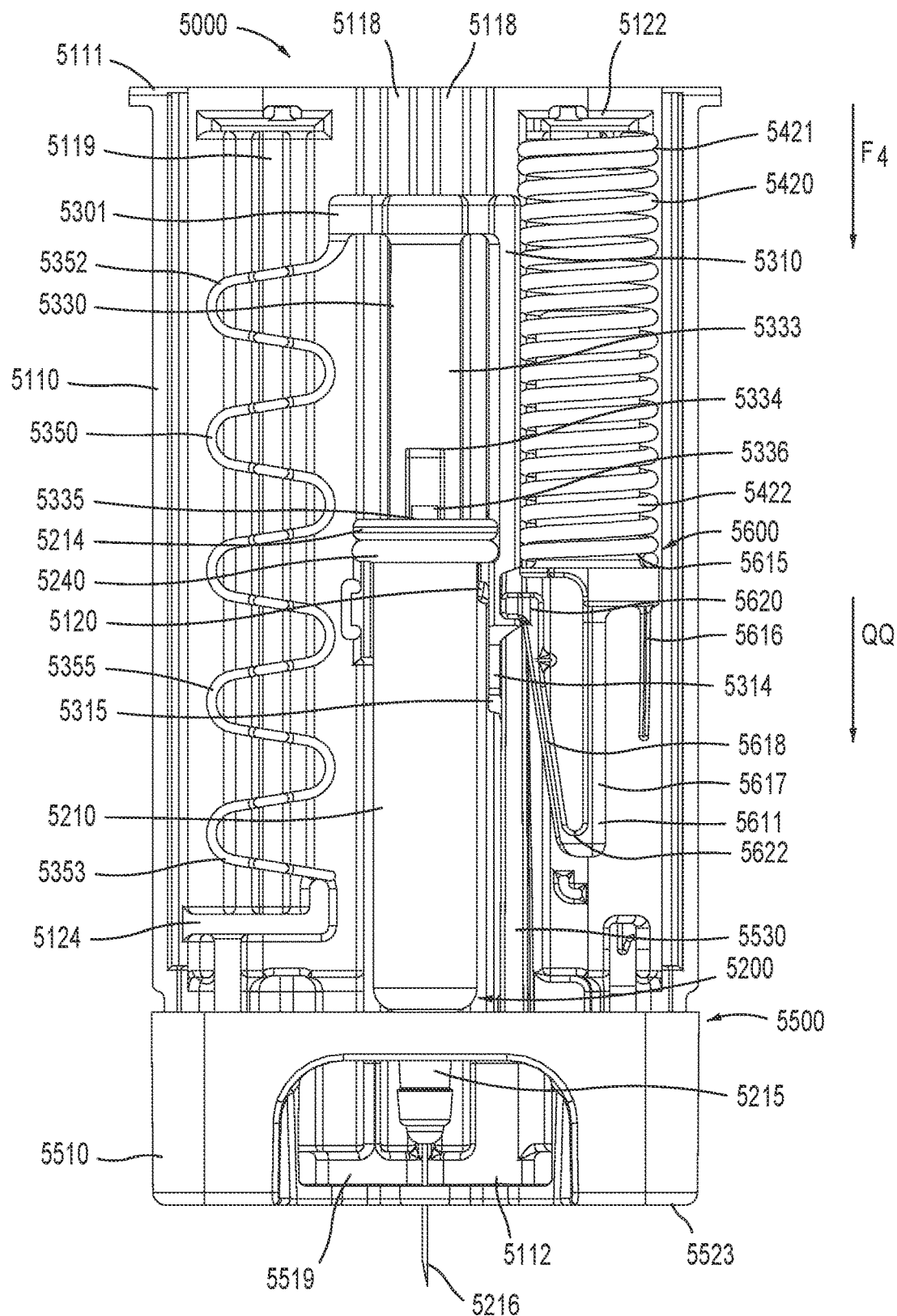
FIG. 93 is a front view of a portion of the medical injector illustrated in FIG. 60 in the fourth configuration (i.e., the needle insertion configuration).
Figure 94:
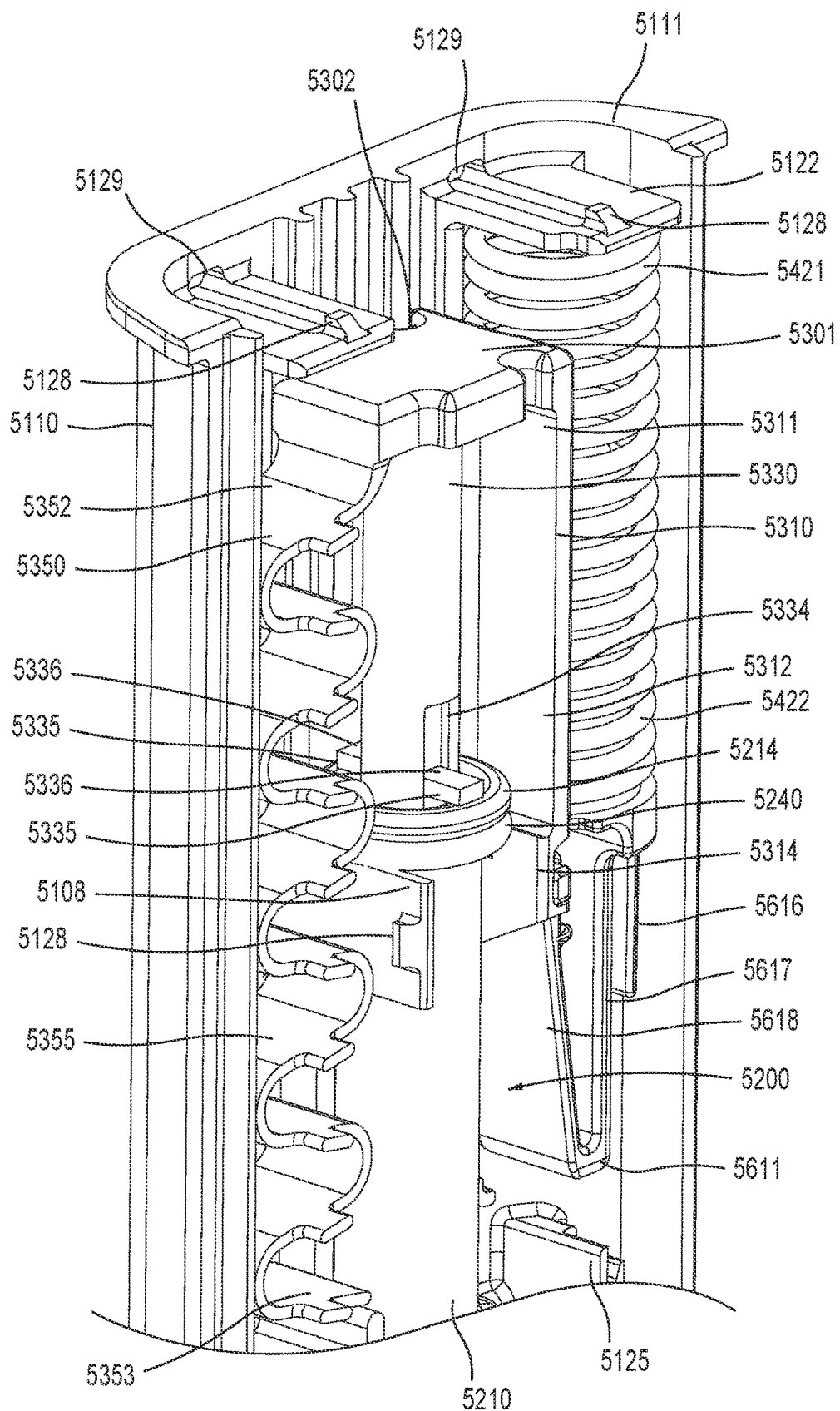
FIG. 94 is an enlarged perspective view of a portion of the medical injector illustrated in FIG. 60 in the fourth configuration (i.e., the needle insertion configuration).

When the base 5510 is moved from the first position to the second position, the system actuator 5500 actuates the medicament delivery mechanism 5300, thereby placing the medical injector 5000 in its fourth configuration (i.e., the needle insertion configuration), as shown in FIGS. 92-94. More specifically, the proximal movement of the system actuator 5500 and/or the base 5510 moves the release member 5530 in the proximal direction within the housing 5100, thereby allowing the first latch protrusion 5315 to be disengaged from the system lock surface 5534 of the proximal end portion 5533 of the release member 5530. Similarly stated, when the system actuator 5500 is moved in the proximal direction, the system lock surface 5534 disengages the first latch protrusion 5315. Moreover, when the system lock surface 5534 moves in the proximal direction relative to the first latch protrusion 5315, the first latch protrusion 5315 moves into the channel 5533 defined by the release member 5530.

When the first latch protrusion 5315 is disposed within the channel 5533, the force applied by the system lock surface 5534 of the base 5510 to maintain the first latch protrusion 5315 within the latch member notch 5120 is removed and the first latch protrusion 5315 is allowed to disengage the latch member notch 5120. Therefore, the engagement surface 5109 of the latch member notch 5120 no longer applies the reaction force to the first latch protrusion 5315; thus, the spring 5420 is allowed to expand. As described above, the proximal end portion 5421 of the spring 5420 is in contact with the upper spring plate 5122 of the first housing member 5110 such that the spring 5420 expands in the direction shown be the arrow QQ in FIG. 93. With the distal end portion 5422 of the spring 5420 in contact with the spring seat 5615 of the transfer member 5600, a force $F_4$ produced by the expansion of the spring 5420 is applied to the transfer member 5600, which moves the transfer member 5600 in the direction shown by the arrow QQ. In this manner, the latch 5620 of the transfer member 5600 transfers at least a portion of the force $F_4$ to the second latch protrusion 5317 of the latch portion 5310 of the medicament delivery mechanism 5300 such that the portion of the force moves the medicament delivery mechanism 5300 in the distal direction, shown by the arrow QQ in FIG. 93. Thus, the medicament delivery mechanism 5300 (the first movable member) and the transfer member 5600 (the second movable member) move together distally within the housing.

When the medicament delivery mechanism 5300 is moving distally, the piston portion 5330 of the medicament delivery mechanism 5300 applies a portion of the force $F_4$ to the medicament container 5200. More specifically, as shown in FIG. 94, the first shoulder 5335 of each engagement member 5336 contacts the flange 5214 of the medicament container 5200. The movement of the medicament delivery mechanism 5300 moves the piston portion 5330 in the distal direction. Therefore, with the first shoulder 5335 of each engagement member 5336 in contact with the flange 5214 of the medicament container 5200, the first shoulder 5335 transfers a portion of the force $F_4$ to the medicament container 5200 to move the medicament container 5200 in the distal direction. The movement of the medicament container 5200 within the housing 5100 results in the needle insertion operation.

As shown in FIG. 78, the distance between the end surface of the piston rod 5333 and the engagement members 5336 is such that when the first shoulder 5335 of each engagement member 5336 contacts the flange 5214, the distal end portion 5332 of the piston rod 5333 is spaced apart from the elastomeric member 5217 within the medicament container 5200. This arrangement prevents any portion of the force $F_4$ from being applied or transferred to the plunger 5217. Said another way, during the needle insertion operation (i.e., when the medical injector is being moved to its fourth configuration) the plunger 5217 is isolated from the piston portion 5330. Accordingly, this arrangement reduces and/or eliminates leakage and/or injection of medicament 5220 from the medicament container 5200 during the needle insertion operation.

After the transfer member 5600, the medicament delivery mechanism 5300 and the medicament container 5200 move in the distal direction a given distance, the damping member 5240 of the medicament container 5200 contacts the proximal surface 5108 of the medicament container holder 5127 and 5157 of the first housing portion 5110 and the second housing portion 5140, respectively. The proximal surface 5108 prevents the medicament container 5200 from moving further in the distal direction. Thus, when the flange 5214 and/or the damping member 5240 contact the proximal surface 5108, the needle 5216 is fully inserted into the target location of a patient. At this point, the medical injector 5000 can be moved from the fourth configuration to the fifth configuration (i.e., the medicament delivery configuration), shown in FIGS. 95 and 96.

When the damping member 5240 of the medicament container 5200 is in contact with the proximal surface 5108 of the medicament container holders 5127 and 5157, the medicament container 5200 is prevented from moving in the distal direction. The portion of the force $F_4$ applied by the spring 5420, however, continues to urge the transfer member 5600 and the medicament delivery mechanism 5300 in the direction shown by the arrow RR in FIG. 95. More specifically, when the medicament container 5200 is in contact with the medicament container holders 5127 and 5157, the force $F_4$ applied by the spring 5420 moves the transfer member 5600 and the medicament delivery mechanism 5300 in the distal direction, relative to the medicament container 5200. In this manner, the portion of the force $F_4$ applied to the medicament delivery mechanism 5300 causes the deformable portion 5338 of the engagement members 5336 to deform and/or bend inward (see e.g., FIG. 96). Similarly stated, the deformable portion 5338 of each of the engagement members 5336 is configured to deform when the damping member 5240 of the medicament container 5200 is in contact with the proximal surface 5108 of the medicament container holders 5127 and 5157. When the deformable portion 5338 is deformed, the engagement members 5336 are disposed within the recesses 5334 defined by the piston rod 5333 (see e.g., FIG. 96). In this manner, the piston rod 5333 is configured to move within the medicament container 5200 into contact with the elastomeric member 5217 to deliver the medicament 5220. Similarly stated, the piston portion 5330 is moved from its first configuration, in which the engagement members 5336 collectively have a size that is greater than the size (i.e., diameter) of the inner bore of the medicament container 5200 to its second configuration, in which the engagement members 5336 collectively have a size that is less than the size (i.e., diameter) of the inner bore of the medicament container 5200. This decrease in size (or diameter) allows the piston rod 5333 to move within the medicament container 5200.

When the medicament delivery mechanism 5300 moves in the distal direction to move the elastomeric member 5217 and inject the medicament 5220, the serpentine portion 5355 and/or the bias portion 5350 is also compressed. More specifically, a portion of the force $F_4$ compresses the serpentine portion 5355 and/or the bias portion 5350 between the proximal end portion 5301 of the medicament delivery mechanism 5300 and the lower bias plate 5124. Similarly stated, the bias portion 5350 is configured to compress as the serpentine portion 5355 elastically deforms (e.g., bending, squeezing, or compressing such that the bias portion 5350 returns to a non-deformed configuration when the deforming force is removed). In this manner, the space defined between adjacent portions of the serpentine portion 5355 is reduced.

As the spring 5420 fully expands, the medicament delivery mechanism 5300 moves in the distal direction to fully inject the medicament 5220 within the medicament container 5200 through the needle 5216. Additionally, when the spring 5420 is fully expanded and/or when the medicament delivery mechanism 5300 has moved a desired distance within the housing 5100, the latch arm 5618 of the transfer member 5600 engages the transfer member release protrusion 5121 of the housing 5100. As described above, the transfer member release protrusion 5121 contacts the latch arm 5618 of the transfer member 5600 such that the bendable portion 5622 disposed at the distal end of the latch extension 5617 bends. In this manner, the latch 5620 of the latch arm 5618 is disengaged from the second latch protrusion 5318 of the latch portion 5310 of the medicament delivery mechanism 5300 (see e.g., FIGS. 97 and 98). Similarly stated, the spring 5240 and/or the transfer member 5600 are decoupled from the medicament delivery mechanism 5300. With the latch arm 5618 disengaged from the latch portion 5310, the medical injector 5000 can be moved from the fifth configuration to the sixth configuration (i.e., the retraction configuration).

As shown in FIG. 98, the transfer mechanism 5600 is deformed such that the transfer member 5600 and/or the spring 5420 are no longer engaged with the medicament delivery mechanism 5300. Therefore, the medicament delivery mechanism 5300 is configured to move within the housing 5100 in the direction shown by the arrow SS in FIG. 97 in response to the force produced by the bias portion 5350. Similarly stated, with the medicament delivery mechanism 5300 disengaged from the transfer member 5600 and/or the spring 5420, the force $F_4$ is no longer applied to the medicament delivery mechanism 5300. In this manner, the bias portion 5350 is configured to expand in the direction of the arrow SS shown in FIG. 97 to apply a retraction force to the medicament delivery mechanism 5300. Similarly stated, with the portion of the force $F_4$ configured to compress the bias portion 5350 removed, the bias portion 5350 expands, returning to its uncompressed (i.e., non-deformed) configuration.

During the retraction operation, the second shoulder 5313 included in the latch portion 5310 is configured to engage a distal surface of the damping member 5240 and/or the flange 5214. The second shoulder 5313 is further configured to transmit the retraction force produced by the expansion of the bias portion 5350 to the flange 5214, thereby moving the medicament container 5200 proximally. Similarly stated, the medicament container 5200 is moved in the proximal direction towards the first position of the medicament container 5200. This motion, removes the needle 5216 from the target location of the patient and retracts the needle into the housing 5100, as shown in FIG. 97.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although the first surface 3341 of the piston member 3330 is shown as being substantially parallel to the second surface 3342 of the piston member 3330, in other embodiments, the first surface of a movable member can be at any suitable angular orientation to a second surface of the movable member.

Although the carrier 3370 is shown as substantially surrounding the medicament container 3200, in other embodiments, a carrier and/or the contact shoulders (analogous to the first shoulder 3377 and the second shoulder 3381) need not substantially surround the medicament container 3200. For example, in some embodiments, a carrier can be a single piece member that only partially surrounds the flange 3214 of the medicament container 3200. Similarly stated, in some embodiments, a carrier need not be movable between an opened configuration and a closed configuration, but rather can receive and/or retain the medicament container in a single configuration.

Although the carrier 4370 is described above as being configured to accommodate an o-ring or other suitable damping member to reduce the forces exerted on the medicament container 4200 during insertion and/or injection, in other embodiments, any suitable mechanisms or structures for reducing the energy, impulse and/or forces applied to the carrier, the medicament container, the housing and/or the actuation member can be employed. For example, in some embodiments, a carrier can include a deformable portion (e.g., a "crush rib") configured to deform when contacting the housing during an insertion event. In this manner, the deformable portion can absorb at least a portion of the energy and/or force generated during the impact, thereby reducing the magnitude of the energy, impulse and/or force applied to the medicament container. Similarly, in some embodiments, a portion of a medicament delivery mechanism, such as medicament delivery mechanism 4300 can include a crush rib or an impact portion configured to plastically and/or elastically deform to absorb and/or dampen the forces from the needle insertion operation.

In some embodiments, the outer surface 3815 of the needle sheath 3810 can include a cap or cover that has different material properties than the remainder of the needle sheath 3810. For example, in some embodiments, the outer surface 3815 can be constructed of a material having greater hardness and/or rigidity than the remainder of the needle sheath 3810. This arrangement allows for sufficient structural rigidity to assembly the needle sheath 3810 within the engagement portion 3720 of the safety lock 3700. In other embodiments, however, any of the needle sheaths described herein need not include an outer cover or cap. The use of a cap-less design can reduce manufacturing and/or assembly costs.

Although the medical injector 3000 is shown above as including a gas container 3410 that is actuated by a puncturer that moves within the housing 3100 with the release member 3550, in other embodiments a system actuation assembly 3500 can include a puncturer that is substantially fixed within the housing and a gas container that moves within the housing into contact with the puncturer upon actuation of the device.

Although the medicament delivery mechanism 5300 is shown above as being a monolithically constructed member (i.e., a "first movable member"), in other embodiments, the medicament delivery mechanism 5300 can include multiple members that are separately constructed and/or that are coupled together. For example, in some embodiments, a medicament delivery mechanism can include a first member that corresponds to the latch portion 5310 and the piston portion 5330, and a second, separately constructed member that produces a retraction force (e.g., similar to the function of the bias portion 5350. In such embodiments, for example, second member can be a separately constructed coil spring or the like.

Any of the devices and/or medicament containers shown and described herein can be constructed from any suitable material. Such materials include glass, plastic (including thermoplastics such as cyclic olefin copolymers), or any other material used in the manufacture of prefilled syringes containing medications.

Any of the devices and/or medicament containers shown and described herein can include any suitable medicament or therapeutic agent. In some embodiments, the medicament contained within any of the medicament containers shown herein can be a vaccine, such as, for example, an influenza A vaccine, an influenza B vaccine, an influenza A (H1N1) vaccine, a hepatitis A vaccine, a hepatitis B vaccine, a *haemophilus* influenza Type B (HiB) vaccine, a measles vaccine, a mumps vaccine, a rubella vaccine, a polio vaccine, a human papilloma virus (HPV) vaccine, a tetanus vaccine, a diphtheria vaccine, a pertussis vaccine, a bubonic plague vaccine, a yellow fever vaccine, a cholera vaccine, a malaria vaccine, a smallpox vaccine, a pneumococcal vaccine, a rotavirus vaccine, a varicella vaccine, a rabies vaccine and/or a meningococcus vaccine. In other embodiments, the medicament contained within any of the medicament containers shown herein can be a catecholamine, such as epinephrine. In other embodiments, the medicament contained within any of the medicament containers shown herein can be an opioid receptor antagonist, such as naloxone, including any of the naloxone formulations described in U.S. Pat. No. 8,627,816 entitled, "Medicament Delivery Device for Administration of Opioid Antagonists Including Formulation for Naloxone," filed on Feb. 28, 2011. In yet other embodiments, the medicament contained within any of the medicament containers shown herein can include peptide hormones such as insulin and glucagon, human growth hormone (HGH), erythropoiesis-stimulating agents (ESA) such as darbepoetin alfa, monoclonal antibodies such as denosumab and adalimumab, interferons, etanercept, pegfilgrastim, and other chronic therapies, or the like. In yet other embodiments, the medicament contained within any of the medicament containers shown herein can be a placebo substance (i.e., a substance with no active ingredients), such as water.

Although the medical injector 3000 includes the electronic circuit system cavity 3153, the gas cavity 3154 and/or the medicament cavity 3157 that are shown and described as being fluidically and/or physically isolated from each other, in other embodiments, any of the electronic circuit system cavity 3153, the gas cavity 3154 and/or the medicament cavity 3157 can be fluidically coupled to and/or share a common boundary with each other. In some embodiments, for example, a housing can define a single cavity within which a medicament container, an energy storage member and an electronic circuit system are disposed.

The medicament containers and/or medicament delivery devices disclosed herein can contain any suitable amount of any medicament. For example, in some embodiments, a medicament delivery device as shown herein can be a single-dose device containing an amount medicament to be delivered of approximately 0.4 mg, 0.8 mg, 1 mg, 1.6 mg or 2 mg. As described above, the fill volume can be such that the ratio of the delivery volume to the fill volume is any suitable value (e.g., 0.4, 0.6 or the like). In some embodiments, an electronic circuit system can include "configuration switch" (similar to the configuration switch 3974 shown and described above) that, when actuated during the assembly of the delivery device, can select an electronic output corresponding to the dose contained within the medicament container.

Although the electronic circuit system 3900 is shown and described above as having two irreversible switches (e.g., switch 3972 and switch 3973), in other embodiments, an electronic circuit system can have any number of switches. Such switches can be either reversible or irreversible.

Although the electronic circuit system 3900 is shown and described above as producing an electronic output in response to the actuation of two switches (e.g., switch 3972 and switch 3973), in other embodiments, an electronic circuit system can produce an electronic output in response to any suitable input, command or prompt. Suitable input for prompting an output can include, for example, an audible input by the user (e.g., the user's response to a voice prompt produced by the electronic circuit system), an input from a "start button" depressed by the user, an input from a sensor (e.g., a proximity sensor, a temperature sensor or the like), movement of (e.g., shaking) of the medicament delivery device, or the like. In some embodiments, an electronic circuit system can include a microphone and/or a voice recognition module to detect a user's vocal input.

Although medical devices having two LEDs and an audio output device have been shown, in other embodiments the medical device might have any number of LEDs and/or audio output devices. Additionally, other types of output devices, such as haptic output devices, can be used. In some embodiments, outputs from an electronic circuit system can include, for example, an audible or visual output related to the composition of the medicament (e.g., an indication of the expiration date, the symptoms requiring treatment with the medicament or the like), the use of the medicament delivery device, and/or post-administration procedures (e.g., a prompt to call 911, instructions for the disposal of the device or the like).

Any of the medicament delivery devices shown and described herein can include any of the electronic circuit systems shown and described herein. For example, although the medical injector 5000 is shown as being devoid of an electronic circuit system, in other embodiments, the medical injector 5000 can include an electronic circuit system similar to the electronic circuit system 3900 shown and described above with reference to FIGS. 29-39. Moreover, although the electronic circuit systems (e.g., the electronic circuit system 3900) are shown and described herein as being coupled the housing of the medicament delivery device, in other embodiments, all or a portion of an electronic circuit system can be coupled to a removable cover (e.g., cover 3190). For example, in some embodiments, the cover can include an electronic circuit system (the "master ECS") including an audible output device, and the electronic circuit system can be configured to receive on or more signals from an electronic circuit system (the "slave ECS") coupled to the medicament delivery device. In this manner, the master ECS can receive indications of when the safety tab has been removed, when the device has been actuated or the like, and can produce an audible output as described herein. In some such embodiments, the master ECS and the slave ECS can be similar to the electronic circuit systems shown and described in U.S. Pat. No. 8,172,082 entitled, "Devices, Systems and Methods for Medicament Delivery," filed on Feb. 5, 2007, which is incorporated herein by reference in its entirety.

Although the electronic circuit system 3900 is shown and described above as producing an electronic output in response to the removal of the safety lock 3700 and/or movement of the base 3510, in other embodiments, any suitable component within a medicament delivery device can function to actuate the electronic circuit system. For example, in some embodiments, a carrier (similar to the carrier 3370) can include a protrusion configured to engage a portion of an electronic circuit system such that the electronic circuit system produces an output in response to movement of the carrier. In other embodiments, an electronic circuit system can produce an electronic output in response to the deformation of a portion of a movable member (e.g., the engagement portion 3379 of the carrier 3370). In such embodiments, the deformable portion may be configured to engage a portion of the electronic circuit system or may be configured such that a portion of the electronic circuit system is disposed therein (e.g., a copper trace) to activate the electronic circuit system.

In some embodiments, the electronic circuit system 3900 of the types shown and described herein can be used in either an actual medicament delivery device or a simulated medicament delivery device. A simulated medicament delivery device can, for example, correspond to an actual medicament delivery device and can be used, for example, to train a user in the operation of the corresponding actual medicament delivery device.

The simulated medicament delivery device can simulate the actual medicament delivery device in any number of ways. For example, in some embodiments, the simulated medicament delivery device can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device can include components that correspond to the components of the actual medicament delivery device. In this manner, the simulated medicament delivery device can simulate the look, feel and sounds of the actual medicament delivery device. For example, in some embodiments, the simulated medicament delivery device can include external components (e.g., a housing, a needle guard, a sterile cover, a safety lock or the like) that correspond to external components of the actual medicament delivery device. In some embodiments, the simulated medicament delivery device can include internal components (e.g., an actuation mechanism, a compressed gas source, a medicament container or the like) that correspond to internal components of the actual medicament delivery device.

In some embodiments, however, the simulated medicament delivery device can be devoid of a medicament and/or those components that cause the medicament to be delivered (e.g., a needle, a nozzle or the like). In this manner, the simulated medicament delivery device can be used to train a user in the use of the actual medicament delivery device without exposing the user to a needle and/or a medicament. Moreover, the simulated medicament delivery device can have features to identify it as a training device to prevent a user from mistakenly believing that the simulated medicament delivery device can be used to deliver a medicament. For example, in some embodiments, the simulated medicament delivery device can be of a different color than a corresponding actual medicament delivery device. Similarly, in some embodiments, the simulated medicament delivery device can include a label clearly identifying it as a training device.

Although various embodiments have been described as having particular features and/or combinations of components, other embodiments are possible having a combination of any features and/or components from any of embodiments where appropriate. For example, any of the devices shown and described herein can include an electronic circuit system as described herein. For example, although the medicament delivery device 4000 shown in FIGS. 56 and 57 is not shown as including an electronic circuit system, in other embodiments, a medicament delivery device similar to the device 4000 can include an electronic circuit system similar to the electronic circuit system 3900 shown and described above.

Any of the medicament containers described herein can include any of the elastomeric members described herein. For example, the medicament container 5200 can include an elastomeric member 5217 that is formulated to be compatible with the medicament contained therein. Although the medical injector 5000 includes a single elastomeric member 5217, in other embodiments, any number of elastomeric members 5217 can be disposed within the medicament container 5200. For example, in some embodiments, a medicament container can include a dry portion of a medicament and a fluid portion of the medicament, configured to be mixed before injection. The piston portion 5330 of the medicament delivery mechanism 5300 can be configured to engage multiple elastomeric members 5217 associated with the portions of the medicament. In this manner, multiple elastomeric members 5217 can be engaged to mix the dry portion with the fluid portion of the medicament before the completion of an injection event. In some embodiments, for example, any of the devices shown and described herein can include a mixing actuator similar to the mixing actuators shown and described in U.S. Patent Publication No. 2013/0023822 entitled, "Devices and Methods for Delivering Medicaments from a Multi-Chamber Container," filed Jan. 25, 2012, which is incorporated herein by reference in its entirety.

What is claimed is:
1. An apparatus, comprising:
a housing defining a gas chamber;
a medicament container assembly disposed within the housing, the medicament container assembly including a container body and an elastomeric member disposed within the container body, the container body including a flange, the medicament container assembly including a needle coupled to a distal end portion of the container body; and a carrier assembly coupled to the medicament container assembly, the carrier assembly including a carrier body and a movable member, the carrier body configured to move within the housing from a first carrier position to a second carrier position in response to actuation of an energy storage member, the needle disposed within the housing when the carrier assembly is in the first carrier position, a portion of the needle disposed outside of the housing when the carrier assembly is in the second carrier position, the carrier body defining an internal volume sized to receive a portion of the container body and having a shoulder defining a recess, the carrier assembly including a first seal member and a second seal member, the first seal member in sliding contact with an inner surface of the housing to fluidically isolate the gas chamber, the second seal member being positioned at least partially within the recess defined by the carrier body, the second seal member being in contact with a proximal end portion of the container body, the shoulder, the carrier body, and a distal-most surface of the flange.

2. The apparatus of claim 1, wherein the medicament container assembly includes a needle sheath disposed about the needle, a surface of the needle sheath configured to engage a safety lock such that a movement of the safety lock removes the needle sheath from the medicament container assembly.

3. The apparatus of claim 1, wherein the medicament container assembly is a prefilled syringe, the needle being staked to the distal end portion of the container body.

4. The apparatus of claim 1, wherein the carrier body is configured to move within the housing in a distal direction from the first carrier position to the second carrier position, the apparatus further comprising:

a retraction spring coupled to the carrier assembly, the retraction spring configured to urge the carrier body in a proximal direction from the second carrier position towards the first carrier position, the carrier body including a first stop surface configured to engage a first portion of the housing to limit movement of the carrier body in the proximal direction when the carrier body is in the first carrier position, the carrier body including a second stop surface configured to engage a second portion of the housing to limit movement of the carrier body in the distal direction when the carrier body is in the second carrier position.

5. The apparatus of claim 1, wherein:
the second seal member is an o-ring disposed between the shoulder of the carrier body and the flange.

6. The apparatus of claim 1, wherein:
the proximal end portion of the container body is disposed within the internal volume;
the carrier body includes a distal end surface; and
the distal end portion of the container body extends outside of the distal end surface of the carrier body.

7. The apparatus of claim 6, wherein the distal end surface of the carrier body is configured to contact a portion of the housing to limit distal movement of the carrier body when the carrier body is in the second carrier position.

8. The apparatus of claim 1, wherein the carrier body is configured to move within the housing in a distal direction from the first carrier position to the second carrier position, the apparatus further comprising:

a retraction spring coupled to the carrier assembly, the retraction spring configured to urge the carrier body in a proximal direction from the second carrier position towards the first carrier position; and a valve configured to allow fluid communication between the gas chamber and an area outside the gas chamber when the valve is actuated, the carrier assembly including an actuator configured to actuate the valve.

9. The apparatus of claim 1, wherein the container body contains a monoclonal antibody.

10. An apparatus, comprising:
a housing defining a gas chamber;
a prefilled syringe assembly disposed within the housing, the prefilled syringe assembly including a syringe body and an elastomeric member disposed within the syringe body, the prefilled syringe assembly including a needle staked to a distal end portion of the syringe body;

an energy storage member configured to produce a pressurized gas within the gas chamber when the energy storage member is actuated;

a system actuator assembly configured to actuate the energy storage member, the system actuator assembly including a release member and a first seal member positioned between the release member and an inner surface of the housing, the first seal member being in sliding contact with the inner surface to fluidically isolate the gas chamber; and a carrier assembly coupled to the prefilled syringe assembly, the carrier assembly including a carrier body and a movable member, the carrier body configured to move within the housing from a first carrier position to a second carrier position in response to a force exerted on an outer surface of the carrier assembly by the pressurized gas, the needle disposed within the housing when the carrier body is in the first carrier position, a portion of the needle disposed outside of the housing when the carrier body is in the second carrier position, the carrier body defining an internal volume sized to receive a portion of the syringe body and having a shoulder defining a recess, the carrier assembly including a second seal member and a third seal member, the second seal member surrounding the outer surface of the carrier assembly to fluidically isolate the gas chamber, the third seal member being positioned at least partially within the recess defined by the carrier body, the third seal member being in contact with an inner surface of the carrier assembly, the shoulder, the syringe body and a distal-most surface of a flange assembly, the shoulder, and the syringe body.

11. The apparatus of claim 10, wherein the second seal member is in sliding contact with the inner surface of the housing, a shape of the outer surface of the carrier assembly being non-circular.

12. The apparatus of claim 10, wherein:
a proximal end portion of the syringe body of the prefilled syringe assembly the flange; and
the third seal member is disposed within the recess such that the third seal member is between the shoulder of the carrier body and the flange.

13. The apparatus of claim 10, wherein:
a proximal end portion of the syringe body of the prefilled syringe assembly the flange; and
the proximal end portion of the syringe body is disposed within the internal volume such that the third seal member is between the shoulder and the flange.

14. The apparatus of claim 10, wherein:
- the elastomeric member is configured to move within the syringe body from a first elastomeric member position to a second elastomeric member position in response to a force from the pressurized gas to expel a medicament from the syringe body via the needle when the carrier assembly is in the second carrier position; and
- an actuator of the carrier assembly is a protrusion configured to move relative to a valve to actuate the valve when the elastomeric member moves to the second elastomeric member position.

15. The apparatus of claim 10, wherein the syringe body contains a monoclonal antibody.

\* \* \* \* \*

UNITED STATES PATENT AND TRADEMARK OFFICE
CERTIFICATE OF CORRECTION

| | | |
|---|---|---|
| PATENT NO. | : 12,420,016 B2 | Page 1 of 1 |
| APPLICATION NO. | : 17/869570 | |
| DATED | : September 23, 2025 | |
| INVENTOR(S) | : Eric S. Edwards et al. | |

It is certified that error appears in the above-identified patent and that said Letters Patent is hereby corrected as shown below:

In the Claims

Claim 10, Line 39, Column 60, Line 51, delete "assembly, the shoulder, and the syringe body"

Claim 12, Line 3, Column 60, Line 58, change "syringe assembly the flange" to --syringe assembly includes the flange--

Claim 13, Line 3, Column 60, Line 64, change "syringe assembly the flange" to --syringe assembly includes the flange--

Signed and Sealed this
Eleventh Day of November, 2025

John A. Squires
*Director of the United States Patent and Trademark Office*